(12) United States Patent
Luy et al.

(10) Patent No.: US 7,939,305 B2
(45) Date of Patent: May 10, 2011

(54) PUFA-PKS GENES FROM *ULKENIA*

(75) Inventors: Markus Luy, Ried-Brig (CH); Matthias Rüsing, Köln (DE); Thomas Kiy, Frankfurt/Main (DE)

(73) Assignee: Nutrinova Nutrition Specialties & Food Ingredients GmbH, Frankfurt (DE)

( * ) Notice: Subject to any disclaimer, the term of this patent is extended or adjusted under 35 U.S.C. 154(b) by 788 days.

(21) Appl. No.: 11/547,921

(22) PCT Filed: Apr. 8, 2005

(86) PCT No.: PCT/EP2005/003701
§ 371 (c)(1),
(2), (4) Date: May 21, 2007

(87) PCT Pub. No.: WO2005/097982
PCT Pub. Date: Oct. 20, 2005

(65) Prior Publication Data
US 2009/0093033 A1    Apr. 9, 2009

(30) Foreign Application Priority Data

Apr. 8, 2004 (DE) .................. 10 2004 017 370

(51) Int. Cl.
*C12N 9/00* (2006.01)
(52) U.S. Cl. .......... 435/183; 435/189; 435/193; 435/232
(58) Field of Classification Search .................. None
See application file for complete search history.

(56) References Cited

U.S. PATENT DOCUMENTS

| | | |
|---|---|---|
| 5,798,259 A | 8/1998 | Yazawa et al. |
| 6,566,583 B1 | 5/2003 | Facciotti et al. |

FOREIGN PATENT DOCUMENTS

WO    WO 02/083870 A2    10/2002

*Primary Examiner* — Nashaat T Nashed
(74) *Attorney, Agent, or Firm* — Hammer & Associates, P.C.

(57) ABSTRACT

The invention relates to genes which are coded for sequences specific to polyketide synthases (PKS). The thus synthesized PKS is characterized by the enzymatic capacity thereof to produce PUFAs (polyunsaturated fatty acids). The invention also relates to the identification of the corresponding DNA-sequences, in addition to the use of said nucleotide sequences for the production of recombined and/or transgenic organisms.

6 Claims, 15 Drawing Sheets

```
Ulkenia        1   -MQRENRLESNMDTRIAIIGMSAILPCGTTVRESWEAIRDGIDCLSDLPEDRVDVTAYF
Schizochytrium 1   MAARLQEQKGEEMDTRIATIGMSAILPCGTTVRESWETIRAGIDCLSDLPEDRVDVTAYF
consensus      1   . *       . ****** ******************  ** ******************

Ulkenia        60  DPVKTTKDKIYCKRGGFIPEYDFDAREFGLNMFQMEDSDANQTWLLKVKEALEDAGIIA
Schizochytrium 61  DPVKTTKDKIYCKRGGFIPEYDFDAREFGLNMFQMEDSDANQTRLLKVKEALQDAGIIA
consensus      61  ******************************************  ******** ***** *

Ulkenia        120 LGKEKKNIGCVLGIGGGQKSSHEFYSRLNYVVVEKVLRKMGMPEEDVQAAVEKYKANFPE
Schizochytrium 121 LGKEKKNIGCVLGIGGGQKSSHEFYSRLNYVVVEKVLRKMGMPEEDVKVAVEKYKANFPE
consensus      121 *  ********************************************  **********

Ulkenia        180 WRLDSFPGFLGNVTAGRCTNTFNLDGMNCVVDAACASSLIAVKVAIDELLGGDCDMMITG
Schizochytrium 181 WRLDSFPGFLGNVTAGRCTNTFNLDGMNCVVDAACASSLIAVKVAIDELLVGDCDMMVTG
consensus      181 ************************************************* ****** **

Ulkenia        240 ATCTDNSIGMYMAFSKTPVFSTDPSVRAYDEKTKGMLIGEGSAMLVLKRYADAVRDGDEI
Schizochytrium 241 ATCTDNSIGMYMAFSKTPVFSTDPSVRAYDEKTKGMLIGEGSAMLVLKRYADAVRDGDEI
consensus      241 ************************************************************

Ulkenia        300 HAVIRGCASSSDGKASGIYTPTISGQEEALRRAYMRANVDPATVTLVEGHGTGTPVGDRI
Schizochytrium 301 HAVIRGCASSSDGKAAGIYTPTISGQEEALRRAYNRACVDPATVTLVEGHGTGTPVGDRI
consensus      301 *************** ****************** **  *********************

Ulkenia        360 ELTALRNLFDSAYGN-EKEKVAVGSIKSNIGHLKAVAGLAGMIKVIMALKHKTLPFTINV
Schizochytrium 361 ELTALRNLFDKAYGEGNTEKVAVGSIKSSIGHLKAVAGLAGMIKVIMALKHKTLEGTINV
consensus      361 **********  ***    ********* ************************  ****

Ulkenia        419 DEPFKLYDNTPITQSSLYINTMNRPWFPAPGVPRRAGISSFGFGGANYHAVLEEAEPEHQ
Schizochytrium 421 DNPPNLYDNTPINESSLYINTMNRPWFPPPGVPRRAGISSFGFGGANYHAVLEEAEPEHT
consensus      421 * ** ******* ************** ********************************

Ulkenia        479 KAYRLNKRPQPVLMMASFTQAIASLCEAQLKEFEKAIEENKTVKNTAYIKCVDFCEKFKF
Schizochytrium 481 TAYRLNKRPQPVLMMAAFPAAIQSLCEAQLKEFEAAIKENETVKNTAYIKCVKFGEQFKF
consensus      481 ************ **   *  ********** ** ** ** ***********    * ***

Ulkenia        539 PGSIFSSNARLGFLVKEAPDATETLRAIVAQFQKSAGKESFLPRQGVSFRACGINTTGG
Schizochytrium 541 PGSIPATNARLGFLVKTADDACSTLRAICAQFAKDVTKEAWLPREGVSFRAKGIATNGG
consensus      541 ****   ********* *  ** ***** ***  *  **   *** ****** **  *

Ulkenia        599 VAALFSGQGAQYTHMFSEVAMNWPQFREISDMDRAQAKVAGADKDIERVSQVLYPRKPY
Schizochytrium 601 VAALFSGQGAQYTHMFSEVAMNWPQFRCSIAAMDAAQSKVAGSDKDIERVSQVLYPRKPY
consensus      601 ***************************  **  ** ** *** ***.***********

Ulkenia        659 NSEPEQDHKKISLTSVSQPSTLACALGAEEIFKQAGEKPDFAAGHSLGEFAALYAADCVN
Schizochytrium 661 EREPEQNPKKISLTAYSQPSTLACALGAEEIFKEAGEIPDFAAGHSLGEFAALYAAGCVD
consensus      661 ****  ****** ********************.*** *****************  **

Ulkenia        719 RDILFELVCRRARIMGGKDAPATPKGCMAAVIGPNAEKIQTRTADVWLGNCNSPSQTVIT
Schizochytrium 721 RDELFELVCRRARIMGGKDAPATPKGCMAAVIGPNAENIKVQAAVVWLGNSNSPSQTVIT
consensus      721 ** ********************************* *      *****.*********
```

Figure 4A

```
Ulkenia        779  GSVEGIKKESELLQSEGFRVVPLACESAFHSPQMQNASSAFKDVLSKVAFRQPSAQTKLF
Schizochytrium 781  GSVEGIQAESARLQKEGFRVVPLACESAFHSPQMENASSAFKDVLSKVSFRTPKAETKLF
consensus      781  ***** ** ** ****************** ************ *** ** *  ****

Ulkenia        839  SNVSGETYSNNAQDELKEHMTSSVKFLLQVRNMHSAGARIFVEFGPKQVLSKLVSETLKD
Schizochytrium 841  SNVSGETYPTDAREMLTQHMTSSVKFLLQVRNMHQAGARIFVEFGPKQVLSKLVSETLKD
consensus      841  ********    *  * **********.******.*************************

Ulkenia        899  DPSETTHSVNPSSGKDADIQLREAAVQLVVAGVNLQGFDKWDAPDATRLQPIKKKTTLR
Schizochytrium 901  DPSWATRSVNPASGTDSDIQLREAAVQLVVAGVNLQGFDKWDAPDATRLQAIKKKTTLR
consensus      901  ***  * **** ** * ***************************** * *********

Ulkenia        959  LSAATYVSDKTKKAREAAMNDGRMESCVS-KVIAPPDAKPVDTKAQEEVARLQKQLQDA
Schizochytrium 961  LSAATYVSDKTKKVREAAMNDGRCVIYEKGAAPLIKAPEPVDEAAKREAERLQKELQDA
consensus      961  ************* ********  .      .    .   * ** * *  **** ****

Ulkenia        1018 QAQIQKAKADAAEADKKLAAAKEAKRAAASAPVQKQVDTIIVEKHRAILKSMLAELDGY
Schizochytrium 1021 QRQIDDAKRAAAEANSKLAAAKEBAKTAAASA--KPAVDTAWVRKHRAILKSMLAELDGY
consensus      1021 * *  ** ** ****  ****** ** ****.. *** .*.*****************.*

Ulkenia        1078 STPGAVSSS-----FQAEVAATPAPVAAPVAAAPAPAVNNALLAKAESVVMEVLAAKTGY
Schizochytrium 1079 GSVDASSLQQQQQQQTAPAPVKAAAPAAPVASAPAPAVSNELLEKAEIVVMEVLAAKTGY
consensus      1081   *  *  ..... **     *   ***** *.**  * **   *.***********

Ulkenia        1133 ETDMIEPDMELETELGIDSIKRVEILSEVQAQLNVEAKDVDALSRTRTVGEVVNAMKAEI
Schizochytrium 1139 ETDMIEADMELETELGIDSIKRVEILSEVQAMLNVEAKDVDALSRTRTVGEVVNAMKAEI
consensus      1141 ****** *********************** ****************************

Ulkenia        1193 AGSSS---AAAAAPAPVAAPAAAPAPAVNSALLAKAETVVMEVLAAKTGYETDMIEPDMEL
Schizochytrium 1199 AGSSPAPAAAAPAPAKAAPAAAAPAVSNELLEKAETVVMEVLAAKTGYETDMIESDMEL
consensus      1201 ****...*****  *****  *** **   * ****************  ****

Ulkenia        1251 ETELGIDSIKRVEILSEVQAQLNVEAKDVDALSRTRTVGEVVNAMKAEIAGSSSAAAAAP
Schizochytrium 1259 ETELGIDSIKRVEILSEVQAMLNVEAKDVDALSRTRTVGEVVNAMKAEIAGGSAPAPAAA
consensus      1261 ******************** ***************************** *. * **

Ulkenia        1311 AP-VAAAPAPVAAAAPAVSSALLEKAESVVMEVLAAKTGYETDMIEADMELETELGIDSI
Schizochytrium 1319 APGPAAAAPAPAAAAPAVSNELLEKAEIVVMEVLAAKTGYETDMIESDMELETELGIDSI
consensus      1321 **. *** ******** ******** ****************  ***************

Ulkenia        1370 KRVEILSEVQAQLNVEAKDVDALSRTRTVGEVVNAMKAEIAGSS---AAAPAPVAAAPA
Schizochytrium 1379 KRVEILSEVQAMLNVEAKDVDALSRTRTVGEVVDAMKAEIAGGSPAPAAAAPAPAAAAP
consensus      1381 *********** ******************** ********* ...*** ***   ***

Ulkenia        1427 PVAAAAPAVNSALLEKAETVVMEVLAAKTGYETDMIEPDMELETELGIDSIKRVEILSEV
Schizochytrium 1439 APAAPAPAVSSELLEKAETVVMEVLAAKTGYETDMIESDMELETELGIDSIKRVEILSEV
consensus      1441  * ****  * ********************************  **************

Ulkenia        1487 QAQLNVEAKDVDALSRTRTVGEVVNAMKAEIAGSSSAAAAAPAPVAAAPAVAAPAVSSA
Schizochytrium 1499 QAMLNVEAKDVDALSRTRTVGEVVDAMKAEIAGGSPAPAAAAPAPAAAAPAAPAP--
consensus      1501 ** ******************** ********* * ** ** **  **  **  ..

Ulkenia        1547 LLEKAESVVMEVLAAKTGYETDMIEADMELETELGIDSIKRVEILSEVQAQLNVEAKDVD
Schizochytrium 1557 ------------------------------------------------------------
consensus      1561 ............................................................
```

Figure 4B

```
Ulkenia       1607 ALSRTRTVGEVVNAMKAEIAGSSGAAAAAPAPVAASPAPVAAAAPAVSSALLEKAESVVM
Schizochytrium 1557 ------------------------------AAP------APAVSSELLEKAETVVM
consensus     1621 ..............................**.......******.******.***

Ulkenia       1667 EVLAAKTGYETDMIEADMELETELGIDSIKRVEILSEVQAMLNVEAKDVDALSRTRTVGE
Schizochytrium 1577 EVLAAKTGYETDMIESDMELETELGIDSIKRVEILSEVQAMLNVEAKDVDALSRTRTVGE
consensus     1681 *************** ********************************************

Ulkenia       1727 VVNAMKAEIAGSSEAAAAAPAPVAAAPAPVTAAAP-AVSSALLEKAESVVMEVLAAKTGY
Schizochytrium 1637 VVDAMKAEIAGSSTSAPAAAAPAPAAAAPAPAAAAPAVSNELLEKAETVVMEVLAAKTGY
consensus     1741 ** *********. * ** ** ** ** *** .*** ******.**************

Ulkenia       1786 ETDMIEADMELETELGIDSIKRVEILSEVQAMLNVEAKDVDALSRTRTVGEVVNAMKAEI
Schizochytrium 1697 ETDMIESDMELETELGIDSIKRVEILSEVQAMLNVEAKDVDALSRTRTVGEVVDAMKAEI
consensus     1801 ****** ********************************************** ******

Ulkenia       1846 ASSSGAAAPAPAAAVAPAPAAAPAVSSALLEKAESVVMEVLAAKTGYETDMIEADMELET
Schizochytrium 1757 AGG---SAPAPAAAAPAPAAAAPAVSNELLEKAETVVMEVLAAKTGYETDMIESDMELET
consensus     1861 *  ... ******  *******  ******.******************** ******

Ulkenia       1906 ELGIDSIKRVEILSEVQAMLNVEAKDVDALSRTRTVGEVVNAMKAEIASSSE----AAAP
Schizochytrium 1814 ELGIDSIKRVEILSEVQAMLNVEAKDVDALSRTRTVGEVVDAMKAEIAGSSSPAPAAAAP
consensus     1921 **************************************** ******.  .....****

Ulkenia       1962 APAAAAAPAPAAAPAVSSALLEKAESVVMEVLAAKTGYETDMIEADMELETELGIDSIKR
Schizochytrium 1874 APAAAAPAPAAAPAVSSELLEKAETVVMEVLAAKTGYETDMIESDMELETELGIDSIKR
consensus     1981 ****** ********.******.****************** *****************

Ulkenia       2022 VEILSEVQAMLNVEAKDVDALSRTRTVGEVVNAMKAEIASSSGAAAPAPAAAAAPAPAAA
Schizochytrium 1934 VEILSEVQAMLNVEAKDVDALSRTRTVGEVVDAMKAEIAG---CSAPAPAAAAPAPAAAA
consensus     2041 ****************************** ****** ....*******  ***  ***

Ulkenia       2082 PAVSSALLEKAESVVMEVLAAKTGYETDMIEADMELETELGIDSIKRVEILSEVQAMLNV
Schizochytrium 1991 PAVSNELLEKAETVVMEVLAAKTGYETDMIESDMELETELGIDSIKRVEILSEVQAMLNV
consensus     2101 ****.******.****************** ****************************

Ulkenia       2142 EAKDVDALSRTRTVGEVVNAMKAEIAG-SSGAATASAPAAAAAAPAAKISTVHGADCDDL
Schizochytrium 2051 EAKDVDALSRTRTVGEVVDAMKAEIAGGSAPAPAAAPASASAAPAVKIDSVHGADCDDL
consensus     2161 ****************** ********.* * *** ** *.**** ** .*********

Ulkenia       2201 SNMSAEYVDIRRADELLLERPENRPVLIVDDGTELTSALVRVLGACAVVLTFEGLQLAQR
Schizochytrium 2111 SLMHAKYVDIRRPDELLLERPENRPVLAVDDGSELTLALVRVLGACAVVLTFEGLQLAQR
consensus     2221 *.* * .*****.************** **** *** **************.*******

Ulkenia       2261 AGAAVR-HVQVKDLSAESAEKAIKEAEQRFGQLGGFISQQAERFAPAILGFTLMCAKFA
Schizochytrium 2171 AGAAIRHVLAKDLSAESAEKAIKEAEQRFGALGGFISQQAEREPAILGFTLMCAKFA
consensus     2281 ****.***.*** ***************** **************  **.*********

Ulkenia       2320 KASLCTPVQGGRAFIGVARLDGRLGPTSQGESLTRAQRGAIFGLCKTIGLEWSANEV
Schizochytrium 2231 KASLCTAVAGGRPAIGVARLDGRLGPTSQGESDALKRAQRGAIFGLCKTIGLEWSESLV
consensus     2341 ****** * *** * ****************..* * ******************** .*

Ulkenia       2380 FARGIDIAREVHPEDAAVATREMSCADNRIREVGIGLNQKRCTIRAVDEKPGAPKIQIS
Schizochytrium 2291 FSRGEDIAQGMHPEDAAVATVREMACADIRIREVGIGANQQRCTIRAAKIETGNPQRQIA
consensus     2401 *.**.***. ********** ***.***.*********.**.*******  *  ** **
```

Figure 4C

```
Ulkenia       2440 QDDVLLVSGGARGITPLCIREITRQM RGGKYILLGRSKV PAGEPAWCNG SDD-D GKAA
Schizochytrium 2351 KDDVLLVSGGARGITPLCIREITRQ A GGKYILLGRSKV ASBPAWCAG DEKA QKAA
consensus     2461 ********************** . *********** *  *****  *  *    ***

Ulkenia       2499 MQELKRAFSAGEGPKPTP MTHK KLVG T A GAREVRSSIA IEALGGKAIYSSCDVNSAAD
Schizochytrium 2411 TQELKRAFSAGEGPKPTP RAVT KLVG VL GAREVRSSIA LEALGGKAIYSSCDVNSAAD
consensus     2521 *****************     ****  . ********** ********************

Ulkenia       2559 VAKAVR AB QLGARV G VHASGVLRDRLIE QKR PDEFDAVFGTKVTGLENI FGA DM
Schizochytrium 2471 VAKAVR AES QLGARV G VHASGVLRDRLIE KKL PDEFDAVFGTKVTGLENI LAA DRA
consensus     2581 ****** ** ****** * ************* *  ******************** .*.* *

Ulkenia       2619 NLKH VLFSSLAGFHGN GQSDYAMANEAINKMGLEL SDR VSVKSICFGPWDGGMVTPQL
Schizochytrium 2531 NLKI VLFSSLAGFHGN GQSDYAMANEAINKMGLEL AKD VSVKSICFGPWDGGMVTPQL
consensus     2641 **** *************. ****************    ********************

Ulkenia       2679 KKQFQ MGVQIIPREGGADTVARIVLGSSPAEILVGNW TP KKVGS P VV HRKISA S
Schizochytrium 2591 KKQFQ MGVQIIPREGGADTVARIVLGSSPAEILVGNW RTP KKVGS T T HRKISA S
consensus     2701 ***** *************************** **.***** .  . ****** *

Ulkenia       2739 NPFL KDHVIQGR VLPMT A GC LAETCLG FPGYSLWAI DAQLFKGVTVDGDVNCE T
Schizochytrium 2651 NPFL EDHVIQGR RVLPMT A GS LAETCLGL FPGYSLWAI DAQLFKGVTVDGDVNCE T
consensus     2761 **** ******** *****.* . ******* **********.****************.*

Ulkenia       2799 LKPS Q TAGRVM QATLKTF ASGKLVPAYRAVIVLST QGK PPAATT SQ PSL QADPAARG
Schizochytrium 2711 LT PST PS GRVN QATLKTF SSGKLVPAYRAVIVLS NQGA PPANA TM PPSL DADPAL QG
consensus     2821 *  **   ***  ******  ***************  **  *** *  * *** ****  *

Ulkenia       2859 NP YDGKTLFHGPAF GLKE SQNKSQLVAE C FIPSE SAG-EFA DYSF NPFVND A
Schizochytrium 2771 SV DGKTLFHGPAF RG DVSCTKSQLVAK QSA P SD ARGEEAI DT AE DPFVND A
consensus     2881 *  ************  *   .  .** ****** * . *  *   .** . .* ***** *

Ulkenia       2918 FQAMLVW RRTLGQAALPNSIQRIVQHRA PQDKPFY TL SNSASGHSQHK TS QFHNE
Schizochytrium 2831 FQAMLVW RRTLGQAALPNSIQRIVQHRP PQDKPFY TL SNQSGGHSQHK HAL QFHNE
consensus     2941 *******.*******************  ******.** **  *****  .  *****

Ulkenia       2978 QGDLF D QASV TS DSLAF
Schizochytrium 2891 QGDLF D QASV IA DSLAF
consensus     3001 *****.*.****  .*****
```

Figure 4D : Orf 1 Ulkenia-Orf A Schizochytrium Alignment (amino acid sequence)

```
Ulkenia       1   MASRKNVSAAHEMHDEKRIAVVGMAVQYAGCKDKEEFWKVVMGGEAAWTKISDKRLGSNK
Schizochytrium 1  -MAAKNVSAAHEMHDEKRIAVVGMAVQYAGCKTKEEFWKEVLMNGKVESKVISDKRLGSNY
consensus     1    .***********************  *.*** *.* *        *********

Ulkenia       61  RAEHKKAERSKEADTFCNENYGCVDDS-VDNEHELLLKLSKKALSETSVSDSTRCGIVSG
Schizochytrium 60  RAEHKKAERSKLADTFCNETYGTLDSNEIDNEHELLLNLAKQALAETSVKDSTRCGIVSG
consensus     61  *****.****** *******  **.*.  . ********  *  ** **** **********

Ulkenia       120 CLSFPMDNLQGELLNVYQNHVEKKLGARVFKDASRWSEREQSDNPEAGDRRIFMDPASFV
Schizochytrium 120 CLSFPMDNLQGELLNVYQNHVEKKLGARVFKDASRWSEREQSNKPEAGDRRIFMDPASFV
consensus     121 ****************************************** .*******.*****************

Ulkenia       180 AEELNLGPLHYSVDAACATALYVLRLAQDHLVSGAADVMLAGATCFPEPFFILSGFSTFQ
Schizochytrium 180 AEELNLGALHYSVDAACATALYVLRLAQDHLVSGAADVMLQGATCLPEPFFILSGFSTFQ
consensus     181 ******* ******************************** **** **************

Ulkenia       240 AMPVSG-DGISYPLHKDSQGLTPGEGGAIMVLKRLDDAIRDGDHIYGTLLGATISNAGCG
Schizochytrium 240 AMPVGTGQNISMPLHKDSQGLTPGEGGSIMVLKRLDDAIRDGDHIYGTLLGANISNSGTG
consensus     241 ****   .  ** ************* ************************* .*  * *

Ulkenia       299 LPLKPHLPSEKSCLIDTYKRINVHPHKIQYVECHATGTPQGDRVEIDAVKACFEGKVPRF
Schizochytrium 300 LPLKPLLPSEKKCLIDTYTRINVHPHKIQYVECHATGTPQGDRVEIDAVKACFEGKVPRF
consensus     301 ***** ***** ****** *.***************************************

Ulkenia       359 CEEKGNFGHTLVAAGFAGMCKVLIAMKHGIPPTPGVDGSSQMDPLVVS-EPIPWPETEG
Schizochytrium 360 CLEKGNFGHTLXAAGFAGMCKVLISMKHGIPPTPGIDDEKMDPLVVSGEAIPWPETNG
consensus     361 *  ******** ************ ********** *  .***** .*****.*

Ulkenia       418 EPKRAGLSAFGFGGTNAHAVFEEFDRSKAACATHDSISSLSSRCGGECNMRIAITGMDAT
Schizochytrium 420 EPKRAGLSAFGFGGTNAHAVFEEFDPSNAACTGHDSISALSARCGGESNMRIAITGMDAT
consensus     421 ************************* * *** **** **.******* *************

Ulkenia       478 FGSLKGLDAFERAIYNGQHGAVPLPEKRWRFLGKDKDFLDLCGVKEVPHGCYIEDVEVDF
Schizochytrium 480 FGALKGLDAFERAIYTGAHGAIPLPEKRWRFLGKDKDFLDLCGVKATPHGCYIEDVEVDF
consensus     481 ** ************ * ***.***********************  *************

Ulkenia       538 SRLRTPMTPDDMLRPMQLLAVTTIDRAILNSGIKKGGKVAVFVGLGTDLELYRHRARVAL
Schizochytrium 540 QRLRTPMTPEDMLLPQQLLAVTTIDRAILDSGVKKGGNVAVFVGLGTDLELYRHRARVAL
consensus     541 ********* .***  ************ **  *** ***********************

Ulkenia       598 KERARPEAASALNDMMSYINDCGTATSYTSYIGNLVATRVSSQWGFEGPSFTITEGNNSV
Schizochytrium 600 KERVRPEASKKLNDMMQYINDCGTSTSYTSYIGNLVATRVSSQWGFTGPSFTITEGNNSV
consensus     601 *** ****    ***** ****** *********************  *************

Ulkenia       658 YRCAELGKYLLETGEVRVVIAGVDLCSSAENLYVKSRRFKVSEQDSPRASFDSGADGYF
Schizochytrium 660 YRCAELGKYLLETGEVDGVVIAGVDLCCSAENLYVKSRRFKVSTDSPRASFDAAADGYF
consensus     661 ****************  ** *****.***.**********    ******   .****

Ulkenia       718 VGEGCGALVLKRESDCTKDERIYACMDAIVPGNMPAACVEEALAQARVNPKDEEMLELSA
Schizochytrium 720 VGEGCCAFVLKREISCTKDERIYACMDAIVPGNVPSACREALDQARVKPGDEEMLELSA
consensus     721 ***** * ***** *****.************.*  *  *** **** * * **********

Ulkenia       778 DSARHLKNPSVLPKELTABEEIRGTEAILSQRSSNEAVEPINVAVSSVKSTVGDTGYASG
Schizochytrium 780 DSARHLKDPSVLPKELTABEEIGGEQTILR--DDD--KLEVNVATGSVKATVGDTGYASG
consensus     781 *******.************* *.  ** ..  ..  *.***  *** ************

Ulkenia       838 AASLIKTALCEYNRYLPSNGASMEEPAPETQWGKELVACQSSRAWLKNPGARRHAAVSGV
```

Figure 5A

```
Schizochytrium   836  AASLIKAALCYYNRYLPSNGDDWEEPAPEAPWDSLLEACQESRAWLKNPGERRYAAVSGV
consensus        841  *** .*** ********   *.*****  *   *.*** ********  ** ******

Ulkenia          898  SETRSCYTVLLSPVEGHHETKSRISLDDDAVKLTVTRCDSHEAITQRVDKERERLAQPS-
Schizochytrium   896  SETRSCYSVLLSAAEGHYDRENRISLDEDAPKLTVLREDSHEEILGREDKRERFLQPIG
consensus        901  ******* ****. *** . *** *****. ** ** *.*** . * *.**.***  **..

Ulkenia          957  ---------ANVRLAFYELLGESEAQETKTP--LPAFALCLVTSPSKLQEEELASKGIP
Schizochytrium   956  AAPRESELKADARRIFLELLGEILAQLAASSGSQKPLALSLVSSPSKLQEVELAAKGIP
consensus        961  .........*.   * .*****  **  ..   . ** ** **.***** *** ****

Ulkenia         1006  RSLKMGRDWLSPSGSSEAFKPLSSDRVAFMYGEGRSPYYGIGLDIHRIWPELHFFVNAKT
Schizochytrium  1016  RCLKMRRDWSSPAGSLMAFEPLASDRVAFMYGEGRSPYYGITQDIHRIWPELHFVFNEKT
consensus       1021  * *** ***.**  *. **.** *****************  ************.* **

Ulkenia         1066  MELWDQGDRWLLPRASTKEELKAQEDEFNRNQVEMFRLGILMSACFTFHARDVLGIQPKA
Schizochytrium  1076  NSLWAEGDRWVLPRASFKSELESQQQEFDRNMGEMFRLGILTSAAFTNLARDVLNITPKA
consensus       1081  *.**  **** ******  ** .*** * **   ********* *  **  ***** * ***

Ulkenia         1126  AFGLSLGEISMFFAFSEKNGLVSEELTTKLRNSEVWRKALAVEFDALRKAWNIPQDTEVS
Schizochytrium  1136  AFGLSLGEISMFFAFSKKNGLMSEQLTKDLRESLVWNKALAVEENALREAWGIPQSVPKD
consensus       1141  **************.**** *** ***  **  .**. ****** .***. ** **

Ulkenia         1186  EFWQGYVVRGTREAEEAAIGPNNKYVHLTIYNDANSALISGKPEDCKAAIARLSSNEPAL
Schizochytrium  1196  EFWQGYTVRGTHQDLEAAIEPDSKYVRLTIYNDANIALISGKPECKAAIARLGGNEPAL
consensus       1201  ****** ****.   .****.*   ***.***.******* ******** **..****

Ulkenia         1246  PVDLGMCGHCPVVEPYGKQIAETHSVLETFEVAGLDLYITSNNQKILVNKSTGASDEYAP-
Schizochytrium  1256  PVTQGMCGHCPEVGPYTKDIAKEHANLEFEVVDGLDLATMNQKELVPRATGARDEWAPS
consensus       1261  ** *******  * ** *.**  *  .** ** *****  ****   *** .** *** .

Ulkenia         1305  SFGEYAAQLVTVQADFPKIAKTVSDKNIDVFVETGPNAHRSAAERATLGNSDPFVTGSED
Schizochytrium  1316  SFGEYAQQLYEKQANFPCIVETIYKQNLDVFVEVGPNNERSTAVRTTLCPQGNILAGAID
consensus       1321  ****** .***  *** *  ** *.* *.***** *** .**** ***    ..  . * *

Ulkenia         1365  RQNENAWTTYVKLVASLQAHRVPGVKVSPLYEPETVEEATQSYNDVVAGKKFTINKFERK
Schizochytrium  1376  RQNEDAWTTEVKLVASLKAELVPGVTTSPLYHSKLVAEAQACYAALCKQEKEKINKFMRK
consensus       1381  .*** **** ****** ** ** **  ****. .  * *   .*   . *  ** ****.**

Ulkenia         1425  IVINGREDPKKQLPPQVLAKLPPADPKIEALIQARKMQELAPKFMERLDIQEQDATRDP
Schizochytrium  1436  IQINGRINSKADPLSSADLASFPPADPAIEAAISSRIMKEAAPKFYARLNIDEQDETRDP
consensus       1441  * ***    *        *   *****  **.     *. ** *.   ** *.*** ****

Ulkenia         1485  ILNKDNKPSAAPALAPAAPARSVSG---------------AVVASSHALRAKLLELNS
Schizochytrium  1496  ILNKDNAPSSSSSSSSSSSSSSPSPAPSAPVQKKAAPAAETKAVASAALRSALLLLDS
consensus       1501  ****** **                  .................   *** . *** **.* *

Ulkenia         1528  TLMLG-VNANGDLVEASPSEASERVPKCDLKDLGSRAFMETYGVSAFMYTGAMAKGIASA
Schizochytrium  1556  MIALSSASASGNLIVETAPSEASWIVPPCNIADLGSRAFMKTYGVSAPIYTGAMAKGIASA
consensus       1561  * .  * *.*** **.** * .**    * *********.******* **********

Ulkenia         1587  ENVIAAGRRGILESLGAGGLPLATVRKAIEAIQAELPKGPYAVNLIHSPFDSNLEKGNVD
Schizochytrium  1616  DLVIAAGROGILESFGAGGLPMQVVRESIEKIQAALPNGPYAVNLIHSPFDSNLEKGNVD
consensus       1621  ..*****. ***.* ****** .  **.   ** .* .********************

Ulkenia         1647  LFLEKGVTVVEASAFMTLTPQFVRYRAAGILSRAADGSTVIENRNTGKVSRTELAAMFERP
Schizochytrium  1676  LFLEKGVTFVEASAFMTLTPQVVRYRAAGLTRNADGSVNLINRTIGKVSRTELAEMFERP
```

Figure 5B

```
consensus      1681 ********  ************* ********* * ****   *.** ********** **.**

Ulkenia        1707 APENLIEKLIKSGEITQEQAALARLVPVADDIAVEADSGGHTDNRPIHVILPLIVNLRDR
Schizochytrium 1736 APEHLLQKLTASGEINQEQAELARRVPVADDIAVEADSGGHTDNRPIHVILPLIHNLRDR
consensus      1741 *** ** **. **** **** *** *********************** .****

Ulkenia        1767 LHHECGYPAHLRVRVGAGGGIGCPQAAHATFNMGAAFIVTGTVNQMSKCAGTCDTVRKQL
Schizochytrium 1796 LHHECGYPANLRVRVGAGGGIGCPQAAHATFNMGASFIVTGTVNQVAKQSGTCDNVRKQL
consensus      1801 **.****** ***************** ******* ******** .  **  **** *****

Ulkenia        1827 SQATYSDHCMAPAADMFEEGVKLQVLKKGTMFPSRANKLYELFVKYDSFESMAPGEIERV
Schizochytrium 1856 AKATYSDHCMAPAADMFEEGVKLQVLKKGTMFPSRANKLYELFCKYDSFESMPPAEIARV
consensus      1861 ***** .****************************** ******* * ** **

Ulkenia        1887 EKRIEKKSLSEVWHETKDFYINRLQNPEKIERAERDPKLKMSLCFRWYLGLASFWANAGL
Schizochytrium 1916 EKRIPSRALEEVWHETKNFYINRLHNPEKIQRAERDPKLKMSLCFRWYLSLASRWANTCA
consensus      1921 ****   *  *** *** ****** ***** *****************  *** *** *

Ulkenia        1947 PDRAMDYQVWCGPAIGSFNDFIKGTYLDPAVANEYPDVVQINLQILRGACFLRRLEAVRN
Schizochytrium 1976 SDRVMDYQVWCGPAIGSFNDFIKGTYLDPAVANEYPCVVQINKQILRGACFLRRLEIIRN
consensus      1981 ** ******************************** ***** ************** .**

Ulkenia        2007 APLKANAKQVAAEIDDIVVPTEHL
Schizochytrium 2036 ARLSDGAAALVASIDDTYVPAEHL
consensus      2041 * *   *  . * *** *** *.*
```

Figure 5C : Orf 2 Ulkenia-Orf B Schizochytrium Alignment (amino acid sequence)

```
Ulkenia        1  MATRVKTNKKPCWEMTKEELTSGKNVFDYDELLEFAEGDISKVFGPEFSQIDQYKRRVR
Schizochytrium 1  MALRVKTNKKPCWEMTKEELTSGKTEVFNYEELLEFAEGDIAKVFGPEFAVIDKYPRRVR
consensus      1  ** ******************** * * ********** ******* * *  ****

Ulkenia        61 LPAREYLLVTRVTLMDAEVNNYRVGARMVTEYDLPVNGELSEGGDCPWAVLVESGQCDLM
Schizochytrium 61 LPAREYLLVTRVTLMDAEVNNYRVGARMVTEYDLPVNGELSEGGDCPWAVLVESGQCDLM
consensus      61 ************************************************************

Ulkenia        121 LISYMGIDFQNKSDRVYRLLNTTLTFYGVAQEGETLEYDIRVTGFAKRLDGDISMFFFEV
Schizochytrium 121 LISYMGIDFQNQGDRVYRLLNTTLTFYGVAPEGETLEYDIRVTGFAKRLDGGISMFFFEV
consensus      121 ***********   ****************** ******************* *******

Ulkenia        181 DCYVNGRLLIEMRDGCAGFFTNEELAAGKGVVFTRADLAREKTKQDLSPYAIAFRLNK
Schizochytrium 181 DCYVNGRLLIEMRDGCAGFFTNEELDAGKGVVFTRGDLAARAKIPKQDLSPYALAICLHK
consensus      181 ************************* ******** **  *  ***  ***.** * *

Ulkenia        241 TVLNETEMQSLVDKNATKVFGPENGMDQINYKLCARKMLMIDRVTKIDYTGGPYGLGLLV
Schizochytrium 241 TKLNEFEMQILVDKDWASVFGSKNGMPEINYKLCARKMLMIDRVTSIDHKGGVYGLGQLV
consensus      241 * *** *** **** *  ***  ***  ********************* *  ******

Ulkenia        301 GEKILERDHWYFPCHFVGDQVMAGSLVSDGCSQILKMYMDWLGLHLRTGPFDFRPVNGHP
Schizochytrium 301 GEKILERDHWYFPCHFVKDQVMAGSLVSDGCSQLLKMYMDWLGLHLTTGPFDFRPVNGHP
consensus      301 ***************** **************.***** ****** *************

Ulkenia        361 NKVRCRGQISPHKGKLVYVMEIKEMGKDEAGDPYAIADVNIEDIDFEKGQTFDLANEHIV
Schizochytrium 361 NKVRCRGQISPHKGKLVYVMEIKEMGDDEDNDPYAIADVNIEDIDFEKGQDLSLDREGIY
consensus      361 ************************** ** ********** ********   ** * *

Ulkenia        421 GKGDLNKKIVVDFKGIALKLQKRSGPAVVAPEKPIALN------------------
Schizochytrium 421 GKGDLNKIIVVDFKGIALKLQKRSTNKNPSKVQPIFANGAATVGPEASKASSGASASASA
consensus      421 ******* *************** ****  *  *  *  .............

Ulkenia        459 --------KDECAPAVRPIPEHILKGDALAPNQMTHPMSAIAGNPTPSEPSAYPKRPI
Schizochytrium 481 APAKPAFSADVLAPKPVALPEHILKGDALAPKEVSWHPMARLPGNPTPSEAPSAYKPRNI
consensus      481 ........  *.** *.************  *  ****   * ********  ****  *

Ulkenia        511 TFTPFPGNKMDNNEVPGEMPLEWINMAEFMAGKVSICLGPEFAKFDDSNTSRSPAWDLAI
Schizochytrium 541 AFTPFPGNPNDNDETPGKMPLTWINMAEFMAGKVSICLGPEFAKFDDSNTSRSPAWDLAI
consensus      541 ******* *** * * ** *** *.**********.*************************

Ulkenia        571 VTRVVSVSDMEWVEWINKDCNPSKGTMVGEFDCFIDAWFDQGSCNDEHMPYSILMEIALQ
Schizochytrium 601 VTRAVSVSDIKHVERWMRLDLDPSKGTMVGEFDCFADAWFYKGACNDEHMPYSILMEIALQ
consensus      601 *** *****. ** .   ...* *************  ****  * *** ***********

Ulkenia        631 TSGVLTSVLKAPLTMEKRDILFRNLDANAEMVRSDEDLRGKTIENUTKCTGYSMLGIMGV
Schizochytrium 661 TSGVLTSVLKAPLTMEKDDILFRNLDANAEFVRADEDYRGKTIKSWTKCTGYSMLGEMGV
consensus      661 **************** ************ ** **.* ***** .* **********.***

Ulkenia        691 HRFSFEISVDGVIFYKGITSFGWFVPEVFISCTGLDNGREKQPVHIESKVESAQVLRDDV
Schizochytrium 721 HRFSFEIYVDVVLFYKGKTSFGWFVPEVFAAQAGLDNGRKSEVFIENKVPASQVSSEDV
consensus      721 ***.*** ** * **** **********    ******   . ** *** ** **  .**

Ulkenia        751 TPNGAGRLQLEANAPKGAQLTRRWNQCQYLDTEDLVVAGGSAGLGYEHGRKQVNPEDWFF
Schizochytrium 781 RFNGSCRTALEANAPSGAQLNRRTDQGQVLDALDMVSGCKKSLGYTHGSKTVNENDWFF
consensus      781 *** *** ..****** ***** * * **** .*.*      ***.** * ** ******

Ulkenia        811 SCHFWFDSVMPGSLGVESMFQLVESIAVKQDLAGKYGITETFAHAP-SKISWKYRGQLT
```

Figure 6A

Figure 6B : ORF 3 Ulkenia-ORF C Schizochytrium Alignment (amino acid sequence)

FASTX compares a DNA sequence to a protein sequence data bank version 3.4t21
May 14, 2003

Pearson et al, Genomics (1997) 46:24-36

1>>>Sequence - 357 aa
vs SWISS-PROT All library
414613972 residues in 1289149 sequences FASTX (3.46 May 2003) function [optimized, BL50 matrix (o=15:-5:-1)] ktup: 2
 join: 37, opt: 31, open/ext: -12/-2 shift: -20, width: 16

The best scores are:                                              opt bits E(1289149)

SWALL:Q94FB8 Q94FB8 Polyunsaturated fatty acid (2910) [f]  604 113.5 9.4e-23
SWALL:O33904 O33904 Hypothetical protein (Acyl  (2756) [f]  309  63.8 7.8e-08
SWALL:Q9RA21 Q9RA21 Genes, similar to eicosape  (2652) [f]  292  60.9 5.5e-07
SWALL:Q93CG8 Q93CG8 Omega-3 polyunsaturated fa  (2573) [f]  208  46.8 0.0097
SWALL:Q93HH9 Q93HH9 Modular polyketide synthas  (2365) [f]  200  45.4 0.023
SWALL:Q8YWG7 Q8YWG7 Heterocyst glycolipid synt  (1263) [f]  196  44.5 0.024

>>SWALL:Q94FB8 Q94FB8 Polyunsaturated fatty acid synthas  (2910 aa)
 initn: 357 init1: 357 opt: 604  Z-score: 550.6  bits: 113.5 E(): 9.4e-23
Smith-Waterman score: 608; 89.516% identity (94.068% ungapped) in 124 aa overlap
(1-357:1815-1937)

10        40        70       100       130       160
Sequen LGIDSIKRVEILSEVQAMLNVEAKDVDALSRTRTVGEVVNATKAEIASSS----GAAAPA
       ::::::::::::::::::::::::::::::::::::::::::.::  :::::.    ::::::
SWALL: LGIDSIKRVEILSEVQAMLNVEAKDVDALSRTRTVGEVVDAMKAEIAGSSAPAPAAAAPA
           1820      1830      1840      1850      1860      1870

190       220       250       280       310       340
Sequen PAAAVAPAP-AAAPAVSSALLEKAESVVMEVLAAKTGYETDMIEADMELETELGIDSIKR
       ::::  ::::  :::::::::::  ::::::.::::::::::::::::.:::::::::::::::
SWALL: PAAA-APAPAAAAPAVSSELLEKAETVVMEVLAAKTGYETDMIESDMELETELGIDSIKR
           1880      1890      1900      1910      1920      1930

Sequen VEIL
       ::::
SWALL: VEIL

Figure 7:

BLASTX
Reference: Gish, W. (1996-2003) http://blast.wustl.edu
Gish, Warren and David J. States (1993). Identification of protein coding
regions by database similarity search. Nat. Genet. 3:266-72.

```
Sequences producing High-scoring Segment Pairs:              Score    P(N)       K SWALL:Q94FB6  Q94FB6 Polyunsaturated fatty acid synthase s...  473    2.9e-57
SWALL:O33906  O33906 Hypothetical protein.                     232    2.2e-22
SWALL:Q93CG6  Q93CG6 Omega-3 polyunsaturated fatty acid sy...   206    1.5e-20
SWALL:Q9RA19  Q9RA19 ORF10.                                    213    1.9e-19
SWALL:Q8EGK2  Q8EGK2 Multi-domain beta-ketoacyl synthase.      180    7.7e-18
SWALL:Q7WYA1  Q7WYA1 Omega-3 polyunsaturated fatty acid sy...   178    9.2e-18
SWALL:Q8YWH0  Q8YWH0 Hypothetical protein All1643.             158    4.3e-11

>SWALL:Q94FB6 Q94FB6 Polyunsaturated fatty acid synthase subunit C.
        Length = 1503

Minus Strand HSPs:

Score = 473 (171.6 bits), Expect = 2.9e-57, Sum P(3) = 2.9e-57
  Identities = 88/114 (77%), Positives = 97/114 (85%), Frame = -1

Query:    342  NEELAAGKGVVPTRADLLARERTKKQDITPYAIAPRLNKTVLNETEMQSLVDKNWTKVFG  163
               NEEL AGKGVVPTR DL AR K  KQD++PYA+AP L+KT LNE EMQ+LVDK+W   VFG
Sbjct:    202  NEELDAGKGVVPTRGDLAARAKIPKQDVSPYAVAPCLHKTKLNEKEMQTLVDKDWASVFG  261

Query:    162  PENGMDQINYKLCARKMLMIDRVTKIDYTGGPYGLGLLVGEKILERDHWYFPCH  1
               +NGM +INYKLCARKMLMIDRVT ID+ GG YGLG LVGEKILERDHWYFPCH
Sbjct:    262  SKNGMPEINYKLCARKMLMIDRVTSIDHKGGVYGLGQLVGEKILERDHWYFPCH  315
```

Figure 9:

SEQUENCE LISTING

<160> NUMBER OF SEQ ID NOS: 91

<210> SEQ ID NO 1
<211> LENGTH: 43372
<212> TYPE: DNA
<213> ORGANISM: Ulkenia sp.

<400> SEQUENCE: 1

```
ggatccacag cgttcattta ctcaagatca cactcgtgtg cagtccttga accttgggaa      60
agctcatgtc tctaggtatt gctgtcatgg tttgaaattt tgtcctcaaa agaatcgctt     120 gtaattttc acttggtggg gtgcacaatg gtctctcaga accatctgct ctaaggagtc      180
ctactgacac ctacctacca cccttccttc atacccatgc ctactaacca acctattgat     240
aactctaacc agggttctat gataggcaaa tcagccaatc tcccgtggaa attagtcttt     300
tcaatcgttg gccagcaagc accatcgcaa cgacagcgct gcatcagcag gaactcgagt     360
acgcttcacc gtcatcgtca tcggtatcac cactattcat gaaatcagaa cctagtcacc     420
cagttacttt ttacgaggca gttgattctg tggagagatg ctcctgatca atggatatgt     480
ctattttatc tacaggtcac acataatcaa tcattcgggg tcatgatttt ccgccatggc     540
gatagtccaa aaaaactcag gaggcaaaat cattgttcaa tttacaacta cccacggagt     600
aaattaatgt aagagctcca atttacaggc aggtatatca tcacggtgtg ctgcagtagg     660
ttctgggtta tcatcctcaa tcattcataa acataacatt cattcataaa cataacattc     720
attcattcat aaacataaca ttcattcatt cattcactca ttcactcatt cattcattca     780
ctcattaatc cgcttaattt aactttaaat tgattgattg attgattgat ggcagaacca     840
cctattagca attggttact ccttgtattg aaaggcctga ataagtaagc aagcaagcca     900
ttggtaaacc ttcctcgccg cgactcgagc gacctcgaga gcggtctgag tgagtctctc     960
acgcaggccc cccgcctcct gagccgtctg tctcgctcaa ctgaagctcc gacaagccaa    1020
gctcacagct gcaagcttgc aagcaagctc gcttctgtct actcgtcctg catcgaatca    1080
acaaccttct cttacgccat gacggacgcc tcttccgaga tgcgcaagcg taagcgctac    1140
gcataccgca tcctcactga tgagtcatcc tcctcccatg caccctctgc tgaggatggt    1200
tccgtgcagg actctcgtat gctccgccat gccggcagca tctgggatgc cgaagagcgc    1260
cgccgcgctg gcaaaatgtc ctcttccgca actgcagcca tgtccagtgt acctcctgga    1320
gaggaactct ggcttgtgtc tatccctgcg gacttcgacg cccatgacct caatggcctt    1380
```

```
cgcctgtctg ggaagaagcc cctcgcggac caagaaatcc aaattggcgc tacccacacg    1440
ctcactgctg acctgctctc gggctcttct caggtgcggt gcctgcgccc tactagctcc    1500
tatgtcaacg gcctgaggct acaccgcct gccgcgcgtg ttttccacgt cgtagagcgt     1560
gatgccgcta tgatgaggc cagtgaagcg ggaggcagtg cccaagagga ggaggagcgc     1620
ctgcgcaagg ctgaagaggt cgtcaagaga cttttgccga agccgcgtga gcaaattgaa    1680
tttaggactt tttctatggc cgacaaagag gaactgctga agcgcatgca aaaggcaaag    1740
gcgcgtggag agaagaagag gggcagaaac gcgattaagg aagaagcaga agacgaggag    1800
gacaaggagg aagagaagtt ggtggccaag acagcaaaga aggacaagaa gaagggcaag    1860
aaggaaaagg agaaaaggcg caagtctgtg gcctgagctg gaaacccctt taaagtgaat    1920
aaaggctgtc ttgacatgtt caagaacgct tattcgatac atgaagacgt gctctggggt    1980
tatttcgatg aagcctgatc taaatactag tctgcttcag aatcatgcac agtgttcaaa    2040
ttgattctta actacagcct acgctgaagt tcagcttcaa attttggtct attttgaagt    2100
tcttcaccga aagtcatttc tagagtcccg ccccaaagtc tgatctacac tctctactcc    2160
attaccgcta atatccttta caactcttat ctttttcgac ttcttcaagc gctaaggagc    2220
ggaccactaa actgatgcaa gcttgcatca actctacgac ctttttatg tcaacacaag     2280 ttctggcctt acgctgaact cgtctctgat acacaatatg caacgaacac cgccaagacg    2340
gtcgctcatg cacatacgca cacatatata caaccaaaca tacaaataaa cacataagca    2400
ttggtcaagc cagctacagg accaatattc catcttttgc tgcttttctg caatttgggc    2460 cgcttttta tgtttggctg tatatatttt tcttggcatg caacctaaca agacacatga     2520
gcagaaaaaa taaatacggt caaagtcttg tctctgatgc tcatgtcttt cttctaatct    2580
taccagcgag aagaccttc taaagaataa tatcacatat actcaattgt ccaaattgct     2640
ttcaataagc attctttact ggatagctct cgccaaactg tcattcttag gaacactgct    2700
aatacgtggc tgaaagcact cccaacatgc acttttattc ctatgcattt tcttcttgga    2760
gctcaatttg acaaaatgcc ggtcgataag ctcgcggtct tgactttgat gcttacttcc    2820
ttgtttaact cgaaaacctt ctcatggctc attggaaaat catcaaatgg attatctatc    2880
atcttcactt aacccaattt ttgtttctct aaaacagccc caactatttt ttaaagaaat    2940
ttgtgtgctc tatcttctgt ttgcaactca aactaacaag ccacatcaac aaacatttat    3000
ttttttcaaa cttgataact ttagaccaac tttgcatcct cgatgctcgg gactccatct    3060 tacccettgt caggtatgaa gcatctgatg aagcttgcag tattattacc ttttccagaa    3120
cactactgct accttcaaag atttgttcat ttcttttctt tgggggaaac aatgaatgct    3180
gattacccga agcgtaatat ggttgttgca tatattcaaa tattttaaac cttctaagta    3240
tttatatgat aggtatatgt tatttttaaa gacctttaat gcagttattt catatcaata    3300
accaagctct cgcagttttg cgctgtactg gcagtggtgg aggacccgtt gatctttata    3360
aaataggatc actggaggaa ggtgagacca ggaaactaag actatataag tttgtgggtt    3420
tctgtcattg tcactgacaa ggatcaaagt tatcctaatg cagagcatcc aacctttgtc    3480
tcagggaccc acccaatcca ctcttcaagt tttcactttc aatttcaggc caatttaaga    3540
caggaataca actcaaacta aatcaggatt cttcttttt aactcccagt catgcgatct     3600
ttaaaattga tcacattgcc ggcataataa ccatgggttt cgcaacttcc tccctggttt    3660
ctttgccaaa taaacttcc acacactcga gagcaaactc cattgccgtg ccaggccctc     3720
tagacgtcac aattttggcc tcgtgctcaa ccaccacgcg atcctctgaa catcctcctt    3780
```

```
gagcgctctc aagatctttc gcaaatgccg gatggcacgt ggctctgcgc cctttcacaa    3840
tacccaaagg tgctagcacc accgctggag cggcgcaaat tgcggcaacc caggctccgc    3900
gcgagttctg tgccaacaat agcgagcgga gaggctcgct cgcggcgaga tttgaagcgc    3960
cgggcatccc gccaggaacg attacgaggt cgaaagatgg agatgtagaa ctggcatcca    4020
ggaggtcatc caaacgaaca tcagcctcaa tacgcacgcc tcgagaacag gtgagggttt    4080
ttccgctatc gcaaacagcg gcaacaatca cggaggcacg ggctctgcgc aggacatcaa    4140
tcggaatcac gctttccatc tcttcactgc catccgccat gacaaccagc acggacggtg    4200
gggaggaagg ggaagaagac atcgtcgaat tatgggaaac gtcgagactg gagcaagcgg    4260
gggcgattgt ttaagcgagc acaaagtgac gaggaattga gttacaatgt gaatctatag    4320
ataaataggt acctgtgcct tgcgacgaca gaaagatatt ttctcataat aggcctatct    4380
aaaaccaata attttgaaca ttttcatcat tgacgaaaag ctcctgcctt ccaaattgga    4440
agtgactatc cttaatatag tgcaataacg cattggacca aacagaatcc tcctggaggt    4500
gaccaccatg ttaggacctt gaacttcgca attgattggt ttcgaccttt tctccctcct    4560
tttataaaat aagcggctca aattaattag cctatcacgg tttctctagt tttttggggt    4620
ttcgctatta tttggttatt atgaacaaat gtacagcttc ttacttacca gcctcctcgt    4680
tcagcatggt gaatgcatga aataaggaat caacttcatg actcatgctc tgcgtacaac    4740
attagattat ttttgcatgt ggtgttgaaa gtaagtcttc aagtcttttt cgtcaggata    4800
aaaactttct ttcatttgaa gttgtatgca agtcgcacca agatgtgatg actattttgc    4860
ttttcattaa ctttcctttg cagcaaaaaa gctctgtgcc tatgaaagcg ttagaactta    4920
cttatataac ctccaaatgg tagtgactat tccacctaaa ttacatatca taatgattta    4980
agtctttgtt aaaagtggaa tgtttggtaa gaaactggaa taactaaggg accactaagc    5040
tccagacact acaagtgaag caaatcttca atttaaatta tcaaagtact tcaaccaaaa    5100
ttttagcgtc tcaacaagta cccttcgtgt gctatcccgg aggcaatcac atgtgcacaa    5160
gtaacgatgt tgaacgtacc tatggctctg gtttattttg gcagccatga gcaacgcaac    5220
actgaccgta tctttctcta cgctacaatg tcctccgcca agcaaaaaga gaatatccca    5280
gctcatttgc aaagccgaga ttttattcct gccagtggtg tcaactggtc atttacggag    5340
aggattgcac ttcaaagcca tgcaatgaat gtggtattat ccacgacaat cttggaaaat    5400
ccaagctttt aaaatgcccc aaaaccatgc aaacacgtag ccgatcgtga tatccacgcc    5460
ctccagctgc gccacctatc caaggacatg gtttaagaat tgtcgtttgg tcatatgtta    5520
gttttcaacc cgcaattggg ccttagtcca ccttgttacc ataggaaatg caagctttgc    5580
aaattttgta ggctaatctc taagtgtagc ttttgtcatt gtaaagacac aattcattga    5640
catgaggttg aaagctgttc tcatatgtaa caatccgcaa cattgactac gtcacatgtt    5700
cgtgcataga gggaacactt atcttgcata gtatgccctc acaactctcc tcccccgtac    5760
agcaatcgca cgcaccatca tttattcaaa tgagacaata cttgctatcg tcccgattgc    5820
tctttagttg gacatagaac taaatgcgcg tcgcgatgcg accggaaagg tttaccagca    5880
gactgttctg caatcgttcc gtaccctatt tcacaacatt agtcgatcga tcagaacaaa    5940
tcaagataga acctgcagga ggggtcgcgc aaagtttagg cacccaggca cagccgctct    6000
gtaagtggat tttcattcaa ttgtggtcct gtgcattcat tgtttgctcg tgtagcaaat    6060
agaaccacaa ggggttttgc agaaagaaaa caaggatcat ggggcgaaac cgaggccaga    6120
cggcgggacc actcgaccgc cagtcgaggt tcatgaccaa ggttctgcgg caccgcgcgg    6180
```

```
cagacatggg tcttgaaatg cgttcagatg ggtttgtgcg cgtagaagac cttctgaaac    6240
ttcagcaact taaagacatt ggccttgagg atgtcaaagc tattgttgct gctgataaca    6300
aacagcgatt tggccttcag caggaagagg accagacctg gtggattcgt gccaaccaag    6360
gtcactctat ggctagtgtc gagacagaag atcttcttga ggaggttgac ctcgatggga    6420
tttctctctg tttgcacggc acctatttgc ggttctggcc attgatagta cgcgatggtt    6480
taaagcgtat gcaacgtaac catatccact ttgcaacagg ccttcccggg gacgatggtg    6540
tccttagtgg atttcgcaac tctgctgagg tgcttatttta tcttgatacc gtgcaggcga    6600
aaaaagctgg actcaaaatg tatcgctctg caaaccaggt gctcctaagt ccaggtcttg    6660
gcgacagtgg agtaatccct gtcaccttgt ttgctaaggc tgtcgagcgc cgctctggaa    6720
agctactttg gccaatagag gaaggtaaag agtcgcaacc ccctacagcg cctacttcag    6780
accaccaacc tcgacaagga caactagcaa gtaagcgaaa agctggtggc cacaacaaga    6840
aactatcgca catgcttagc cgtgtcctgc ggcactctgc agttgatgaa ggaatcacca    6900
ttcgtgaaga tggcttcgtg cgccttgaag atctccaaac caaactcaag cgtttcgaaa    6960
atgtaactct tgatgacgtt caagctgtgg tgcgtgacaa tgacaaacaa cgcttcacac    7020
tacgccagga gtcagacggg tcctggatta ttcgcgcaaa ccaaggtcat tccatggctg    7080
ttgtcaaaga atctttttctc ttgcgggaac ttgaccctac cacaattgat gtgtgtcttc    7140
atggtactta caaagaagct tgggcaaaga ttcgaaaaac tggtctctcg cgcatgaacc    7200
gaaaccatat tcactttgct cgtggattgc cctccgactc caatggtgtt atcagtggca    7260
tgcggaaatc atgcgaagta catctctata ttgatgcctc tgcagcaggc aaagatggga    7320
ttaaattctt tgaatctgac aacggtgtta tcttaagtcc tggtaatggt gatggcatta    7380
tccctcctaa atactttaag tctgtcacag atcgccaagg cgcttcctta gaaaacctaa    7440
aatgacaaat tatgtagatc ttagttgttg aggacttcat gtccttttttg ttgtttgatt    7500 ccttgtatag cttatacacc ctggttatgt acattgtcat tcttgttaga ggcaattctt    7560
catctttgat tgatattcta tagaacttcc tcatgggtgt acctatacac aattatttat    7620
tataccgtgt gatattgtga ggttctaaag ttagcatcgc ctctgacacc tatgatggat    7680
gcagagtgac gccaatcctt cctctatatt gtgcgtgcct gctcgagaat caaatgatgt    7740
taaaagtcgt cttcattcat tatataacag agcataatgg aataataaaa ggaggcagga    7800
gacaagggta cttctgttgt gtaaaattcc attactatgt tcgtgtatag tagtattcct    7860
tgcctttagg atagtaggga agatattctc tgtgactttc acctacttca ctcttatgca    7920
agctcttatg caatcacaga tggatgtaga ttccgcttct tcattctcac tacgagaaca    7980
gcgcaactac aaatcttaag gactgtcaac tggcctgaaa tagtgaccaa ttatatattc    8040
caaaataaat ttatttgtat aaaattgtaa agatgcagca tgatagctta ggtacacata    8100
aacaacggtt aagtgtatag ggatacgcaa acgcaagcga gaacatgcaa gcgagaccat    8160
cgcctttcac cataatgtta taaatgtcta ttcttctgcc aagagcacga tacactcaac    8220
gttggtctaa gcactaaaga cagcatgtat ttatgtaagg acaacaacaa gcacctatac    8280
ctcaaaactt agtaataggc ttactaaaca ttctaacact atgatcttca tgtgaaaata    8340
ctcagcagca tggatgttga agctccacaa atggaataca gaaaacacaa tctagcaaga    8400
cgatgaaaat tgttcttagg tttcaggatc agaataacca aaatgcgcac cacacctgtt    8460
tctgatgctg tagctgtcat gttatggtaa aaacgtgcac agggcaccac tagcctgtta    8520
ttgtgtcgat tttgatacag tttatcacac gagagcttac tgactatgtt gtagaatgta    8580
```

```
aataccctat tcaaataacc ttgtggacac actcatccaa catactctac tcaactctta    8640
ctaaaacaac caaaagattc cgctgaacta gaccaaaata atttgagtga tatgctgcaa    8700
ttcgtttgaa cacaatacat gtattgatgg ctgagatatg acttgccaaa gattgttcgt    8760
tgcaattaaa gtttactctc tgagtgcata tactcaatac aatgcagctt tatcgtggaa    8820
atccgggcta agcatgccat taggacccta tagcaggctc tgggcacgat ctttatatct    8880
tagcgatagt ttgtgcagca aaataatgga taaatcaaac ttcaacgagt cttaattcat    8940
agtttcgaat ccctacgagg ctatatatat aaagaaggtg tgagtcgaca gcacagttat    9000
gtaggaaaag ttataattat gtggaaaata accttagttg tcgaatcgtg gtgaataaaa    9060
gcttcattta agcgttttca gagatgccgg agcccatacc aaatattaat ttgctcaaag    9120
tcatcaattt cttatttgat agaatctaaa acagctttat attatatgaa gagcatatat    9180
attttaagct agtttagact tcaaccaagg ggatccaatt ttcgctcgtc actctgcgtc    9240
aaggtcgttt gcaaaaacat caaatctggt gcaagctcaa atgactaggg tcaataagga    9300
ctcctactaa ttatagttgt cactattatt tccactagga accgataaaa cagatgtaat    9360
taactctctt ggcgcttacc ttgtatagca agagtaaaga gtaaatgatg cggcaaaaac    9420
tatctctgtt acttatatgt tatagagtgc attggctgcg ccatgccata tgatagtagg    9480
taaactttgg aagttgaaag gggcgagaaa gggatcacag gtgatctata tataaaatgc    9540
aaatgaaaat tttaaagttt ggaaagttta tatgcgacac ataaaattat aatttgcata    9600
tgtggattaa gtgaatggaa tgagtctagc tataactact acctatccct atcataatca    9660
tgggaacaga tcaggagcaa attgggctta caggcgctca gtgggcacgt agatgtcatc    9720
aatctcggca gcaacctgct tggcgttagc cttcagcggg gcattacgga cagcttcgag    9780
gcggcgcaag aagcaggcac cacggaggat ctgcaagttg atttgcacaa catcggggta    9840
ctcgttggca acggcggggt caaggtaggt acccttgatg aagtcgttga aagatccaat    9900
cgctgggcca caccaaacct ggtagtccat ggcacggtcc gggatgccag cgtttgccca    9960
gaagctcgcc aaaccaaggt accagcggaa gcacaaggac atcttaagct tggggtcacg    10020
ctccgcgcgc tcaatcttct ccgggttctg caacctgttg atgtagaagt ccttggtctc    10080
ttcccaaact tctgacagag acttcttgaa aatgcgcttc tccacacgtt ccagctctcc    10140
aggagccatg gactcaaagg agtcatactt gacgaagagc tcatagagct tgttggcacg    10200 cgagggaac atagttccct tcttgagcac ctggagcttg acaccttcct caaacatgtc    10260
agctgctggg gccatgcaga tgtcggagta ggtggcttgt gagagctgct tgcgaacggt    10320
gtcacaggtt ccagcttgct tactcatctg gtttacggta ccagtgacga tgaaggccgc    10380
gcccatgttg aaggtggcaa tggcggcctg agggcatcca atgccaccac cagcaccaac    10440
gcgaacgcga aggtgggcag ggtagccgca ctccttgtgc agacgatcac ggaggttgac    10500
aatgagaggg aggatgacgt ggatggggcg ttatcggtg tggccaccgg agtccgcctc    10560
aacggcaatg tcgtctgcca caggcactgt gcgtgcgaga gcagcctgct cttgggtgat    10620
ctcgccggac ttcagcagct tctcgaggag attctcgggc gcgggacgga taaacattgc    10680
ggcaagctct gtgcgagaaa ccttaccgat gacgcggttc ttaataaccg tggagccatc    10740
agcagcgcga gagagacctg cagcacggta gcgcacgagc tgcggggtca aggtcataaa    10800
ggcggaggct tcaacgacag tgacgccctt ctcgaggaag aggtcgacgt tacccttctc    10860
gaggttgctg tcgaagggag agtggatgag gttgacagcg taagggccct tgggcagttc    10920
agcctggata gcttcgagag ccttgcgtac ggtggcgata ggaagaccac cagcaccgag    10980
```

```
agaaccaagg atgccgcgct ttccggcagc gataaccatc tcagcggatg caatgccctt   11040
tgccatggcg ccggtgtaca tgggggcgga tacaccatat gtctccatga aggcacggct   11100
gccaagatcc ttgatatcgc acttgggcac aacaatagat gcttcacttg ggcttgcttc   11160
aacgagatca ccgttggcgt tgacaccaag catcaaagtg ctgttgagct ccaaaagttt   11220
ggcacggaga gcctcagagg aagccacaac agctccggag acgctgcggg ccggagcagc   11280
aggggcaagg gcaggagcag cggaaggttt gttatccttg ttgagaatag ggtcgcgtgt   11340
ggcgtcttgc tcctgaatgt cgagacgctc catgaacttg ggggcaatag gctgcatctt   11400
gcgagcctgg ataagagcct cgatcttggg gtccgcagga ggaagcttag ctagcacctg   11460
gggcggcacg agctgctttt tggggtcata gcgaccattg accacaatct tacgcaagaa   11520
cttgttctta gtaggcttct tgccagccac catatcgttg taactctgcg tagcctcctc   11580
aacagtctcg gggtggtaca gaggggagac cttcacgcca ggcacgcggt gggcttggag   11640
agaggcaacc agcttgacca tggttgtcca agcattctcg ttctggcggt ccatggatcc   11700
ggtgacaaaa ggcttgctat ttccaagggt ggcgcgaatt gcggcgctac ggtgggcgtt   11760
gggaccagtc tcaacaaaga cgtcaaagtt cttgtcgcta acggtcttgg cgatcttagg   11820
aaagtctgcc tgaacagtgt acagctgtgc tgcgtattca ccaaagctgg gtgcgtactc   11880
gtcgctggct ccagtggact tgttaacaag cttcttctgg ttgacgctcg tgtacaggtc   11940
aaggccggca acctcgggaa tctcgaggac gctatggatc tcagcgatct gcttgccgta   12000
cggctcgacc acggggcagt ggccacacat accaaggtcc acgggcaaag cagggaggtt   12060
gctgctcagg cgagcaatgg cagccttgca atcttcaggc ttgccactga tgagagcact   12120
gttggcatcg ttgacaatgg tcaagtgcac gtacttattg ttggggccga tggccgcttc   12180
aacggcctcg cgggttccac gtaccacgta tccttgccag aactcgctga caggggtatc   12240
ttggggaata ttccaggcct tgcggagggc gtcaaactca acgcgagggg ccttacgcca   12300
gacctccgag ttgcggagtt tagttgtcag ctcctcagac acaaggccgt tcttctcaga   12360
aaaggcaaaa accatggaaa tctctccaag gctcagtccg aaagcagcct tgggctggat   12420
gccaagcacg tcgcgagcga tgtgggtgaa gcacatggca atgagaatac cgagtcggaa   12480
catctccacc tggttgcggt tgaactcatc ttcctgcgcc ttaagctcct ccttcgtcga   12540
ggcgcgcggg atcaaccatc tgtcgccttg atcccaaagc ttgttggtct tggcgtttac   12600
aaactcgtga agttcgggcc agatgcggtg aatgtcaagg ccgataccat agtaagggct   12660
tcggccttcg ccgtacataa acgcaacgcg atcgcttgac agtggcttgg gtgcaaagtg   12720
gctgcccgag ggtgatgtcc agtcgcggcc catcttaaga ctccgcggga tgcccttgga   12780
ggcgagttca agctccttct ggagcttact aggagaggtc accaggcaca gagcgaaggc   12840
cggcaacggg gtcttggtct cctgggcaat gctctcgccg agcaactcca taaaagcaag   12900
acgtacatta gcgctaggct gggcgaggcg ctcgcggagc ttgtcaacac gctgcgtgat   12960
agcgtcatgg gagtctccgc ggattacgag gagtttgacg gcatcgtcat cgagcgaaat   13020
gcggctcttg gtctcgtggt ggccctccac atcagagagc agcaccgtgt agcatgaacg   13080
ggtctcggaa acacctgaga cagctgcgtg gcggcgagct ccagggttct tcaaccaggc   13140
ccgcgaggac tggcacgcgt acagagactt gccccactgt gtctcaggtg caggctcctc   13200
ccaggaggcg ccgtttgagg gcaagtagcg gttgtacaga cagagagccg tcttgatgag   13260
actggcagct cctgaggcgt agccggtgtc accgacagtg gacttgacgc tgctgacagc   13320
gacgttgtgg ggctccacag cttcgttgct agagcgctgg ctgagaatgg cctcaatgcc   13380
```

```
gcggatttcc tcctcagcag tgagttcctt aggcagaacg gaggggttct tgaggtggcg    13440
ggcagagtca gcggagagct cgagcatctc aacgtccttg gggttgacgc gagcctgggc    13500
gagagcctcc tccatgcagg ctgccggcat gttgccgggc acgatagcgt ccatgcaggc    13560
gtaaatgcgt tcgtccttgg tgcagtcgct ctcgcgcttg aggacgaggg caccacatcc    13620
ctcaccaaca aagtagccgt cagcgccgga gtcgaagctg gcccgcgggc tctcctgctc    13680
cgagaccttg aaacgacgcg acttcacgta gagattctca gcgctggcgc aaagatccac    13740
accggcgatc actacggcct cgacctcgcc agtctcgagc aagtacttgc ccaactctgc    13800
gcaacggtag acgagttgt tgccctctgt gatggtgaaa aaggaccct cgaaacccca    13860
ttgtgaagac acgcgggtgg ccacgaggtt gccgatgtag gatgtgtacg aggtagcggt    13920
accgcaatcg ttgatgtagg acatcatatc attgagggct gaagcggctt cgggacgagc    13980
acgctccttg agggcaacgc gggcgcggtg acggtagagc tcaaggtcag tgccaaggcc    14040
gacgaagaca gcgaccttac ctcccttctt gaggccagag ttgagaatgg cacggtcgat    14100
ggttgtgaca gcaagtagct gcatggggcg caacatgtcg tctggcgtca tgggcgtgcg    14160
caggcggcta aagtccacct cgacgtcctc aatgtagcat ccgtggggca cctccttgac    14220
accgcacagg tccaaaaagt ccttgtcttt accaaggaaa cgccagcgct tctcaggcaa    14280
tggcacagca ccatgttggc cattgtagat ggcacgctca aaggcgtcca ggcccttgag    14340
ggagccgaag gtggcatcca taccggtaat agcaatgcgc atgttgccct ccccgccaca    14400
acgtgagctg agggaactga tgctatcgtg ggtggcacag gcagccttgg agcggtcaaa    14460
ctcctcaaag actgcgtggg cgttggtgcc accaaagccg aaagcggaga gaccagcgcg    14520
cttgggctcg ccctcagtgt cgggccatgg gatgggctca gagaccacaa gcgggtccat    14580
ttgggaagat ccatcgacac caggagtggg cgggatcaca ccatgcttca tggcaaggag    14640
taccttgcac atgcctgcga aaccagctgc aacgagtgtg tggccaaagt tacccttgga    14700
gcttccaaag cgaggcacct tgccctcgaa gcaagccttg acggcatcaa tctcaacgcg    14760
gtctccctgg ggagtacccg ttgcgtggca ctcgacgtac tggatcttgt gcgggtgcac    14820
gttgacgcgc ttgtaggtat caatgaggca ggacttctcg ctgggcaagt gcggcttgag    14880
gggaagacca cagccagcat tgctgatggt agcaccgagc agagtaccgt aaatgtggtc    14940
tccatcgcga atagcgtcgt caaggcgctt gagaaccata atggcaccac cttcaccagg    15000
ggtgagaccc tgactgtcct tgtgaagcgg gtacgagatg ccgtctcccg atacaggcat    15060
ggcctggaaa gtggagaatc cggagagaat gaaaaagggc tccggaaagc aagttgcacc    15120
agcgagcatg acatcagcag caccggaaac gaggtggtcc tgggcgaggc gaaggacgta    15180
aagggcggtg gcacaggcag catcgacaga gtagtgaaga ggaccgaggt tgagctcttc    15240
tgctacgaag gatgccgggt ccataaagat gcggcggtca ccagcctcgg ggttctgcga    15300
ctgctcacgc tcggaccact tggaggcatc cttgaagacg cgagcgccga gtttcttttc    15360
gacgtggttt tggtacacat tgaggagttc gccctggagg ttgtccatgg aaaggacag    15420
gcatccgctc acaataccgc accttgtaga gtcggagacc gatgtctcgg agagagcctt    15480
cttggagagc ttaaggagaa gctcgtgttc gttatcgacg gagtcatcga cgcagccgta    15540
gttctcgttg caaaaggtat ctgcaaattt gctacgctct gctttgaagt gctcggctcg    15600
cttgttggat ccgaggcgtt tatcgctaat cttagtccat gcagcctcac cgcccatgac    15660
tactttccag aactcttcct tgtctttgca gcccgcgtat tgcacggcca tgcccaccac    15720
ggcaatgcgc ttctcgtcgt gcatttcgtg agcagcgctc acattcttgc gagaggccat    15780
```

```
cttttttgctt tcttgttgct gcttactgta aacaaaaaaa agagcttgcg tgtcacctga    15840
ccggcacttt tagatcgatc aaaaagcggt cgtgtagatg gtttgctttg gaggagatgt    15900
ataaatgatg tgattgacta ccttgagcaa gtgattacag ggatgccaga gcaatcaaat    15960
aatcaatcag ttaatcaacg ccgtaataaa ggctatcaat caatcaatca atcaatcagc    16020
caactagcta gccgaagctg cgatggactg gcgtttggac agcgcgaagc tgtaggaact    16080
ggcgccgcac gagctgcgag gctgccaagc tagaggctgt ctgcctttgt ctcactcctt    16140
ttccgaggaa ggagagagag agagagagag agagagagag tgggggatg aaagtttgga    16200 tgcacgatgc gtgctttgtg gtttgtttcc ttgtttcttt ctttgcttgt tttttctctc    16260
tttttctttg ttattttgtc tctcttgaag caaatagaaa gaacctcgaa ctagacgctc    16320
caaagggtct tcaagaggtc tcgaaggcta ggctggcgaa agcgcgcacg ctggtcaagc    16380
aagcaagcaa agcaagcagg caagcaagca agcaagcaag caagcaaagc aagcagggg    16440 tggattccac gaatgcgaga agtcaaaact ctgcttcaaa cagagaacaa atgggcaaac    16500
gaatgaggat aaatgagcaa ctaagtgaag tttacatttt caaaactcaa caaaacgatt    16560
acccaatcaa ctatgagacg cgcagacgtc tgcggcagca tctctttttat gattttcaaa    16620 aacaaaaaca aaaaccaaaa caaaataatt tgcaacaaat taatgaaaag cgaaacaaca    16680
aacagaaaca ttgttaaaac taaaaagtca ttttttattga aaatctgttc ttttcatctg    16740
tacgtatgta tgtttgtatg tacacacttt gcttcatcgg tttattcgag tgctcttcat    16800
tcttgaaatt gccttagttc ttgctgttat aactgtcaaa caaacctcgc gaccttgaca    16860
agcagctcca cctcaccttc gggcctgctc gtttgccttt ctcgcttttt tcgcgatctt    16920
ctgccatcct tgcctactct gtccttatct catcaggctg ctgcggcctc ttgacctagc    16980
agttcaagta taattaattt gaaaataaac aaaaaaacac tgccacttat tatgcagatg    17040
gcactctctc agtgttgcaa aagtagagtg aaattctggt ttacaaaaaa tatttattta    17100
ataaacaaat aaaataaata taaattcatg ttatgttaga tcattttatt ttgttttctg    17160
agggcgcgat aaacgcttac ttgagaacca agaaaagcaa gaaaagcaaa ggtgcgaaag    17220
aagcaaacac attgatttcc ctagttccca ccacttcttt ctttctttgt ttgtatattt    17280
gtttgtttct ttcttttcctg ctttgttttg tttgttttgt ttgttttgtt tgtttgtctg    17340
tttgtctgtt tatctgtttg ttagtttgtt agttactaga ctgctaattg atttgaaaac    17400
caagccaaac ccacgcaatg aatacgcaga agcacagct aaaagaaga agaagaggag    17460 gaattccgaa tcaggcgaga aagtctcgaa agcagtgcac caaaatcctc atttggaatc    17520
aaagccctcc ttcccagcga ctacggaggc ccacgacgac gacgacgccg acgacgccgc    17580
ccgcccgccc atcctcctct ctctccgcct gctcctcgtc ttctccctcc ctccctcct    17640 ccctcgcgca cgccgctccg aatggaatga catgactgac gcaagcgcgc aatggccgcc    17700
gtgcgatggc tcgaagcagc atcgcatcgc attgcattgg cattattcat tgattcattc    17760
attgattcat tcattaattt attcatttta attcattcat tcattcaatc attcatttat    17820
tcattcattc attaatttat tcattttaat tcattcatta atttatttcat taatttattc    17880 attttttattc attcatactc ccgagcgcta cccggcgcta ggtgggtgct aggcgtggat    17940
ggagcggacc tctctgccag cagaaagagg aatgaatcta tctggatact gcgcgcagct    18000
tcttgcttgc tttgcttcaa cttgcttgca aacagccagg aggccgaacg gcttcgaccg    18060
ctcagcgtgt tcgccagcaa agaaccacct ccgcccctcgc agtcgccgga tggatgaacg    18120
agcgaatgcg aatcctcctc cgatcttgaa cctcgaacct tcaatcaact tgccttaatt    18180
```

```
ttactttcat gactctcact attttaaata tacatgtatg tatgtatgta tgtatgtatg   18240
tatgtatgaa tgcacctcat actgataggg acctgcgggg gactgatacc acctgtctga   18300
atcaatttgc gagaccgcga gactgagtgg caggtagtag ctagctaagt agctgcctaa   18360
gagtctatcg gcatgcatga atcaaaaact atcatgtcaa tgttcctttg aggcttcgaa   18420
gtccgtcatt tgtcacgaaa ggttttgggt gaacgatcca ctgtttcgag agagatggtg   18480
tgaatgtata ggtgatagtt gccgagctgg cgagccgtcc caagcggtgc cggcactcac   18540
ccggctgaag cttcttacat gctctccgtt cataatcgtc caaattgatc ctgattcatg   18600
attcatgatt catgattcat gatgacacga gttggagttg gacgataagt cagcgctcgc   18660
tcaaccaaac tacctctgct cgcctagctg ctgttaggta gtgctactga ggcaggaccc   18720
aacttgaagc tacctactgc ctaggtattc ctacgctgtt tcgctgattt gcaatctctt   18780
cgttaccaag agataaaatt aacgagttat gacattgcgt atgcagacta cataataaag   18840
attgtgtcat ttatttataa gtggaaaggt gtaagatcaa gaactaagca ctaggtagca   18900
attaggcgtt atttgttagc gcgtggaaga aaatgcctct ggacagatag ctattaatag   18960
ctattaatag ccggtgttgt atttacaacc ttctgaaaga atttctccat agaggaaagt   19020
aaagaaacat cttattctgt gaaaagagat aaacaacttt ctagaaaatg gatgacagag   19080
caaagaaggt cgatcgtctt caaccgcaga tctgggaatg ctaaggttgg cgccaggctt   19140
acattatgcg tcatgctgac caaagggcgt aaagtgccga tgggcatccg atatatgcgc   19200
gttcaaggtg aggaattcaa gatcatcaag ttttgtttgaa tttcgaggtt gaaaacacag   19260
agttttgaca atcgatcaat caatcaatca atcaatcaat caatttaaaa ccaatttaaa   19320
accaaatgaa tgagtgaatg agtgaatgac tgaatcaatt taaactaaat gaatgaatga   19380
atttaaaacc aaatgaatga gtccttagcg atttcaagtt ctgcagtgaa atctacaaat   19440
ctacgacgaa agtagtgaga tcgtatcaac gtgtatagac agacaatgat gctgcggata   19500
cctaagtgct tgcgtggagg gactacgatg cagatcccga gttttaggtc ctagttcctc   19560
cgttctctgg taaaaagaa agcctctcct tcttgacgcc attcagcgac gtggaacaag   19620
cgagacagag gcacaagttt tggagtcatt gagtcgggtc tgctctgctt tgaggatgaa   19680
ccaacgacct tcggagtctt gcagatagat ggtccattct tcaaacgaca cagagatcgt   19740
cgtctcgcgt aagttggcag tgggtctaga gctagctaaa aacatctgac agagagcaca   19800
tacagagcta aagaggagtg tactcggcaa aatagcgtgg acggatgaca tcatcaatcg   19860
ctcagctttt tcgtttctta ccaaaaaatt gacaaaccag agaaataaat agattgactc   19920
aacaaattaa attaaaacaa taaattaaaa aagatctctt aaagaagttt tctgaaagaa   19980
accaaaaaca ataaactctg cgacaagaac ttgaggccag aagggatgaa gaaggtacgt   20040
atctagatgg tgactgggga cacaaagaag caaggtctga attctcagaa gccagctgca   20100
gccagccagc tactaggagt gtctgccagc tccgtcgtca tgccacgagt gtccctgcca   20160
acgcttcaag cgtacttgca actttatttt gattactaca ttactacatt ataacttcat   20220
ctatagcttt aaaaggaaa taaggaaat aataaaataa atcaaataat ggtaaaaagt   20280
tataaataat caacgactaa aaaggaattt tattcgaagg tcctcggcag gaaataagtg   20340
gaatcaaaga gaaggcggga acggtaggga ccatacatga tagtcccaaa ctgaggaact   20400
acgaattgcg gggctaagca aattcatagg atcccagtta gggacagacc ctcgaggtcc   20460
gagttggtat cctgggccaa agcttgcgca agggtgctct agagctacaa ctcaatacca   20520
gtagttgcat ggccatctct gatagctttc ttcatgaata tggggtgagc ttagagacaa   20580
```

```
gcagtagaca ctctgtgacc tacgagctat atttgctgtc gcagagcatc tcctcaaaat   20640
aattcatcga agaaagacgg attgaaagtt ttgccttatt tgaacaaagt taatattta    20700 actctcggta gttaaaccat gatagctcat ttatagcgta ggctgacaca gaagcgtagg   20760
ggcttagacg tcatgatgat tcgtgatgaa ataaatcaag gattctcgaa cgttgacacg   20820
cgcaatggag cgtgccaatg tcaaagggt attgctgtat catcaacgta ggtaggtagt    20880
caaacgggct acagctctgt cctattcact cactaagaca aaatgttttc tctcaaacgg   20940
ccagctcgaa agtaatattg ggagcaagaa tgaaaatcat tctccagtac acttgcagtg   21000
agatcaagtt tcaagaccat caaacgatac gatacaggag gtactatctt tgctgaagtc   21060
agtagcagca gcattacgag cctggtagat ataaattgat aaaaagacaa gaggtatatc   21120
atatttcaga gtagagtaca tactgagctg gaaacataaa actagtgcac gcaatcgacg   21180
gttcaacttt tctcaagacg cttccagtcg tttcttaatt agctcagatg gtagcaaaag   21240
tgatatgcgc atcagacttt cgtaaacgta aaactcggca tctgtagatg ttgagtcatt   21300
gttttcttca ataatttact tctcgcagca gtgcacttgg aaaggtttgt caagtttgac   21360
ccagctaatg aaacacaaca tcatcaggcg gggctcgaaa agtagatctg aaagtctata   21420
aagaatgaaa gttactctca acacagaaag caatttgtgc aaacataaga gagaatggcg   21480
tctatgctgc aagagaaaat tcgacggtcg catcatagtc gtctacactg ctgtgcatgg   21540
gcaatttata atatcatgtc tgatcacggt ttctgagaac atttaaacga aataagtcaa   21600
aacgaatgcg ctctgtcgcg attatagttt tgttctgaca gtaactccta accaaagggc   21660
caaataagga cgagagaata aaatagattg ctctctcact tcggacccag gaatcccgaa   21720
tttatataat ttcaatgtac tcacgtaaca ctgacaagct atgcggcgtc ataactcat    21780 ccacgttggg agaatctcga acaacgcaa cgagttattt tatcctgatt aataatctag    21840
cttgaaccgt tgttgtaac tagaacccaa gctgcaaaga gctacaacca aggtttgatt     21900
tcgttccaag ctaacatgaa actctcaaac ttcgtcgatt tttttaatgt ttgtcaaaaa   21960
cctagtacag cggtcctagg taccgatttg agaagcaggc aacccgctta taaataaaag   22020
aaaaagagtc tttattattt tataaataga aaaaacttta attgggacaa tattcttta    22080 gtgttctctg tcttcttcct tcatgtatga cgtaatgatc atgctccttt catctccttc   22140
cttccaaaaa gttcatttt cctactaggt cttttcaaa attaaaaata taattaagta      22200
agaaagaaag aaggaaagaa agaaaaacct gggtactaat cagtgtgata tgaggtgaat   22260
ggtggttttg ttttacttct cggaagtgtc gagtcctata aggagcacta tacctatcct   22320
agacgctttt ggtaccaagc cctgcgcggc aggcatacgt cagcaagcta cgatagcagt   22380
acacgctact cagaaaggcc tagtgaggta ggcgagcagg aagtagtgct cttgcgtcat   22440
gcttatgatg gcatcagcca cgcgagaacc tcattcgaat agtcctttg caattcattc     22500 acgcatgcat gcattgatgc ctgctacaga gtagctagtg agagagtatg atacttagtt   22560
agtgctactt atgcgttgtc acctatgcaa tagcattgga tagaaggaat cagattcacc   22620
gctgactctc gctgagagta agggccatac gcagtgctcc tgagttgttt cattaaacgg   22680
acttcaagct gagttctggc taggcacctg gtagctgggg ctagagggta cctacctacc   22740
tacctactga tagctaactt tcaaatgagg aaagattgga gattgaatag aaagaaagtg   22800
atacatactg tcagccgtat cgaaactccg aagtggcacg cggatggcgt cagcaaactg   22860
ccgtagcaag tgaataacgc acatctcaat tgggacgtcc atgaaaacaa aaaacaaaaa   22920
agcaaaaaaa agttgcaatc gatcatgaat cgtgctgatt catgggttgc ttgcttagtt   22980
```

```
gttatgctgg agggtgtcga gacttggatc tggtgagcag tgcgctctcc actcaagttg   23040
gaccctttgg tatcagggga gtgcgagtgg gcacactacc atagtatcct aaattacctc   23100
tacgttttga ttgcctttga tcacagcaga taattttcaa tttaaataaa aatcataaaa   23160
agaagaagaa gaagaagaaa gaaagtgaag gtggcgtttc tgatgtcatc attttcgcag   23220
tgcttcccag cgaagattta ctgtgaacta ctacgcatgt gagtatggca agcactgggt   23280
aagtaggtac ctaccactac catgttgtaa aacaaaacaa ggaatatgtt agctagaaca   23340
gagcgaatcc ggtgtgagtg ggagtcatca tcagatattg aaagttgtcc tctcaattaa   23400
tataaatatt tctaactaaa gcaattaaac atatatttat taatttaatt ataaattaaa   23460
taaatatgct gggtgggtcc gagtcattct gactatcatc tatgatgttt aataataaaa   23520
tattgaaagc agtcaaggtt atttggaatt atgggatgat cgtgatctgt gtatcattct   23580
gcatcattgt ggatgctggc ctacgaaact acgacggcat tgcaattgcc acctggcggt   23640
gcgatcgcgt gcactcctgc aattgcgagt gtcttccgcc ggcttcaagt tgaggtgctg   23700
cgacagtgcg ggcccagagc tcctaacatt tcgtggatga ccgactgact cagacagagg   23760
tctctcaagc ttagaaagtg cgctgcaaaa aagggcgcta gctagataag atacgagtga   23820
gtgagtgagt gagtgagtga gtgagtgagg ttctagctag tgctcctccc aaatcttgga   23880
gtgccgatgc tcgagaatac atacatactt caagacacga agaacttgaa cccgaagacg   23940
aatgccgtct tcgacgtcat ctttgccgtc gtcatggccc actgcagcaa cgatccagtg   24000
cgtgcgagca gcagggccag cccacgatca cgcagctcgt cgggctggac ttggctcaat   24060
gaatgaatga atcaatcaat gaaagaatga ctcaatgaat caatgaatca gcaagttgcc   24120
accaaagccc atcgcaacga cgggtcctgc ctgcgtgcgc cattcttagg atccagagca   24180
agcaagatct tcttcaccta tcgctcagca agcgagaacg caacctccct ctgcatcatg   24240
atgcaggata agtaagataa atccatcttg gacctcgagc tcaaatcgac gcttgctgca   24300
tctatctatc tttgtatcta tctatgtatc tatctttgta tctatgtgtc tatctatctc   24360
tctgcgtgcc tcgtcgtgtt tttgaaaagg agtttcgatc gtggcccaat cggaagagaa   24420
ggctctctct ccctctctct ctctctctct ctctctgcat cgcacagacc aatgagcctt   24480
gcggcaacac agcttcaact tcattgcagg atccaatcca tccaaggcat cgcttgggct   24540
ctcagtgaat gaattcgacc aaagctcgtt ggcaggcaga caaggcctgg acaacataaa   24600 gcaaggggc acgaaggcaa gatggcaagg aggcagagca ggcaccagcg actgcgatgc   24660
tggcgagaga agatcaaggc aaagcagagg ctgcaagcaa gctctgcagt agccacctcc   24720
tcagcagatt cgtcaagatc gggcaaactt cgtctgtggc tgccacgcca gagcagagca   24780
tgcctgcttc atgatccatg ctcaagaaag aaagacagac aagacagaca agacagatag   24840
atggatgaca gcgaacttac atttgcagac ttcgaaggtg cctgacgggt attggtgcca   24900
ctaagacgag aaggagcact tgcttccaga tcgctcacgc cgctcacatc accatgctac   24960
gtcttcaata cgcctggtcc ggttcgcaag agccgcgcgc cggcgattgg gcgaaaggcg   25020
gaggagtcga ggtacgcgtt atcagcagaa tgtaggaaca ccgcgacgcg gccgacgacg   25080
ctggtgagga ggaagaaaga cctggcgcct gtacgtacgt acctacgttc tagcagtagc   25140
ttgaagtgga ctgtgggtcc cctccatctt cttcaagacc ttcaagttgc ttgctgacgg   25200
catcgctgtt tgtttgtggc tgttaggtag gtaggtagct agctagctat agctgtgtcc   25260
tagctgcaca gggagcactc agcctctttc ctagtttctt tggttctgtg cttgtttttc   25320
tagcgagtcg tgcaaataac ctgcggcggc cacgagaagt ccgcgttgag gcgatcttgc   25380
```

```
gccagtgcgg cagttgccat cactcgtgca gacagagttg agttgcttct caatcgttac  25440
caatcgctcc aagcaggcct agacatagat tttccttctc tggaccatct actaaaatga  25500
tcaagttaga taggtagata gatagataga tagatagcta gggagatact aggcaccttc  25560
tatgccggca cgtctcgaac aaagcgaaga aagagctgtg ggcaagagca ctcattttga  25620
tcgtagatga tcgtagacgc gctgtagagg agagctctta gtggcggcta ctgtgatgga  25680
ctatgagagg ggacttcgca agacctgtct cggtcgcacg tagctgtggg aagcgagaac  25740
ccgcagagga ctgattctga ttagtgcgga taacttggtc gaggaagagc ggggacccgc  25800
agggaacccg catagcagcg acgttggcac ccgacgacgc tagggcaaag acgcagcatg  25860
cgtgcgaggt gcctataagc tgcgcaattc agagaattaa gacagcagcg ctgggaagga  25920
aggaggagat ttgaaggctc ggcgggagct gtcgagatgg aggcaggcag gcaagcaagc  25980
aagcaagcga aagaggcggc cagggctcgc gtcgaagccg ctgatggacg agagaatcgc  26040
acgaagaaga atacggagtg tttgttttca aagccaaaga aagccaaagc caaagccaat  26100
tcgttcgttc gtgagttaac ttattattta atttaattga catcttcatt tactactgtt  26160
gttatctatt atttatttat ttatttattt atttatttat ttattattt atttatttat  26220 ttatttattt atttatttat ttatttattt atttatttat tgtttatatt tttttaaatt  26280
aaaaaaattc aaaattcaaa attcaaaatt cacgaataaa ttgcacttga aggagatgaa  26340
gcaaagcttt gtttcttcta aaaagagtat aaataataca aagtgatgac ggaaagaagc  26400
atcattctga tggtaagcac ttcggcaaga tgcacgcact agcacttgtc gccttgcttg  26460
cgatccgcgg aggtaatagt ggaggcgaaa gaaggagttc attcctgtta tttcgcgctg  26520
gggttacagc agtgccaaga tttcgaatat ttgaattttt gaatttttga attttttggat  26580 cttcgttccc cttcttcctg aactgttcaa acgactcgga ggttgtcgat cggatcactc  26640
aatctctcaa tctctcactc actcactcac tcacttttc tcagctgcct gatccttcgc  26700
aatgctcgcg aagcgcgagg gatatgcgtg ggcgagcacg caccatcttc tctccacgcg  26760
taaagaagag cagagccaga ggcaggtagg tatctccacc catctcaggc tgtgacttct  26820
ttgtttcttt ctttctttgc ttgttttctg ttctctctct gtgctctgtc cacacgagaa  26880
agagaaagag agagagaaag aaccacgggt ttatagagcg cactcgtcct tcctgcttca  26940
gcagaaagca ctgcgtagga gaactacggg ggaggaggaa gcacgcacgg aggaggcgtg  27000
gaaggaagga ggagacagag agagagagac actgagggac agaggggag aggcagaggg  27060 agaggcatct gatgtttgcg agaaaccaat aagttttgaa agtgatttga tttagctgat  27120
tgactgatct atggcctgaa agaaagcttt taaagcggag ggagatagat gacgagggca  27180
gctgcgatgc cgtacggcgc atccgtctct ctctgtgtct ctctctcttt ctctctcgtc  27240
agggcgtgga gacctcggaa gctgcacgcg gcgcggtgag gaggcagggc agcagaggga  27300
gaggagagat cccagagtcg aagagcattg attgattgca gatgatcttg ggcaacgcgc  27360
gtcagcttga gcgaggaatg ctttggactt caggttcttc gcttctgtgt ttcattcttt  27420
ctcgaagaaa gaaagaatga aagaagaga gaaagaaaga aagaaagaaa gaagaaaga  27480 aagaaagaaa gaatgaatga atgaaagaaa gagagaaaga aagaacgaat gaaagaaaga  27540
gagaaagaat caaagagaaa gcgcattcgc agttcttctt cgtgaaagaa aaggaaaaga  27600
gaggcgatgg taggctctga tctcatcatt tctggtttct ctgttgtacc tgtactctgt  27660
gcttgtggcc ttgcgaaggc tgaagacgcc atgcagacaa ccacgcctcc gcagagactt  27720
tgcgggaaag cagagggctt ctcgccactc tcgaagaaac gagctcgcca gttttcgggg  27780
```

```
ttgttctcag aattgcgagt gttggcttta tatgggatga tggtatggca cttcgtcatc    27840
gttactctcg ctcgcttgct tacgaagatt ttcaaaaggg cgaaagaagt gctcagcttt    27900
taaaataaag tcacaccaaa gactaggccg catagcagaa agctaaagta aacccaatct    27960
gtctgaagag agtgtcgtgg ttagatactt acgcaagagt ttaaaagctg taaatagtac    28020
aggaacaaaa acaaataaat atatatatat tctttttttat tagtaaaaca tgaaaccaaa    28080
aaactccttt aaaataaaat aaaataaaat aaaataaaat aaaataaaat aaatttacta    28140
ctatatatac atatatatat acaataaata aaaacaactt tttcagacca gaaaaagact    28200
gagaaaaaag gaaactaatg actctcgagc accgagagcg atataagagt ggattatatt    28260
tgctaggccc accacgagtg agtcccctag gaggaagcgc cctctgagac aggagcagag    28320
gcgtcgctgg tgctccaaaa agcgacggcg aatggaaagc aaaaccctttt cgagggaggc    28380 ttgtggccgt gactattcaa atctccagca tctcagctcc agcacagcag aagctacctc    28440
gcttctcagc tctagctatc acatcgatcg cagcatctag ctcgtagaca gctagcgccg    28500
caccttcccc caaatcaact tgggcaactt aactcttttt tcaccagaac tcctcttttc    28560
ctttaatctt cgaaaagaag acgaataaaa gagataatcc tctgccgcag cacattctaa    28620
aagaaaagcg gcatactggc gtaggcaaga cttcaagct cttcctcgcc tccacccgt     28680 atttccctgt tcatctttgt gaaacgagga acaagaaat tttataggac aagatggctc    28740
aacgtgagaa ccgtctcgag gccaacatgg ataccgcat cgctgtgatc ggcatgtccg    28800
ccatcctccc ctgcggtacc accgttcgtg agtcttggga ggctatccgc gatggtatcg    28860
actgcctcag tgatctcccc gaggaccgcg tcgatgtgac cgcctactcc gacccggtca    28920
agaccaccaa ggataagatc tactgcaaac gtggtggatt catccctgag tacgacttcg    28980
acgcccgtga gttcggcctc aacatgtttc agatggagga ctccgacgca aaccaaaccg    29040
tcaccctcct caaggtcaag gaggccctcg aggacgctgg catcgaagcc ctcagcaagg    29100
aaaagaagaa cattggatgt gttctcggta tcggtggtgg ccagaagtcc agccacgagt    29160
tctactcccg cttaaactat gttgtcgttg agaaggtcct tcgcaagatg ggcatgcctg    29220
aggaggatgt tcaagctgct gttgagaagt acaaggccaa cttccctgag tggcgccttg    29280
actccttccc cggtttcctc ggcaacgtta ctgccggtcg ctgtaccaac accttcaacc    29340
tcgatggtat gaactgtgtc gtcgatgctg cctgtgctag ttctctcatc gccgttaagg    29400
ttgccattga tgagcttctc cacggagact gtgacatgat gatcactggt gctacctgca    29460
cggataactc catcggtatg tacatggcct tctccaagac cccggtgttc tctaccgacc    29520
ctagcgtccg cgcatacgat gagaagacca agggtatgct tattggcgaa ggctctgcca    29580
tgcttgtgct taaacgttac gccgacgctg ttcgtgatgg tgacgagatt cacgctgtca    29640
ttcgcggctg cgcctcttcc tctgacggta aggcctccgg tatttacacc ccgaccatct    29700
ctggtcaaga ggaggctctt cgccgtgcct acatgcgcgc taacgtcgat cccgccaccg    29760
tcactcttgt tgagggccac ggtaccggta cccccgttgg tgaccgtatt gagctcaccg    29820
ctctccgtaa cctcttcgac agtgcctacg gcaacgagaa ggagaaggtc gctgttggca    29880
gcattaagtc caacatcggt cacctcaagg ctgtcgccgg tcttgccggt atgatcaagg    29940
tcatcatggc cctcaagcat aagactcttc cggccaccat caacgttgat gagcccccta    30000
agctttacga caacactccc atcaccgact catcgctgta cattaacacg atgaaccgtc    30060
cgtggttccc tgctccgggt gtgccccgtc gcgctggtat ctccagtttc ggttttggtg    30120
gtgccaacta ccacgccgtt cttgaggaag ccgagcccga gcaccagaag gcttaccgtc    30180
```

```
tcaacaaacg ccccagccg gtgcttctga tggcatcttc aacccaggct cttgcttccc    30240
tctgtgaagc ccagcttaag gaattcgaga aggctatcga ggagaacaag accgtcaaga    30300
acactgctta catcaagtgc gtcgacttct gtgagaagtt caagttccct ggatctatcc    30360
cgagctctaa cgctcgcctc ggttttcttg tcaaggaggc cgatgatgcc accgagaccc    30420
tccgtgccat cgttgcccag ttccaaaagt cagctggcaa ggattcttgg caccttcccc    30480
gccagggtgt gagctttcgt gctcagggca tcaacaccac tggtggtgtc gctgccctct    30540
tctctggcca gggtgctcag tacacccaca tgttcagcga ggtcgccatg aactggcctc    30600
agttccgtga gagcatctct gacatggatc gtgcccaggc taaggttgct ggcgctgaca    30660
aggactacga gcgtgtctcc caagtcctct acccgcgtaa gccttataac tctgagcccg    30720
agcaggacca caagaagatc tccctgacct catactctca gccctctacc ctcgcctgcg    30780
ctcttggtgc ctacgagatc ttcaagcagg ctggtttcaa gcccgacttc gctgccggtc    30840
actctctcgg tgagtttgcg gccctctacg ctgctgactg cgtcaaccgt gacgacctct    30900
ttgagctcgt gtgccgtcgt gcccgcatca tgggtggcaa ggatgcacct gctaccccca    30960
agggatgcat ggctgctgtc attggaccca atgccgagaa gatccagatt cgcactgctg    31020
atgtctggct cggcaactgc aactcccctt cgcagactgt catcaccggc tctgttgagg    31080
gtatcaagaa ggagtccgag cttctccaga gtgagggctt ccgtgttgtc ccctcgcct    31140 gcgagagtgc cttccactca ccgcagatgc aaaacgcctc ctctgccttc aaggatgttc    31200
tctccaaggt tgccttccgt cagcctagcg cccagaccaa gctcttcagc aacgtgtctg    31260
gcgagaccta ctccaacaat gcccaggacc tccttaagga gcacatgacc agcagtgtta    31320
agttcatctc tcaggttcgc aacatgcact ctgctggtgc tcgcatcttt gtcgagtttg    31380
gccccaagca ggtgctctct aagcttgttt ccgagaccct caaggacgat ccttccatta    31440
tcactatctc tgtcaaccct tcctctggca aggatgccga tattcagctt cgcgaggctg    31500
ctgtgcagct cgttgttgct ggagtcaacc ttcagggctt cgacaagtgg gacgcacctg    31560
acgccacccg ccttcagccg attaagaaga gaaagactac tcttcgtctc tcggctgcca    31620
cttacgtgtc tgacaagacc aagaaggctc gcgaggctgc catgaacgac ggccgcatgc    31680
tcagctgtgt cagcaaggtc atcgccccc ctgacgccaa gcccattgtg gacaccaagg    31740
ctcaggagga ggttgctcgt ctccagaagc agcttcagga tgcccaggcc cagatccaga    31800
aggccaaggc cgatgctgct gaggctgaca agaagcttgc cgctgctaag gatgaggcca    31860
agcgtgccgc cgcttctgca cctgtgcaga agcaggttga caccaccatt gttgataagc    31920
accgtgctat cctcaagtct atgcttgctg agcttgactg ctactccact cctggtgctg    31980
tgtccagctc tttccaggca cctgttgctg ctacccctgc tccggtcgct gcgcctgttg    32040
cagctgctcc tgctccggct gtcaacaatg ctctccttgc caaggctgag tctgttgtca    32100
tggaggttct tgccgccaag actggttacg agactgacat gatcgagccc gacatggagc    32160
tcgagactga gctcggcatt gactctatca gcgtgtcga gattctctct gaggtccagg    32220
cccagctcaa cgtcgaggcc aaggatgttg atgctcttag ccgcacccgc accgtcggtg    32280
aggttgtcaa cgccatgaag gctgagatcg ctggcagctc tggtgctgcc gctgctgccc    32340
cggccccggt tgctgctgct cccgctgccc ctgccctgc tgtcaacagc gctcttcttg    32400
ccaaggctga gactgttgtc atggaggttc ttgccgccaa gactggttac gagactgaca    32460
tgattgagcc cgacatggag ctcgagactg agctcggcat tgactccatc aagcgtgtcg    32520
agattctctc tgaggttcag gcccagctca acgttgaggc caaggatgtt gatgctctta    32580
```

```
gccgcacccg caccgttggt gaggttgtca acgccatgaa ggctgagatc gctggcagct    32640
ctggtgctgc cgctgctgcc ccggcccctg ttgctgctgc tccggcgccc gtcgctgccg    32700
ctgcccctgc tgtcagcagc gctctccttg agaaggctga gtctgttgtc atggaggttc    32760
ttgccgccaa gactggttac gagactgaca tgattgaggc cgacatggag ctcgagactg    32820
agctcggcat tgactccatc aagcgtgtcg agattctctc tgaggtccag gcccagctca    32880
acgtcgaggc caaggatgtc gatgctctta gccgcacccg caccgttggt gaggttgtca    32940
acgccatgaa ggctgagatc gctggcagct ctggtgctgc tgccccggcc ccggtcgctg    33000
cggcccctgc tccggtcgct gccgctgccc tgctgtcaa cagcgctctt cttgagaagg    33060
ctgagactgt tgtcatggag gttcttgccg ccaagactgg ttacgagact gacatgatcg    33120
agcccgacat ggagctcgag actgagctcg gcattgactc tatcaagcgt gtcgagattc    33180
tctctgaggt ccaggcccag ctcaacgttg aggccaagga tgttgatgct cttagccgca    33240
cccgcaccgt tggtgaggtt gtcaacgcca tgaaggctga gatcgctggc agctctggtg    33300
ctgccgctgc tgccccggcc ccggttgctg ctgctcccgc tcccgtcgct gcccctgctg    33360
tcagcagcgc tctccttgag aaggctgagt ctgtcgtcat ggaggttctt gccgccaaga    33420
ctggttacga gactgacatg attgaggccg acatggagct cgagactgag ctcggcattg    33480
actccatcaa gcgtgtcgag attctctctg aggtccaggc ccagctcaac gttgaggcca    33540
aggatgtcga tgctcttagc cgcacccgca ccgttggtga ggttgtcaac gccatgaagg    33600
ctgagatcgc tggcagctct ggtgctgccg ctgctgcccc ggcccctgtt gctgcctctc    33660
ccgctcccgt cgctgccgct gcccctgctg tcagcagcgc tctccttgag aaggccgaat    33720
ctgttgtcat ggaggttctc gccgccaaga ctggttacga gactgacatg attgaggctg    33780
acatggagct cgagactgag ctcggcattg actctatcaa gcgtgtcgag attctctctg    33840
aggtccaggc tatgcttaac gttgaggcca aggatgttga tgctcttagc cgcacccgca    33900
ccgttggtga ggttgtcaac gccatgaagg ctgagatcgc tggcagctct ggtgccgccg    33960
ctgctgcccc ggccccggtt gctgctgctc cggcgcccgt cactgccgct gcccctgctg    34020
tcagcagcgc tctccttgag aaggccgaat ctgttgtcat ggaggttctc gccgccaaga    34080
ctggttacga gactgacatg attgaggccg acatggagct cgagactgag cttggcattg    34140
actccatcaa gcgtgtcgag attctctctg aggtccaggc tatgcttaac gtcgaggcca    34200
aggatgttga tgctcttagc cgcacccgca ccgttggtga ggttgtcaac gccatgaagg    34260
ctgagattgc tagcagctct ggtgctgctg cccctgctcc ggctgctgcc gttgcaccgg    34320
cccctgctgc tgcccctgct gtcagcagcg ctctccttga aaggccgaa tctgttgtca    34380 tggaggttct cgccgccaag actggttacg agactgacat gattgaggcc gacatggagc    34440
tcgagactga gctcggcatt gactctatca agcgtgtcga gattctctct gaggtccagg    34500
ctatgcttaa cgttgaggcc aaggatgttg atgctcttag ccgcacccgc accgttggtg    34560
aggttgtcaa cgccatgaag gctgagattg ctagcagctc tggtgctgct gcccctgctc    34620
ctgctgctgc cgctgcaccg gcccctgctg ctgcccctgc tgtcagcagc gctcttcttg    34680
agaaggctga gtctgttgtc atggaggttc tcgccgccaa gactggttac gagactgaca    34740
tgattgaggc cgacatggag ctcgagactg agcttggcat tgactccatc aagcgtgtcg    34800
agattctctc tgaggtccag gctatgctta acgttgaggc caaggatgtt gatgctctta    34860
gccgcacccg caccgttggt gaggttgtca acgccatgaa ggctgagatt gctagcagct    34920
ctggtgctgc tgcccctgct cctgctgctg ccgctgcacc ggcccctgct gctgcccctg    34980
```

```
ctgtcagcag cgctcttctt gagaaggctg agtctgttgt catggaggtt ctcgccgcca    35040
agactggtta cgagactgac atgattgagg ccgacatgga gctcgagact gagcttggca    35100
ttgactccat caagcgtgtc gagattctct ctgaggtcca ggctatgctt aacgttgagg    35160
ccaaggatgt tgatgctctt agccgcaccc gcaccgttgg tgaggttgtc aacgccatga    35220
aggctgagat cgctggcagc tctggtgctg ctactgcctc tgcccctgct gctgcagctg    35280
ccgcccctgc tatcaagatc tccactgttc acggtgctga ctgcgatgac ctctctgtga    35340
tgtctgctga gcttgtcgac attcgtcgcg ctgatgagct ccttcttgag cgccctgaga    35400 accgccggt cctattgtc gatgatggta ccgagctcac ctctgctctg gttcgtgttc    35460
ttggtgctgg tgctgtagtt cttacctttg acggtcttca gttggctcag cgtgctggtg    35520
ctgctgttcg ccatgtccag gtgaaggacc tctccgctga gagtgccgag aaggctatca    35580
aggaggctga gcaacgcttc ggccagcttg gaggcttcat ctctcagcag gctgagcgct    35640
ttgcccctgc tgacattctt ggtttcaccc tcatgtgcgc taagtttgcc aaggcttccc    35700
tctgcacccc tgtgcagggt ggccgtgcct tcttcattgg tgtggcccgt cttgacggtc    35760
gccttggttt cacctcccag ggatctactg actccctcac acgtgcccag cgtggtgcta    35820
tcttcggcct ctgcaagacc attggccttg agtggtctgc taacgaagtg ttcgcccgcg    35880
gtattgatat tgctcgtgag gtccacccctg aagatgctgc cgtcgccatc actcgcgaaa    35940
tgtcctgcgc tgacaaccgt atccgcgagg tcggcattgg cctcaaccag aagcgctgca    36000
ccatccgtgc tgtggacctc aagccgggtg ccccccaagat ccagatcagc caggatgacg    36060
ttctccttgt gtctggtggt gctcgtggta ttactcctct ctgcatccgt gagatcaccc    36120
gtcaggtccg cggtggtaag tacattctcc tcggtcgctc caaggtccct gctggtgagc    36180
ctgcttggtg caacggtgtt tctgatgacg atcttggcaa ggctgctatg caggagctga    36240
agcgtgcttt ctccgccggt gagggcccca agcccacccc gatgacccac aagaagctcg    36300
ttggcactat tgctggtgcc cgtgaggttc gttcctcaat tgctaacatt gaggctctcg    36360
gtggcaaggc aatctactcc tcttgtgatg tgaactctgc tgctgatgtc gccaaggctg    36420
ttcgcgaggc tgaggctcag cttggcgccc gtgtaactgg tgtcgtccac gcttctggtg    36480
tccttcgtga ccgcctcatt gagcagaagc gccccgatga gtttgatgct gtcttcggca    36540
ccaaggtgac tggtctcgag aacctctttg gtgccattga catggccaac cttaagcacc    36600
tcgtcctctt cagctctctt gctggttttcc acggcaacat tggtcagtct gactacgcca    36660
tggctaacga ggccctcaac aagatgggtc ttgagctctc tgaccgtgtg tccgtgaagt    36720
ctatttgctt cggcccctgg gatggtggca tggttacccc ccagctcaag aagcagttcc    36780
agtctatggg tgttcagatc atcccccgtg agggtggtgc cgatactgtg gctcgcattg    36840
tcctcggctc ctcccctgct gagatccttg ttggcaactg gaccactccc accaagaagg    36900
ttggcagtga gcccgttgtg atccaccgca agatcagcgc tgcatccaac ccttttctta    36960
aggaccacgt catccagggt cgctgtgtgc tccccatgac cattgctgtg gctgcctttg    37020
ctgagacctg cctgggtcag ttccctggat actccctctg ggctattgag gatgctcaac    37080
tcttcaaggg tgtcaccgtt gacggtgatg tcaactgtga gatcactctc aagccttccc    37140
agggtactgc cggccgcgtt atgattcagg ccacccctgaa gaccttcgct agcggcaagc    37200
ttgttccggc ttaccgtgcc gtgatcgttc tctccactca gggaaagccc cctgctgcta    37260
ctacttccca gaccccctct ctccaggctg atcctgctgc ccgtggcaac ccttacgacg    37320
gcaagaccct cttccacggc cctgccttcc agggtcttaa ggagatcatc tcttgcaaca    37380
```

```
agtctcagct tgtcgccgag tgcacttca  ttccgtcttc cgagagcgct ggtgagttcg   37440
cttctgacta cgagtcccac aacccttcg  tcaacgacat tgctttccag gccatgctcg   37500
tctggattcg ccgcaccctc ggccaggctg ccctccccaa ctctatccag cgcattgtgc   37560
agcaccgtgc tcttccccag gacaagccct tctacttgac cctcaagagc aacagcgcga   37620
gtggccactc tcagcacaag acctccgttc agtttcacaa cgagcagggt gacctcttcg   37680
tggacatcca ggcttccgtc acctcttctg actcccttgc cttctaaagt tgtgaggctg   37740
tcttgtcttg tcagtcgcga aagtgtaagc aagaactttg tcatacaaag aagcaaccaa   37800
cttccgaacc aacacacctt gtaggattac aaccacaact ttctataaat agtgcgcaag   37860
aataaccagt aagctatcct tcgtgtacct gttacaacaa cgacattttt acttgatctt   37920
cctacttgtg atgggtagtc ccggcttgta ctgacagtga tgccacagca gagtagatca   37980
ctgtgaataa gtaaataagc ctacttatta tattcccaaa gtactcgctg ggatattatt   38040
agtatcacga aaagtgatat gttttataac tcgcttgtct tgccaagatc taaccttttt   38100
tttttaaatg gccaaaaagt cgccagaaca catcttacaa taaacaaaaa tttagattat   38160
atcgtatgta taatgtataa tatattatat tattatatac atacgatata atctaaagcc   38220
attccagact tattcggtga tgaaaaatgc tttcccagct ttatacaaac tattcaaaaa   38280
gttgcatgac ccattttcag atatatttaa tagtataaga ttatgtccat ttgttttcaa   38340
agttattcaa gagtttacat cttgaagttt catcccttta ctactacact gttttttcgtt  38400 tgggttttt  ctctaacggc gaaagaaaca agtcaccaag cttaactagt aggcatcttt   38460
gtggtgacga aattaaagtt gaatatataa attatagtta gtcattatgg aatctcagtt   38520
tgaacgaagc taagctattt ataaaaatca ctgcatggag ataatacttg aattttgatg   38580
atagtgttta tgaagaagtt taatcttgct ttttattaat gttattctct aatatagaaa   38640
tatttcaata aaaaaatcat atgaagggat aataaataca gagaatgatc gttatcattt   38700
gatatgtcga acgctaatct atcatcttat ctaggaaaca aaggtggaaa taaaggaaag   38760
ccctacacga gttaattcct caaacgaact actttggatt atcaaatcca actgctgaca   38820
ctggatacat gcatgtattt agtgggtgtt actgtacttc cttatttcct ttaattcaat   38880
tgtcttgatt tttacttcgg agattctact tgaaaatcat ctcccttcac ttccggttat   38940
acagaaagac ccttcaattc gaatgctggc caggtacaat aactatcagc gattcccctc   39000
cactagacat gaccgactgt aagcacctca acccgatttc aagcaacaca tgatgactag   39060
ctgtttccgc aaaacaacaa ataagagagg tagtggaaaa cacccagttc gctcgagctc   39120
ccctagtaga ttcgacattc actttctatt tgattgctaa ttgtgggtcc ggctatttaa   39180
ggaaagaact gatgaaagtc cacctcacgc aatcaaatcg cggtctagtt ggaagctaca   39240
atggccgacg tatgcgcgcc tctatctttt aggattgtag aacagggcgg caatctgcta   39300
acataaattt aataccttgc tcaagctgct ttccatactt ttcaatccat ttgtgataat   39360
cttgcaatgg accaatctcc aaatctgtag aagcaataac aaggacatcg cagggtcccg   39420
gttcgtttgc atgctcgtct tctggtgcca caacaatgct gcctgttatt atctcatgag   39480
agtctttata ctgcggatcc gtggctatag cgtgaataaa cgttgtgcgc aagcctatat   39540
cctcgcgatg gagatactgg cctgctcag  tttgcgttcg tctgcctacg acaacgcatg   39600
gaacattctt tggtgtgcga gtgggccgta gcgttcgacc ctgggcaagg aagccatgca   39660
gacgtgattc cgagaggcca tctcgcgtgt aagacttatc ccaattttct ggatcctcta   39720
atttccagct agccataagc tcagtcaaca gaccaagcgt tcttgatctt ctttctaggt   39780
```

```
caaatacatc ttgatggaag cctgcagtaa tttctttgta agatttggaa acgacgttct    39840
tgaaatgaac acaaactgat attgcattca tgggtgcagg tgacagttgc aaatgaactg    39900
aaatgtctgg agaaaagttg aggaagcgtg gtttataaag cggccaagct gtcctcgcat    39960
gcgcaagacc tagtatatta ctaatgactc tgcgaccaca atcctccatg cgttcaaact    40020
tgctatgcgg aattccacga atgatgttac cttgaggatt tggggctctc caaggagct    40080
gttgcagttg ctgtacgtat tcgcggtgtt cgcggacctg atctcgaagt cgggcatttt    40140
cctctgagca aggccctaca ggtggaaatc tgcacagcat attgtatgtt ctctctagat    40200
gtactgcccg ttgccgcaaa tgagctacat ccatctccag tttatttact gtgtcttcga    40260
gcgcaaacct ttcacagcgc ctgcgtttgc gttcatttct cgaaatctct cgccgccgct    40320
gcctgattcg ttctgcgcga tcaactcggt catccctgt gtagcttggt gatgacgtgg    40380
atccatcttg tgaggcgtca agccagaca ctgcctttac ttctaaatct cgccattcat    40440
ctgcaaaatc cctatatcct tccccataag tgtaatcgtc actacctatc aattctgtag    40500
atgccgcatc tacagtccta attatttgag gatttccttg cattgtaaag caaagatact    40560
cggaggctgg atttgtcaca aaaggtacga cagccctatt gatcaaattg aaggaagggg    40620
attgcttta ccagtacacg atgttactgt tgttgctatt gttgttgttc ccaatttctt    40680
cagacgtagc gtgccgcttc tgacattgcc aatagctgct tgtctttggt cttctttggg    40740
gaatgggcca gtaaaagaaa ccctaggcag ttcgattatc tactaatcta aagaacctgt    40800
ggccccttc ccctcaaccc acgcccttcg ttgctctctt cggtcggtga agcgtttaga    40860
tgcgaggttt cctccactac gtgcttcttc aatgctaaac gcccaagtca actgaggaca    40920
ctgaaagcct gcacggagca gaagaccac acagacggtc gcaggatcaa ccctacctac    40980
gcctcgttgc cacgatggtc gctgccgatc ctcgatctct cgtcgattat tggtctcctg    41040
ttgcgctctt ggccacgcgg ccactcgac tctgcttctg tggcttctca ctgacgtgat    41100
gtagaaagaa atagaaagca cagagccact ttaaaaggaa aaggggaaag cagagaggaa    41160
agggaaaaag aagacctcag attgactcag agattgactc aatcgacgag agaatggaag    41220
ggaatggacg ccacggagac agaggcgcag cgagacggag cgagacggag gtaggcagag    41280
gcagaggcag aggtggaggc gaggggccgg gttgtcggca ctggcagagg gagagagaga    41340
gaaggagagg cggaccagtt tgaaaactct cgccagcttc gatagccgta ctcggtatgt    41400
atgtatgtat gtatgtatgt atgtatgtat gtatgtatgt atgtatgtat gcactcttct    41460
acttgttttcc aatgtgctgt tctatgcttt acagtgtttt ccgcgctcgc tacttgctac    41520
tttcatcagt ctgtctgcct gaggcggcgg tgatgcagaa tgcacctagg tacctatttg    41580
tcgccaactt tggatttgcg tggcggcagg attcctcttc tcctgcactt tgtttcgact    41640
cgccttagaa gggttgttgg aagacgccta acgggtatt gcccggagat aggtgctgct    41700
ggtagctcat gtagatagtt cgttaggtag ttacactgga acagacagac gctctgtgtt    41760
tcgtggtgtt gcaggtcatg gactcagagg ggctgcgtga gttttgtgtt cgagagcaga    41820
gtgttgatat tcttttatgg gcaggacaca ttgcaacttg aagtaccgtg gttgtaacta    41880
caggacctcc atctgaagcg cggcatcacg tgaaaaagaa atgaaatgaa gagggaaagg    41940
acacccaaag gttcataatg tttggttttgc aaaggttatt cgaaagacac cttcttcgtg    42000
gtagatggtg attctgtcga aactgccgag attttgctga gagtgaacca aagcagggtt    42060
ttgagatgga agaatcaatc gtgcatggac aacctattcg taggattgtt atagctgttg    42120
tttgttatag gtcaaacttt atagcttcaa cccctcgctg gcaagtacga agggaaagtg    42180
```

-continued

```
taaatataca ttcttggttt aacgcataat ctcaagagct tccatgctga aaagttagat    42240
agtatattct tctgatttta catatttaaa ccaagtaaac aagttccacc aagggactta    42300
cttggcaact taaccatggt catcataatt tgcgcatcac ttagatcact acgttaacat    42360
tcgttcttga tctcttcgag cgcctaaata agcaaactgg cagcgaatta ggtcaccata    42420
tttttccaag gaggaaaaac tgtattgtgc tacccgttgt ggtgtaaaac ttgtaattct    42480
tcgcatctct aattcctatc gttaaacttg tcatcttact ttctggaagg aagcttggta    42540
tctcagaaaa tcgaactttg caataatacg aaagcacaag taagggttta tggcagcata    42600
acattgtctt aagaaattga atttaaaagc agaccgaatg caccgcagaa tacattgtaa    42660
attggtgcca atattatga gtagcaatca tcaatctaac gcacgatttt ttgaagaagt    42720
acaatacaaa tttccccgtc gtagagaatc aaatggtttt acacatctat ttcaacactt    42780
ttcttggatt gtgatttcat atcaagacaa ggcttaaatg atcttggctt tctctgcaag    42840
agcggttctc caaatttcct ctcctgtttc tggattcatg tcaaaacata gtttaacaat    42900
agaaagaagg tgaccaggta ggtacgcaat aatagtttcc gcaatgaatt ggggcttgta    42960
gcgtgcagag aaatgcatga gatatagggc ctggcagttg tccaatgcac ctcgttttgc    43020
aaacctcgcg agctcttcaa tgtggatgtg gccacgctct ctagcaaagg agatatcgcc    43080
atcaaaaaat gtaagctcca tgcaaagtgt ggcagcctga agaaatagag cctcaggat    43140 atccagggcg tctataattg tgtcacctgt atatgcaaat tcaatcgttt ctctgtacac    43200
gaaatcctca ggcataggag gtgacttttg aaagcgcttt cgtttctctt ctggactgag    43260
gttggcaagc tctgacctaa gctcttttcg tttcgtcttc accgcatagc ctacagaggg    43320
aactctatgc atcgtcttgc acaccacaac acttgcatct cctcctagat cc            43372
```

```
<210> SEQ ID NO 2
<211> LENGTH: 39976
<212> TYPE: DNA
<213> ORGANISM: Ulkenia sp.
<220> FEATURE:
<221> NAME/KEY: misc_feature
<222> LOCATION: (32084)..(32084)
<223> OTHER INFORMATION: n stands for any Base
<220> FEATURE:
<221> NAME/KEY: misc_feature
<222> LOCATION: (32086)..(32086)
<223> OTHER INFORMATION: n stands for any Base
<220> FEATURE:
<221> NAME/KEY: misc_feature
<222> LOCATION: (32086)..(32086)
<223> OTHER INFORMATION: n stands for any Base

<400> SEQUENCE: 2
```

```
tcaagaattc gcggccgcaa ttaaccctca ctaaagggat ctgatgaact tggagcaaga      60
ataagaaatc catccattca agtcagcaca cccgatggca tcatcaatct tcgtcaactc     120
tttgtgcagg cagattggtg cttcgggcaa tcaatcggtt gacggattga ttgatcaatc     180
gctttgcttg cttgcttgct tgcttgcttg caattgatcg gcaaagagg ccatccatcg      240 tagagcgtgc aatcttcaat gctctagcta gaggcgccat caggtagtta gttagctagc     300
tcgttagtta gttgctcttc ctgaaactaa caatgtatga catcagcatc atcgttcttt     360
cttctttatc catccaggat ccttcttttc aattcgtttg ttttgttttg tcttgttttg     420 tcttttttctt tcaatgcaag catctcttaa ttcaacaaac caaacgaacc aagagatgaa     480
actcaaaaaa cgtttaaaaa taacaaaca attaaaatca aatagaaaat gaaattgaaa     540
gcacttttgt tttcgcctct ctagagagct agctatagct acctactatt cgttctcgct     600
```

```
cttcgtcgtc gggactgctg catcctgtca ttatcgggcc ctaagagtgc cctagtctta    660
gaaattgatg gcgataagat ggcggtcttt cttatccttc ttctcgttgc tgctgctgtg    720
ctctttgcct ctcggatcct tttgtttaca gctggccagt cagtcagaca gtcagttaat    780
cgattaacag gcaagcaagc aagcaagcaa gcacgcaagt cagccagctg gatagacagt    840
tagatagatc gtggcgtcgt cgttggcttc gtcgctgttt tggtgcttga ggattcgaag    900
tgcacgaggt tccttctacc tacagctctt cctttcactc ttcacctatt attatgcgct    960
gcaagttctt ttcgaaaggc ttttcttct ttcattctct ttcttttggc ctttgcgtta   1020
cagagcggag acgcctagtt ttatagatct aaataaacaa gagggaggac aacagaggcg   1080
gaaaacaagc aagttcaaga cggcaagaaa gcagcgcctt tgtttctttg tttctttttgt  1140 ttcttttcaa aagagccctt cctcggaaag ctttctttct ctcttgagcc aacttgaatt   1200
cgaatctgat cttcaaagcg agttagttcc tcaggcgcca ggcacctctc tccctccctc   1260
cctccctcta tcgcaggcag gccagcgtga cacctgtgac agcaggcagc tcaggcgtgc   1320
atgcaacgaa ggcgttgact catgcattgg cgctcactca ctcactcact cactcactca   1380
ctcgcgtacg tacgcacgca cactcacgca ctcacgcact caatcactca atcactcact   1440
cactcactca ctcactcacg ccagcattct cgaggagagg ccatgcgtag gtgaggtacg   1500
aaggaaagga gtccatagtt tggaggcgat gatggcgaat tgcagagcat aacagtgcag   1560
agggagaaac ttacatccat tcatacgtag ggaggcgcat acttacgtaa ctaagtgcaa   1620
tcggtggatc aagaaagaag gaatgaaaga atgaatgaag gaatgaatga aagaaagaaa   1680
gaaagaataa atgaataaat gaatgaatga atgaatgaat gaatgaatag ataaatgaat   1740
gaaagaaaga gccccgctta tttggtatcg atctcattgc aaatgttcct gaaagttgct   1800
tatttgcctc acaactatga gtaggtagtg atgataataa tagtaattgc tattgctatt   1860
acttgaattt gaatttgaat ttgaattcag gtagacaata aaataagatt agcaaaacat   1920
tttgagagga agcagaggat atgcagtgca aaaggaggtc ccgagtttcg atcttctttg   1980
cacctgctac gtatctagtg cacgtagagc aagaaagaat gaaagaaaga acgaaagaaa   2040
gaaagagaga gagagagaga gagagagaga gaaagcgaag atgatagcgg agagaactct   2100
tcttcgcagt cactctgttt ctcagtcagt cccgcaacca ataacaactc gaactcgcag   2160
cagtgttctt cggagtgcca gcgctcgctc gcactgcgtc ggcacagcag cagcagcagc   2220
aggccccgcg ctcgctgcac tcagcccggg caggagcaac agctgctgag cagctgaggc   2280
cagctggctg gcggctcgcc tcgcctcgcc tcgcgtcgcg tcgcgagaga aagcgatcga   2340
ccaactgtca atcgattatt cgagtccttc gagcgcttta tagggcactg attgatcact   2400
cattgattca ttgactcatt tattctttgc gtggtcagcc aaacggcgtt agcattgggc   2460
aaagcgggtc tttgctttgc tctaaaatag atttgctcgc gagagtacgt acttgcagga   2520
gtaggtaggc tctgcctagt acctgggcat ttgaatattt gaacttcgaa cttcgttgag   2580
tatctgaata tttgaatatc tgaatatttg aatttcgaaa gtttgaatat ttgaatattt   2640
gaattttgga atattggaat agctgggttt ggagataaga cttactaagc taagcgccga   2700
cgtaagagcg gcgagtaaat ccacacacaa gagagaggca gagagagagg gagggagaca   2760
actcgcgcag gcaagctgag cccactggac gcacggggcg cgtccccct gacgggcgct    2820 ctggtggtgg cgtgtttggg agggttttgc atgcttgtga taggggctct ggcgcgggct   2880
ctgtacggtg cttggagatg cacgggcagg gcgagagagg ggacgggttc ccggaggcg    2940 ctgcttggag gtgctgagag ggagggagaa ggcgtgcttt gcgatgcgcg gggcgaccta   3000
```

```
ggcgctgctg cgcggtgcag cagcagggac ctcggacgtg agtcgaagcc gtctgcagag    3060
gagatggtag aagggccgcg gattggtagc agagaagagg aaatagaaga agaagaagaa    3120
atagaagaag aagaaataga agaagaagaa atagaagaag aagaggagga cgggcaggcg    3180
ggaaagatgg agaaaggact cgcggcggga aaacaagaga atgtgaactt gggcttgaac    3240
tttggtttga atttgaatgt ggagaacgag gggttgaatt tgagtttgaa tttgaaagaa    3300
aacttacgga aagaaagttt agttgaaagt gagaaagaaa aaaatgagaa agaaaaagag    3360
aaagaaaaag agaagaaaaa agagaaagaa aagagaaaag aaaagagaaa agaaaaagag    3420
aaagaaaaag agaagaaaaa agagaaagaa aagagaaaag aaaagagaaa agaaaaagag    3480
aaagaaaaag agaagaaaaa agaagaagaa aagagaaaag aaaagagaaa agaaaaagag    3540
aaagaaaaag aagaaggaga tttaaaaagt tgtttagttg aaaaaggaga aggaggaaga    3600
agcagcgaca gcggcagaag aagaagtagt tgttgtaaga ggggaacgga ggcagtagca    3660
gtggagcagg cggaggcgac agcaaacctc gaactcgacc ccgtcgagcc gcagcaagaa    3720
caagagcccg accaggtgga cgaggacgag gtccgcttgt tgtcaggaac aacagaagtt    3780
gcaggactag ccgagagtgc taccactgca attcttagat ccacagacgc aagagcagaa    3840
aacttacaac tgctcgccac aacacaagaa ccaccttcag atacaaccag gttcgagaac    3900
tccacaagtc tagaagcagc aacagctcta gcagataatc aaacaggtcc agaaaaagct    3960
acgactagaa gagaaattat cgagtcgcaa cttgcaacca tggccactcg cgtgaagacc    4020
aacaagaaac catgctggga gatgaccaag gaggagctca ccagcggcaa gaacgtcgtt    4080
ttcgactatg acgagctcct tgagttcgcc gagggtgaca tcagcaaggt cttcggcccc    4140
gaattcagcc agatcgacca gtacaagcgt cgcgttcgtc tccccgcccg cgagtacctc    4200
ctcgtcaccc gcgtcaccct catggacgcc gaggtcaaca actaccgcgt cggtgcccgc    4260
atggtcactg agtacgacct ccccgtcaac ggtgagctct ctgagggtgg tgactgcccc    4320
tgggccgtgc tcgtcgagag tggtcagtgt gatctcatgc tcatctccta catgggtatt    4380
gacttccaga acaagagcga ccgcgtctac cgtctgctca acaccaccct caccttctac    4440
ggtgttgccc aggagggcga gaccctggag tacgacatcc gcgtgaccgg cttcgccaag    4500
cgtctcgacg gtgacatctc catgttcttc ttcgagtacg actgctacgt caacggccgt    4560
ctcctcatcg agatgcgcga cggctgtgcc ggtttcttca ccaacgagga gctcgccgcc    4620
ggcaagggtg tcgtctttac ccgcgctgat ctcctcgccc gcgagaagac caagaagcag    4680
gacatcaccc cgtacgccat tgccccgcgt cttaacaaga ccgttctcaa cgagactgag    4740
atgcagtccc tcgtggacaa gaactggacc aaggttttcg gccccgagaa cggcatggac    4800
cagatcaact acaaactctg cgcccgtaag atgctcatga ttgaccgcgt caccaagatt    4860
gactacaccg gtggccccta cggccttggt cttctcgttg gtgagaagat cctcgagcgc    4920
gaccactggt actttccgtg ccacttcgtc ggagaccagg tcatggctgg atccctcgtg    4980
tctgacggct gcagccagct cctcaagatg tacatgctct ggctcggcct ccaccttaag    5040
accggtccct tcgacttccg ccccgtcaac ggccaccccca acaaggtccg ctgccgtggc    5100
cagatctccc cgcacaaggg taagctcgta tacgtcatgg agatcaagga gatgggctac    5160
gacgaggctg gtgacccgta cgccatcgcc gatgtcaaca ttctcgacat tgacttcgag    5220
aagggccaga ctttcgacct tgccaacctc cacgagtacg gcaagggcga cctcaacaag    5280
aagatcgtcg tcgacttcaa gggtattgcc ctcaagctcc agaagcgctc tggccctgcc    5340
gttgtcgctc ccgagaagcc cctcgctctc aacaaggacc tttgcgcccc ggctgttgag    5400
```

```
gccatccctg agcacatcct caagggcgat gctcttgccc ctaaccagat gacctggcac    5460
ccgatgtcca agatcgctgg caaccccacg ccctcgttct ctccctcggc ctaccctccc    5520
cgtcccatca ccttcacccc gttccccggc aacaagaacg acaacaacca cgtgcccggc    5580
gagatgccgc tctcgtggta caacatggct gagttcatgg ccggcaaggt cagcctctgc    5640
ctcggccctg agttcgccaa gttcgatgac tccaacacca gccgcagccc tgcatgggac    5700
cttgctcttg tgactcgtgt ggtctccgtt tctgacatgg agtgggtcca gtggaagaac    5760
gtggactgca acccgtccaa gggaaccatg gttggcgagt tcgactgccc catcgacgcc    5820
tggttcttcc agggatcttg taacgacggc acatgccgt actccatcct catggagatc    5880
gccctccaga cctctggtgt cctcacctct gtgctcaagg ccccgctcac catggagaag    5940
aaggacattc tcttccgcaa ccttgacgcc aacgccgaga tggttcgctc tgatattgac    6000
ctccgcggca agaccatcca caacctcacc aagtgtaccg gctacagcat gctcggagac    6060
atgggtgtcc accgcttcag cttcgagctc tctgttgatg tgtagtctt ctacaagggt    6120
accacctcct tcggctggtt cgtccctgag gtcttcatct cccagactgg tctcgacaac    6180
ggtcgccgca cccagccctg gcacattgag tccaaggtgc cttccgccca ggtcctcacc    6240
tacgacgtta cccccaacgg tgccggtcgc acccagctct acgccaacgc ccccaagggc    6300
gctcagctca ctcgccgctg gaaccagtgc cagtaccttg acaccatcga ccttgtggtc    6360
gccggtggct ccgccggtct tggctacggt catggccgca agcaggtgaa ccccaaggac    6420
tggttcttct cgtgccactt ctggttcgac tccgtcatgc ccggctcgct cggtgtggag    6480
tctatgttcc agctcgtcga gtccatcgct gtcaagcagg acctcgccgg caagtacggc    6540
atcaccaacc cgaccttcgc tcatgctccg ggcaagatct cctggaagta ccgtggtcag    6600
ctcaccccca cctccaagtt catggactcc gaggcccaca ttgtctccat cgaggcccac    6660
gacggcgtcg tcgacatcgt tgccaatggt aacctctggg ctgatggcct ccgcgtctac    6720
aacgtcagca acatccgtgt gcgcattgtt gctggcgccg cccctgctgc tgctgctgct    6780
gctgctgctg ttgctgctcc ggctgccgcc cctgctccgg ttgctgcatc tggccctgcc    6840
cagaccatca ccctcaagca gctcaaggct gagcttcttg acgttgagaa gcctctctac    6900
atctcctcca gcaacggcca ggtcaagaag cacgccgatg tggctggtgg ccaggccacc    6960
attgtgcagg cttgcagcct cagtgacctc ggtgatgaag gcttcatgaa gacctacggt    7020
gttgtggctc ctctctacac cggtgccatg gccaagggta ttgcctctgc tgaccttgtg    7080
attgccactg gtaagcgcaa gatcctcggt tccttcggtg ctggcggtct ccccatgcac    7140
attgtccgtg ccgctgttga aaagatccag gctgagctcc gaacggcccc cttcgccgtc    7200
aacctcatcc actccccctt cgatagcaac cttgagaagg gcaacgttga cctcttcctc    7260
gagaagggcg ttactgtcgt cgaggcctcc gccttcatga ccttgacccc gcaagtcgtc    7320
cgctaccgtg ctgctggtct ttcccgtaac gctgatggct ccattaacat caagaaccgc    7380
atcatcggta aggtctcccg taccgagctc gctgagatgt tcatccgccc tgccccgcag    7440
aacctcctcg acaagctcat ccagtctggt gagattacca aggagcaggc tgagcttgcc    7500
aagctcgtcc ccgtcgccga cgacatcgcc gtcgaggccg actctggtgg ccacaccgac    7560
aaccgcccca tccacgtcat cctccccctt atcatcaacc tccgcaaccg cctccacaag    7620
gagtgcggct accccgctca cctccgcgtg cgcgttggag ctggtggtgg tgttggatgc    7680
ccccaggccg ctgccgctgc tctcgctatg ggtgctgcct tccttgttac cggcactgtc    7740
aaccaggtcg ccaagcagtc cggcacctgc gacaatgtcc gcaagcagct ctgcatggcc    7800
```

```
acctactctg acgtctgcat ggctcccgct gctgacatgt tcgaggaggg cgtcaagctc    7860
caggtcctca agaagggaac catgttcccg tccagggcta acaagctcta cgagctcttc    7920
tgcaagtacg actccttcga gtccatgcct gccacagagc tcgagcgtgt tgagaagcgc    7980
atcttccagt gccctcttgc tgatgtctgg gctgagacct ccgacttcta catcaaccgc    8040
ctccacaacc cggagaagat cacccgtgcc gagcgtgacc ccaagctcaa gatgtctctc    8100
tgcttccgct ggtaccttgg tcttgcctct cgctgggcca acaccggtga ggctggacgc    8160
gtcatggact accaggtctg tgtggccct gccattggag ccttcaacga cttcatcaag    8220
ggctcctacc ttgacccggc cgtctctggt gagtacccgg acgtcgtgca gatcaacttg    8280
cagatccttc gcggtgcctg ctacctccgc cgtctcaatg tcatccgcaa cgacccgcgt    8340
gtcagcattg aggtcgagga tgctgagttc gtctacgagc ccaccaacgc cctctaagcg    8400
agttatatct gtctagaaaa cttggcatgg ctagcaattt atgtctagct attccataca    8460
cacggtaatg ccagtagcct gttagttata gctcttttgg ttgttgtctc acaatacact    8520
gacatcagca gaacaaaatg aaaggggcct tggctaccat gaaatcaata cttcaaaagg    8580
tctcttggtt tctttactcg catgtcgcta tttacttaca ttcctcgagt acataacata    8640
tcatacatca agaaattaa aaagaaaaca aacattcaaa tatgcattac tttccctact    8700
gtactagtaa gtacgtttct ggtattaagt tgttttttct caaaagaaca atgtgcttac    8760
ttgtaaaatc cacagctgct tacttgtaag cctcaactag ttagtgatgt gattatcata    8820
aaatgttcga cactgtacct ccttcccagc tatcttccta cacctcctct gacgcaggtt    8880
gacggaggag gcgtgggggt tgattgaagt gcaacacaac gttttgttta agatattcct    8940
tgccttggcc gactccaaat ggatagcaca gaagcctaat gataaattga attaatttta    9000
tttcgagctt atttaatgct cttatcagag tccgtaggta tctcttttcc tactaattgt    9060
tgaaaaggaa tgttttggac atagcaggtc atcatactat ttggttccat caaattcata    9120
tccatttctt tcgttcaagt gcttcccttc ctacttatta tatatattat atatccataa    9180
atgtaaaaga gacgattacg aatactttgc atacatgtat agcgaaacag agatggtagc    9240
aaaagttcac cttcactaat ctaagaatct ctccacgtgg gtaaaaactt cagcagtaag    9300
attgtaaatg atgtccaaga acaaaacgtc atgctagtcc aggggttact gagctaacga    9360
ttaataatgt ttcgtagtct tcctaattgc accatcaaaa cttgtctgca caagttttaa    9420
agtattggag cctttactga agaatcagag gacatagatg gggcacgttc gccttgaaaa    9480
aaatagtctt ctttacctgc atggtgttac aaacaaaaac gagttgaaaa tagctgtgca    9540
aggaggcaaa catgattgga aaagaaaaac gaggggaccc ttatacagga gggcgccaca    9600
tagtagaatg agtagattgt tagagtaggg tacgctttat gtgattgatt gaatgggcga    9660
gtgaaagttg ctgtcaaggt tctaaacaaa aggatgtttg agtttgtgag tattgtttgc    9720
ggcaaaaaga ttcagtagag agaaatgcac aaaaagataa tacgtgtgta gggcgattat    9780
ggaggcatgc atttggggga aatcatcgca tgcgcatgag tttctccatc tgccgaatct    9840
ttgcaaaggc attttcaagc tccatttgca tagcgtaggc ttgctgctca aactgagcgc    9900
gctgatgcgc cagattttct tcatgtcttt tgttcaaact acgctcaaga ccctcaagag    9960
ccgcaacctt gagcttgcgt tccttttgct gaatctccat aactcttcgt ttcacctgga   10020
gctcaatttc tgcagcatcc gtggtctttg cagcggcctg tgcgtcttgt gcggcctgtg   10080
cgttgtttgc gagctccttt cgcagctcct ccatctccgc gttctttttc tcctccatcc   10140
atttggcacc gagtttggca gcttgatcga tgcggccctt gagaacttct tcgttctcct   10200
```

```
caagttctgc gatacgcgcg tgtaagccga ggatctcctc cgagacagcc tcgccattga    10260
tcattatttc acttcccgag tcttgaatga caacatcagc cttggtgcca ggttcaccgg    10320
tatctcgctc gcaaccctgc tggcgcatag acagcataag gcgcgcatta tcctcacgca    10380
gatcatccac ctgttctgat aaaagtttga ctgcctgctc aagattacgg gggttcactt    10440
cgtgaaaaat ttcttgaagg tctcgaagct cagaaagctt ggcagagcaa gtgtgcatcg    10500
ctctgcactt tttaagacgt gcaagtgcat catcaagttt ggcattattt accttcatgg    10560
aggcttcagc tacttcggct tcttcgatta caattttctg cagctctaca acatcatggc    10620
caattaactt gcgatgcagc tcggcaatca ccccatgcat cttttcggta tggcctggac    10680
gcgcctcatc ctgcgttctt cggatctcct cctctagttc tcgatttaga cgaagggctg    10740
gtccaagggg cgggtaatta gcctgagtca agccaagctc tgttgctagt ccaaggcagt    10800
cggaaagtcg cagccggtcc ctatcagaaa cagccttttg caagtctacg ctcaaacgca    10860
cttcttgagc cttgcgcacc atcttcggtt ctgcctgtcg cagaagtttc gagtcgtagc    10920
cagcttgcca cgctagcacg atggcacgcg caagtgacct cagttgaccg ctgttcatgg    10980
cagacttgag caacattttg atttgcacaa ataccteate tgattcatca tcttcagctt    11040
cctcaagctc tgcaggtgtc ttgcgctctc cagagacttg aagagcaggg ttcaaaccgc    11100
cctccaggac ctcgctcgca agcgcctcct ctgtctcagc tttgcgcaat agcgcagcag    11160
cattctccgc cattgtgttt gtcactcacg agattaatat cgttgccaga gtatacggta    11220
atgcgagtta aggattcaca gaatctctca aattaatctt ttcacctaat gatatccaca    11280
aaacgttgca atcgctcagc ccaacgacaa gcgtgcttct tgttttaaga ctgcaactgc    11340
tccttttcct attagtcaat atggaccgtc ctccaaacgt ccagaaaata gcacagaatt    11400
taccagcagc cgctgcagac aagaagtgca agagagcagg caagcaagtg agggtttgag    11460
caaataggcc aacctctcca cgcagaattc tagggtcgca accggaactc acagtccttta   11520 gaaaccgtgc gaagccctgg gctcaacttc aatttgtcca cgggaccttc agcaagcacc    11580
aagctcagca gcgtgaaggc aggcgctgac cacagtttga gctcagaggg cttggtgtgc    11640
ctcgcgattg atattgaagt caattgcgca ggacggcagc aacggaccag gtggtgaaga    11700
aggtaatctc cagcggagtg atgatggagc tcgaccgact actccggaat cgaccagggg    11760
aggtgcgggc gcccttcaca agcgggcgag aggcagggga gagaaggctc gactccacgt    11820
cttgaagcgt gtacgtgtgc gcgctcacgc gtgcgacacg ccggcaaggg cgccttagtg    11880
gcctgctgct gctgctggtc gccacgctgc gagcccaaga gatttgaatt gaactcgaag    11940
aaaataacta tcatttatca attccaatca atcaatgcat tatgaagcac ctctgaagtg    12000
aactattctc ctctccaata tacaacaaaa aacacacaca gtgggtttta ccctataacc    12060
tattgttccg cgagcgatca actactctat agagcgaatg accagttttt ctttctttct    12120
ttctttcttt ctttctttct ttctttcttt ctttctttct ttctttcttt ctttctgttt    12180
tcctatctaa taaccccttt aatcgaggaa acctttcgat ttaaaaggaa agctctgtct    12240
gtatatatct gttacagata ctgctatcat gccatgcaga aagaaacaca aaagaaaaac    12300
aaaagaaaga gagaaagaga gaaagaaaga gagaaagaaa gaaagaaaga aagaaagaag    12360
agcttttctc aatcggtttc ctcatcgacc gctcacatat ctacgattgt ggcaaagaaa    12420
gaaagaaaga aagaaggaaa gcctcagcag agtccgcacg aaagccttca ttgagccacc    12480
atgtcgtggt ccgctgcagt cagtgccgcc tctctgtgaa ttgagtgagt gagtgagtga    12540
gtgagttggt tggttagtta gttagtgcct cttcagctca aagcctttca cggtcgctct    12600
```

```
tcgagcgttt gcttttcat  aaacaaataa  acaaaccatc  gaacgaacca  tcgaacgaac   12660
gaacaatggt  accccagaat  agacggaatt  aattgctaag  taaaccagta  acagtaagtt   12720
agtgtttctg  acctgagccg  ttttctttat  ttattcctct  cagctctgtg  aagagaattt   12780
gggatgaaaa  gaaacgtttt  tatttattta  aaagtttagt  aacaagaaaa  acatggtccc   12840
tcttcttcct  tcatgtaaaa  ataagtaagt  aaaaaaaaga  aaagaaaaaa  aaaaagctt    12900 ttaaagtagt  aaagcgaggt  agagataaaa  gttctttctc  agggctccta  gtaggcactt   12960
aggaggtacg  tctaagaccg  cctcgtggga  agaaagaga   aaacaagaag  agaaaagaga   13020
gagagaaaca  gcgctgaccc  gagaggctca  tgcgcagagc  ccaaatctgc  ccaactttgg   13080
caaaatgcag  cgccgcctct  gcggcggaga  cggtcatgtg  aatccgcaga  gctgcacgca   13140
cgcgtcacag  gctacagctg  gatatttttt  atacgagccc  gcgcgagacc  gcggcggaga   13200
aacggggtcc  cgcgcgaagg  gcctctgaaa  agcaggcagc  gaaccaggcc  tgcaccagcg   13260
ccgacctccg  cgagacttcc  ttcgatctca  ggaaggacct  tctgaagagt  ggctcaaagc   13320
agcgcaggcg  gaggcagcgg  cggagggcac  gcccagcgag  ggcatcggct  cgaggctcca   13380
gggctgccag  gtcgcgaggc  atgcacggcc  tcggttcgtg  atcttggccc  tgccgggtgt   13440
gccgggatcc  aatatggtgc  gcaccgtttt  tgaagctgtc  gctcttttct  cgcgtcgcac   13500
attacgatgc  gcagaactga  gtgagtggac  aaacgaagag  ggcgatcgat  ggcttggaat   13560
gcgaactccg  tccatcgaca  tcgacatcga  tcaacccatc  gacccatcca  ctccgtgcac   13620
aagctgcact  ccgtgcacaa  gctggagacg  agcgaccgaa  gaggtgacga  ttcgctctcg   13680
ctcgggatgc  ttggatgatt  ggatgattgg  gtgcacgagc  tgccacttgt  tgttcttgtg   13740
ttgttcttgt  tgctgttctt  cttcttcttg  gcggtcgttg  agcgaatgcg  ctgtttgtcg   13800
agaaccatga  aatgagcgtc  ttgaatatgg  gtggcctcgg  gaatccgcag  aacgatggta   13860
tcgcattcgc  atccctggtt  gcaagaaggc  ttgcgatgag  gtaagcacat  gccgactcgc   13920
cgatcgacca  gcgcgggcct  ctgtgccgaa  ggagcgacag  cttggacgca  ggggaatggg   13980
gcctcgaagt  tcttgtggtc  actcaggaca  gaaactcttg  ttttaatttt  tctagttgct   14040
tagctcaagt  tagttagcca  gttggctagt  ttgcttttaa  ttaaaaatga  agaaaactaa   14100
aattgagttc  tcaagtctga  aagaacaagc  aaacaaaagc  gaaggatgtg  ctgtgcatgc   14160
acgagcttcg  gctcaggcag  aggaagattg  ccagctcgca  tgaccttgga  tcttccatac   14220
tgcgtaatgc  tgagcgtcag  agaaagatgc  gggccaggtg  ccggaagata  taccttcatg   14280
gactttccgc  agaggtgaag  atcagcgatg  atcatgtgga  agtgacacga  cgcacctcga   14340
gcatcccagg  aattgcagtg  tttgcccagg  caggcagtga  gtgcctggtc  aattatggaa   14400
tagtcaatct  agtaatatga  gtgagtgaa  ggcagaaaat  aatttccatt  ccttcattcc    14460
atgactagct  gcatcaacat  catgatgttg  cttcagctcg  tcagcagggt  gaacaacgtg   14520
cgggctagaa  gaattagaaa  agaacaatga  gtgtctatga  atgcatgaga  atcgagtgta   14580
atgcaataca  gaaacgtgag  aaattgcagg  attgattaga  aagtattagt  agggcaagaa   14640
cagagagatt  agagaagtga  aaagggatga  cggtgaaacc  agtgtagtcg  tagtaaagag   14700
tggcttgcaa  ataggtgcac  cgcatccatc  aattggtcaa  cgagcaaatt  agtgcagcca   14760
gcgtactagc  tatttactgc  gacgatgtaa  cgaagtcctc  caaggacgcg  tacacggtgg   14820
ccggcaagtc  ttcattggcc  ttgagcttgt  ccaagataat  gcggggaaac  tggattgcct   14880
ggtcaatcac  agccttacgg  gcctgctcat  cgttgacaag  tgtagggtcg  cgctcgaggt   14940
ggtcggtgaa  gcgagagtgc  aaatcaagag  ctacagcaat  gatgcgctca  gccttgagct   15000
```

```
catcacggtc ccactcaact tcctgttgca taagcgaacg gatgcgcttt acaaggcagt    15060
ctcggacctt gggcaggtca ttaataccat cgtaataaat actcatgacc ttccacatgt    15120
tgggctcact cttacactta gaacgcattt tgtcaaagag ttcctccaat tgtgcgcgca    15180
aactagacac aagttcaggg ctcatctcct tacgagggc ctccggcgtg tgcgggtctt    15240
cactagaggt ctgagaatcc gacttacgga cagagaccaa ggcatctaca actacaagga    15300
gactctgtaa gtcaaccatc tcagcaatgg cctcacgagt gccagcgcgc acatccacaa    15360
ggttgctcat accatcaatg gccataccc actgatgagt gttgacagcc aacataatgt    15420
agttctccca aatacgccag ttggaacgtg actgacgaac ggcctcaata acagccttca    15480
aggcagcagg gtagtcgttg agctgaatca aaatcgaact caagttagcc caagcatcac    15540
cgctatccgg atcctggcga gtcacatgcg caaaggctgt acgggccaag gtccactgtt    15600
caaggcgcat agcgcatgag ccaaggcgga accacgactc cgggtacaac gggttgatct    15660
taagggcatc ctgaagatgg tcaatactct cctgcaaatc accgcggtca aatgccatga    15720
gggccaattc acgcttagca cgcgcatggc gcttgccaga aaactcccac gccttgctga    15780
accagtcctc atcctgaagc aaagagccca aacgcacat aaggtgtgca gtgggctcaa    15840
ccgcaaggcg ctcacggatc aacttctcag cacgagcgcg cttgtccatg atcacaaggc    15900
agtccacagc ctcttcccaa agacgaacct cctcaaagat ctgcaacgca ctaccagcag    15960
cgcccacttc atagtacaat gcgcgaggc gcgcttgag ctcccaaact gcgggccagg    16020
atagcgcgtg cagaaaggcg agacgctcgg tcactgggc agcgttgtcc acgtcacgct    16080
ggcgaggctg tgttggtgtg agccggtcag tctgctggtc aacgaggact tgcatctgta    16140
aaatggcacg ctccttggtc ttgttgcgct caaactcaag ctgagactta attagaagtg    16200
cagtggagta ccatccag ttttcaggac tctggaggac acgctccacg taagcaagca    16260
tctcctctgc agtgagagcc tccatagcgt agctgttctt cacatccata cacaagccga    16320
gcacgataca ttggtccaaa aggctcaacg ttccgcggcg catgcgagcc tcctcatcac    16380
tggtctcctt tgcgtactgg atctcctcgt gaagtggagt ctcagcgtca acttcttcga    16440
ggcgcacctt ggggataccg agaacagaag tggatcctac aatctcgcca ccgttctctt    16500
cctcagttgc atcattatca tcctctgcca caatctcgtt gggtacctcg gtctcgatgg    16560
ccttgactgc agggaatta gaattcttag gagcttcagt gtcttgctcg cgattttctg    16620
ggtctttggt ggtagctgac gatgcaagaa gaataagctg ggtcttctct tgtttctgaa    16680
acttggtacg ctttcccatt acaccagtca tctgaatatt cagctgtgct gtttcctttg    16740
cctttgcaaa agcacgctta gctccatctg cagccttgaa cttgtgccgt gctacaccgc    16800
attcaaccca cacgagggac tccagaagtt tatcatctgg gtacatgatc tgcactgctc    16860
ggaccgtgcg agcaaatcct ctctctgcct cctgctcgag gctaggagcc gctgcctcct    16920
tggcttcaag ggtctcctgg tgaacaacag cagatcgtgc tgcccaccag ctaggtgtca    16980
gcaaatgccg aagagctccg cggactgtgt tggagatctg ttcatgaggg ttagcgctca    17040
tgccgccgtt ggtctttccg ggaagatcgt cctcgccatc ttcttcatct tcatcagcgc    17100
caatgacagc cccgttctcg tccacaaggc gagcctcagc gagcatatca gttgggtcca    17160
cagcaccagg ggttactgtc ggattagcga cgacgcgaag aatgacgcga gcaacaagca    17220
agaagtgaag gtacttggca tcacggtaaa cctcctcacc gttcgcgcca agcataagag    17280
ctgttcttgc gtggagctcc ggatacgcgt ccaactgtga ctcgtggaag ctggcatcct    17340
tgccagacac agcggcagca gccttagcat cggaggcgag agcggagaga gcagtctcca    17400
```

```
cataccctgag acccggctca gaggcagact tggagctagt atctacagaa ttcttggggg    17460
cattggggtt gtcgtagacg ccgcgaacaa aagggagggg gtagaacttg tcaataccat    17520
ggctagagac aggaggacct gtccagttgg cctggacgaa gatgtgaaga caagcaacac    17580
ctgcgaacat gcaggccata gctcgcgagg cacgttggtt tacgtggtcc tcaggactcg    17640
agacactcgg gtccttgaag gagctgcgac ctgtgcaggg gccaatacca gtctcgatgt    17700
gctcaacaac acgctcatga agaaaacgac cttcacggtt tttaacgcga cttacagagt    17760
atcccttctt aagatcttct gcggcaaaga ggccttgcgc cgcaggagag gcgaggacct    17820
cgaagaaatc gccttgggca agagcgcacg ccatacgaag gacctcaagt tggagctctt    17880
tcacttcagg ctcgtcacgg agctcctcgc ggtcatctgc agcagccgat gcagccacaa    17940
gaacatcttc gagacccctcg gcattgctct cgagagcgag acgctcgaca agtcgcagcg    18000
agtaaagagg tttcgcaact ccagagccct ttttggagtt gaagacacca gcgccgttaa    18060
gatcaccatc gtcagcctcg tcgatctcat catcaggacc gtcagggagc tcaaagtcct    18120
gtggaaggcc taggaactcg ttcaggtctg cgtcagagct cgaatccgac gcgtagtccg    18180
ccatcctggc ctacaggacc gccgaaacag gttgcggcag ccgcccaaag tctaagctgc    18240
aagagtcaac cctcaatcgc gagcttgcgg cacaacgtcg ccgcaggatc tcgcgccaag    18300
acgtctccaa atgcaagtct ggtgctcaag tcatcctggc cacccgcgcc tttgccctt     18360
aagctaggtc acctacctta aaccagagtt gccccgcggt gtcatattgt aaacatttta    18420
taacaatata cgtcatatta aaaacctaga tgtggggaca atgttataaa taagtaacaa    18480
atatagacta catcgagaag aaagaattct tcggcactcc gtgtgagttt gggcgaaact    18540
gcaatcacga agccatgcaa agtcttcgta tatctgagtg gagcctcgct ggagagaaga    18600
ccccatgtga atgggtgtag aacgacgaat ctacgcagcg ttgtctccgt tgagacgctc    18660
tgtccagata tgaggtccct cactattctc gtatttgatc atgccaagca tctccagttc    18720
caacaatgga gttttctatt gaaagaacat agacatgttt ggaacggttc ctttcagagg    18780
ggaaaaacta atcaaaaatc aattgaggaa tgcaggggggg ttatttgctg cagttttagc    18840
aataaaataa aaatcctttg ttgatgtgat ttcattcgtt cctttgacat tcaatcattg    18900
aattgctctt caccggagct tttcaaggtg cccaactgcg atctccgctg cggctgctcg    18960
cggccgggct ctgagctcta tctccgtgtg ggaggcggga agccagcagg tgcggcgacc    19020
ctctccaaat agaggccgcg gcgaccttga ggcactcgcg tggcgggcgg attggcgatt    19080
ctgtgttcaa ccgagatatt tcatacatat tatttgctaa ttattagcaa atagaaataa    19140
atatacagac tttgcaagct cagtagagaa agtgaagatc caaaatgtcg gcctcttcct    19200
cgcaatctac ttcggagcag cgcaagtcac gcgtggcgta cttttacaaa cctgagattg    19260
gcagctacta ctatgggtaa gttagtatgg gaaaattggc gacagaaaaa tataataaaa    19320
aaagcaactg tatcgccacc gtttattcac ggtagttaga aggtatttgc ttcctgcgca    19380
cactcgatct gcaggatgta catgtcttga gtggcattgt ccaacgatcg ttctgtttgg    19440
cggaacattg cttttaaaca aaaacgagat agtgaatata ttctacccaa ctaccaccat    19500
ccggtttaag gagacaaata aatctgtctt tcgacccagg ataaggaggc ttgcatggga    19560
atcttttata atctagtctt tatgtcaaat tttcgcaggt tccagcctac catctctcat    19620
gctatttgtg attgcacaag atgatatgaa agtaaagaaa caaggcaaag gatataagat    19680
gcataaggat gtgcagaaaa ctaactagaa acattcatgt gatgaaacct tcctcttgaa    19740
aactcacctc ggtttgtttt ggatcttggt ttgtctttgc tcacttttt tcattattta     19800
```

```
cagcccgtcc catccgatga agcctcaccg cctgaaactg actcacaacc tgcttcttac    19860
atacggactc ttccgacaca tggaagttct gcgcccgcac gacgcgactg cggaagacat    19920
ggagcgtttc cactcgcacg aatatgttga cttctaaag cgcatttctc ccgacaccga     19980
gcaagagttc gagaagcaaa tgacccgttt caacgttggt ccctattctg attgccctat    20040
ttttgacggc ttatacaatt ttatgtctag ctgctccggc gcatcgttgg atgccgcaat    20100
taagatcaac cacggacagg ccgatgtttg tgtcaactgg tctggtggtc ttcaccacgc    20160
aaagaagggt gaagcttctg gtttttgcta catcaacgat attgttctct gtattgttga    20220
gctcctcaag tatcaccctc gtgtactcta tgtggatatc gacattcacc atggtgacgg    20280
agttgaggaa gcgttttaca caaccaatcg tgtgatgacc tgctcttttc acaagtatgg    20340
tgacttcttt cccggtagtg gtgcctacac agataccggc gctcgcgctg gtaagaacta    20400
cgccgtaaac tttccgctca aggatggtct tgacgatgcc agctttgaga gcatcttcaa    20460
gcctgttctt gatggcatca tgaagcactt tcagcccgt gctgtggtga tgtgctgtgg     20520
tgctgattcc atctctggtg atcgccttgg gtgctggaac atgtcattgc gaggccatgg    20580
ctacgctgta cagtacgtga aatcctttgg cgtacctgtt gtgcttcttg gtggtggagg    20640
ttacaccccg cgtaacgtgg ctcgctgctg ggcttacgaa accggcattg cactcggcaa    20700
gcatgaggat atgcagaatg atattccatg gaacaactac cacaactact ttggccctaa    20760
ccatcttctt cacattactc ctgacccgca gatgaagaac gccaattcac gcacctacat    20820
ggacaagtac accaacatta ttctcgagaa cctttcgaag cttgaagcgg tgcccagtgt    20880
acagttccaa gatcgcccta cgactttgc aaacccagat gagcgtgctc gtattgctct     20940
tgacaacgct gaccctgatg aaaaggatta cattcaacgt cctcagcacg aggccgaata    21000
ttacgaagac gagaaacacc aagactcgga ccgtcccaat ccggctgatg gtggtgccga    21060
ctcaaaggta aagtctgaaa atcctcagg cgatggagct gcggacgaag cggagaccgg     21120
atccagaaag cctacaaaa agggcactga atgcggtggt ctacttgaaa ttgacgaggc     21180
tgtcatggaa gtggactcca tgaagcgcc caaggagact gctcctgctt cagattctgc     21240
tatcaagact gaggatgctc ctgctgctga gtctgctgcc tccccctcgg atgccaaggc    21300
ctaaacatga agactttgtt ttaatgcaat agacgtgctc ttttgctgct cgagtagcgg    21360
caaccctagt gccatgtcct ccttttttct tactcacttc tctctctacc tttgaaagag    21420
accaagtgga accaagcagc catttctgtg ttccacattg caatagatta tcttttaaca    21480
attctcatac atacatattt tcttcatttt tcttttctat gtattttaa aataaaatat     21540 aacaacaaag tagtagtttg tatgaatttc ggccatgcag gtgacaaaag gtgaaagtaa    21600
tgagcgtcat tttggatcac attaccagcg aatccactca acgactcttc tcttctcgag    21660
ctttagaagc tgactgtgag ataatagaac agagcacggt ccatcaatca aaatacataa    21720
ttagctcgca atagcttcgc ctcacagtga tcgtttcacc tcatgatacc cttgttgggc    21780
gctcgctctt aggctctccc ttgttgttat atgatgcaac gatcatctaa gtgctgtccg    21840
cagtcatcaa gacatcctat tctgtagcaa gcaagcaagc aagcaagcta gctagtttag    21900
ctggctagct agtttagctg ctgagttcg cagtgaataa acaattaaca cctcaagtct      21960
tgaaggagca ggaaacttgg ctcctatgat atgccatcct ggaaggccat gttttggggg    22020
gtatgagaga caggtctttc cttttctact ctggttcggt ggatgacgag acaacaacca    22080
gacgtcccgc ctagtacctg gtggtcgat ctgtcctccg ttcactccga gtgcagggct      22140
tgtgggacga ctcgctctgt tgaattgagg tccttcacgc gagcctatct gggcatcgat    22200
```

```
cgacctcatc catcaacaca cacacatatg ttcaatccgc gccaccctcg ctgactccca   22260
gactgcccag cgaaactttg aaaacttccc catctcgaaa cagcactccc aaaagacgca   22320
cacaagcaac gcttgagcct aggcaggctc tccgctggac gcacaaacca cctcgcagcc   22380
atccactctc tgactcccca agcatgcatg gccttctccc tcgatttggc gcttcgcgtt   22440
gctgtcttcg aagtcctcaa acacgaactt tcactaatc atcctcgacc tcagcaggat   22500
gccccccctc ctaagctctg tttgctatgt atttattaga ggaaggacgg caagctgggg   22560
gtctgcggaa cgcattttgg gggtttgaaa attttcgaat tttcaaactc cccgaaacgg   22620
ccatggtttc ttccgagaag cggtagttag gtggggaaat gagagcacgg cggagttggc   22680
gagaagcata atctgggcg gcaagcaaa ccccaaacta tcctgcaatc aacaaaacac   22740
acgcactccg caatcaactt gcaccgtaag tctttggaat tgattatggt atctgcttcg   22800
ccgtcttcaa ctttaacttt gcgcctcgca acgagacttt gttttgtaat gtgcctttag   22860
atttgacgaa acatctttaa gcgagatagt acagcagcgc gttggtacca agagagatag   22920
atcctgggac cttttgaaat aaataaactg tgtgatgaac ggtcgactaa ctgggcttgt   22980
aattgatata ttgatgatac tcttggtcca catgggagtg agcacagtcc acaaacaact   23040
tgctaaccca cacaaaaacc tcccaaactt gcagacccgt tctgcattct tgtaaacaca   23100
taatcacaca gcacacataa tcacaatgac ctacggcaca gcacacaact acgtgcagga   23160
gcagattgag ttggacgaat gcttcaacaa cttttggcgaa gaagtgagca gctctgttga   23220
gcctcggtgg cagcgcaagg ccttggccgc tcgcactccc aagtctagcc gcaagcgtag   23280
ccgcaccggc aagaccccga gcaagggcaa gtctacgccc cagcacgacc gattcatccc   23340
caaccgtggc gccatggacc tcgctaacgc tcacttcaac ctcatgaagg agaacagcag   23400
ctccgcctct aaccagtgcg agtcccctac tcgtgctgaa ttcaacaagg ctttggcgtc   23460
cagcatgggt gcgggtgagt cccgtgtttt ggccttcaag aagaaggctc cggcaccgcc   23520
tgagggatat gaaaactccc tcaaggtttt gtacacgcag aacaaggaga agatggcgcg   23580
cactcagaag cccgttcgtc acattccttg gcaccggag cgtatcctcg acgcacccga   23640
cctcttggac gactactacc tcaaccttgt cgactggggc gcctccaaca tgctcgccgt   23700
ggcccttggc cagacggtgt acttgtggaa cgccgagacc ggcggcattg aggagctctg   23760
ccagtgtgat gccgaggatg actacatcac ctcggttaag tttgttcagg agggcggtgg   23820
ctacttggct gtgggcacga acttcagcga gaccaagctc tttgatgtgg agacctgcaa   23880
gcttctccgc aacatggacg gtcacagctc tcgcgtgtcc tcgctctcgt ggaaccagca   23940
catcctttcc agtggcagcc gcgactcgac tattgtgcac cacgacgttc gcgtggccag   24000
ccacaaggtc ggtgttcttg agggtcacgt gcaggaggtc tgtgggcttt catggtcccc   24060
ggatggccag accttggcct ccggaggcaa cgacaacctg ctgtgcctct gggacgctcg   24120
ttactctggc gacggtcgct cccagcagac cgtgcagacc ccgcgtctta agatcgctga   24180
ccacctcgct gctgtgaagg ctcttgcctg gtgcccgcac cagcgcaatg tccttgccag   24240
cggaggtggt actgccgatc gcacgattaa gatctggaac gctgccaatg gcgcctgcct   24300
caacagcgtc gacactggat cccaggtgtg ctccctcctc tggaacccac acgagaagga   24360
gcttctgtct tctcacggct tcagtgagaa ccagctcagt tctctggaagt tcccttccat   24420 ggctcgtgtc aaggatcttc gcagccactc cgctcgcgtt ctccacttgg cgatgtctcc   24480
ggacggaacc actgtctgct ccgctgctgc tgacagacc cttcgattct ggaaggtctt   24540
cgaggcagct aacccggtca agcgcaacaa gcgcgccgct ggagctgcca ctgcctctca   24600
```

```
cggtggcctc gcccgcatga gcatccggta agtttccccc cttcccttgt ccggttaatt    24660
cactttcgac tactgtctta cacagaagca aagcatggtt atgcaagcaa acttgctggc    24720
atgctctctt ttgtctcttc agtagcgaga ggccgtggtc aaggggctca tgcgggagct    24780
ccaatgtaat ctaccaccac ccggcctctc atgtatacat atatatatat ctatttatat    24840
gctgatcatg atgcaaaaaa atcccacgcc gtcatactaa agcgcgtcag tgtttacaat    24900
actgttggcg tatagttcgg tagtgaaaat taaaatcctt cagggtttgt acctatagct    24960
tttggtgatg aatgtgatct actactactg acgtgacaga agcaacaatt cttgtgaatc    25020
tgacttcttt tttgtgtatt ctatttcgca tgactgcctg attgtatgat atgggtctga    25080
tttggtcgac tgtactctat tttgcatgcc atgtaacttt tgttcgatt atactatgaa     25140 tctgtggcaa cttttgctga gaagaaggga tggcagacag tttgattttc ttgatcaatg    25200
tgtttcgctg tcccgctgtg ttgaaagaat gcagtaaatg acccgagtat cggactggag    25260
tgcgtatgtt tcacgctgcc ttatgaatcc ccaggggttc gcagcagcac tttccctcgt    25320
ctgtctctgt gtttgctgtt tgttcgctcg taaatgtgtt ttgcctgtat catatgcatg    25380
taggatagaa agttattacg cagtgtgtat tatagattta tggaagatca ggtggactcg    25440
tatatgctga ctggtgggta tgcttcacgg gatactcgca ttaagttcaa attcgaggca    25500
atggttgctg ctgaagtcgc tgacgaagga gagctcattg ttcttgtcgc caatttgtaa    25560
gtaggtggca cctgattcct cttttcctctg ggaagagatg cagcgctctt gggatcagtt   25620
tctctctcaa tcacgcttgc cgagcagttt ttagtagcaa gcaataggtc tttaatgact    25680
tctagaacta gatgagcagg tatttgcatc atgcaaggct ggcatgtttg gtggctttgc    25740
aatttctctg tcttgaactt agctggatag atagcgagag agtgaagttg gtacaaacat    25800
aaccgacagc atgtagccgc tgccttcgct cgcagctcta gcgctcgcct gcagagacgg    25860
aagagtgtat aattgcccag tgtcaacttt tgggtggtgg gtctgactca caatcaatgg    25920
taccgttcag gtatctttcg gtagattatg acactggcca cttttctgaa gtgatttgag    25980
atttggtatc gatgatgaag agtgagagaa ttttgaaaga aatacctcat taacttccaa    26040
tagtcagtat cttgatgaaa aacgctgacc tgaaagctgc gcgtgttttg ttgacacggt    26100
cctttatttt tgttttttga tgatctattg gtacttatac ctgcgatttt tcttttgcaa    26160
gctaaggcac attcgacttt gtctagaagg aaagtgatca tcacgcttcg gcacacatct    26220
gttttcctca gttaagttttt cttcttggtt caggtatggt attacatgca ggaagaaagg    26280
ggatgcgggg acagccgtat agatgccacc aactttaaca tggtttgtgt tttgggggaaa   26340 caaggaaaga gagcatacgc tatgagctac ttaaactagt gacacaagaa gcaacttatc    26400
ataccggaga tcacaatgga gtgattaggt tctatcagat agtagaagca gagtatgcga    26460
cctgcggtgg ctacgtacat gggtgaaaat aatagaacac ctcgcgtagc gtcgaaaacc    26520
gcctcgtaga ctctgtgtca ggtatgaacc acccactttt tttgtcctct ttatctccac    26580
actatttcct tcatggagac aaactcattc tcgaaagaca aacaatcaaa tcaatccatt    26640
accctcatgt tctcatgatg ggtatgttat acatatatgt ctcagacata tgtttatcct    26700
ttttaaaaca catacttaat aggcacttag cactgttact gctatagaaa actcatccat    26760
tcaagaggag ggagagaaca gagttggcaa atcttggaa gggcaaagtt tatagcaagt     26820
aagtagtagc acagagagag tattatgtat gtgttcatct agcaaaatct aaatagaaga    26880
gccgatcgac tcagtcagtt gtaattagga ctagtcgtta atcatgacat ggctcataaa    26940
caactagtca gtttcttgat ttacttggca ctcaggaaca aagtatgttg ccatccctgg    27000
```

```
gcaatagatt tgatcccgtg cgttgagata aagcttgcca aggtcgggtc atgtaactgc   27060
agaggcactg ggcgtagatt ccagtcccag acataaggaa cagcaagatc ctcaccaacc   27120
acgcaaatgc cctcagttcc aattgtaact tcaagctgag gagtcttgtg ctcggcggaa   27180
agctcgaaag gggtaaaaac aggtacaggg tcaaggactg tgcgagctgt ggccttgtat   27240
ttgttggtgg acttccaaaa tccctcctcc atgaatggtt caatctgctt ggtcacagcc   27300
tcggagcttg aagtttcctt gtcggacatg agaccccact ggtaaagctt gcagccgtgg   27360
ccctgagaat ctttaactaa agcgacataa ctctgcgggc ctgcccaaat gtcaagcacc   27420
gggcccgcct cagggccgaa ctcgacctct cttggtgaaa cctggtcctc gtagttgctt   27480
ttggcctcgt ccaactggcg agattgcatc ttgccccaca caaagacacg accatccttg   27540
agcaaggctg cgctgctgtt catgccagca gcaaccttga tggccggtcc aggtagatct   27600
ctgacctctt gcatgacgaa gaagtcgtca ataccgcgca gaccgattcc gagttgaccg   27660
cgctgtccct tgccccacgc gaagactttg ccgctcactt tcgtagccac aactccgtgt   27720
ctgaatccca acgcaacgct ggccacggca tcatcatctt caggaagacc aattgtagtc   27780
cttgggtccc agaagtacga gtctgtggtt cccgtcgcgc actgtccata gacattctcg   27840
ccaaatacaa aaagcgtgtc cgtttccttc gtaatgaaag ctgtcacacc ggcaccacac   27900
acaacttccc gaataggttc tgtcgagtaa ccctcaaact ttgtctcaag accccttttc   27960
cgtgagtcct gctcaatatc gtcctcacca aggtccttgt acaccttgta gctcaatacc   28020
tcctttggct caatcgcatc cacagatgtc tccacaccca tcatccgcat gacatactgc   28080
atcaccatgc ttgatttcgc atagcgaccc agacgcacag taagccgggt atcgtgggtg   28140
cgaccaaaga gataaacgcg accttgggcg tcaagaacgg cgctgtggcc aaagcccgct   28200
gcaagtttta caggctgggc ctgcttggtg tcgaggtcgc cgtggatctg tgtagggctg   28260
tcagcgttat cgagactacc tgtaccgagg gcaccgttga taccaatgcc tcgagcccat   28320
acgccgcgaa gggcggttcc ggcagaagag ctaagcatcc gcttggcacc tgttagggag   28380
cccagcgccg tcatggtggt ggtctgtatg tcaatgtatc tgtagaaagg cagccagcta   28440
actaaccagc tgtactgtga accacagaag aggcttttgc aaaagatgct cgagagcaaa   28500
atggatgatc ggtggagatg cggagaagcg cacagcacga tccgagtccg aacttgattg   28560
aactcaagtt cggagtttgc aattttttcta caactaggta taccttcgta gtatcacgta   28620
gtaggtggta gtactagtag tcctttgaat tgcggcaggg aatttacgac agcaactctg   28680
gtaaattaat ttaggacgcc tcttttgtac taaagtcctt ctcttagaa cggaaagaac   28740 atatgatatt gagacatcat gaggacatgg gaaagggttg tgcatctttg gaactgtatt   28800
gcccagtatg gctggacttc accttggact tattcataga atgaccacag ctattcctgg   28860
ggtagatgga ggtctgacaa tgctcgagct aaccctgccc atccatgatc aagacgcacc   28920
caagcactat ggccgcaagt ttcagttcat ggagagcaga gctgctcaaa tttagcttct   28980
gcggtcgatt ggtcttggca caaccgctct taagagtcat ctacgacagg ctaccatcca   29040
ctcaagataa aaatggactc acagatagat agatagatag atagatagat agatagatgc   29100
caggcgacca atcgcagcgc actctcgctc tcaagatatg cccgcccatc gaaacacggc   29160
cttctcatgc ggcctgtttc gtctcaagct cgagcaggcg tcggcccatg ctccagcgca   29220
acgggcccgc aactttcagt ttcgagcttg gtcttgcttt tgagtttgct tttgcttttg   29280
agtttgagtt tgagtttgag tttgagttca aaattcaaat tcttcaaatt caaattcttc   29340
gaattcaaac tcaaattgga gaatccatct tttcaaaaac tcaattcacg ctctcgaaga   29400
```

```
agttcaaact ccgcagtcgc atccagctga ggcacgcact ccccatcgca tcgccggcgc    29460
tctctcctcg ctcctgccgc gtctaagcgt gctcgcgtct ctgtcctgct gctgcttgct    29520
tgccagtatc tccacttctc gcgagcagaa ggaggacgag cagaagaaga aggaaggatc    29580
aagaatcatc aagaaggaac actctctttg tttctgtggt tcgtcattag tttgttgtag    29640
cttgaaggag aaggagaaga cggagaagat ggagaagaag ggaatgaaca gcagtggcgt    29700
ttatctgtct ctagctagct aggtacctta cctaccaggt agagttagga ggagaggata    29760
gccgagacta aggaagcaag ccgtagtttt attttactat gtctgttgtt ctttctctcg    29820
actaccttct ctcgctaccc ccgtgggaag gaggtctctt gtgtcgagtc tgatccacgt    29880
ggacgcctcg aggatcttcc ctcgcacccc gggcccggtc gctgccggtg caaaacctcc    29940
tcagtggcct tgctcgcgct gtgtgctttc gttcctgcgt ctggaacgtc agatagcaga    30000
taaagagata taagatagtt agttgacgga agcagtcaaa gcaaacctcg aacggattga    30060
agcgaagcga ggacgctctc gcctctttgc tgactgctcc gccattgct gctctggccc    30120 tcactctgag atattactat gtctgaacct gccgcagccg caccgccggc cgagcccaaa    30180
tcgtcgtggg cggatgaagt cgataatgac acggagggag acgctgtggc cgctctgagc    30240
gaacatgcgg ctaagttgga cctcgacgtc cacggagctc cagacctgca cagcggtgct    30300
cttgtagtac gcgaggccgg gtgccccgtg gacgagccca agacgcaggc agtgacaagt    30360
ttctcagccc ttgcgattga tgacgacctc aagaagtcta tcgcgaacgt caagggctgg    30420
agcactatgt ctaagatcca gcaaattgga cttccgcttg tgatcagcga ccctccacga    30480
aaccttatcg ggcaggctca agccggcacg ggtaagaccg gtacctttgt catctctatg    30540
cttgcaagga tctctgcaga taagaagccc agcacgcctc aggccattat cttggctgta    30600
actcaggagc tgtgcacgca gattgcacag gaggtcaacg cactgggatc cgacaagggc    30660
attaaagcac gcagagttat gtctgctagg tccaaaaatg gacccctcgc ggaagggagc    30720
gcggcggcgc cgtgggcact tagtgaaggt gaagactttg atgagcaggt cgttgtggga    30780
acacctggaa tggtcaagaa ctacctcaaa aatgccatgg gacgcaagaa gcgcaagccc    30840
atgatcgatc cgtctgagtg ccgcgttctt attcttgatg aagctgacaa gatggtgcag    30900
cagccacctc acggatttgg acaggacgtt caggagattc gcgacattat tctcaagaag    30960
cgcaaggaca agccgtgcca aattttgctc ttttcggcca ccttcaccga aaatgtacga    31020
cagattgccc gccagttcgt tggtggacat gacatggacg agtccaagta ccacgagatc    31080
acgctgcgca aggaggatgt cactctcgac aaagtcgtca acttcgttgt ctatattgga    31140
gacgagaatg agcgcaacga agaggaaatc tataagaaga gtttgaggc cattaatgag    31200 atctgggaga acctctctca gctcagcgag gggcagtccg ttatcttttg caatcgtaaa    31260
gatcgtgtac aacgcctcgc ggattatctt cgcgggctaa acttcccggt cggtcagatc    31320
catggtgaca tggataaggc cgagcgtgac attgtgctca gtgagttcaa gcgcggtgag    31380
cgcaaggctc tcgtttctac tgatgtcacc tcgcgcggta ttgacaaccc caatgtgact    31440
ttagttatta atgtcgacct tcctgttaac cgcgagcagg aagctgaccc ggagaatttt    31500
gtgcacagga taggccgctc gggacgttgg actaagaagg gtgcttctgt ttctcttgtg    31560
gctcgcagcc ctgccttccg tgaccttggc ctcatgaagg acattgagcg tgcactcttc    31620
gctaatgcag aggtaaaccg tccgcttatc cccgtcgatg atctctccaa ccttgagagc    31680
aagatcattt ctgctcttga agcatacaac taagtgccta cctaccttaa tcagcccta    31740 tcacttgcat tgccgagccg ggtttccgca gcgcttgccc tgtgttgcta gagactgggc    31800
```

```
aagctggctc gcctgtctct ttctcgcatt caacaatgca ttcaccgttt ctcctagctg   31860
cacccgccct ctctcttgcg cccacgacaa gaaaaataca gttcatatca gcatcccccc   31920
caaaacaacc ataacaatta cgtaaatgaa ggccgtttat tctaccgtgc atcatgagca   31980 ctgcacctt tctctcctcc atcgcgcctt ataccgataa acaaaaaata gataacacct    32040
ttttgtagag caaccaccac cattgtttcc cttccctccc tccncnctcc ctcccaaaat   32100
aacttgcttt gtttgtacgg cgttccttct atctactttt tctttaatct tcaatcatgt   32160
ctgacggttc ctttacttat tatgcgttgt tttattcggt cacaaggagg tacagccttg   32220
atggtcctgc gatagatgcc gtactttatt gtcatatgtt tataacttt aaaaaattaa    32280 tttttagta cttatattca aaattcaaaa ttcaaatat aaaattcaaa attcaaaaat    32340
tcaaaaattc gaaattcgaa attcgaaatt caatttagat tgtaatctga ttatctttga   32400
atccgtcacc ttcttttat tattttttaa aataatttat ttttaatgtt tttagttaag    32460
ctaattttgt aaaacaatt atattgttat aataaccta tcacctgaat aataagatag     32520
aaaacgaaga tgcatcctta cctcagcata agaccaaaca gactaaaacg aaacatcttg   32580
gattgcattt tgtctcgact atatcccatc tcaagagagc aataaaagtt attactgagc   32640
cttttcaagt cagaaatgtg tagtcgtgtt caaatttgaa ctttagttt cgctaaataa    32700 catataagat ctgaattttg caacgactgt gacacaacac tttggttctc aagagaacac   32760
aagttcttgg ttggccagtg cttgttattc cgtatagtat tttgggataa tggacaagga   32820
tccaaaccaa gcacaattga gaagcataat tgcaacacca aacctgaaaa gtaactattt   32880
tgaagacatt accttgtggt gcagtttgat cgatacgaga gcaacgaacg gagcattgag   32940
gttaagcgag gggagtcaaa gaaagttatg ggacaggcac tcaactccac gatgaatgcc   33000
atgcatgtat ccaaggctgg ctgctcctct gggtggatgg gtgtcggggc acatgattat   33060
gtagaggaca aagatgtccc ttctcttgag ccttctgagc atagccaggc acctttcgt    33120 tgttcttgcg tacaatctcg ggttgtaggc cccaaaagtc acgttgaaaa ggtaatgggc   33180
tcacgatgtt gtcaaagccc tcgatgtagc gcgggcaaag gcacgcttgc agaactcgac   33240
gaggtcatgg acaacaaagt ccgaatttct ctagacgttg gcgaagacgt cgatgtcggc   33300
catgaagtcg gcaaagaaga taagacgagg ggcaaggcga ctcttcatga tggaggtgtt   33360
agagacaaac tcagaatcgc tgatggtgtt attggctcta attatgttga tctcaaggcc   33420
aaagaaagtc atcaagcacc aggctcggtt atccaatcgc agcggcactc tcgagccgag   33480
aagtaccgcc gagcagacgc tgttcgcgaa gctcttcgcg atttgtcttc tttctcgcca   33540
agtacttcaa tgaatacttt tcctgactct tcgagccgaa caacacctgc atgctcccct   33600
gaatcagaaa ctagccttga tgaggagaag gagaatatag ggctggtaaa taacgttcta   33660
cttgaggaag aacacgttag tcgcccacga tcaatgacgt ttgatgcttc actttcgatg   33720
acggagctga aaaccaaaa cgaagtggag cacgctgtgt tgacttcgtc tgtcatgtat   33780
gcagccgaga aaactctaag ttttattaag gagaattccg gagaattggg caaacatatc   33840
ggaaccgaag gcggaagtaa tatcaaagac attgttgaag aacatgcaaa tcaaaaatcg   33900
caagaaagtg ataatgaaat gtttatgagg ttgcttgaag atctgcctac tcaggcccaa   33960
caagtagttt ccgaaagttt gggaacacct actaccaaac atcattactt ttccagcgcc   34020
aacacgagca gtggagcatc gcgaagcttg cagtcaggtc gatcaagcac cccaaactgt   34080
gtcacggtat ctccatgcac agagctgggc tctcctcgtt gcgggcttga ctctgtactt   34140
ggtaaccaaa ttgatgaaaa acatggtgaa gggcttgacg atcaccatag gatcccgcag   34200
```

```
tttgatctct tacaacatga gcttttacaa gatagcaact ctattacagc acacagagat   34260
ggtgaaacga cttcgtcccc agttgcctgg gctggagatc ttcaagatga tcttacgcgc   34320
tctctgttga cagaagttga acatcctttc atctgtcgag aaacaaatat accaccggtc   34380
cattcaaaag ggaacgaggg tttgagaaca tgcaatggtt cgtcgcatag atctagtctg   34440
ggagcaattt tgcacgagat tctcgaaacc aagggagact ttcgtaaaaa cggtgaactg   34500
atcaccgacc tcgacatctt cctaggcgat aaattgccaa aaggcaaaac attttggtcg   34560
ctcttgacaa gtagcgagct aggtgagctt ggtgaaagag ttgaactcga ataatgagc   34620 cgcccctcg cgcaccagcc ttaccgagaa tcactctggt gtgttgcatt tcagacaatc   34680
cagctcactc cctatcgcca aagattggcg ctcagctgtc gcgatagact tttgcctcac   34740
gagcgggctt aagcgggtt ctccattgct caactaggtc gtgcgtgttt tgtacttcgg   34800
caaaggctcg tagactgctt ccaccacaac ggcaggataa agttcaaatg ttacaggcga   34860
acatgcaagt tgctggaagc aaggatgtgg caatgagcct caaaacatag gcttggcaca   34920
gggtgttgaa gcgcctttct gagacccatg aaactcctag tttgtttgct ttgcatcgct   34980
ctgtatcaat cgtgccgcat gcaaatgcaa taagctaaca ctcaaatcat ggtacagtct   35040
tttaatttgg accgagtcta gggcacccga ggcatttcga tgcaaacatc tttctcatca   35100
aagacttatt taggcgagtt aggcattgga gctcaccttc cctggcaggt cgcctttacg   35160
tggtaagtta tataagtcaa gaggaaaacc cgagcgacgc tggtctctat aagattgaca   35220
gatccctgga ggtgataaag gttgtatcgt acaacttgtt ctacgagaat caaatcttgt   35280
acgctccaag ccagcagctt gaaattggca gatgagttgt atctgcgtca ggagttatca   35340
gagagcttac tggactatca aatggtagac atgttgacac tgcgcacctg aaaagctctg   35400
ccaagcacct ccgctcccca gaaagcctgg tttacatgaa gtgtgatgta gtctgcagtt   35460
caagatctaa tctcatcaga gagcgcttag tacccattgg tgatctgtca cattttgagg   35520
ctacgcacag tttggatgac gctcttcgcg ctgtatgcaa cacatccgac gaacgagatg   35580
aacctacttc caaagactcg tgtgctggtt ggcgcgcggc ctagacctgg tcggggcact   35640
ggcgcatgct atgagattgc tggacgcgaa aaatgtggcg aagctgtgta cgcagtgaac   35700
tggggtgcca aatcaatgat tctaagagtg tttgccccaa agtatggctt aaaatgtttc   35760
aaactaccca agggttcccc gacatgaggc cacatgtggg aagtgtattt gccccccatt   35820
tgagaagttg ggacagagcg cttcgtcagg gatgatcatg aagcatgttc tatgaacttg   35880 cacccacttgt ttagaacgga agtgtggctg gaatgaaacc tatatgtcag catatctgcg   35940
ggtaatcccc aactacataa tatttgctgg tatgcttgct ttaagcagca atcaagtttc   36000
tagcaacagg gtaataacca ggtcaccggt caatcgcaca atggcctttt tagttcggaa   36060
aatttgacaa cctgtggatg tttggggagt ccatggataa atgtggagct gtttggtgta   36120
acagaacatt gcaaagggtg acgccttaga tcctttctc atgacaggct tcgatcacaa   36180
agttgtacac tttcaaggtt gtaggtgcgt attgaacttg gcatttctgg aacaaacaga   36240
cactatatct cgaatctggg tctgcctgcc cctctagctc aggccctgat agtttgacta   36300
gagcatcgcc gtctcgtgta ttctctccga atctttctgc acattgagtt agacttctcg   36360
tcgtgtttgg agcatgtgta aatacatcag cgatattttt ttactcctaa aaatggcaaa   36420
ttcgcattta cctactgcaa ataatgaatc aaaatgagga acaatgtgc tatatgaacc   36480 gtgctctttg gaacacaaat aaaaaataaa taaagtcaaa gatcgtgcca aatccgccca   36540
acttgagaga aaggcttggc tggtgacctg ccctgttgtg gcatcatcct atcttggctg   36600
```

```
ccgccctcca aagagaaatg tgagcctcgg aagagcgggc taggctggta accaatgaga   36660
gctatgtaaa tagcaaagga agagagaata aatctttggg aataaacctg tcagcaaggc   36720
tccaaagctt gctttctggg caaggcttac atgttgcttg atatgatttc acagaagcat   36780
ttggacacgc caaactctgc tactttgact gtgcctaggt ggtaaaccaa gcaactgcta   36840
tctttgacgc caccatgcag gtttccatca aaatagagat agaggagaag ttaccatatt   36900
tgaatccacc aattcttcaa gtgtgtggag acgctcgagt aatgagcata cttgaggaag   36960
atgctcatgg accttccgtg tgttttctc ccgaggtatt acacgatatt ttcgtatttg    37020
caatgttgca gagtcttgat atcgtgtgac agtggaaaca aatgctacag ttgattcctt   37080
gatccccttc atcgcaaaga gcttgttatt ctctataata agagctagtt accggcaccg   37140
tagtcgcttt tgctcagcaa gtggcccttt tccagcatga gataagacct cctaattttg   37200
gctcgttttc tgattacaaa tgaaggtcct tgccaactac accatggtca cagcttttctc  37260
tgccgagctc agggatgcaa ctgtcggctt agacaccaag tcagcgtcgg ttgcaagtgc   37320
tgcttctgag agctgactgc tgtagtgtgt gggtttgctc cacctatgag tgggtatgag   37380
taggtctgct ccacctatga ggaccaccaa gtttgctctc catgtgctac agcgcctgcg   37440
tctcttgtgc ggtgagacat atttttgag cttggtcttt acgaaatgaa ggcctgcgac    37500
agacaacgat cgcaacaatt ctgcctcgaa ggcgcttatc cctacgtaga cgtaggtctc   37560
tgttcccact aaagccactc ctgcgtcaat agaacaaaag caaaagctct tatggctgct   37620
gtacaaatag agtaaaactt caccttcta ctcgtaacac tacagttata agtagcaagt    37680
caatcagagc aagacctttg cgagtaaacc tgcattgctc tatcgcagtc ttccagcatc   37740
ttcgcgaggc ggtctcgcac aacttcagtc agtctgtaat aacaggagct ttagcaccag   37800
ccaaagcagt tgcgttgcaa ccagcagaag acttggcatc atgctcattc ccgctgtgga   37860
cgtggccgtg ggcggtgctg tggcgtcctc tgagaagttt gatctcctca aacgcctgag   37920
ttggtgcggc ccccttcgca tcatcccttc acttgactct gtctccgcac caagtgtggg   37980
tgcccctgag gagaaggact tctggaaatc tgctgttcgc aagtggggca aagctttgtg   38040
ttcgtaccct tgccaagttg gtcccatcgc cgctacaagc gttgaggaag tgacgcaatg   38100
gctcaacgaa ggcgctgtcc aagtcattgt tgagggttct ttcgacgacc tcgaggacat   38160
tgcttcgcag cttcctcgtg aacgtcttgt tgccagattt ccgagaaggg tccttgaaga   38220
cgacggtctc ctgagcaaac tttctggcag cgttgggggc gtttcaatta tttctgaggc   38280
caaaaattct gaagaagtcg tcaaggtcgc agagagggca tggcagcttt tgggaaaacg   38340
ccttgctatc gcattagagg tccccgagat cgaggccgga ggcgaggcgc agaagattaa   38400
caaccagctt gttggtaagc tccatggact ccactccaca gactttcctg tgaacgttgt   38460
gtctgagaac gtttccatgc aacagaagg gtctcttgcg acagatactg actcagaagc    38520
tgccttttgc gtggcaaggt cttttgtagc gtgccttcgc accgaccgta cagatggtct   38580
ctttgcgacg gtcgtcaccg atgagaatgg cgtggcactt ggcctcgtgt actccagcga   38640
acagtctgtg gttgcctcgt tggcgtgtgg ccgcggcgtg tactggtcaa gatccaggca   38700
gagtctgtgg cgcaagggcg acacaagcgg tgcctttcag gagcttgtgt ctatcgcatt   38760
tgactgtgat gccgacgcga tgaggttcaa ggtgcgccag cgtggaaacc ctcctgcatt   38820
ttgccatcaa cagacccgca catgctgggg ttatgacggt ggcatccccc acctctttcg   38880
cactcttgag tcccgcaagc ttaacgcccc agaaggatca tacacaaaac gtctttttga   38940
ggacaaggca ttgctgcgta acaagctcat tgaggaggca caagaggtaa ttgaggctat   39000
```

```
tgaggagaat gacccagagc atgttgcccg cgaggtcgca gacctcgcat acttcctctt   39060
tgccgcgtgc acgtgcggaa atgcgtcgct cgaggacgtt acacggcagc ttgacatgcg   39120
ttccctcaag gtcaagcgga ggccaggcaa tgcaaaggca gatcgcatcg ctgctggtga   39180
ggcagttctc caggctcagc agcagaaaaa gtctgcagag gagcccccag cagctcccaa   39240
ggaccaggcc taaattgcat gcttattatt acacccaaat cctgcttatt gtgacttgtc   39300
tgcacccttt tcacattgaa gaagcgtgtt ttcttacccg tcacaccacc actaagtctc   39360
atcctttctt tcttaccttt ttactagtcc gaacgatata aactttatct ttgcaaggct   39420
cttgttatac tgcaattgtt atttagtttg ttttctattg ataggcaaac cagacgtaat   39480
cgtctgagag tgtttgaaga ggataaaaca aagaatcatt aacaggtttt gtgtttctgt   39540
acacttgaat agttttatgc ctatctactt ctagagcctg gcggagttg gcatttgtat    39600 aatctcaaca ttcgataaca aattgcttca aatgaagaac aaaaacagga aatgatttga   39660
attaaaatct aatatttgta gaaaagaaaa agcgagctga catcattcca tcaaattgac   39720
caattgactc cttagcacag tagatatttc ctaaacgact tcaactcatt cctcattatc   39780
ctcgctgttc ctgcttccgt gagtacccTt gctgattcgt acttccaaat cgccgccatc   39840
ctcccggtca tcatcatctt cgtcatcttc gtcttcatca tcagcccctg acgaggagta   39900
aatgtcaagg taaggtttgg gattctcgag cttTcgcaat tctccaatac ttattggttg   39960
gccacagacc ggatcc                                                   39976

<210> SEQ ID NO 3
<211> LENGTH: 8994
<212> TYPE: DNA
<213> ORGANISM: Ulkenia sp.

<400> SEQUENCE: 3
atggctcaac gtgagaaccg tctcgaggcc aacatggata cccgcatcgc tgtgatcggc     60
atgtccgcca tcctcccctg cggtaccacc gttcgtgagt cttgggaggc tatccgcgat    120
ggtatcgact gcctcagtga tctccccgag gaccgcgtcg atgtgaccgc ctacttcgac    180
ccggtcaaga ccaccaagga taagatctac tgcaaacgtg gtggattcat ccctgagtac    240
gacttcgacg cccgtgagtt cggcctcaac atgtttcaga tggaggactc cgacgcaaac    300
caaaccgtca ccctcctcaa ggtcaaggag gccctcgagg acgctggcat cgaagccctc    360
agcaaggaaa agaagaacat tggatgtgtt ctcggtatcg gtggtggcca gaagtccagc    420
cacgagttct actcccgctt aaactatgtt gtcgttgaga aggtccttcg caagatgggc    480
atgcctgagg aggatgttca agctgctgtt gagaagtaca aggccaactt ccctgagtgg    540
cgccttgact cctTccccgg tttcctcggc aacgttactg ccggtcgctg taccaacacc    600
ttcaacctcg atggtatgaa ctgtgtcgtc gatgctgcct gtgctagttc tctcatcgcc    660
gttaaggttg ccattgatga gcttctccac ggagactgtg acatgatgat cactggtgct    720
acctgcacgg ataactccat cggtatgtac atggccttct ccaagacccc ggtgttctct    780
accgacccta cgctccgcgc atacgatgag aagaccaagg gtatgcttat tggcgaaggc    840
tctgccatgc ttgtgcttaa acgttacgcc gacgctgttc gtgatggtga cgagattcac    900
gctgtcattc gcggctgcgc ctcttcctct gacggtaagg cctccggtat ttacaccccg    960
accatctctg gtcaagagga ggctcttcgc cgtgcctaca tgcgcgctaa cgtcgatccc   1020
gccaccgtca ctcttgttga gggccacggt accggtaccc cgttggtga ccgtattgag    1080 ctcaccgctc tccgtaaccT cttcgacagt gcctacggca acgagaagga gaaggtcgct   1140
```

```
gttggcagca ttaagtccaa catcggtcac ctcaaggctg tcgccggtct tgccggtatg    1200
atcaaggtca tcatggccct caagcataag actcttccgg ccaccatcaa cgttgatgag    1260 cccctaagc tttacgacaa cactcccatc accgactcat cgctgtacat taacacgatg     1320
aaccgtccgt ggttccctgc tccgggtgtg ccccgtcgcg ctggtatctc cagtttcggt    1380
tttggtggtg ccaactacca cgccgttctt gaggaagccg agcccgagca ccagaaggct    1440
taccgtctca acaaacgccc ccagccggtg cttctgatgg catcttcaac ccaggctctt    1500
gcttccctct gtgaagccca gcttaaggaa ttcgagaagg ctatcgagga gaacaagacc    1560
gtcaagaaca ctgcttacat caagtgcgtc gacttctgtg agaagttcaa gttccctgga    1620
tctatcccga gctctaacgc tcgcctcggt tttcttgtca aggaggccga tgatgccacc    1680
gagaccctcc gtgccatcgt tgcccagttc caaaagtcag ctggcaagga ttcttggcac    1740
cttccccgcc agggtgtgag ctttcgtgct cagggcatca acaccactgg tggtgtcgct    1800
gccctcttct ctggccaggg tgctcagtac acccacatgt tcagcgaggt cgccatgaac    1860
tggcctcagt tccgtgagag catctctgac atggatcgtg cccaggctaa ggttgctggc    1920
gctgacaagg actacgagcg tgtctcccaa gtcctctacc cgcgtaagcc ttataactct    1980
gagcccgagc aggaccacaa gaagatctcc ctgacctcat actctcagcc ctctaccctc    2040
gcctgcgctc ttggtgccta cgagatcttc aagcaggctg gtttcaagcc cgacttcgct    2100
gccggtcact ctctcggtga gtttgcggcc ctctacgctg ctgactgcgt caaccgtgac    2160
gacctctttg agctcgtgtg ccgtcgtgcc cgcatcatgg gtggcaagga tgcacctgct    2220 accccaagg gatgcatggc tgctgtcatt ggacccaatg ccgagaagat ccagattcgc    2280
actgctgatg tctggctcgg caactgcaac tccccttcgc agactgtcat caccggctct    2340
gttgagggta tcaagaagga gtccgagctt ctccagagtg agggcttccg tgttgtcccc    2400
ctcgcctgcg agagtgcctt ccactcaccg cagatgcaaa acgcctcctc tgccttcaag    2460
gatgttctct ccaaggttgc cttccgtcag cctagcgccc agaccaagct cttcagcaac    2520
gtgtctggcg agacctactc caacaatgcc caggacctcc ttaaggagca catgaccagc    2580
agtgttaagt tcatctctca ggttcgcaac atgcactctg ctggtgctcg catctttgtc    2640
gagtttggcc ccaagcaggt gctctctaag cttgtttccg agaccctcaa ggacgatcct    2700
tccattatca ctatctctgt caaccctccc tctggcaagg atgccgatat tcagcttcgc    2760
gaggctgctg tgcagctcgt tgttgctgga gtcaaccttc agggcttcga caagtgggac    2820
gcacctgacg ccacccgcct tcagccgatt aagaagaaga agactactct tcgtctctcg    2880
gctgccactt acgtgtctga caagaccaag aaggctcgcg aggctgccat gaacgacggc    2940
cgcatgctca gctgtgtcag caaggtcatc gcccccctg acgccaagcc cattgtggac    3000
accaaggctc aggaggaggt tgctcgtctc cagaagcagc ttcaggatgc ccaggcccag    3060
atccagaagg ccaaggccga tgctgctgag gctgacaaga agcttgccgc tgctaaggat    3120
gaggccaagc gtgccgccgc ttctgcacct gtgcagaagc aggttgacac caccattgtt    3180
gataagcacc gtgctatcct caagtctatg cttgctgagc ttgactgcta ctccactcct    3240
ggtgctgtgt ccagctcttt ccaggcacct gttgctgcta cccctgctcc ggtcgctgcg    3300
cctgttgcag ctgctcctgc tccggctgtc aacaatgctc tccttgccaa ggctgagtct    3360
gttgtcatgg aggttcttgc cgccaagact ggttacgaga ctgacatgat cgagcccgac    3420
atggagctcg agactgagct cggcattgac tctatcaagc gtgtcgagat tctctctgag    3480
gtccaggccc agctcaacgt cgaggccaag gatgttgatg ctcttagccg cacccgcacc    3540
```

```
gtcggtgagg ttgtcaacgc catgaaggct gagatcgctg gcagctctgg tgctgccgct    3600
gctgccccgg ccccgttgc tgctgctccc gctgccctg ccctgctgt caacagcgct      3660 cttcttgcca aggctgagac tgttgtcatg gaggttcttg ccgccaagac tggttacgag    3720
actgacatga ttgagcccga catggagctc gagactgagc tcggcattga ctccatcaag    3780
cgtgtcgaga ttctctctga ggttcaggcc cagctcaacg ttgaggccaa ggatgttgat    3840
gctcttagcc gcacccgcac cgttggtgag gttgtcaacg ccatgaaggc tgagatcgct    3900
ggcagctctg gtgctgccgc tgctgccccg ccctgttg ctgctgctcc ggcgcccgtc      3960
gctgccgctg ccctgctgt cagcagcgct ccttgaga aggctgagtc tgttgtcatg       4020
gaggttcttg ccgccaagac tggttacgag actgacatga ttgaggccga catggagctc    4080
gagactgagc tcggcattga ctccatcaag cgtgtcgaga ttctctctga ggtccaggcc    4140
cagctcaacg tcgaggccaa ggatgtcgat gctcttagcc gcacccgcac cgttggtgag    4200
gttgtcaacg ccatgaaggc tgagatcgct ggcagctctg gtgctgctgc cccggccccg    4260
gtcgctgcgg cccctgctcc ggtcgctgcc gctgcccctg ctgtcaacag cgctcttctt    4320
gagaaggctg agactgttgt catggaggtt cttgccgcca agactggtta cgagactgac    4380
atgatcgagc ccgacatgga gctcgagact gagctcggca ttgactctat caagcgtgtc    4440
gagattctct ctgaggtcca ggcccagctc aacgttgagg ccaaggatgt tgatgctctt    4500
agccgcaccc gcaccgttgg tgaggttgtc aacgccatga aggctgagat cgctggcagc    4560
tctggtgctg ccgctgctgc cccggccccg gttgctgctg ctcccgctcc cgtcgctgcc    4620
cctgctgtca gcagcgctct ccttgagaag gctgagtctg tcgtcatgga ggttcttgcc    4680
gccaagactg gttacgagac tgacatgatt gaggccgaca tggagctcga gactgagctc    4740
ggcattgact ccatcaagcg tgtcgagatt ctctctgagg tccaggccca gctcaacgtt    4800
gaggccaagg atgtcgatgc tcttagccgc acccgcaccg ttggtgaggt tgtcaacgcc    4860
atgaaggctg agatcgctgg cagctctggt gctgccgctg ctgccccggc ccctgttgct    4920
gcctctcccg ctcccgtcgc tgccgctgcc cctgctgtca gcagcgctct ccttgagaag    4980
gccgaatctg ttgtcatgga ggttctcgcc gccaagactg gttacgagac tgacatgatt    5040
gaggctgaca tggagctcga gactgagctc ggcattgact ctatcaagcg tgtcgagatt    5100
ctctctgagg tccaggctat gcttaacgtt gaggccaagg atgttgatgc tcttagccgc    5160
acccgcaccg ttggtgaggt tgtcaacgcc atgaaggctg agatcgctgg cagctctggt    5220
gccgccgctg ctgccccggc cccggttgct gctgctccgg cgcccgtcac tgccgctgcc    5280
cctgctgtca gcagcgctct ccttgagaag gccgaatctg ttgtcatgga ggttctcgcc    5340
gccaagactg gttacgagac tgacatgatt gaggccgaca tggagctcga gactgagctt    5400
ggcattgact ccatcaagcg tgtcgagatt ctctctgagg tccaggctat gcttaacgtc    5460
gaggccaagg atgttgatgc tcttagccgc acccgcaccg ttggtgaggt tgtcaacgcc    5520
atgaaggctg agattgctag cagctctggt gctgctgccc ctgctccggc tgctgccgtt    5580
gcaccggccc ctgctgctgc ccctgctgtc agcagcgctc ccttgagaa ggccgaatct    5640 gttgtcatgg aggttctcgc cgccaagact ggttacgaga ctgacatgat tgaggccgac    5700
atggagctcg agactgagct cggcattgac tctatcaagc gtgtcgagat tctctctgag    5760
gtccaggcta tgcttaacgt tgaggccaag gatgttgatg ctcttagccg cacccgcacc    5820
gttggtgagg ttgtcaacgc catgaaggct gagattgcta gcagctctgg tgctgctgcc    5880
cctgctcctg ctgctgccgc tgcaccggcc cctgctgctg ccctgctgt cagcagcgct    5940
```

```
cttcttgaga aggctgagtc tgttgtcatg gaggttctcg ccgccaagac tggttacgag    6000
actgacatga ttgaggccga catggagctc gagactgagc ttggcattga ctccatcaag    6060
cgtgtcgaga ttctctctga ggtccaggct atgcttaacg ttgaggccaa ggatgttgat    6120
gctcttagcc gcacccgcac cgttggtgag gttgtcaacg ccatgaaggc tgagattgct    6180
agcagctctg gtgctgctgc ccctgctcct gctgctgccg ctgcaccggc ccctgctgct    6240
gcccctgctg tcagcagcgc tcttcttgag aaggctgagt ctgttgtcat ggaggttctc    6300
gccgccaaga ctggttacga gactgacatg attgaggccg acatggagct cgagactgag    6360
cttggcattg actccatcaa gcgtgtcgag attctctctg aggtccaggc tatgcttaac    6420
gttgaggcca aggatgttga tgctcttagc cgcacccgca ccgttggtga ggttgtcaac    6480
gccatgaagg ctgagatcgc tggcagctct ggtgctgcta ctgcctctgc ccctgctgct    6540
gcagctgccg cccctgctat caagatctcc actgttcacg gtgctgactg cgatgacctc    6600
tctgtgatgt ctgctgagct tgtcgacatt cgtcgcgctg atgagctcct tcttgagcgc    6660
cctgagaacc gcccggtcct tattgtcgat gatggtaccg agctcacctc tgctctggtt    6720
cgtgttcttg gtgctggtgc tgtagttctt acctttgacg tcttcagtt ggctcagcgt    6780
gctggtgctg ctgttcgcca tgtccaggtg aaggacctct ccgctgagag tgccgagaag    6840
gctatcaagg aggctgagca acgcttcggc cagcttggag gcttcatctc tcagcaggct    6900
gagcgctttg cccctgctga cattcttggt ttcaccctca tgtgcgctaa gtttgccaag    6960
gcttccctct gcacccctgt gcagggtggc cgtgccttct tcattggtgt ggcccgtctt    7020
gacggtcgcc ttggtttcac ctcccaggga tctactgact ccctcacacg tgcccagcgt    7080
ggtgctatct tcggcctctg caagaccatt ggccttgagt ggtctgctaa cgaagtgttc    7140
gcccgcggta ttgatattgc tcgtgaggtc caccctgaag atgctgccgt cgccatcact    7200
cgcgaaatgt cctgcgctga caaccgtatc cgcgaggtcg gcattggcct caaccagaag    7260
cgctgcacca tccgtgctgt ggacctcaag ccgggtgccc ccaagatcca gatcagccag    7320
gatgacgttc tccttgtgtc tggtggtgct cgtggtatta ctcctctctg catccgtgag    7380
atcacccgtc aggtccgcgg tggtaagtac attctcctcg gtcgctccaa ggtccctgct    7440
ggtgagcctg cttggtgcaa cggtgtttct gatgacgatc ttggcaaggc tgctatgcag    7500
gagctgaagc gtgctttctc cgccggtgag ggccccaagc ccaccccgat gacccacaag    7560
aagctcgttg gcactattgc tggtgcccgt gaggttcgtt cctcaattgc taacattgag    7620
gctctcggtg gcaaggcaat ctactcctct tgtgatgtga actctgctgc tgatgtcgcc    7680
aaggctgttc gcgaggctga ggctcagctt ggcgcccgtg taactggtgt cgtccacgct    7740
tctggtgtcc ttcgtgaccg cctcattgag cagaagcgcc ccgatgagtt tgatgctgtc    7800
ttcggcacca aggtgactgg tctcgagaac ctctttggtg ccattgacat ggccaacctt    7860
aagcacctcg tcctcttcag ctctcttgct ggtttccacg gcaacattgg tcagtctgac    7920
tacgccatgg ctaacgaggc cctcaacaag atgggtcttg agctctctga ccgtgtgtcc    7980
gtgaagtcta tttgcttcgg cccctgggat ggtggcatgg ttacccccca gctcaagaag    8040
cagttccagt ctatgggtgt tcagatcatc ccccgtgagg gtggtgccga tactgtggct    8100
cgcattgtcc tcggctcctc ccctgctgag atccttgttg caactggac cactcccacc    8160
aagaaggttg gcagtgagcc cgttgtgatc caccgcaaga tcagcgctgc atccaaccct    8220
tttcttaagg accacgtcat ccagggtcgc tgtgtgctcc ccatgaccat tgctgtgggc    8280
tgccttgctg agacctgcct gggtcagttc cctggatact ccctctgggc tattgaggat    8340
```

```
gctcaactct tcaagggtgt caccgttgac ggtgatgtca actgtgagat cactctcaag    8400
ccttcccagg gtactgccgg ccgcgttatg attcaggcca ccctgaagac cttcgctagc    8460
ggcaagcttg ttccggctta ccgtgccgtg atcgttctct ccactcaggg aaagcccct    8520 gctgctacta cttcccagac cccctctctc caggctgatc ctgctgcccg tggcaaccct    8580
tacgacggca agaccctctt ccacggccct gccttccagg gtcttaagga gatcatctct    8640
tgcaacaagt ctcagcttgt cgccgagtgc accttcattc cgtcttccga gagcgctggt    8700
gagttcgctt ctgactacga gtcccacaac cctttcgtca cgacattgc tttccaggcc    8760 atgctcgtct ggattcgccg caccctcggc caggctgccc tccccaactc tatccagcgc    8820
attgtgcagc accgtgctct tccccaggac aagcccttct acttgaccct caagagcaac    8880
agcgcgagtg ccactctca gcacaagacc tccgttcagt ttcacaacga gcagggtgac    8940
ctcttcgtgg acatccaggc ttccgtcacc tcttctgact cccttgcctt ctaa          8994

<210> SEQ ID NO 4
<211> LENGTH: 6093
<212> TYPE: DNA
<213> ORGANISM: Ulkenia sp.

<400> SEQUENCE: 4
atggcctctc gcaagaatgt gagcgctgct cacgaaatgc acgacgagaa gcgcattgcc      60
gtggtgggca tggccgtgca atacgcgggc tgcaaagaca aggaagagtt ctggaaagta     120
gtcatgggcg gtgaggctgc atggactaag attagcgata acgcctcgg atccaacaag     180 cgagccgagc acttcaaagc agagcgtagc aaatttgcag ataccttttg caacgagaac     240
tacggctgcg tcgatgactc cgtcgataac gaacacgagc ttctccttaa gctctccaag     300
aaggctctct ccgagacatc ggtctccgac tctacaaggt gcggtattgt gagcggatgc     360
ctgtcctttc ccatggacaa cctccagggc gaactcctca atgtgtacca aaaccacgtc     420
gaaaagaaac tcggcgctcg cgtcttcaag gatgcctcca gtggtccga gcgtgagcag     480 tcgcagaacc ccgaggctgg tgaccgccgc atctttatgg accggcatc cttcgtagca     540 gaagagctca acctcggtcc tcttcactac tctgtcgatg ctgcctgtgc caccgccctt     600
tacgtccttc gcctcgccca ggaccacctc gtttccggtg ctgctgatgt catgctcgct     660
ggtgcaactt gcttcccgga gcccttttc attctctccg gattctccac tttccaggcc     720
atgcctgtat cgggagacgg catctcgtac ccgcttcaca aggacagtca gggtctcacc     780
cctggtgaag gtggtgccat tatggttctc aagcgccttg acgacgctat cgcgatgga     840 gaccacattt acggtactct gctcggtgct accatcagca atgctggctg tggtcttccc     900
ctcaagccgc acttgcccag cgagaagtcc tgcctcattg atacctacaa gcgcgtcaac     960
gtgcacccgc acaagatcca gtacgtcgag tgccacgcaa cgggtactcc ccagggagac    1020
cgcgttgaga ttgatgccgt caaggcttgc ttcgagggca aggtgcctcg ctttggaagc    1080
tccaagggta actttggcca cactcgtt gcagctggtt tcgcaggcat gtgcaaggta    1140
ctccttgcca tgaagcatgg tgtgatcccg cccactcctg tgtcgatgg atcttcccaa    1200 atggacccgc ttgtggtctc tgagcccatc ccatggcccg acactgaggg cgagcccaag    1260
cgcgctggtc tctccgcttt cggctttggt ggcaccaacg cccacgcagt cttgaggag    1320 tttgaccgct ccaaggctgc ctgtgccacc cacgatagca tcagttccct cagctcacgt    1380
tgtggcgggg agggcaacat gcgcattgct attaccggta tggatgccac cttcggctcc    1440
ctcaagggcc tggacgcctt tgagcgtgcc atctacaatg ccaacatgg tgctgtgcca    1500
```

-continued

```
ttgcctgaga agcgctggcg tttccttggt aaagacaagg acttttttgga cctgtgcggt    1560 gtcaaggagg tgcccacgg atgctacatt gaggacgtcg aggtggactt tagccgcctg     1620
cgcacgccca tgacgccaga cgacatgttg cgcccatgc agctacttgc tgtcacaacc     1680
atcgaccgtg ccattctcaa ctctggcctc aagaagggga gtaaggtcgc tgtcttcgtc    1740
ggccttggca ctgaccttga gctctaccgt caccgcgccc gcgttgccct caaggagcgt    1800
gctcgtcccg aagccgcttc agccctcaat gatatgatgt cctacatcaa cgattgcggt    1860
accgctacct cgtacacatc ctacatcggc aacctcgtgg ccacccgcgt gtcttcacaa    1920
tggggtttcg agggtccttc tttcaccatc acagagggca acaactccgt ctaccgttgc    1980
gcagagttgg gcaagtactt gctcgagact ggcgaggtcg aggccgtagt gatcgccggt    2040
gtggatcttt cgccagcgc tgagaatctc tacgtgaagt cgcgtcgttt caaggtctcg    2100
gagcaggaga gcccgcgggc cagcttcgac tccggcgctg acggctactt tgttggtgag    2160
ggatgtggtg ccctcgtcct caagcgcgag agcgactgca ccaaggacga acgcatttac    2220
gcctgcatgg acgctatcgt gcccggcaac atgccggcag cctgcatgga ggaggctctc    2280
gcccaggctc gcgtcaaccc caaggacgtt gagatgctcg agctctccgc tgactctgcc    2340
cgccacctca agaacccctc cgttctgcct aaggaactca ctgctgagga ggaaatccgc    2400
ggcattgagg ccattctcag ccagcgctct agcaacgaag ctgtggagcc ccacaacgtc    2460
gctgtcagca gcgtcaagtc cactgtcggt gacaccggct acgcctcagg agctgccagt    2520
ctcatcaaga cggctctctg tctgtacaac cgctacttgc cctcaaacgg cgcctcctgg    2580
gaggagcctg cacctgagac acagtggggc aagtctctgt acgcgtgcca gtcctcgcgg    2640
gcctggttga agaaccctgg agctcgccgc cacgcagctg tctcaggtgt tccgagacc     2700 cgttcatgct acacggtgct gctctctgat gtggagggcc accacgagac caagagccgc    2760
atttcgctcg atgacgatgc cgtcaaactc ctcgtaatcc gcggagactc ccatgacgct    2820
atcacgcagc gtgttgacaa gctccgcgag cgcctcgccc agcctagcgc taatgtacgt    2880
cttgctttta tggagttgct cggcgagagc attgcccagg agaccaagac cccgttgccg    2940
gccttcgctc tgtgcctggt gacctctcct agtaagctcc agaaggagct tgaactcgcc    3000
tccaagggca tcccgcggag tcttaagatg ggccgcgact ggacatcacc ctcgggcagc    3060
cactttgcac ccaagccact gtcaagcgat cgcgttgcgt ttatgtacgg cgaaggccga    3120
agcccttact atggtatcgg ccttgacatt caccgcatct ggcccgaact tcacgagttt    3180
gtaaacgcca agaccaacaa gctttgggat caaggcgaca gatggttgat cccgcgcgcc    3240
tcgacgaagg aggagcttaa ggcgcaggaa gatgagttca accgcaacca ggtggagatg    3300
ttccgactcg gtattctcat gtccatgtgc ttcacccaca tcgctcgcga cgtgcttggc    3360
atccagccca aggctgcttt cggactgagc cttggagaga tttccatggt ttttgccttt    3420
tctgagaaga acgccttgt tctctgaggag ctgacaacta aactccgcaa ctcggaggtc    3480
tggcgtaagg ccctcgctgt tgagtttgac gccctccgca aggcctggaa tattccccaa    3540 gataccctg tcagcgagtt ctggcaagga tacgtggtac gtggaacccg cgaggccgtt    3600
gaagcggcca tcggccccaa caataagtac gtgcacttga ccattgtcaa cgatgccaac    3660
agtgctctca tcagtggcaa gcctgaagat tgcaaggctg ccattgctcg cctgagcagc    3720
aacctccctg ctttgcccgt ggaccttggt atgtgtggcc actgccccgt ggtcgagccg    3780
tacggcaagc agatcgctga gatccatagc gtcctcgaga ttcccgaggt tgccggcctt    3840
gacctgtaca cgagcgtcaa ccagaagaag cttgttaaca agtccactgg agccagcgac    3900
```

```
gagtacgcac ccagctttgg tgaatacgca gcacagctgt acactgttca ggcagacttt    3960
cctaagatcg ccaagaccgt tagcgacaag aactttgacg tctttgttga gactggtccc    4020
aacgcccacc gtagcgccgc aattcgcgcc acccttggaa atagcaagcc ttttgtcacc    4080
ggatccatgg accgccagaa cgagaatgct tggacaacca tggtcaagct ggttgcctct    4140
ctccaagccc accgcgtgcc tggcgtgaag gtctcccctc tgtaccaccc cgagactgtt    4200
gaggaggcta cgcagagtta caacgatatg gtggctggca agaagcctac taagaacaag    4260
ttcttgcgta agattgtggt caatggtcgc tatgacccca aaaagcagct cgtgccgccc    4320
caggtgctag ctaagcttcc tcctgcggac cccaagatcg aggctcttat ccaggctcgc    4380
aagatgcagc ctattgcccc caagttcatg gagcgtctcg acattcagga gcaagacgcc    4440
acacgcgacc ctattctcaa caaggataac aaaccttccg ctgctcctgc ccttgcccct    4500
gctgctccgg cccgcagcgt ctccggagct gttgtggctt cctctgaggc tctccgtgcc    4560
aaacttttgg agctcaacag cactttgatg cttggtgtca acgccaacgg tgatctcgtt    4620
gaagcaagcc caagtgaagc atctattgtt gtgcccaagt gcgatatcaa ggatcttggc    4680
agccgtgcct tcatggagac atatggtgta tccgccccca tgtacaccgg cgccatggca    4740
aagggcattg catccgctga gatggttatc gctgccggaa agcgcggcat ccttggttct    4800
ctcggtgctg gtggtcttcc tatcgccacc gtacgcaagg ctctcgaagc tatccaggct    4860
gaactgccca agggccctta cgctgtcaac ctcatccact ctcccttcga cagcaacctc    4920
gagaagggta acgtcgacct cttcctcgag aagggcgtca ctgtcgttga agcctccgcc    4980
tttatgacct tgaccccgca gctcgtgcgc taccgtgctg caggtctctc tcgcgctgct    5040
gatggctcca cggttattaa gaaccgcgtc atcggtaagg tttctcgcac agagcttgcc    5100
gcaatgttta tccgtcccgc gcccgagaat ctcctcgaga agctgctgaa gtccggcgag    5160
atcacccaag agcaggctgc tctcgcacgc acagtgcctg tggcagacga cattgccgtt    5220
gaggcggact ccggtggcca caccgataac cgccccatcc acgtcatcct ccctctcatt    5280
gtcaacctcc gtgatcgtct gcacaaggag tgcggctacc ctgcccacct tcgcgttcgc    5340
gttggtgctg gtggtggcat tggatgccct caggccgcca ttgccacctt caacatgggc    5400
gcggccttca tcgtcactgg taccgtaaac cagatgagta agcaagctgg aacctgtgac    5460
accgttcgca agcagctctc acaagccacc tactccgaca tctgcatggc cccagcagct    5520
gacatgtttg aggaaggtgt caagctccag gtgctcaaga agggaactat gttcccctcg    5580
cgtgccaaca agctctatga gctcttcgtc aagtatgact cctttgagtc catggctcct    5640
ggagagctgg aacgtgtgga agagcgcatt ttcaagaagt ctctgtcaga agtttgggaa    5700
gagaccaagg acttctacat caacaggttg cagaacccgg agaagattga gcgcgcggag    5760
cgtgacccca gcttaagat gtccttgtgc ttccgctggt accttggttt ggcgagcttc    5820
tgggcaaacg ctggcatccc ggaccgtgcc atggactacc aggtttggtg tggcccagcg    5880
attggatctt tcaacgactt catcaagggt acctaccttg accccgccgt tgccaacgag    5940
taccccgatt ttgtgcaaat caacttgcag atcctccgtg gtgcctgctt cttgcgccgc    6000
ctcgaagctg tccgtaatgc cccgctgaag gctaacgcca agcaggttgc tgccgagatt    6060
gatgacatct acgtgcccac tgagcgcctg taa                                 6093
```

<210> SEQ ID NO 5
<211> LENGTH: 4398
<212> TYPE: DNA
<213> ORGANISM: Ulkenia sp.

<400> SEQUENCE: 5

```
atggccactc gcgtgaagac caacaagaaa ccatgctggg agatgaccaa ggaggagctc      60
accagcggca agaacgtcgt tttcgactat gacgagctcc ttgagttcgc cgagggtgac     120
atcagcaagg tcttcggccc cgaattcagc cagatcgacc agtacaagcg tcgcgttcgt     180
ctccccgccc gcgagtacct cctcgtcacc cgcgtcaccc tcatggacgc cgaggtcaac     240
aactaccgcg tcggtgcccg catggtcact gagtacgacc tccccgtcaa cggtgagctc     300
tctgagggtg gtgactgccc ctgggccgtg ctcgtcgaga gtggtcagtg tgatctcatg     360
ctcatctcct acatgggtat tgacttccag aacaagagcg accgcgtcta ccgtctgctc     420
aacaccaccc tcaccttcta cggtgttgcc caggagggcg agaccctgga gtacgacatc     480
cgcgtgaccg gcttcgccaa gcgtctcgac ggtgacatct ccatgttctt cttcgagtac     540
gactgctacg tcaacggccg tctcctcatc gagatgcgcg acggctgtgc cggtttcttc     600
accaacgagg agctcgccgc cggcaagggt gtcgtcttta cccgcgctga tctcctcgcc     660
cgcgagaaga ccaagaagca ggacatcacc ccgtacgcca ttgccccgcg tcttaacaag     720
accgttctca cgagactgat gatgcagtcc ctcgtggaca agaactggac caaggttttc     780
ggccccgaga acggcatgga ccagatcaac tacaaactct gcgcccgtaa gatgctcatg     840
attgaccgcg tcaccaagat tgactacacc ggtggcccct acggccttgg tcttctcgtt     900
ggtgagaaga tcctcgagcg cgaccactgg tactttccgt gccacttcgt cggagaccag     960
gtcatggctg gatccctcgt gtctgacggc tgcagccagc tcctcaagat gtacatgctc    1020
tggctcggcc tccaccttaa gaccggtccc ttcgacttcc gccccgtcaa cggccacccc    1080
aacaaggtcc gctgccgtgg ccagatctcc ccgcacaagg gtaagctcgt atacgtcatg    1140
gagatcaagg agatgggcta cgacgaggct ggtgacccgt acgccatcgc cgatgtcaac    1200
attctcgaca ttgacttcga agagggccag actttcgacc ttgccaacct ccacgagtac    1260
ggcaagggcg acctcaacaa gaagatcgtc gtcgacttca agggtattgc cctcaagctc    1320
cagaagcgct ctggccctgc cgttgtcgct cccgaggaag ccctcgctct caacaaggac    1380
cttttgcgccc cggctgttga ggccatccct gagcacatcc tcaagggcga tgctcttgcc    1440
cctaaccaga tgacctggca cccgatgtcc aagatcgctg gcaaccccac gccctcgttc    1500
tctccctcgg cctaccctcc ccgtcccatc accttcaccc cgttccccgg caacaagaac    1560
gacaacaacc acgtgcccgg cgagatgccg ctctcgtggt acaacatggc tgagttcatg    1620
gccggcaagg tcagcctctg cctcggccct gagttcgcca agttcgatga ctccaacacc    1680
agccgcagcc ctgcatggga ccttgctctt gtgactcgtg tggtctccgt ttctgacatg    1740
gagtgggtcc agtggaagaa cgtggactgc aacccgtcca agggaaccat ggttggcgag    1800
ttcgactgcc ccatcgacgc ctggttcttc cagggatctt gtaacgacgg ccacatgccg    1860
tactccatcc tcatggagat cgccctccag acctctggtg tcctcacctc tgtgctcaag    1920
gccccgctca ccatggagaa gaaggacatt ctcttccgca accttgacgc caacgccgag    1980
atggttcgct ctgatattga cctccgcggc aagaccatcc acaacctcac caagtgtacc    2040
ggctacagca tgctcggaga catgggtgtc caccgcttca gcttcgagct ctctgttgat    2100
ggtgtagtct tctacaaggg taccacctcc ttcggctggt cgtccctga ggtcttcatc     2160
tcccagactg gtctcgacaa cggtcgccgc acccagccct ggcacattga gtccaaggtg    2220
ccttccgccc aggtcctcac ctacgacgtt accccccaacg tgccggtcg cacccagctc    2280
tacgccaacg ccccccaaggg cgctcagctc actcgccgct ggaaccagtg ccagtacctt    2340
```

```
gacaccatcg accttgtggt cgccggtggc tccgccggtc ttggctacgg tcatggccgc    2400
aagcaggtga accccaagga ctggttcttc tcgtgccact tctggttcga ctccgtcatg    2460
cccggctcgc tcggtgtgga gtctatgttc cagctcgtcg agtccatcgc tgtcaagcag    2520
gacctcgccg gcaagtacgg catcaccaac ccgaccttcg ctcatgctcc gggcaagatc    2580
tcctggaagt accgtggtca gctcaccccc acctccaagt tcatggactc cgaggcccac    2640
attgtctcca tcgaggccca cgacggcgtc gtcgacatcg ttgccaatgg taacctctgg    2700
gctgatggcc tccgcgtcta caacgtcagc aacatccgtg tgcgcattgt tgctggcgcc    2760
gcccctgctg ctgctgctgc tgctgctgct gttgctgctc cggctgccgc ccctgctccg    2820
gttgctgcat ctggccctgc ccagaccatc accctcaagc agctcaaggc tgagcttctt    2880
gacgttgaga agcctctcta catctcctcc agcaacggcc aggtcaagaa gcacgccgat    2940
gtggctggtg gccaggccac cattgtgcag gcttgcagcc tcagtgacct cggtgatgaa    3000
ggcttcatga agacctacgg tgttgtggct cctctctaca ccggtgccat ggccaagggt    3060
attgcctctg ctgaccttgt gattgccact ggtaagcgca agatcctcgg ttccttcggt    3120
gctggcggtc tccccatgca cattgtccgt gccgctgttg agaagatcca ggctgagctc    3180
ccgaacggcc ccttcgccgt caacctcatc cactcccccct tcgatagcaa ccttgagaag    3240
ggcaacgttg acctcttcct cgagaagggc gttactgtcg tcgaggcctc cgccttcatg    3300
accttgaccc cgcaagtcgt ccgctaccgt gctgctggtc tttcccgtaa cgctgatggc    3360
tccattaaca tcaagaaccg catcatcggt aaggtctccc gtaccgagct cgctgagatg    3420
ttcatccgcc ctgccccgca gaacctcctc gacaagctca tccagtctgg tgagattacc    3480
aaggagcagg ctgagcttgc caagctcgtc ccgtcgccg acgacatcgc cgtcgaggcc    3540
gactctggtg gccacaccga caaccgcccc atccacgtca tcctccccct tatcatcaac    3600
ctccgcaacc gcctccacaa ggagtgcggc taccccgctc acctccgcgt gcgcgttgga    3660
gctggtggtg gtgttggatg cccccaggcc gctgccgctg ctctcgctat gggtgctgcc    3720
ttccttgtta ccggcactgt caaccaggtc gccaagcagt ccggcacctg cgacaatgtc    3780
cgcaagcagc tctgcatggc cacctactct gacgtctgca tggctcccgc tgctgacatg    3840
ttcgaggagg gcgtcaagct ccaggtcctc aagaagggaa ccatgttccc gtccagggct    3900
aacaagctct acgagctctt ctgcaagtac gactccttcg agtccatgcc tgccacagag    3960
ctcgagcgtg ttgagaagcg catcttccag tgccctcttg ctgatgtctg ggctgagacc    4020
tccgacttct acatcaaccg cctccacaac ccggagaaga tcacccgtgc cgagcgtgac    4080
cccaagctca agatgtctct ctgcttccgc tggtaccttg gtcttgcctc tcgctgggcc    4140
aacaccggtg aggctggacg cgtcatggac taccaggtct ggtgtggccc tgccattgga    4200
gccttcaacg acttcatcaa gggctcctac cttgacccgg ccgtctctgg tgagtacccg    4260
gacgtcgtgc agatcaactt gcagatcctt cgcggtgcct gctacctccg ccgtctcaat    4320
gtcatccgca acgacccgcg tgtcagcatt gaggtcgagg atgctgagtt cgtctacgag    4380
cccaccaacg ccctctaa                                                   4398

<210> SEQ ID NO 6
<211> LENGTH: 2997
<212> TYPE: PRT
<213> ORGANISM: Ulkenia sp.

<400> SEQUENCE: 6

Met Ala Gln Arg Glu Asn Arg Leu Glu Ala Asn Met Asp Thr Arg Ile
1               5                   10                  15
```

-continued

```
Ala Val Ile Gly Met Ser Ala Ile Leu Pro Cys Gly Thr Thr Val Arg
             20                  25                  30
Glu Ser Trp Glu Ala Ile Arg Asp Gly Ile Asp Cys Leu Ser Asp Leu
         35                  40                  45
Pro Glu Asp Arg Val Asp Val Thr Ala Tyr Phe Asp Pro Val Lys Thr
     50                  55                  60
Thr Lys Asp Lys Ile Tyr Cys Lys Arg Gly Gly Phe Ile Pro Glu Tyr
 65                  70                  75                  80
Asp Phe Asp Ala Arg Glu Phe Gly Leu Asn Met Phe Gln Met Glu Asp
                 85                  90                  95
Ser Asp Ala Asn Gln Thr Val Thr Leu Leu Lys Val Lys Glu Ala Leu
            100                 105                 110
Glu Asp Ala Gly Ile Glu Ala Leu Ser Lys Lys Lys Asn Ile Gly
        115                 120                 125
Cys Val Leu Gly Ile Gly Gly Gly Gln Lys Ser Ser His Glu Phe Tyr
    130                 135                 140
Ser Arg Leu Asn Tyr Val Val Glu Lys Val Leu Arg Lys Met Gly
145                 150                 155                 160
Met Pro Glu Glu Asp Val Gln Ala Ala Val Glu Lys Tyr Lys Ala Asn
                165                 170                 175
Phe Pro Glu Trp Arg Leu Asp Ser Phe Pro Gly Phe Leu Gly Asn Val
            180                 185                 190
Thr Ala Gly Arg Cys Thr Asn Thr Phe Asn Leu Asp Gly Met Asn Cys
        195                 200                 205
Val Val Asp Ala Ala Cys Ala Ser Ser Leu Ile Ala Val Lys Val Ala
    210                 215                 220
Ile Asp Glu Leu Leu His Gly Asp Cys Asp Met Met Ile Thr Gly Ala
225                 230                 235                 240
Thr Cys Thr Asp Asn Ser Ile Gly Met Tyr Met Ala Phe Ser Lys Thr
                245                 250                 255
Pro Val Phe Ser Thr Asp Pro Ser Val Arg Ala Tyr Asp Glu Lys Thr
            260                 265                 270
Lys Gly Met Leu Ile Gly Glu Gly Ser Ala Met Leu Val Leu Lys Arg
        275                 280                 285
Tyr Ala Asp Ala Val Arg Asp Gly Asp Glu Ile His Ala Val Ile Arg
    290                 295                 300
Gly Cys Ala Ser Ser Ser Asp Gly Lys Ala Ser Gly Ile Tyr Thr Pro
305                 310                 315                 320
Thr Ile Ser Gly Gln Glu Glu Ala Leu Arg Arg Ala Tyr Met Arg Ala
                325                 330                 335
Asn Val Asp Pro Ala Thr Val Thr Leu Val Glu Gly His Gly Thr Gly
            340                 345                 350
Thr Pro Val Gly Asp Arg Ile Glu Leu Thr Ala Leu Arg Asn Leu Phe
        355                 360                 365
Asp Ser Ala Tyr Gly Asn Glu Lys Glu Lys Val Ala Val Gly Ser Ile
    370                 375                 380
Lys Ser Asn Ile Gly His Leu Lys Ala Val Ala Gly Leu Ala Gly Met
385                 390                 395                 400
Ile Lys Val Ile Met Ala Leu Lys His Lys Thr Leu Pro Ala Thr Ile
                405                 410                 415
Asn Val Asp Glu Pro Pro Lys Leu Tyr Asp Asn Thr Pro Ile Thr Asp
            420                 425                 430
Ser Ser Leu Tyr Ile Asn Thr Met Asn Arg Pro Trp Phe Pro Ala Pro
```

435                 440                 445
Gly Val Pro Arg Arg Ala Gly Ile Ser Ser Phe Gly Phe Gly Gly Ala
450                 455                 460
Asn Tyr His Ala Val Leu Glu Glu Ala Glu Pro Glu His Gln Lys Ala
465                 470                 475                 480
Tyr Arg Leu Asn Lys Arg Pro Gln Pro Val Leu Leu Met Ala Ser Ser
                485                 490                 495
Thr Gln Ala Leu Ala Ser Leu Cys Glu Ala Gln Leu Lys Glu Phe Glu
                500                 505                 510
Lys Ala Ile Glu Glu Asn Lys Thr Val Lys Asn Thr Ala Tyr Ile Lys
                515                 520                 525
Cys Val Asp Phe Cys Glu Lys Phe Lys Phe Pro Gly Ser Ile Pro Ser
530                 535                 540
Ser Asn Ala Arg Leu Gly Phe Leu Val Lys Glu Ala Asp Ala Thr
545                 550                 555                 560
Glu Thr Leu Arg Ala Ile Val Ala Gln Phe Gln Lys Ser Ala Gly Lys
                565                 570                 575
Asp Ser Trp His Leu Pro Arg Gln Gly Val Ser Phe Arg Ala Gln Gly
                580                 585                 590
Ile Asn Thr Thr Gly Gly Val Ala Ala Leu Phe Ser Gly Gln Gly Ala
                595                 600                 605
Gln Tyr Thr His Met Phe Ser Glu Val Ala Met Asn Trp Pro Gln Phe
610                 615                 620
Arg Glu Ser Ile Ser Asp Met Asp Arg Ala Gln Ala Lys Val Ala Gly
625                 630                 635                 640
Ala Asp Lys Asp Tyr Glu Arg Val Ser Gln Val Leu Tyr Pro Arg Lys
                645                 650                 655
Pro Tyr Asn Ser Glu Pro Gln Asp His Lys Lys Ile Ser Leu Thr
                660                 665                 670
Ser Tyr Ser Gln Pro Ser Thr Leu Ala Cys Ala Leu Gly Ala Tyr Glu
                675                 680                 685
Ile Phe Lys Gln Ala Gly Phe Lys Pro Asp Phe Ala Ala Gly His Ser
690                 695                 700
Leu Gly Glu Phe Ala Ala Leu Tyr Ala Ala Asp Cys Val Asn Arg Asp
705                 710                 715                 720
Asp Leu Phe Glu Leu Val Cys Arg Arg Ala Arg Ile Met Gly Gly Lys
                725                 730                 735
Asp Ala Pro Ala Thr Pro Lys Gly Cys Met Ala Ala Val Ile Gly Pro
                740                 745                 750
Asn Ala Glu Lys Ile Gln Ile Arg Thr Ala Asp Val Trp Leu Gly Asn
                755                 760                 765
Cys Asn Ser Pro Ser Gln Thr Val Ile Thr Gly Ser Val Glu Gly Ile
770                 775                 780
Lys Lys Glu Ser Glu Leu Leu Ser Glu Gly Phe Arg Val Val Pro
785                 790                 795                 800
Leu Ala Cys Glu Ser Ala Phe His Ser Pro Gln Met Gln Asn Ala Ser
                805                 810                 815
Ser Ala Phe Lys Asp Val Leu Ser Lys Val Ala Phe Arg Gln Pro Ser
                820                 825                 830
Ala Gln Thr Lys Leu Phe Ser Asn Val Ser Gly Glu Thr Tyr Ser Asn
                835                 840                 845
Asn Ala Gln Asp Leu Leu Lys Glu His Met Thr Ser Ser Val Lys Phe
850                 855                 860

```
Ile Ser Gln Val Arg Asn Met His Ser Ala Gly Ala Arg Ile Phe Val
865                 870                 875                 880

Glu Phe Gly Pro Lys Gln Val Leu Ser Lys Leu Val Ser Glu Thr Leu
                885                 890                 895

Lys Asp Asp Pro Ser Ile Ile Thr Ile Ser Val Asn Pro Ser Ser Gly
            900                 905                 910

Lys Asp Ala Asp Ile Gln Leu Arg Glu Ala Ala Val Gln Leu Val Val
            915                 920                 925

Ala Gly Val Asn Leu Gln Gly Phe Asp Lys Trp Asp Ala Pro Asp Ala
        930                 935                 940

Thr Arg Leu Gln Pro Ile Lys Lys Lys Thr Thr Leu Arg Leu Ser
945                 950                 955                 960

Ala Ala Thr Tyr Val Ser Asp Lys Thr Lys Lys Ala Arg Glu Ala Ala
            965                 970                 975

Met Asn Asp Gly Arg Met Leu Ser Cys Val Ser Lys Val Ile Ala Pro
            980                 985                 990

Pro Asp Ala Lys Pro Ile Val Asp  Thr Lys Ala Gln Glu  Glu Val Ala
        995                1000                1005

Arg Leu Gln Lys Gln Leu Gln  Asp Ala Gln Ala Gln  Ile Gln Lys
    1010                1015                1020

Ala Lys  Ala Asp Ala Ala Glu  Ala Asp Lys Lys Leu  Ala Ala Ala
    1025                1030                1035

Lys Asp  Glu Ala Lys Arg Ala  Ala Ala Ser Ala Pro  Val Gln Lys
    1040                1045                1050

Gln Val  Asp Thr Thr Ile Val  Asp Lys His Arg Ala  Ile Leu Lys
    1055                1060                1065

Ser Met  Leu Ala Glu Leu Asp  Cys Tyr Ser Thr Pro  Gly Ala Val
    1070                1075                1080

Ser Ser  Ser Phe Gln Ala Pro  Val Ala Ala Thr Pro  Ala Pro Val
    1085                1090                1095

Ala Ala  Pro Val Ala Ala Ala  Pro Ala Pro Ala Val  Asn Asn Ala
    1100                1105                1110

Leu Leu  Ala Lys Ala Glu Ser  Val Val Met Glu Val  Leu Ala Ala
    1115                1120                1125

Lys Thr  Gly Tyr Glu Thr Asp  Met Ile Glu Pro Asp  Met Glu Leu
    1130                1135                1140

Glu Thr  Glu Leu Gly Ile Asp  Ser Ile Lys Arg Val  Glu Ile Leu
    1145                1150                1155

Ser Glu  Val Gln Ala Gln Leu  Asn Val Glu Ala Lys  Asp Val Asp
    1160                1165                1170

Ala Leu  Ser Arg Thr Arg Thr  Val Gly Glu Val Val  Asn Ala Met
    1175                1180                1185

Lys Ala  Glu Ile Ala Gly Ser  Ser Gly Ala Ala Ala  Ala Ala Pro
    1190                1195                1200

Ala Pro  Val Ala Ala Ala Pro  Ala Ala Pro Ala Pro  Ala Val Asn
    1205                1210                1215

Ser Ala  Leu Leu Ala Lys Ala  Glu Thr Val Val Met  Glu Val Leu
    1220                1225                1230

Ala Ala  Lys Thr Gly Tyr Glu  Thr Asp Met Ile Glu  Pro Asp Met
    1235                1240                1245

Glu Leu  Glu Thr Glu Leu Gly  Ile Asp Ser Ile Lys  Arg Val Glu
    1250                1255                1260

Ile Leu  Ser Glu Val Gln Ala  Gln Leu Asn Val Glu  Ala Lys Asp
    1265                1270                1275
```

```
Val Asp Ala Leu Ser Arg Thr Arg Thr Val Gly Glu  Val Val Asn
    1280                1285                1290

Ala Met Lys Ala Glu Ile Ala Gly Ser Ser Gly Ala  Ala Ala Ala
    1295                1300                1305

Ala Pro Ala Pro Val Ala Ala Ala Pro Ala Pro Val  Ala Ala Ala
    1310                1315                1320

Ala Pro Ala Val Ser Ser Ala Leu Leu Glu Lys Ala  Glu Ser Val
    1325                1330                1335

Val Met Glu Val Leu Ala Ala Lys Thr Gly Tyr Glu  Thr Asp Met
    1340                1345                1350

Ile Glu Ala Asp Met Glu Leu Glu Thr Glu Leu Gly  Ile Asp Ser
    1355                1360                1365

Ile Lys Arg Val Glu Ile Leu Ser Glu Val Gln Ala  Gln Leu Asn
    1370                1375                1380

Val Glu Ala Lys Asp Val Asp Ala Leu Ser Arg Thr  Arg Thr Val
    1385                1390                1395

Gly Glu Val Val Asn Ala Met Lys Ala Glu Ile Ala  Gly Ser Ser
    1400                1405                1410

Gly Ala Ala Ala Pro Ala Pro Val Ala Ala Ala Pro  Ala Pro Val
    1415                1420                1425

Ala Ala Ala Ala Pro Ala Val Asn Ser Ala Leu Leu  Glu Lys Ala
    1430                1435                1440

Glu Thr Val Val Met Glu Val Leu Ala Ala Lys Thr  Gly Tyr Glu
    1445                1450                1455

Thr Asp Met Ile Glu Pro Asp Met Glu Leu Glu Thr  Glu Leu Gly
    1460                1465                1470

Ile Asp Ser Ile Lys Arg Val Glu Ile Leu Ser Glu  Val Gln Ala
    1475                1480                1485

Gln Leu Asn Val Glu Ala Lys Asp Val Asp Ala Leu  Ser Arg Thr
    1490                1495                1500

Arg Thr Val Gly Glu Val Val Asn Ala Met Lys Ala  Glu Ile Ala
    1505                1510                1515

Gly Ser Ser Gly Ala Ala Ala Ala Ala Pro Ala Pro  Val Ala Ala
    1520                1525                1530

Ala Pro Ala Pro Val Ala Ala Pro Ala Val Ser Ser  Ala Leu Leu
    1535                1540                1545

Glu Lys Ala Glu Ser Val Val Met Glu Val Leu Ala  Ala Lys Thr
    1550                1555                1560

Gly Tyr Glu Thr Asp Met Ile Glu Ala Asp Met Glu  Leu Glu Thr
    1565                1570                1575

Glu Leu Gly Ile Asp Ser Ile Lys Arg Val Glu Ile  Leu Ser Glu
    1580                1585                1590

Val Gln Ala Gln Leu Asn Val Glu Ala Lys Asp Val  Asp Ala Leu
    1595                1600                1605

Ser Arg Thr Arg Thr Val Gly Glu Val Val Asn Ala  Met Lys Ala
    1610                1615                1620

Glu Ile Ala Gly Ser Ser Gly Ala Ala Ala Ala Ala  Pro Ala Pro
    1625                1630                1635

Val Ala Ala Ser Pro Ala Pro Val Ala Ala Ala Ala  Pro Ala Val
    1640                1645                1650

Ser Ser Ala Leu Leu Glu Lys Ala Glu Ser Val Val  Met Glu Val
    1655                1660                1665

Leu Ala Ala Lys Thr Gly Tyr Glu Thr Asp Met Ile  Glu Ala Asp
```

```
             1670              1675              1680

Met Glu Leu Glu Thr Glu Leu Gly Ile Asp Ser Ile Lys Arg Val
    1685              1690              1695

Glu Ile Leu Ser Glu Val Gln Ala Met Leu Asn Val Glu Ala Lys
    1700              1705              1710

Asp Val Asp Ala Leu Ser Arg Thr Arg Thr Val Gly Glu Val Val
    1715              1720              1725

Asn Ala Met Lys Ala Glu Ile Ala Gly Ser Ser Gly Ala Ala Ala
    1730              1735              1740

Ala Ala Pro Ala Pro Val Ala Ala Pro Ala Pro Val Thr Ala
    1745              1750              1755

Ala Ala Pro Ala Val Ser Ser Ala Leu Leu Glu Lys Ala Glu Ser
    1760              1765              1770

Val Val Met Glu Val Leu Ala Ala Lys Thr Gly Tyr Glu Thr Asp
    1775              1780              1785

Met Ile Glu Ala Asp Met Glu Leu Glu Thr Glu Leu Gly Ile Asp
    1790              1795              1800

Ser Ile Lys Arg Val Glu Ile Leu Ser Glu Val Gln Ala Met Leu
    1805              1810              1815

Asn Val Glu Ala Lys Asp Val Asp Ala Leu Ser Arg Thr Arg Thr
    1820              1825              1830

Val Gly Glu Val Val Asn Ala Met Lys Ala Glu Ile Ala Ser Ser
    1835              1840              1845

Ser Gly Ala Ala Ala Pro Ala Pro Ala Ala Ala Val Ala Pro Ala
    1850              1855              1860

Pro Ala Ala Ala Pro Ala Val Ser Ser Ala Leu Leu Glu Lys Ala
    1865              1870              1875

Glu Ser Val Val Met Glu Val Leu Ala Ala Lys Thr Gly Tyr Glu
    1880              1885              1890

Thr Asp Met Ile Glu Ala Asp Met Glu Leu Glu Thr Glu Leu Gly
    1895              1900              1905

Ile Asp Ser Ile Lys Arg Val Glu Ile Leu Ser Glu Val Gln Ala
    1910              1915              1920

Met Leu Asn Val Glu Ala Lys Asp Val Asp Ala Leu Ser Arg Thr
    1925              1930              1935

Arg Thr Val Gly Glu Val Val Asn Ala Met Lys Ala Glu Ile Ala
    1940              1945              1950

Ser Ser Ser Gly Ala Ala Ala Pro Ala Pro Ala Ala Ala Ala Ala
    1955              1960              1965

Pro Ala Pro Ala Ala Ala Pro Ala Val Ser Ser Ala Leu Leu Glu
    1970              1975              1980

Lys Ala Glu Ser Val Val Met Glu Val Leu Ala Ala Lys Thr Gly
    1985              1990              1995

Tyr Glu Thr Asp Met Ile Glu Ala Asp Met Glu Leu Glu Thr Glu
    2000              2005              2010

Leu Gly Ile Asp Ser Ile Lys Arg Val Glu Ile Leu Ser Glu Val
    2015              2020              2025

Gln Ala Met Leu Asn Val Glu Ala Lys Asp Val Asp Ala Leu Ser
    2030              2035              2040

Arg Thr Arg Thr Val Gly Glu Val Val Asn Ala Met Lys Ala Glu
    2045              2050              2055

Ile Ala Ser Ser Ser Gly Ala Ala Ala Pro Ala Pro Ala Ala Ala
    2060              2065              2070
```

```
Ala Ala Pro Ala Pro Ala Ala Ala Pro Ala Val Ser  Ser Ala Leu
2075                2080                2085

Leu Glu Lys Ala Glu Ser Val Val Met Glu Val Leu  Ala Ala Lys
2090                2095                2100

Thr Gly Tyr Glu Thr Asp Met Ile Glu Ala Asp Met  Glu Leu Glu
2105                2110                2115

Thr Glu Leu Gly Ile Asp Ser Ile Lys Arg Val Glu  Ile Leu Ser
2120                2125                2130

Glu Val Gln Ala Met Leu Asn Val Glu Ala Lys Asp  Val Asp Ala
2135                2140                2145

Leu Ser Arg Thr Arg Thr Val Gly Glu Val Val Asn  Ala Met Lys
2150                2155                2160

Ala Glu Ile Ala Gly Ser Ser Gly Ala Ala Thr Ala  Ser Ala Pro
2165                2170                2175

Ala Ala Ala Ala Ala Ala Pro Ala Ile Lys Ile Ser  Thr Val His
2180                2185                2190

Gly Ala Asp Cys Asp Asp Leu Ser Val Met Ser Ala  Glu Leu Val
2195                2200                2205

Asp Ile Arg Arg Ala Asp Glu Leu Leu Leu Glu Arg  Pro Glu Asn
2210                2215                2220

Arg Pro Val Leu Ile Val Asp Asp Gly Thr Glu Leu  Thr Ser Ala
2225                2230                2235

Leu Val Arg Val Leu Gly Ala Gly Ala Val Val Leu  Thr Phe Asp
2240                2245                2250

Gly Leu Gln Leu Ala Gln Arg Ala Gly Ala Ala Val  Arg His Val
2255                2260                2265

Gln Val Lys Asp Leu Ser Ala Glu Ser Ala Glu Lys  Ala Ile Lys
2270                2275                2280

Glu Ala Glu Gln Arg Phe Gly Gln Leu Gly Gly Phe  Ile Ser Gln
2285                2290                2295

Gln Ala Glu Arg Phe Ala Pro Ala Asp Ile Leu Gly  Phe Thr Leu
2300                2305                2310

Met Cys Ala Lys Phe Ala Lys Ala Ser Leu Cys Thr  Pro Val Gln
2315                2320                2325

Gly Gly Arg Ala Phe Phe Ile Gly Val Ala Arg Leu  Asp Gly Arg
2330                2335                2340

Leu Gly Phe Thr Ser Gln Gly Ser Thr Asp Ser Leu  Thr Arg Ala
2345                2350                2355

Gln Arg Gly Ala Ile Phe Gly Leu Cys Lys Thr Ile  Gly Leu Glu
2360                2365                2370

Trp Ser Ala Asn Glu Val Phe Ala Arg Gly Ile Asp  Ile Ala Arg
2375                2380                2385

Glu Val His Pro Glu Asp Ala Ala Val Ala Ile Thr  Arg Glu Met
2390                2395                2400

Ser Cys Ala Asp Asn Arg Ile Arg Glu Val Gly Ile  Gly Leu Asn
2405                2410                2415

Gln Lys Arg Cys Thr Ile Arg Ala Val Asp Leu Lys  Pro Gly Ala
2420                2425                2430

Pro Lys Ile Gln Ile Ser Gln Asp Asp Val Leu Leu  Val Ser Gly
2435                2440                2445

Gly Ala Arg Gly Ile Thr Pro Leu Cys Ile Arg Glu  Ile Thr Arg
2450                2455                2460

Gln Val Arg Gly Gly Lys Tyr Ile Leu Leu Gly Arg  Ser Lys Val
2465                2470                2475
```

-continued

```
Pro Ala Gly Glu Pro Ala Trp Cys Asn Gly Val Ser Asp Asp Asp
    2480            2485                    2490

Leu Gly Lys Ala Ala Met Gln Glu Leu Lys Arg Ala Phe Ser Ala
    2495            2500                    2505

Gly Glu Gly Pro Lys Pro Thr Pro Met Thr His Lys Lys Leu Val
    2510            2515                    2520

Gly Thr Ile Ala Gly Ala Arg Glu Val Arg Ser Ser Ile Ala Asn
    2525            2530                    2535

Ile Glu Ala Leu Gly Gly Lys Ala Ile Tyr Ser Ser Cys Asp Val
    2540            2545                    2550

Asn Ser Ala Ala Asp Val Ala Lys Ala Val Arg Glu Ala Glu Ala
    2555            2560                    2565

Gln Leu Gly Ala Arg Val Thr Gly Val Val His Ala Ser Gly Val
    2570            2575                    2580

Leu Arg Asp Arg Leu Ile Glu Gln Lys Arg Pro Asp Glu Phe Asp
    2585            2590                    2595

Ala Val Phe Gly Thr Lys Val Thr Gly Leu Glu Asn Leu Phe Gly
    2600            2605                    2610

Ala Ile Asp Met Ala Asn Leu Lys His Leu Val Leu Phe Ser Ser
    2615            2620                    2625

Leu Ala Gly Phe His Gly Asn Ile Gly Gln Ser Asp Tyr Ala Met
    2630            2635                    2640

Ala Asn Glu Ala Leu Asn Lys Met Gly Leu Glu Leu Ser Asp Arg
    2645            2650                    2655

Val Ser Val Lys Ser Ile Cys Phe Gly Pro Trp Asp Gly Gly Met
    2660            2665                    2670

Val Thr Pro Gln Leu Lys Lys Gln Phe Gln Ser Met Gly Val Gln
    2675            2680                    2685

Ile Ile Pro Arg Glu Gly Gly Ala Asp Thr Val Ala Arg Ile Val
    2690            2695                    2700

Leu Gly Ser Ser Pro Ala Glu Ile Leu Val Gly Asn Trp Thr Thr
    2705            2710                    2715

Pro Thr Lys Lys Val Gly Ser Glu Pro Val Val Ile His Arg Lys
    2720            2725                    2730

Ile Ser Ala Ala Ser Asn Pro Phe Leu Lys Asp His Val Ile Gln
    2735            2740                    2745

Gly Arg Cys Val Leu Pro Met Thr Ile Ala Val Gly Cys Leu Ala
    2750            2755                    2760

Glu Thr Cys Leu Gly Gln Phe Pro Gly Tyr Ser Leu Trp Ala Ile
    2765            2770                    2775

Glu Asp Ala Gln Leu Phe Lys Gly Val Thr Val Asp Gly Asp Val
    2780            2785                    2790

Asn Cys Glu Ile Thr Leu Lys Pro Ser Gln Gly Thr Ala Gly Arg
    2795            2800                    2805

Val Met Ile Gln Ala Thr Leu Lys Thr Phe Ala Ser Gly Lys Leu
    2810            2815                    2820

Val Pro Ala Tyr Arg Ala Val Ile Val Leu Ser Thr Gln Gly Lys
    2825            2830                    2835

Pro Pro Ala Ala Thr Thr Ser Gln Thr Pro Ser Leu Gln Ala Asp
    2840            2845                    2850

Pro Ala Ala Arg Gly Asn Pro Tyr Asp Gly Lys Thr Leu Phe His
    2855            2860                    2865

Gly Pro Ala Phe Gln Gly Leu Lys Glu Ile Ile Ser Cys Asn Lys
```

-continued

```
                2870                2875                2880

Ser  Gln  Leu  Val  Ala  Glu  Cys  Thr  Phe  Ile  Pro  Ser  Ser  Glu  Ser
         2885                2890                2895

Ala  Gly  Glu  Phe  Ala  Ser  Asp  Tyr  Glu  Ser  His  Asn  Pro  Phe  Val
         2900                2905                2910

Asn  Asp  Ile  Ala  Phe  Gln  Ala  Met  Leu  Val  Trp  Ile  Arg  Arg  Thr
         2915                2920                2925

Leu  Gly  Gln  Ala  Ala  Leu  Pro  Asn  Ser  Ile  Gln  Arg  Ile  Val  Gln
         2930                2935                2940

His  Arg  Ala  Leu  Pro  Gln  Asp  Lys  Pro  Phe  Tyr  Leu  Thr  Leu  Lys
         2945                2950                2955

Ser  Asn  Ser  Ala  Ser  Gly  His  Ser  Gln  His  Lys  Thr  Ser  Val  Gln
         2960                2965                2970

Phe  His  Asn  Glu  Gln  Gly  Asp  Leu  Phe  Val  Asp  Ile  Gln  Ala  Ser
         2975                2980                2985

Val  Thr  Ser  Ser  Asp  Ser  Leu  Ala  Phe
         2990                2995

<210> SEQ ID NO 7
<211> LENGTH: 2030
<212> TYPE: PRT
<213> ORGANISM: Ulkenia sp.

<400> SEQUENCE: 7

Met  Ala  Ser  Arg  Lys  Asn  Val  Ser  Ala  Ala  His  Glu  Met  His  Asp  Glu
1                   5                   10                  15

Lys  Arg  Ile  Ala  Val  Val  Gly  Met  Ala  Val  Gln  Tyr  Ala  Gly  Cys  Lys
                    20                  25                  30

Asp  Lys  Glu  Glu  Phe  Trp  Lys  Val  Val  Met  Gly  Gly  Glu  Ala  Ala  Trp
            35                  40                  45

Thr  Lys  Ile  Ser  Asp  Lys  Arg  Leu  Gly  Ser  Asn  Lys  Arg  Ala  Glu  His
50                  55                  60

Phe  Lys  Ala  Glu  Arg  Ser  Lys  Phe  Ala  Asp  Thr  Phe  Cys  Asn  Glu  Asn
65                  70                  75                  80

Tyr  Gly  Cys  Val  Asp  Asp  Ser  Val  Asp  Asn  Glu  His  Glu  Leu  Leu  Leu
                    85                  90                  95

Lys  Leu  Ser  Lys  Lys  Ala  Leu  Ser  Glu  Thr  Ser  Val  Ser  Asp  Ser  Thr
            100                 105                 110

Arg  Cys  Gly  Ile  Val  Ser  Gly  Cys  Leu  Ser  Phe  Pro  Met  Asp  Asn  Leu
            115                 120                 125

Gln  Gly  Glu  Leu  Leu  Asn  Val  Tyr  Gln  Asn  His  Val  Glu  Lys  Lys  Leu
            130                 135                 140

Gly  Ala  Arg  Val  Phe  Lys  Asp  Ala  Ser  Lys  Trp  Ser  Glu  Arg  Glu  Gln
145                 150                 155                 160

Ser  Gln  Asn  Pro  Glu  Ala  Gly  Asp  Arg  Arg  Ile  Phe  Met  Asp  Pro  Ala
                    165                 170                 175

Ser  Phe  Val  Ala  Glu  Glu  Leu  Asn  Leu  Gly  Pro  Leu  His  Tyr  Ser  Val
            180                 185                 190

Asp  Ala  Ala  Cys  Ala  Thr  Ala  Leu  Tyr  Val  Leu  Arg  Leu  Ala  Gln  Asp
            195                 200                 205

His  Leu  Val  Ser  Gly  Ala  Ala  Asp  Val  Met  Leu  Ala  Gly  Ala  Thr  Cys
            210                 215                 220

Phe  Pro  Glu  Pro  Phe  Phe  Ile  Leu  Ser  Gly  Phe  Ser  Thr  Phe  Gln  Ala
225                 230                 235                 240

Met  Pro  Val  Ser  Gly  Asp  Gly  Ile  Ser  Tyr  Pro  Leu  His  Lys  Asp  Ser
```

-continued

```
                    245                 250                 255
Gln Gly Leu Thr Pro Gly Glu Gly Gly Ala Ile Met Val Leu Lys Arg
            260                 265                 270

Leu Asp Asp Ala Ile Arg Asp Gly Asp His Ile Tyr Gly Thr Leu Leu
            275                 280                 285

Gly Ala Thr Ile Ser Asn Ala Gly Cys Gly Leu Pro Leu Lys Pro His
            290                 295                 300

Leu Pro Ser Glu Lys Ser Cys Leu Ile Asp Thr Tyr Lys Arg Val Asn
305                 310                 315                 320

Val His Pro His Lys Ile Gln Tyr Val Glu Cys His Ala Thr Gly Thr
                325                 330                 335

Pro Gln Gly Asp Arg Val Glu Ile Asp Ala Val Lys Ala Cys Phe Glu
            340                 345                 350

Gly Lys Val Pro Arg Phe Gly Ser Lys Gly Asn Phe Gly His Thr
            355                 360                 365

Leu Val Ala Ala Gly Phe Ala Gly Met Cys Lys Val Leu Leu Ala Met
            370                 375                 380

Lys His Gly Val Ile Pro Pro Thr Pro Gly Val Asp Gly Ser Ser Gln
385                 390                 395                 400

Met Asp Pro Leu Val Val Ser Glu Pro Ile Pro Trp Pro Asp Thr Glu
            405                 410                 415

Gly Glu Pro Lys Arg Ala Gly Leu Ser Ala Phe Gly Phe Gly Gly Thr
            420                 425                 430

Asn Ala His Ala Val Phe Glu Glu Phe Asp Arg Ser Lys Ala Ala Cys
            435                 440                 445

Ala Thr His Asp Ser Ile Ser Ser Leu Ser Arg Cys Gly Gly Glu
            450                 455                 460

Gly Asn Met Arg Ile Ala Ile Thr Gly Met Asp Ala Thr Phe Gly Ser
465                 470                 475                 480

Leu Lys Gly Leu Asp Ala Phe Glu Arg Ala Ile Tyr Asn Gly Gln His
            485                 490                 495

Gly Ala Val Pro Leu Pro Glu Lys Arg Trp Arg Phe Leu Gly Lys Asp
            500                 505                 510

Lys Asp Phe Leu Asp Leu Cys Gly Val Lys Glu Val Pro His Gly Cys
            515                 520                 525

Tyr Ile Glu Asp Val Glu Val Asp Phe Ser Arg Leu Arg Thr Pro Met
            530                 535                 540

Thr Pro Asp Asp Met Leu Arg Pro Met Gln Leu Leu Ala Val Thr Thr
545                 550                 555                 560

Ile Asp Arg Ala Ile Leu Asn Ser Gly Leu Lys Lys Gly Gly Lys Val
            565                 570                 575

Ala Val Phe Val Gly Leu Gly Thr Asp Leu Glu Leu Tyr Arg His Arg
            580                 585                 590

Ala Arg Val Ala Leu Lys Glu Arg Ala Arg Pro Glu Ala Ala Ser Ala
            595                 600                 605

Leu Asn Asp Met Met Ser Tyr Ile Asn Asp Cys Gly Thr Ala Thr Ser
            610                 615                 620

Tyr Thr Ser Tyr Ile Gly Asn Leu Val Ala Thr Arg Val Ser Ser Gln
625                 630                 635                 640

Trp Gly Phe Glu Gly Pro Ser Phe Thr Ile Thr Glu Gly Asn Asn Ser
            645                 650                 655

Val Tyr Arg Cys Ala Glu Leu Gly Lys Tyr Leu Leu Glu Thr Gly Glu
            660                 665                 670
```

-continued

```
Val Glu Ala Val Val Ile Ala Gly Val Asp Leu Cys Ala Ser Ala Glu
            675                 680                 685

Asn Leu Tyr Val Lys Ser Arg Phe Lys Val Ser Glu Gln Glu Ser
    690                 695                 700

Pro Arg Ala Ser Phe Asp Ser Gly Ala Asp Gly Tyr Phe Val Gly Glu
705                 710                 715                 720

Gly Cys Gly Ala Leu Val Leu Lys Arg Glu Ser Asp Cys Thr Lys Asp
                725                 730                 735

Glu Arg Ile Tyr Ala Cys Met Asp Ala Ile Val Pro Gly Asn Met Pro
            740                 745                 750

Ala Ala Cys Met Glu Glu Ala Leu Ala Gln Ala Arg Val Asn Pro Lys
                755                 760                 765

Asp Val Glu Met Leu Glu Leu Ser Ala Asp Ser Ala Arg His Leu Lys
770                 775                 780

Asn Pro Ser Val Leu Pro Lys Glu Leu Thr Ala Glu Glu Ile Arg
785                 790                 795                 800

Gly Ile Glu Ala Ile Leu Ser Gln Arg Ser Ser Asn Glu Ala Val Glu
                805                 810                 815

Pro His Asn Val Ala Val Ser Ser Val Lys Ser Thr Val Gly Asp Thr
            820                 825                 830

Gly Tyr Ala Ser Gly Ala Ala Ser Leu Ile Lys Thr Ala Leu Cys Leu
            835                 840                 845

Tyr Asn Arg Tyr Leu Pro Ser Asn Gly Ala Ser Trp Glu Glu Pro Ala
850                 855                 860

Pro Glu Thr Gln Trp Gly Lys Ser Leu Tyr Ala Cys Gln Ser Ser Arg
865                 870                 875                 880

Ala Trp Leu Lys Asn Pro Gly Ala Arg Arg His Ala Ala Val Ser Gly
                885                 890                 895

Val Ser Glu Thr Arg Ser Cys Tyr Thr Val Leu Leu Ser Asp Val Glu
            900                 905                 910

Gly His His Glu Thr Lys Ser Arg Ile Ser Leu Asp Asp Asp Ala Val
        915                 920                 925

Lys Leu Leu Val Ile Arg Gly Asp Ser His Asp Ala Ile Thr Gln Arg
    930                 935                 940

Val Asp Lys Leu Arg Glu Arg Leu Ala Gln Pro Ser Ala Asn Val Arg
945                 950                 955                 960

Leu Ala Phe Met Glu Leu Leu Gly Glu Ser Ile Ala Gln Glu Thr Lys
                965                 970                 975

Thr Pro Leu Pro Ala Phe Ala Leu Cys Leu Val Thr Ser Pro Ser Lys
            980                 985                 990

Leu Gln Lys Glu Leu Glu Leu Ala Ser Lys Gly Ile Pro Arg Ser Leu
        995                 1000                1005

Lys Met Gly Arg Asp Trp Thr Ser Pro Ser Gly Ser His Phe Ala
    1010                1015                1020

Pro Lys Pro Leu Ser Ser Asp Arg Val Ala Phe Met Tyr Gly Glu
    1025                1030                1035

Gly Arg Ser Pro Tyr Tyr Gly Ile Gly Leu Asp Ile His Arg Ile
    1040                1045                1050

Trp Pro Glu Leu His Glu Phe Val Asn Ala Lys Thr Asn Lys Leu
    1055                1060                1065

Trp Asp Gln Gly Asp Arg Trp Leu Ile Pro Arg Ala Ser Thr Lys
    1070                1075                1080

Glu Glu Leu Lys Ala Gln Glu Asp Glu Phe Asn Arg Asn Gln Val
    1085                1090                1095
```

```
Glu Met Phe Arg Leu Gly Ile Leu Met Ser Met Cys Phe Thr His
    1100            1105            1110

Ile Ala Arg Asp Val Leu Gly Ile Gln Pro Lys Ala Ala Phe Gly
    1115            1120            1125

Leu Ser Leu Gly Glu Ile Ser Met Val Phe Ala Phe Ser Glu Lys
    1130            1135            1140

Asn Gly Leu Val Ser Glu Glu Leu Thr Thr Lys Leu Arg Asn Ser
    1145            1150            1155

Glu Val Trp Arg Lys Ala Leu Ala Val Glu Phe Asp Ala Leu Arg
    1160            1165            1170

Lys Ala Trp Asn Ile Pro Gln Asp Thr Pro Val Ser Glu Phe Trp
    1175            1180            1185

Gln Gly Tyr Val Val Arg Gly Thr Arg Glu Ala Val Glu Ala Ala
    1190            1195            1200

Ile Gly Pro Asn Asn Lys Tyr Val His Leu Thr Ile Val Asn Asp
    1205            1210            1215

Ala Asn Ser Ala Leu Ile Ser Gly Lys Pro Glu Asp Cys Lys Ala
    1220            1225            1230

Ala Ile Ala Arg Leu Ser Ser Asn Leu Pro Ala Leu Pro Val Asp
    1235            1240            1245

Leu Gly Met Cys Gly His Cys Pro Val Val Glu Pro Tyr Gly Lys
    1250            1255            1260

Gln Ile Ala Glu Ile His Ser Val Leu Glu Ile Pro Glu Val Ala
    1265            1270            1275

Gly Leu Asp Leu Tyr Thr Ser Val Asn Gln Lys Lys Leu Val Asn
    1280            1285            1290

Lys Ser Thr Gly Ala Ser Asp Glu Tyr Ala Pro Ser Phe Gly Glu
    1295            1300            1305

Tyr Ala Ala Gln Leu Tyr Thr Val Gln Ala Asp Phe Pro Lys Ile
    1310            1315            1320

Ala Lys Thr Val Ser Asp Lys Asn Phe Asp Val Phe Val Glu Thr
    1325            1330            1335

Gly Pro Asn Ala His Arg Ser Ala Ala Ile Arg Ala Thr Leu Gly
    1340            1345            1350

Asn Ser Lys Pro Phe Val Thr Gly Ser Met Asp Arg Gln Asn Glu
    1355            1360            1365

Asn Ala Trp Thr Thr Met Val Lys Leu Val Ala Ser Leu Gln Ala
    1370            1375            1380

His Arg Val Pro Gly Val Lys Val Ser Pro Leu Tyr His Pro Glu
    1385            1390            1395

Thr Val Glu Glu Ala Thr Gln Ser Tyr Asn Asp Met Val Ala Gly
    1400            1405            1410

Lys Lys Pro Thr Lys Asn Lys Phe Leu Arg Lys Ile Val Val Asn
    1415            1420            1425

Gly Arg Tyr Asp Pro Lys Lys Gln Leu Val Pro Gln Val Leu
    1430            1435            1440

Ala Lys Leu Pro Pro Ala Asp Pro Lys Ile Glu Ala Leu Ile Gln
    1445            1450            1455

Ala Arg Lys Met Gln Pro Ile Ala Pro Lys Phe Met Glu Arg Leu
    1460            1465            1470

Asp Ile Gln Glu Gln Asp Ala Thr Arg Asp Pro Ile Leu Asn Lys
    1475            1480            1485

Asp Asn Lys Pro Ser Ala Ala Pro Ala Leu Ala Pro Ala Ala Pro
```

-continued

```
                1490                1495                1500

Ala Arg Ser Val Ser Gly Ala Val Val Ala Ser Ser Glu Ala Leu
    1505                1510                1515

Arg Ala Lys Leu Leu Glu Leu Asn Ser Thr Leu Met Leu Gly Val
    1520                1525                1530

Asn Ala Asn Gly Asp Leu Val Glu Ala Ser Pro Ser Glu Ala Ser
    1535                1540                1545

Ile Val Val Pro Lys Cys Asp Ile Lys Asp Leu Gly Ser Arg Ala
    1550                1555                1560

Phe Met Glu Thr Tyr Gly Val Ser Ala Pro Met Tyr Thr Gly Ala
    1565                1570                1575

Met Ala Lys Gly Ile Ala Ser Ala Glu Met Val Ile Ala Ala Gly
    1580                1585                1590

Lys Arg Gly Ile Leu Gly Ser Leu Gly Ala Gly Gly Leu Pro Ile
    1595                1600                1605

Ala Thr Val Arg Lys Ala Leu Glu Ala Ile Gln Ala Glu Leu Pro
    1610                1615                1620

Lys Gly Pro Tyr Ala Val Asn Leu Ile His Ser Pro Phe Asp Ser
    1625                1630                1635

Asn Leu Glu Lys Gly Asn Val Asp Leu Phe Leu Glu Lys Gly Val
    1640                1645                1650

Thr Val Val Glu Ala Ser Ala Phe Met Thr Leu Thr Pro Gln Leu
    1655                1660                1665

Val Arg Tyr Arg Ala Ala Gly Leu Ser Arg Ala Ala Asp Gly Ser
    1670                1675                1680

Thr Val Ile Lys Asn Arg Val Ile Gly Lys Val Ser Arg Thr Glu
    1685                1690                1695

Leu Ala Ala Met Phe Ile Arg Pro Ala Pro Glu Asn Leu Leu Glu
    1700                1705                1710

Lys Leu Leu Lys Ser Gly Glu Ile Thr Gln Glu Gln Ala Ala Leu
    1715                1720                1725

Ala Arg Thr Val Pro Val Ala Asp Asp Ile Ala Val Glu Ala Asp
    1730                1735                1740

Ser Gly Gly His Thr Asp Asn Arg Pro Ile His Val Ile Leu Pro
    1745                1750                1755

Leu Ile Val Asn Leu Arg Asp Arg Leu His Lys Glu Cys Gly Tyr
    1760                1765                1770

Pro Ala His Leu Arg Val Arg Val Gly Ala Gly Gly Ile Gly
    1775                1780                1785

Cys Pro Gln Ala Ala Ile Ala Thr Phe Asn Met Gly Ala Ala Phe
    1790                1795                1800

Ile Val Thr Gly Thr Val Asn Gln Met Ser Lys Gln Ala Gly Thr
    1805                1810                1815

Cys Asp Thr Val Arg Lys Gln Leu Ser Gln Ala Thr Tyr Ser Asp
    1820                1825                1830

Ile Cys Met Ala Pro Ala Ala Asp Met Phe Glu Glu Gly Val Lys
    1835                1840                1845

Leu Gln Val Leu Lys Lys Gly Thr Met Phe Pro Ser Arg Ala Asn
    1850                1855                1860

Lys Leu Tyr Glu Leu Phe Val Lys Tyr Asp Ser Phe Glu Ser Met
    1865                1870                1875

Ala Pro Gly Glu Leu Glu Arg Val Glu Lys Arg Ile Phe Lys Lys
    1880                1885                1890
```

-continued

```
Ser Leu Ser Glu Val Trp Glu Thr Lys Asp Phe Tyr Ile Asn
    1895            1900            1905

Arg Leu Gln Asn Pro Glu Lys Ile Glu Arg Ala Glu Arg Asp Pro
    1910            1915            1920

Lys Leu Lys Met Ser Leu Cys Phe Arg Trp Tyr Leu Gly Leu Ala
    1925            1930            1935

Ser Phe Trp Ala Asn Ala Gly Ile Pro Asp Arg Ala Met Asp Tyr
    1940            1945            1950

Gln Val Trp Cys Gly Pro Ala Ile Gly Ser Phe Asn Asp Phe Ile
    1955            1960            1965

Lys Gly Thr Tyr Leu Asp Pro Ala Val Ala Asn Glu Tyr Pro Asp
    1970            1975            1980

Val Val Gln Ile Asn Leu Gln Ile Leu Arg Gly Ala Cys Phe Leu
    1985            1990            1995

Arg Arg Leu Glu Ala Val Arg Asn Ala Pro Leu Lys Ala Asn Ala
    2000            2005            2010

Lys Gln Val Ala Ala Glu Ile Asp Asp Ile Tyr Val Pro Thr Glu
    2015            2020            2025

Arg Leu
    2030

<210> SEQ ID NO 8
<211> LENGTH: 1465
<212> TYPE: PRT
<213> ORGANISM: Ulkenia sp.

<400> SEQUENCE: 8

Met Ala Thr Arg Val Lys Thr Asn Lys Lys Pro Cys Trp Glu Met Thr
1               5                  10                 15

Lys Glu Glu Leu Thr Ser Gly Lys Asn Val Val Phe Asp Tyr Asp Glu
                20                  25                  30

Leu Leu Glu Phe Ala Glu Gly Asp Ile Ser Lys Val Phe Gly Pro Glu
            35                  40                  45

Phe Ser Gln Ile Asp Gln Tyr Lys Arg Arg Val Arg Leu Pro Ala Arg
        50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
        115                 120                 125

Phe Gln Asn Lys Ser Asp Arg Val Tyr Arg Leu Leu Asn Thr Thr Leu
    130                 135                 140

Thr Phe Tyr Gly Val Ala Gln Glu Gly Glu Thr Leu Glu Tyr Asp Ile
145                 150                 155                 160

Arg Val Thr Gly Phe Ala Lys Arg Leu Asp Gly Asp Ile Ser Met Phe
                165                 170                 175

Phe Phe Glu Tyr Asp Cys Tyr Val Asn Gly Arg Leu Leu Ile Glu Met
            180                 185                 190

Arg Asp Gly Cys Ala Gly Phe Phe Thr Asn Glu Glu Leu Ala Ala Gly
        195                 200                 205

Lys Gly Val Val Phe Thr Arg Ala Asp Leu Leu Ala Arg Glu Lys Thr
    210                 215                 220
```

```
Lys Lys Gln Asp Ile Thr Pro Tyr Ala Ile Ala Pro Arg Leu Asn Lys
225                 230                 235                 240

Thr Val Leu Asn Glu Thr Glu Met Gln Ser Leu Val Asp Lys Asn Trp
            245                 250                 255

Thr Lys Val Phe Gly Pro Glu Asn Gly Met Asp Gln Ile Asn Tyr Lys
        260                 265                 270

Leu Cys Ala Arg Lys Met Leu Met Ile Asp Arg Val Thr Lys Ile Asp
    275                 280                 285

Tyr Thr Gly Gly Pro Tyr Gly Leu Gly Leu Leu Val Gly Glu Lys Ile
290                 295                 300

Leu Glu Arg Asp His Trp Tyr Phe Pro Cys His Phe Val Gly Asp Gln
305                 310                 315                 320

Val Met Ala Gly Ser Leu Val Ser Asp Gly Cys Ser Gln Leu Leu Lys
                325                 330                 335

Met Tyr Met Leu Trp Leu Gly Leu His Leu Lys Thr Gly Pro Phe Asp
            340                 345                 350

Phe Arg Pro Val Asn Gly His Pro Asn Lys Val Arg Cys Arg Gly Gln
        355                 360                 365

Ile Ser Pro His Lys Gly Lys Leu Val Tyr Val Met Glu Ile Lys Glu
    370                 375                 380

Met Gly Tyr Asp Glu Ala Gly Asp Pro Tyr Ala Ile Ala Asp Val Asn
385                 390                 395                 400

Ile Leu Asp Ile Asp Phe Glu Lys Gly Gln Thr Phe Asp Leu Ala Asn
                405                 410                 415

Leu His Glu Tyr Gly Lys Gly Asp Leu Asn Lys Lys Ile Val Val Asp
            420                 425                 430

Phe Lys Gly Ile Ala Leu Lys Leu Gln Lys Arg Ser Gly Pro Ala Val
        435                 440                 445

Val Ala Pro Glu Lys Pro Leu Ala Leu Asn Lys Asp Leu Cys Ala Pro
    450                 455                 460

Ala Val Glu Ala Ile Pro Glu His Ile Leu Lys Gly Asp Ala Leu Ala
465                 470                 475                 480

Pro Asn Gln Met Thr Trp His Pro Met Ser Lys Ile Ala Gly Asn Pro
                485                 490                 495

Thr Pro Ser Phe Ser Pro Ser Ala Tyr Pro Pro Arg Pro Ile Thr Phe
            500                 505                 510

Thr Pro Phe Pro Gly Asn Lys Asn Asp Asn Asn His Val Pro Gly Glu
        515                 520                 525

Met Pro Leu Ser Trp Tyr Asn Met Ala Glu Phe Met Ala Gly Lys Val
    530                 535                 540

Ser Leu Cys Leu Gly Pro Glu Phe Ala Lys Phe Asp Asp Ser Asn Thr
545                 550                 555                 560

Ser Arg Ser Pro Ala Trp Asp Leu Ala Leu Val Thr Arg Val Val Ser
                565                 570                 575

Val Ser Asp Met Glu Trp Val Gln Trp Lys Asn Val Asp Cys Asn Pro
            580                 585                 590

Ser Lys Gly Thr Met Val Gly Glu Phe Asp Cys Pro Ile Asp Ala Trp
        595                 600                 605

Phe Phe Gln Gly Ser Cys Asn Asp Gly His Met Pro Tyr Ser Ile Leu
    610                 615                 620

Met Glu Ile Ala Leu Gln Thr Ser Gly Val Leu Thr Ser Val Leu Lys
625                 630                 635                 640

Ala Pro Leu Thr Met Glu Lys Lys Asp Ile Leu Phe Arg Asn Leu Asp
                645                 650                 655
```

```
Ala Asn Ala Glu Met Val Arg Ser Asp Ile Asp Leu Arg Gly Lys Thr
            660                 665                 670

Ile His Asn Leu Thr Lys Cys Thr Gly Tyr Ser Met Leu Gly Asp Met
        675                 680                 685

Gly Val His Arg Phe Ser Phe Glu Leu Ser Val Asp Gly Val Val Phe
690                 695                 700

Tyr Lys Gly Thr Thr Ser Phe Gly Trp Phe Val Pro Glu Val Phe Ile
705                 710                 715                 720

Ser Gln Thr Gly Leu Asp Asn Gly Arg Arg Thr Gln Pro Trp His Ile
                725                 730                 735

Glu Ser Lys Val Pro Ser Ala Gln Val Leu Thr Tyr Asp Val Thr Pro
                740                 745                 750

Asn Gly Ala Gly Arg Thr Gln Leu Tyr Ala Asn Ala Pro Lys Gly Ala
                755                 760                 765

Gln Leu Thr Arg Arg Trp Asn Gln Cys Gln Tyr Leu Asp Thr Ile Asp
    770                 775                 780

Leu Val Val Ala Gly Gly Ser Ala Gly Leu Gly Tyr Gly His Gly Arg
785                 790                 795                 800

Lys Gln Val Asn Pro Lys Asp Trp Phe Phe Ser Cys His Phe Trp Phe
                805                 810                 815

Asp Ser Val Met Pro Gly Ser Leu Gly Val Glu Ser Met Phe Gln Leu
                820                 825                 830

Val Glu Ser Ile Ala Val Lys Gln Asp Leu Ala Gly Lys Tyr Gly Ile
            835                 840                 845

Thr Asn Pro Thr Phe Ala His Ala Pro Gly Lys Ile Ser Trp Lys Tyr
850                 855                 860

Arg Gly Gln Leu Thr Pro Thr Ser Lys Phe Met Asp Ser Glu Ala His
865                 870                 875                 880

Ile Val Ser Ile Glu Ala His Asp Gly Val Val Asp Ile Val Ala Asn
                885                 890                 895

Gly Asn Leu Trp Ala Asp Gly Leu Arg Val Tyr Asn Val Ser Asn Ile
                900                 905                 910

Arg Val Arg Ile Val Ala Gly Ala Ala Pro Ala Ala Ala Ala Ala Ala
            915                 920                 925

Ala Ala Val Ala Ala Pro Ala Ala Ala Pro Ala Pro Val Ala Ala Ser
930                 935                 940

Gly Pro Ala Gln Thr Ile Thr Leu Lys Gln Leu Lys Ala Glu Leu Leu
945                 950                 955                 960

Asp Val Glu Lys Pro Leu Tyr Ile Ser Ser Asn Gly Gln Val Lys
                965                 970                 975

Lys His Ala Asp Val Ala Gly Gly Gln Ala Thr Ile Val Gln Ala Cys
                980                 985                 990

Ser Leu Ser Asp Leu Gly Asp Glu Gly Phe Met Lys Thr Tyr Gly Val
            995                 1000                1005

Val Ala Pro Leu Tyr Thr Gly Ala Met Ala Lys Gly Ile Ala Ser
   1010                1015                1020

Ala Asp Leu Val Ile Ala Thr Gly Lys Arg Lys Ile Leu Gly Ser
   1025                1030                1035

Phe Gly Ala Gly Gly Leu Pro Met His Ile Val Arg Ala Ala Val
   1040                1045                1050

Glu Lys Ile Gln Ala Glu Leu Pro Asn Gly Pro Phe Ala Val Asn
   1055                1060                1065

Leu Ile His Ser Pro Phe Asp Ser Asn Leu Glu Lys Gly Asn Val
```

```
                1070              1075              1080
Asp Leu Phe Leu Glu Lys Gly Val Thr Val Glu Ala Ser Ala
    1085            1090            1095
Phe Met Thr Leu Thr Pro Gln Val Val Arg Tyr Arg Ala Ala Gly
    1100            1105            1110
Leu Ser Arg Asn Ala Asp Gly Ser Ile Asn Ile Lys Asn Arg Ile
    1115            1120            1125
Ile Gly Lys Val Ser Arg Thr Glu Leu Ala Glu Met Phe Ile Arg
    1130            1135            1140
Pro Ala Pro Gln Asn Leu Leu Asp Lys Leu Ile Gln Ser Gly Glu
    1145            1150            1155
Ile Thr Lys Glu Gln Ala Glu Leu Ala Lys Leu Val Pro Val Ala
    1160            1165            1170
Asp Asp Ile Ala Val Glu Ala Asp Ser Gly Gly His Thr Asp Asn
    1175            1180            1185
Arg Pro Ile His Val Ile Leu Pro Leu Ile Ile Asn Leu Arg Asn
    1190            1195            1200
Arg Leu His Lys Glu Cys Gly Tyr Pro Ala His Leu Arg Val Arg
    1205            1210            1215
Val Gly Ala Gly Gly Gly Val Gly Cys Pro Gln Ala Ala Ala Ala
    1220            1225            1230
Ala Leu Ala Met Gly Ala Ala Phe Leu Val Thr Gly Thr Val Asn
    1235            1240            1245
Gln Val Ala Lys Gln Ser Gly Thr Cys Asp Asn Val Arg Lys Gln
    1250            1255            1260
Leu Cys Met Ala Thr Tyr Ser Asp Val Cys Met Ala Pro Ala Ala
    1265            1270            1275
Asp Met Phe Glu Glu Gly Val Lys Leu Gln Val Leu Lys Lys Gly
    1280            1285            1290
Thr Met Phe Pro Ser Arg Ala Asn Lys Leu Tyr Glu Leu Phe Cys
    1295            1300            1305
Lys Tyr Asp Ser Phe Glu Ser Met Pro Ala Thr Glu Leu Glu Arg
    1310            1315            1320
Val Glu Lys Arg Ile Phe Gln Cys Pro Leu Ala Asp Val Trp Ala
    1325            1330            1335
Glu Thr Ser Asp Phe Tyr Ile Asn Arg Leu His Asn Pro Glu Lys
    1340            1345            1350
Ile Thr Arg Ala Glu Arg Asp Pro Lys Leu Lys Met Ser Leu Cys
    1355            1360            1365
Phe Arg Trp Tyr Leu Gly Leu Ala Ser Arg Trp Ala Asn Thr Gly
    1370            1375            1380
Glu Ala Gly Arg Val Met Asp Tyr Gln Val Trp Cys Gly Pro Ala
    1385            1390            1395
Ile Gly Ala Phe Asn Asp Phe Ile Lys Gly Ser Tyr Leu Asp Pro
    1400            1405            1410
Ala Val Ser Gly Glu Tyr Pro Asp Val Val Gln Ile Asn Leu Gln
    1415            1420            1425
Ile Leu Arg Gly Ala Cys Tyr Leu Arg Arg Leu Asn Val Ile Arg
    1430            1435            1440
Asn Asp Pro Arg Val Ser Ile Glu Val Glu Asp Ala Glu Phe Val
    1445            1450            1455
Tyr Glu Pro Thr Asn Ala Leu
    1460            1465
```

<210> SEQ ID NO 9
<211> LENGTH: 5547
<212> TYPE: DNA
<213> ORGANISM: Ulkenia sp.

<400> SEQUENCE: 9

| | | | | | |
|---|---|---|---|---|---|
| atgcttgtga | tagggctct | ggcgcgggct | ctgtacggtg | cttggagatg | cacgggcagg | 60 |
| gcgagagagg | ggacgggttc | ccgggaggcg | ctgcttggag | gtgctgagag | ggagggagaa | 120 |
| ggcgtgcttt | gcgatgcgcg | gggcgaccta | ggcgctgctg | cgcggtgcag | cagcagggac | 180 |
| ctcggacgtg | agtcgaagcc | gtctgcagag | gagatggtag | aagggccgcg | gattggtagc | 240 |
| agagaagagg | aaatagaaga | agaagaagaa | atagaagaag | aagaaataga | agaagaagaa | 300 |
| atagaagaag | aagaggagga | cgggcaggcg | ggaaagatgg | agaaaggact | cgcggcggga | 360 |
| aaacaagaga | atgtgaactt | gggcttgaac | tttggtttga | atttgaatgt | ggagaacgag | 420 |
| gggttgaatt | tgagtttgaa | tttgaaagaa | aacttacgga | aagaaagttt | agttgaaagt | 480 |
| gagaaagaaa | aaaatgagaa | agaaaaagag | aagaaaaag | agaagaaaa | agagaaagaa | 540 |
| aaagagaaag | aaaagagaa | agaaaaagag | aagaaaaag | agaagaaaa | agagaaagaa | 600 |
| aaagagaaag | aaaagagaa | agaaaaagag | aagaaaaag | aagaagaaa | agaagaagaa | 660 |
| aaagagaaag | aaaagagaa | agaaaaagag | aagaaaaag | aagaaggaga | tttaaaaagt | 720 |
| tgtttagttg | aaaaaggaga | aggaggaaga | agcagcgaca | gcggcagaag | aagaagtagt | 780 |
| tgttgtaaga | ggggaacgga | ggcagtagca | gtggagcagg | cggaggcgac | agcaaacctc | 840 |
| gaactcgacc | ccgtcgagcc | gcagcaagaa | caagagcccg | accaggtgga | cgaggacgag | 900 |
| gtccgcttgt | tgtcaggaac | aacagaagtt | gcaggactag | ccgagagtgc | taccactgca | 960 |
| attcttagat | ccacagacgc | aagagcagaa | aacttacaac | tgctcgccac | aacacaagaa | 1020 |
| ccaccttcag | atacaaccag | gttcgagaac | tccacaagtc | tagaagcagc | aacagctcta | 1080 |
| gcagataatc | aaacaggtcc | agaaaaagct | acgactagaa | gagaaattat | cgagtcgcaa | 1140 |
| cttgcaacca | tggccactcg | cgtgaagacc | aacaagaaac | catgctggga | gatgaccaag | 1200 |
| gaggagctca | ccagcggcaa | gaacgtcgtt | ttcgactatg | acgagctcct | tgagttcgcc | 1260 |
| gagggtgaca | tcagcaaggt | cttcggcccc | gaattcagcc | agatcgacca | gtacaagcgt | 1320 |
| cgcgttcgtc | tccccgcccg | cgagtacctc | ctcgtcaccc | cgtcaccct | catggacgcc | 1380 |
| gaggtcaaca | actaccgcgt | cggtgcccgc | atggtcactg | agtacgacct | ccccgtcaac | 1440 |
| ggtgagctct | ctgagggtgg | tgactgcccc | tgggccgtgc | tcgtcgagag | tggtcagtgt | 1500 |
| gatctcatgc | tcatctccta | catgggtatt | gacttccaga | caagagcga | ccgcgtctac | 1560 |
| cgtctgctca | acaccaccct | caccttctac | ggtgttgccc | aggagggcga | gaccctggag | 1620 |
| tacgacatcc | gcgtgaccgg | cttcgccaag | cgtctcgacg | gtgacatctc | catgttcttc | 1680 |
| ttcgagtacg | actgctacgt | caacggccgt | ctcctcatcg | agatgcgcga | cggctgtgcc | 1740 |
| ggtttcttca | ccaacgagga | gctcgccgcc | ggcaagggtg | tcgtctttac | ccgcgctgat | 1800 |
| ctcctcgccc | gcgagaagac | caagaagcag | gacatcaccc | cgtacgccat | gccccgcgt | 1860 |
| cttaacaaga | ccgttctcaa | cgagactgag | atgcagtccc | tcgtggacaa | gaactggacc | 1920 |
| aaggttttcg | ccccgagaa | cggcatggac | cagatcaact | acaaactctg | cgcccgtaag | 1980 |
| atgctcatga | ttgaccgcgt | caccaagatt | gactacaccg | gtggcccta | cggccttggt | 2040 |
| cttctcgttg | gtgagaagat | cctcgagcgc | gaccactggt | actttccgtg | ccacttcgtc | 2100 |
| ggagaccagg | tcatggctgg | atccctcgtg | tctgacggct | gcagccagct | cctcaagatg | 2160 |

```
tacatgctct ggctcggcct ccaccttaag accggtccct tcgacttccg ccccgtcaac   2220
ggccacccca acaaggtccg ctgccgtggc cagatctccc cgcacaaggg taagctcgta   2280
tacgtcatgg agatcaagga gatgggctac gacgaggctg gtgacccgta cgccatcgcc   2340
gatgtcaaca ttctcgacat tgacttcgag aagggccaga ctttcgacct tgccaacctc   2400
cacgagtacg gcaagggcga cctcaacaag aagatcgtcg tcgacttcaa gggtattgcc   2460
ctcaagctcc agaagcgctc tggccctgcc gttgtcgctc ccgagaagcc cctcgctctc   2520
aacaaggacc tttgcgcccc ggctgttgag gccatccctg agcacatcct caagggcgat   2580
gctcttgccc ctaaccagat gacctggcac ccgatgtcca agatcgctgg caaccccacg   2640
ccctcgttct ctccctcggc ctaccctccc cgtcccatca ccttcacccc gttccccggc   2700
aacaagaacg acaacaacca cgtgcccggc gagatgccgc tctcgtggta caacatggct   2760
gagttcatgg ccggcaaggt cagcctctgc ctcggccctg agttcgccaa gttcgatgac   2820
tccaacacca gccgcagccc tgcatgggac cttgctcttg tgactcgtgt ggtctccgtt   2880
tctgacatgg agtgggtcca gtggaagaac gtggactgca acccgtccaa gggaaccatg   2940
gttggcgagt tcgactgccc catcgacgcc tggttcttcc agggatcttg taacgacggc   3000
cacatgccgt actccatcct catggagatc gccctccaga cctctggtgt cctcacctct   3060
gtgctcaagg ccccgctcac catggagaag aaggacattc tcttccgcaa ccttgacgcc   3120
aacgccgaga tggttcgctc tgatattgac ctccgcggca agaccatcca aacctcacc   3180 aagtgtaccg gctacagcat gctcggagac atgggtgtcc accgcttcag cttcgagctc   3240
tctgttgatg gtgtagtctt ctacaagggt accacctcct tcggctggtt cgtccctgag   3300
gtcttcatct cccagactgg tctcgacaac ggtcgccgca cccagccctg gcacattgag   3360
tccaaggtgc cttccgccca ggtcctcacc tacgacgtta cccccaacgg tgccggtcgc   3420
acccagctct acgccaacgc ccccaagggc gctcagctca ctcgccgctg gaaccagtgc   3480
cagtaccttg acaccatcga ccttgtggtc gccggtggct ccgccggtct tggctacggt   3540
catggccgca agcaggtgaa ccccaaggac tggttcttct cgtgccactt ctggttcgac   3600
tccgtcatgc ccggctcgct cggtgtggag tctatgttcc agctcgtcga gtccatcgct   3660
gtcaagcagg acctcgccgg caagtacggc atcaccaacc cgaccttcgc tcatgctccg   3720
ggcaagatct cctggaagta ccgtggtcag ctcaccccca cctccaagtt catggactcc   3780
gaggcccaca ttgtctccat cgaggcccac gacggcgtcg tcgacatcgt tgccaatggt   3840
aacctctggg ctgatggcct ccgcgtctac aacgtcagca catccgtgt gcgcattgtt   3900 gctggcgccg ccctgctgc tgctgctgct gctgctgctg ttgctgctcc ggctgccgcc   3960
cctgctccgg ttgctgcatc tggccctgcc cagaccatca ccctcaagca gctcaaggct   4020
gagcttcttg acgttgagaa gcctctctac atctcctcca gcaacggcca ggtcaagaag   4080
cacgccgatg tggctggtgg ccaggccacc attgtgcagg cttgcagcct cagtgacctc   4140
ggtgatgaag gcttcatgaa gacctacggt gttgtggctc ctctctacac cggtgccatg   4200
gccaagggta ttgcctctgc tgaccttgtg attgccactg gtaagcgcaa gatcctcggt   4260
tccttcggtg ctggcggtct ccccatgcac attgtccgtg ccgctgttga agatccag   4320 gctgagctcc cgaacggccc cttcgccgtc aacctcatcc actccccctt cgatagcaac   4380
cttgagaagg gcaacgttga cctcttcctc gagaagggcg ttactgtcgt cgaggcctcc   4440
gccttcatga ccttgacccc gcaagtcgtc cgctaccgtg ctgctggtct ttcccgtaac   4500
gctgatggct ccattaacat caagaaccgc atcatcggta aggtctcccg taccgagctc   4560
```

```
gctgagatgt tcatccgccc tgccccgcag aacctcctcg acaagctcat ccagtctggt    4620
gagattacca aggagcaggc tgagcttgcc aagctcgtcc ccgtcgccga cgacatcgcc    4680
gtcgaggccg actctggtgg ccacaccgac aaccgcccca tccacgtcat cctccccctt    4740
atcatcaacc tccgcaaccg cctccacaag gagtgcggct accccgctca cctccgcgtg    4800
cgcgttggag ctggtggtgg tgttggatgc ccccaggccg ctgccgctgc tctcgctatg    4860
ggtgctgcct tccttgttac cggcactgtc aaccaggtcg ccaagcagtc cggcacctgc    4920
gacaatgtcc gcaagcagct ctgcatggcc acctactctg acgtctgcat ggctcccgct    4980
gctgacatgt tcgaggaggg cgtcaagctc caggtcctca agaagggaac catgttcccg    5040
tccagggcta acaagctcta cgagctcttc tgcaagtacg actccttcga gtccatgcct    5100
gccacagagc tcgagcgtgt tgagaagcgc atcttccagt gccctcttgc tgatgtctgg    5160
gctgagacct ccgacttcta catcaaccgc ctccacaacc cggagaagat cacccgtgcc    5220
gagcgtgacc ccaagctcaa gatgtctctc tgcttccgct ggtaccttgg tcttgcctct    5280
cgctgggcca acaccggtga ggctggacgc gtcatggact accaggtctg gtgtggccct    5340
gccattggag ccttcaacga cttcatcaag ggctcctacc ttgacccggc cgtctctggt    5400
gagtacccgg acgtcgtgca gatcaacttg cagatccttc gcggtgcctg ctacctccgc    5460
cgtctcaatg tcatccgcaa cgacccgcgt gtcagcattg aggtcgagga tgctgagttc    5520
gtctacgagc ccaccaacgc cctctaa                                        5547

<210> SEQ ID NO 10
<211> LENGTH: 837
<212> TYPE: DNA
<213> ORGANISM: Ulkenia sp.

<400> SEQUENCE: 10
acccgcatcg ctgtgatcgg catgtccgcc atcctcccct gcggtaccac cgttcgtgag      60
tcttgggagg ctatccgcga tggtatcgac tgcctcagtg atctccccga ggaccgcgtc     120
gatgtgaccg cctacttcga cccggtcaag accaccaagg ataagatcta ctgcaaacgt     180
ggtggattca tccctgagta cgacttcgac gcccgtgagt tcggcctcaa catgtttcag     240
atggaggact ccgacgcaaa ccaaaccgtc accctcctca aggtcaagga ggccctcgag     300
gacgctggca tcgaagccct cagcaaggaa aagaagaaca ttggatgtgt tctcggtatc     360
ggtggtggcc agaagtccag ccacgagttc tactcccgct taaactatgt tgtcgttgag     420
aaggtccttc gcaagatggg catgcctgag gaggatgttc aagctgctgt tgagaagtac     480
aaggccaact cccctgagtg gcgccttgac tccttccccg gtttcctcgg caacgttact     540
gccggtcgct gtaccaacac cttcaacctc gatggtatga actgtgtcgt cgatgctgcc     600
tgtgctagtt ctctcatcgc cgttaaggtt gccattgatg agcttctcca cggagactgt     660
gacatgatga tcactggtgc tacctgcacg gataactcca tcggtatgta catggccttc     720
tccaagaccc cggtgttctc taccgaccct agcgtccgcg catacgatga aagaccaag     780 ggtatgctta ttggcgaagg ctctgccatg cttgtgctta aacgttacgc cgacgct       837

<210> SEQ ID NO 11
<211> LENGTH: 51
<212> TYPE: DNA
<213> ORGANISM: Ulkenia sp.

<400> SEQUENCE: 11
ggtatgaact gtgtcgtcga tgctgcctgt gctagttctc tcatcgccgt t               51
```

```
<210> SEQ ID NO 12
<211> LENGTH: 12
<212> TYPE: DNA
<213> ORGANISM: Ulkenia sp.

<400> SEQUENCE: 12
gatgctgcct gt                                                            12

<210> SEQ ID NO 13
<211> LENGTH: 522
<212> TYPE: DNA
<213> ORGANISM: Ulkenia sp.

<400> SEQUENCE: 13
cacgctgtca ttcgcggctg cgcctcttcc tctgacggta aggcctccgg tatttacacc         60
ccgaccatct ctggtcaaga ggaggctctt cgccgtgcct acatgcgcgc taacgtcgat        120
cccgccaccg tcactcttgt tgagggccac ggtaccggta ccccgttgg tgaccgtatt         180 gagctcaccg ctctccgtaa cctcttcgac agtgcctacg caacgagaa ggagaaggtc         240 gctgttggca gcattaagtc caacatcggt cacctcaagg ctgtcgccgg tcttgccggt        300
atgatcaagg tcatcatggc cctcaagcat aagactcttc cggccaccat caacgttgat        360
gagcccccta agctttacga caacactccc atcaccgact catcgctgta cattaacacg        420
atgaaccgtc cgtggttccc tgctccgggt gtgccccgtc gcgctggtat ctccagtttc        480
ggttttggtg gtgccaacta ccacgccgtt cttgaggaag cc                            522

<210> SEQ ID NO 14
<211> LENGTH: 1380
<212> TYPE: DNA
<213> ORGANISM: Ulkenia sp.

<400> SEQUENCE: 14
acccgcatcg ctgtgatcgg catgtccgcc atcctcccct gcggtaccac cgttcgtgag         60
tcttgggagg ctatccgcga tggtatcgac tgcctcagtg atctccccga ggaccgcgtc        120
gatgtgaccg cctacttcga cccggtcaag accaccaagg ataagatcta ctgcaaacgt        180
ggtggattca tccctgagta cgacttcgac gcccgtgagt tcggcctcaa catgtttcag        240
atggaggact ccgacgcaaa ccaaaccgtc accctcctca aggtcaagga ggcccctcgag       300 gacgctggca tcgaagccct cagcaaggaa aagaagaaca ttggatgtgt tctcggtatc        360
ggtggtggcc agaagtccag ccacgagttc tactcccgct aaactatgt tgtcgttgag        420 aaggtccttc gcaagatggg catgcctgag gaggatgttc aagctgctgt tgagaagtac        480
aaggccaact cccctgagtg gcgccttgac tccttcccg gtttcctcgg caacgttact         540
gccggtcgct gtaccaacac cttcaacctc gatggtatga actgtgtcgt cgatgctgcc        600
tgtgctagtt ctctccatcg cgttaaggtt gccattgatg agcttctcca cggagactgt        660
gacatgatga tcactggtgc tacctgcacg gataactcca tcggtatgta catggccttc        720
tccaagaccc cggtgttctc taccgaccct agcgtccgcg catacgatga aagaccaag         780 ggtatgctta ttggcgaagg ctctgccatg cttgtgctta acgttacgc cgacgctgtt        840 cgtgatggtg acgagattca cgctgtcatt cgcggctgcg cctcttcctc tgacggtaag        900
gcctccggta tttacacccc gaccatctct ggtcaagagg aggctcttcg ccgtgcctac        960
atgcgcgcta acgtcgatcc cgccaccgtc actcttgttg agggcacgg taccggtacc       1020 cccgttggtg accgtattga gctcaccgct ctccgtaacc tcttcgacag tgcctacggc      1080
```

| aacgagaagg agaaggtcgc tgttggcagc attaagtcca acatcggtca cctcaaggct | 1140 |
| gtcgccggtc ttgccggtat gatcaaggtc atcatggccc tcaagcataa gactcttccg | 1200 |
| gccaccatca acgttgatga gcccctaag  ctttacgaca acactcccat caccgactca | 1260 |
| tcgctgtaca ttaacacgat gaaccgtccg tggttccctg ctccgggtgt gccccgtcgc | 1320 |
| gctggtatct ccagtttcgg ttttggtggt gccaactacc acgccgttct tgaggaagcc | 1380 |

<210> SEQ ID NO 15
<211> LENGTH: 996
<212> TYPE: DNA
<213> ORGANISM: Ulkenia sp.

<400> SEQUENCE: 15

| ctcttctctg gccagggtgc tcagtacacc cacatgttca gcgaggtcgc catgaactgg |  60 |
| cctcagttcc gtgagagcat ctctgacatg gatcgtgccc aggctaaggt tgctggcgct | 120 |
| gacaaggact acgagcgtgt ctcccaagtc ctctacccgc gtaagcctta taactctgag | 180 |
| cccgagcagg accacaagaa gatctcctg  acctcatact ctcagccctc taccctcgcc | 240 |
| tgcgctcttg gtgcctacga gatcttcaag caggctggtt tcaagcccga cttcgctgcc | 300 |
| ggtcactctc tcggtgagtt tgcggccctc tacgctgctg actgcgtcaa ccgtgacgac | 360 |
| ctctttgagc tcgtgtgccg tcgtgcccgc atcatgggtg gcaaggatgc acctgctacc | 420 |
| cccaagggat gcatggctgc tgtcattgga cccaatgccg agaagatcca gattcgcact | 480 |
| gctgatgtct ggctcggcaa ctgcaactcc ccttcgcaga ctgtcatcac cggctctgtt | 540 |
| gagggtatca agaaggagtc cgagcttctc cagagtgagg gcttccgtgt tgtccccctc | 600 |
| gcctgcgaga gtgccttcca ctcaccgcag atgcaaaacg cctcctctgc cttcaaggat | 660 |
| gttctctcca aggttgcctt ccgtcagcct agcgcccaga ccaagctctt cagcaacgtg | 720 |
| tctggcgaga cctactccaa caatgcccag gacctcctta aggagcacat gaccagcagt | 780 |
| gttaagttca tctctcaggt tcgcaacatg cactctgctg gtgctcgcat ctttgtcgag | 840 |
| tttggcccca gcaggtgct  ctctaagctt gtttccgaga ccctcaagga cgatccttcc | 900 |
| attatcacta tctctgtcaa cccttcctct ggcaaggatg ccgatattca gcttcgcgag | 960 |
| gctgctgtgc agctcgttgt tgctggagtc aacctt                           | 996 |

<210> SEQ ID NO 16
<211> LENGTH: 3510
<212> TYPE: DNA
<213> ORGANISM: Ulkenia sp.

<400> SEQUENCE: 16

| gcccaggccc agatccagaa ggccaaggcc gatgctgctg aggctgacaa gaagcttgcc |  60 |
| gctgctaagg atgaggccaa gcgtgccgcc gcttctgcac ctgtgcagaa gcaggttgac | 120 |
| accaccattg ttgataagca ccgtgctatc ctcaagtcta tgcttgctga gcttgactgc | 180 |
| tactccactc ctggtgctgt gtccagctct ttccaggcac ctgttgctgc tacccctgct | 240 |
| ccggtcgctg cgcctgttgc agctgctcct gctccggctg tcaacaatgc tctccttgcc | 300 |
| aaggctgagt ctgttgtcat ggaggttctt gccgccaaga ctggttacga gactgacatg | 360 |
| atcgagcccg acatggagct cgagactgag ctcggcattg actctatcaa gcgtgtcgag | 420 |
| attctctctg aggtccaggc ccagctcaac gtcgaggcca aggatgttga tgctcttagc | 480 |
| cgcacccgca ccgtcggtga ggttgtcaac gccatgaagg ctgagatcgc tggcagctct | 540 |
| ggtgctgccg ctgctgcccc ggccccggtt gctgctgctc ccgctgcccc tgcccctgct | 600 |

```
gtcaacagcg ctcttcttgc caaggctgag actgttgtca tggaggttct gccgccaag      660 actggttacg agactgacat gattgagccc gacatggagc tcgagactga gctcggcatt    720
gactccatca agcgtgtcga gattctctct gaggttcagg cccagctcaa cgttgaggcc    780
aaggatgttg atgctcttag ccgcacccgc accgttggtg aggttgtcaa cgccatgaag    840
gctgagatcg ctggcagctc tggtgctgcc gctgctgccc cggcccctgt tgctgctgct    900
ccggcgcccg tcgctgccgc tgcccctgct gtcagcagcg ctctccttga aaggctgag      960 tctgttgtca tggaggttct gccgccaaag actggttacg agactgacat gattgaggcc    1020
gacatggagc tcgagactga gctcggcatt gactccatca agcgtgtcga gattctctct    1080
gaggtccagg cccagctcaa cgtcgaggcc aaggatgtcg atgctcttag ccgcacccgc    1140
accgttggtg aggttgtcaa cgccatgaag gctgagatcg ctggcagctc tggtgctgct    1200
gccccggccc cggtcgctgc ggcccctgct ccggtcgctg ccgctgcccc tgctgtcaac    1260
agcgctcttc ttgagaaggc tgagactgtt gtcatggagg ttcttgccgc caagactggt    1320
tacgagactg acatgatcga gcccgacatg gagctcgaga ctgagctcgg cattgactct    1380
atcaagcgtg tcgagattct ctctgaggtc caggcccagc tcaacgttga ggccaaggat    1440
gttgatgctc ttagccgcac ccgcaccgtt ggtgaggttg tcaacgccat gaaggctgag    1500
atcgctggca gctctggtgc tgccgctgct gccccggccc cggttgctgc tgctcccgct    1560
cccgtcgctg cccctgctgt cagcagcgct ctccttgaga aggctgagtc tgtcgtcatg    1620
gaggttcttg ccgccaagac tggttacgag actgacatga ttgaggccga catggagctc    1680
gagactgagc tcggcattga ctccatcaag cgtgtcgaga ttctctctga ggtccaggcc    1740
cagctcaacg ttgaggccaa ggatgtcgat gctcttagcc gcaccgcac cgttggtgag    1800 gttgtcaacg ccatgaaggc tgagatcgct ggcagctctg gtgctgccgc tgctgccccg    1860
gcccctgttg ctgcctctcc cgctcccgtc gctgccgctg cccctgctgt cagcagcgct    1920
ctccttgaga aggccgaatc tgttgtcatg gaggttctcg ccgccaagac tggttacgag    1980
actgacatga ttgaggctga catggagctc gagactgagc tcggcattga ctctatcaag    2040
cgtgtcgaga ttctctctga ggtccaggct atgcttaacg ttgaggccaa ggatgttgat    2100
gctcttagcc gcaccgcac cgttggtgag gttgtcaacg ccatgaaggc tgagatcgct    2160
ggcagctctg gtgccgccgc tgctgccccg gcccgttg ctgctgctcc ggcgccgtc       2220 actgccgctg cccctgctgt cagcagcgct ctccttgaga aggccgaatc tgttgtcatg    2280
gaggttctcg ccgccaagac tggttacgag actgacatga ttgaggccga catggagctc    2340
gagactgagc ttggcattga ctccatcaag cgtgtcgaga ttctctctga ggtccaggct    2400
atgcttaacg tcgaggccaa ggatgttgat gctcttagcc gcaccgcac cgttggtgag    2460 gttgtcaacg ccatgaaggc tgagattgct agcagctctg gtgctgctgc cctgctccg      2520 gctgctgccg ttgcaccggc ccctgctgct gccctgctg tcagcagcgc tctccttgag    2580
aaggccgaat ctgttgtcat ggaggttctc gccgccaaga ctggttacga gactgacatg    2640
attgaggccg acatggagct cgagactgag ctcggcattg actctatcaa gcgtgtcgag    2700
attctctctg aggtccaggc tatgcttaac gttgaggcca aggatgttga tgctcttagc    2760
cgcacccgca ccgttggtga ggttgtcaac gccatgaagg ctgagattgc tagcagctct    2820
ggtgctgctg cccctgctcc tgctgctgcc gctgcaccgg ccctgctgc tgcccctgct    2880 gtcagcagcg ctcttcttga gaaggctgag tctgttgtca tggaggttct cgccgccaag    2940
actggttacg agactgacat gattgaggcc gacatggagc tcgagactga gcttggcatt    3000
```

```
gactccatca agcgtgtcga gattctctct gaggtccagg ctatgcttaa cgttgaggcc    3060
aaggatgttg atgctcttag ccgcacccgc accgttggtg aggttgtcaa cgccatgaag    3120
gctgagattg ctagcagctc tggtgctgct gcccctgctc ctgctgctgc cgctgcaccg    3180
gcccctgctg ctgcccctgc tgtcagcagc gctcttcttg agaaggctga gtctgttgtc    3240
atggaggttc tcgccgccaa gactggttac gagactgaca tgattgaggc cgacatggag    3300
ctcgagactg agcttggcat tgactccatc aagcgtgtcg agattctctc tgaggtccag    3360
gctatgctta acgttgaggc caaggatgtt gatgctctta ccgcacccg caccgttggt    3420 gaggttgtca cgccatgaa ggctgagatc gctggcagct ctggtgctgc tactgcctct    3480
gcccctgctg ctgcagctgc cgcccctgct                                    3510

<210> SEQ ID NO 17
<211> LENGTH: 219
<212> TYPE: DNA
<213> ORGANISM: Ulkenia sp.

<400> SEQUENCE: 17
ctccttgcca aggctgagtc tgttgtcatg gaggttcttg ccgccaagac tggttacgag     60
actgacatga tcgagcccga catggagctc gagactgagc tcggcattga ctctatcaag    120
cgtgtcgaga ttctctctga ggtccaggcc cagctcaacg tcgaggccaa ggatgttgat    180
gctcttagcc gcacccgcac cgtcggtgag gttgtcaac                           219

<210> SEQ ID NO 18
<211> LENGTH: 219
<212> TYPE: DNA
<213> ORGANISM: Ulkenia sp.

<400> SEQUENCE: 18
cttcttgcca aggctgagac tgttgtcatg gaggttcttg ccgccaagac tggttacgag     60
actgacatga ttgagcccga catggagctc gagactgagc tcggcattga ctccatcaag    120
cgtgtcgaga ttctctctga ggttcaggcc cagctcaacg ttgaggccaa ggatgttgat    180
gctcttagcc gcacccgcac cgttggtgag gttgtcaac                           219

<210> SEQ ID NO 19
<211> LENGTH: 219
<212> TYPE: DNA
<213> ORGANISM: Ulkenia sp.

<400> SEQUENCE: 19
ctccttgaga aggctgagtc tgttgtcatg gaggttcttg ccgccaagac tggttacgag     60
actgacatga ttgaggccga catggagctc gagactgagc tcggcattga ctccatcaag    120
cgtgtcgaga ttctctctga ggtccaggcc cagctcaacg tcgaggccaa ggatgtcgat    180
gctcttagcc gcacccgcac cgttggtgag gttgtcaac                           219

<210> SEQ ID NO 20
<211> LENGTH: 219
<212> TYPE: DNA
<213> ORGANISM: Ulkenia sp.

<400> SEQUENCE: 20
cttcttgaga aggctgagac tgttgtcatg gaggttcttg ccgccaagac tggttacgag     60
actgacatga tcgagcccga catggagctc gagactgagc tcggcattga ctctatcaag    120
cgtgtcgaga ttctctctga ggtccaggcc cagctcaacg ttgaggccaa ggatgttgat    180
```

```
gctcttagcc gcacccgcac cgttggtgag gttgtcaac                219
```

<210> SEQ ID NO 21
<211> LENGTH: 219
<212> TYPE: DNA
<213> ORGANISM: Ulkenia sp.

<400> SEQUENCE: 21

```
ctccttgaga aggctgagtc tgtcgtcatg gaggttcttg ccgccaagac tggttacgag     60
actgacatga ttgaggccga catggagctc gagactgagc tcggcattga ctccatcaag    120
cgtgtcgaga ttctctctga ggtccaggcc cagctcaacg ttgaggccaa ggatgtcgat    180
gctcttagcc gcacccgcac cgttggtgag gttgtcaac                           219
```

<210> SEQ ID NO 22
<211> LENGTH: 219
<212> TYPE: DNA
<213> ORGANISM: Ulkenia sp.

<400> SEQUENCE: 22

```
ctccttgaga aggccgaatc tgttgtcatg gaggttctcg ccgccaagac tggttacgag     60
actgacatga ttgaggctga catggagctc gagactgagc tcggcattga ctctatcaag    120
cgtgtcgaga ttctctctga ggtccaggct atgcttaacg ttgaggccaa ggatgttgat    180
gctcttagcc gcacccgcac cgttggtgag gttgtcaac                           219
```

<210> SEQ ID NO 23
<211> LENGTH: 219
<212> TYPE: DNA
<213> ORGANISM: Ulkenia sp.

<400> SEQUENCE: 23

```
ctccttgaga aggccgaatc tgttgtcatg gaggttctcg ccgccaagac tggttacgag     60
actgacatga ttgaggccga catggagctc gagactgagc ttggcattga ctccatcaag    120
cgtgtcgaga ttctctctga ggtccaggct atgcttaacg tcgaggccaa ggatgttgat    180
gctcttagcc gcacccgcac cgttggtgag gttgtcaac                           219
```

<210> SEQ ID NO 24
<211> LENGTH: 219
<212> TYPE: DNA
<213> ORGANISM: Ulkenia sp.

<400> SEQUENCE: 24

```
ctccttgaga aggccgaatc tgttgtcatg gaggttctcg ccgccaagac tggttacgag     60
actgacatga ttgaggccga catggagctc gagactgagc tcggcattga ctctatcaag    120
cgtgtcgaga ttctctctga ggtccaggct atgcttaacg ttgaggccaa ggatgttgat    180
gctcttagcc gcacccgcac cgttggtgag gttgtcaac                           219
```

<210> SEQ ID NO 25
<211> LENGTH: 219
<212> TYPE: DNA
<213> ORGANISM: Ulkenia sp.

<400> SEQUENCE: 25

```
cttcttgaga aggctgagtc tgttgtcatg gaggttctcg ccgccaagac tggttacgag     60
actgacatga ttgaggccga catggagctc gagactgagc ttggcattga ctccatcaag    120
cgtgtcgaga ttctctctga ggtccaggct atgcttaacg ttgaggccaa ggatgttgat    180
```

```
gctcttagcc gcacccgcac cgttggtgag gttgtcaac                                219
```

<210> SEQ ID NO 26
<211> LENGTH: 219
<212> TYPE: DNA
<213> ORGANISM: Ulkenia sp.

<400> SEQUENCE: 26

```
cttcttgaga aggctgagtc tgttgtcatg gaggttctcg ccgccaagac tggttacgag         60
actgacatga ttgaggccga catggagctc gagactgagc ttggcattga ctccatcaag        120
cgtgtcgaga ttctctctga ggtccaggct atgcttaacg ttgaggccaa ggatgttgat        180
gctcttagcc gcacccgcac cgttggtgag gttgtcaac                                219
```

<210> SEQ ID NO 27
<211> LENGTH: 609
<212> TYPE: DNA
<213> ORGANISM: Ulkenia sp.

<400> SEQUENCE: 27

```
aagaagctcg ttggcactat tgctggtgcc cgtgaggttc gttcctcaat tgctaacatt         60
gaggctctcg gtgcaaggc aatctactcc tcttgtgatg tgaactctgc tgctgatgtc        120
gccaaggctg ttcgcgaggc tgaggctcag cttggcgccc gtgtaactgg tgtcgtccac        180
gcttctggtg tccttcgtga ccgcctcatt gagcagaagc gccccgatga gtttgatgct        240
gtcttcggca ccaaggtgac tggtctcgag aacctctttg gtgccattga catggccaac        300
cttaagcacc tcgtcctctt cagctctctt gctggtttcc acggcaacat tggtcagtct        360
gactacgcca tggctaacga ggccctcaac aagatgggtc ttgagctctc tgaccgtgtg        420
tccgtgaagt ctatttgctt cggcccctgg gatggtggca tggttacccc ccagctcaag        480
aagcagttcc agtctatggg tgttcagatc atccccgtg agggtggtgc cgatactgtg        540
gctcgcattg tcctcggctc ctcccctgct gagatccttg ttggcaactg gaccactccc        600
accaagaag                                                                 609
```

<210> SEQ ID NO 28
<211> LENGTH: 279
<212> TYPE: PRT
<213> ORGANISM: Ulkenia sp.

<400> SEQUENCE: 28

Thr Arg Ile Ala Val Ile Gly Met Ser Ala Ile Leu Pro Cys Gly Thr
1               5                   10                  15

Thr Val Arg Glu Ser Trp Glu Ala Ile Arg Asp Gly Ile Asp Cys Leu
            20                  25                  30

Ser Asp Leu Pro Glu Asp Arg Val Asp Val Thr Ala Tyr Phe Asp Pro
        35                  40                  45

Val Lys Thr Thr Lys Asp Lys Ile Tyr Cys Lys Arg Gly Gly Phe Ile
    50                  55                  60

Pro Glu Tyr Asp Phe Asp Ala Arg Glu Phe Gly Leu Asn Met Phe Gln
65                  70                  75                  80

Met Glu Asp Ser Asp Ala Asn Gln Thr Val Thr Leu Leu Lys Val Lys
                85                  90                  95

Glu Ala Leu Glu Asp Ala Gly Ile Glu Ala Leu Ser Lys Glu Lys Lys
            100                 105                 110

Asn Ile Gly Cys Val Leu Gly Ile Gly Gly Gly Gln Lys Ser Ser His
        115                 120                 125

```
Glu Phe Tyr Ser Arg Leu Asn Tyr Val Val Glu Lys Val Leu Arg
            130                 135                 140

Lys Met Gly Met Pro Glu Asp Val Gln Ala Val Glu Lys Tyr
145                 150                 155                 160

Lys Ala Asn Phe Pro Glu Trp Arg Leu Asp Ser Phe Pro Gly Phe Leu
                165                 170                 175

Gly Asn Val Thr Ala Gly Arg Cys Thr Asn Thr Phe Asn Leu Asp Gly
                180                 185                 190

Met Asn Cys Val Val Asp Ala Ala Cys Ala Ser Ser Leu Ile Ala Val
            195                 200                 205

Lys Val Ala Ile Asp Glu Leu Leu His Gly Asp Cys Asp Met Met Ile
210                 215                 220

Thr Gly Ala Thr Cys Thr Asp Asn Ser Ile Gly Met Tyr Met Ala Phe
225                 230                 235                 240

Ser Lys Thr Pro Val Phe Ser Thr Asp Pro Ser Val Arg Ala Tyr Asp
                245                 250                 255

Glu Lys Thr Lys Gly Met Leu Ile Gly Glu Gly Ser Ala Met Leu Val
                260                 265                 270

Leu Lys Arg Tyr Ala Asp Ala
            275

<210> SEQ ID NO 29
<211> LENGTH: 17
<212> TYPE: PRT
<213> ORGANISM: Ulkenia sp.

<400> SEQUENCE: 29

Gly Met Asn Cys Val Val Asp Ala Ala Cys Ala Ser Ser Leu Ile Ala
1               5                   10                  15
Val

<210> SEQ ID NO 30
<211> LENGTH: 4
<212> TYPE: PRT
<213> ORGANISM: Ulkenia sp.

<400> SEQUENCE: 30

Asp Ala Ala Cys
1

<210> SEQ ID NO 31
<211> LENGTH: 174
<212> TYPE: PRT
<213> ORGANISM: Ulkenia sp.

<400> SEQUENCE: 31

His Ala Val Ile Arg Gly Cys Ala Ser Ser Asp Gly Lys Ala Ser
1               5                   10                  15

Gly Ile Tyr Thr Pro Thr Ile Ser Gly Gln Glu Glu Ala Leu Arg Arg
                20                  25                  30

Ala Tyr Met Arg Ala Asn Val Asp Pro Ala Thr Val Thr Leu Val Glu
            35                  40                  45

Gly His Gly Thr Gly Thr Pro Val Gly Asp Arg Ile Glu Leu Thr Ala
        50                  55                  60

Leu Arg Asn Leu Phe Asp Ser Ala Tyr Gly Asn Glu Lys Glu Lys Val
65                  70                  75                  80

Ala Val Gly Ser Ile Lys Ser Asn Ile Gly His Leu Lys Ala Val Ala
                85                  90                  95
```

```
Gly Leu Ala Gly Met Ile Lys Val Ile Met Ala Leu Lys His Lys Thr
                100                 105                 110

Leu Pro Ala Thr Ile Asn Val Asp Glu Pro Pro Lys Leu Tyr Asp Asn
            115                 120                 125

Thr Pro Ile Thr Asp Ser Ser Leu Tyr Ile Asn Thr Met Asn Arg Pro
        130                 135                 140

Trp Phe Pro Ala Pro Gly Val Pro Arg Arg Ala Gly Ile Ser Ser Phe
145                 150                 155                 160

Gly Phe Gly Gly Ala Asn Tyr His Ala Val Leu Glu Glu Ala
                165                 170

<210> SEQ ID NO 32
<211> LENGTH: 460
<212> TYPE: PRT
<213> ORGANISM: Ulkenia sp.

<400> SEQUENCE: 32

Thr Arg Ile Ala Val Ile Gly Met Ser Ala Ile Leu Pro Cys Gly Thr
1               5                   10                  15

Thr Val Arg Glu Ser Trp Glu Ala Ile Arg Asp Gly Ile Asp Cys Leu
            20                  25                  30

Ser Asp Leu Pro Glu Asp Arg Val Asp Val Thr Ala Tyr Phe Asp Pro
        35                  40                  45

Val Lys Thr Thr Lys Asp Lys Ile Tyr Cys Lys Arg Gly Gly Phe Ile
50                  55                  60

Pro Glu Tyr Asp Phe Asp Ala Arg Glu Phe Gly Leu Asn Met Phe Gln
65                  70                  75                  80

Met Glu Asp Ser Asp Ala Asn Gln Thr Val Thr Leu Leu Lys Val Lys
                85                  90                  95

Glu Ala Leu Glu Asp Ala Gly Ile Glu Ala Leu Ser Lys Glu Lys Lys
            100                 105                 110

Asn Ile Gly Cys Val Leu Gly Ile Gly Gly Gly Gln Lys Ser Ser His
        115                 120                 125

Glu Phe Tyr Ser Arg Leu Asn Tyr Val Val Val Glu Lys Val Leu Arg
130                 135                 140

Lys Met Gly Met Pro Glu Glu Asp Val Gln Ala Ala Val Glu Lys Tyr
145                 150                 155                 160

Lys Ala Asn Phe Pro Glu Trp Arg Leu Asp Ser Phe Pro Gly Phe Leu
                165                 170                 175

Gly Asn Val Thr Ala Gly Arg Cys Thr Asn Thr Phe Asn Leu Asp Gly
            180                 185                 190

Met Asn Cys Val Val Asp Ala Ala Cys Ala Ser Ser Leu Ile Ala Val
        195                 200                 205

Lys Val Ala Ile Asp Glu Leu Leu His Gly Asp Cys Asp Met Met Ile
210                 215                 220

Thr Gly Ala Thr Cys Thr Asp Asn Ser Ile Gly Met Tyr Met Ala Phe
225                 230                 235                 240

Ser Lys Thr Pro Val Phe Ser Thr Asp Pro Ser Val Arg Ala Tyr Asp
                245                 250                 255

Glu Lys Thr Lys Gly Met Leu Ile Gly Glu Gly Ser Ala Met Leu Val
            260                 265                 270

Leu Lys Arg Tyr Ala Asp Ala Val Arg Asp Gly Asp Glu Ile His Ala
        275                 280                 285

Val Ile Arg Gly Cys Ala Ser Ser Ser Asp Gly Lys Ala Ser Gly Ile
290                 295                 300
```

```
Tyr Thr Pro Thr Ile Ser Gly Gln Glu Glu Ala Leu Arg Arg Ala Tyr
305                 310                 315                 320

Met Arg Ala Asn Val Asp Pro Ala Thr Val Thr Leu Val Glu Gly His
            325                 330                 335

Gly Thr Gly Thr Pro Val Gly Asp Arg Ile Glu Leu Thr Ala Leu Arg
            340                 345                 350

Asn Leu Phe Asp Ser Ala Tyr Gly Asn Glu Lys Glu Lys Val Ala Val
            355                 360                 365

Gly Ser Ile Lys Ser Asn Ile Gly His Leu Lys Ala Val Ala Gly Leu
        370                 375                 380

Ala Gly Met Ile Lys Val Ile Met Ala Leu Lys His Lys Thr Leu Pro
385                 390                 395                 400

Ala Thr Ile Asn Val Asp Glu Pro Pro Lys Leu Tyr Asp Asn Thr Pro
                405                 410                 415

Ile Thr Asp Ser Ser Leu Tyr Ile Asn Thr Met Asn Arg Pro Trp Phe
                420                 425                 430

Pro Ala Pro Gly Val Pro Arg Arg Ala Gly Ile Ser Ser Phe Gly Phe
            435                 440                 445

Gly Gly Ala Asn Tyr His Ala Val Leu Glu Glu Ala
        450                 455                 460

<210> SEQ ID NO 33
<211> LENGTH: 332
<212> TYPE: PRT
<213> ORGANISM: Ulkenia sp.

<400> SEQUENCE: 33

Leu Phe Ser Gly Gln Gly Ala Gln Tyr Thr His Met Phe Ser Glu Val
1               5                   10                  15

Ala Met Asn Trp Pro Gln Phe Arg Glu Ser Ile Ser Asp Met Asp Arg
            20                  25                  30

Ala Gln Ala Lys Val Ala Gly Ala Asp Lys Asp Tyr Glu Arg Val Ser
        35                  40                  45

Gln Val Leu Tyr Pro Arg Lys Pro Tyr Asn Ser Glu Pro Glu Gln Asp
    50                  55                  60

His Lys Lys Ile Ser Leu Thr Ser Tyr Ser Gln Pro Ser Thr Leu Ala
65                  70                  75                  80

Cys Ala Leu Gly Ala Tyr Glu Ile Phe Lys Gln Ala Gly Phe Lys Pro
                85                  90                  95

Asp Phe Ala Ala Gly His Ser Leu Gly Glu Phe Ala Ala Leu Tyr Ala
            100                 105                 110

Ala Asp Cys Val Asn Arg Asp Asp Leu Phe Glu Leu Val Cys Arg Arg
        115                 120                 125

Ala Arg Ile Met Gly Gly Lys Asp Ala Pro Ala Thr Pro Lys Gly Cys
130                 135                 140

Met Ala Ala Val Ile Gly Pro Asn Ala Glu Lys Ile Gln Ile Arg Thr
145                 150                 155                 160

Ala Asp Val Trp Leu Gly Asn Cys Asn Ser Pro Ser Gln Thr Val Ile
                165                 170                 175

Thr Gly Ser Val Glu Gly Ile Lys Lys Glu Ser Glu Leu Leu Gln Ser
            180                 185                 190

Glu Gly Phe Arg Val Val Pro Leu Ala Cys Glu Ser Ala Phe His Ser
        195                 200                 205

Pro Gln Met Gln Asn Ala Ser Ser Ala Phe Lys Asp Val Leu Ser Lys
    210                 215                 220
```

```
Val Ala Phe Arg Gln Pro Ser Ala Gln Thr Lys Leu Phe Ser Asn Val
225                 230                 235                 240

Ser Gly Glu Thr Tyr Ser Asn Asn Ala Gln Asp Leu Leu Lys Glu His
            245                 250                 255

Met Thr Ser Ser Val Lys Phe Ile Ser Gln Val Arg Asn Met His Ser
        260                 265                 270

Ala Gly Ala Arg Ile Phe Val Glu Phe Gly Pro Lys Gln Val Leu Ser
    275                 280                 285

Lys Leu Val Ser Glu Thr Leu Lys Asp Asp Pro Ser Ile Ile Thr Ile
290                 295                 300

Ser Val Asn Pro Ser Ser Gly Lys Asp Ala Asp Ile Gln Leu Arg Glu
305                 310                 315                 320

Ala Ala Val Gln Leu Val Val Ala Gly Val Asn Leu
                325                 330

<210> SEQ ID NO 34
<211> LENGTH: 1170
<212> TYPE: PRT
<213> ORGANISM: Ulkenia sp.

<400> SEQUENCE: 34

Ala Gln Ala Gln Ile Gln Lys Ala Lys Ala Asp Ala Ala Glu Ala Asp
1               5                   10                  15

Lys Lys Leu Ala Ala Lys Asp Glu Ala Lys Arg Ala Ala Ala Ala Ser
            20                  25                  30

Ala Pro Val Gln Lys Gln Val Asp Thr Thr Ile Val Asp Lys His Arg
        35                  40                  45

Ala Ile Leu Lys Ser Met Leu Ala Glu Leu Asp Cys Tyr Ser Thr Pro
    50                  55                  60

Gly Ala Val Ser Ser Ser Phe Gln Ala Pro Val Ala Ala Thr Pro Ala
65                  70                  75                  80

Pro Val Ala Ala Pro Val Ala Ala Pro Ala Pro Ala Val Asn Asn
                85                  90                  95

Ala Leu Leu Ala Lys Ala Glu Ser Val Val Met Glu Val Leu Ala Ala
            100                 105                 110

Lys Thr Gly Tyr Glu Thr Asp Met Ile Glu Pro Asp Met Glu Leu Glu
        115                 120                 125

Thr Glu Leu Gly Ile Asp Ser Ile Lys Arg Val Glu Ile Leu Ser Glu
    130                 135                 140

Val Gln Ala Gln Leu Asn Val Glu Ala Lys Asp Val Asp Ala Leu Ser
145                 150                 155                 160

Arg Thr Arg Thr Val Gly Glu Val Val Asn Ala Met Lys Ala Glu Ile
                165                 170                 175

Ala Gly Ser Ser Gly Ala Ala Ala Ala Pro Ala Pro Val Ala Ala
            180                 185                 190

Ala Pro Ala Ala Pro Ala Pro Ala Val Asn Ser Ala Leu Leu Ala Lys
        195                 200                 205

Ala Glu Thr Val Val Met Glu Val Leu Ala Ala Lys Thr Gly Tyr Glu
    210                 215                 220

Thr Asp Met Ile Glu Pro Asp Met Glu Leu Glu Thr Glu Leu Gly Ile
225                 230                 235                 240

Asp Ser Ile Lys Arg Val Glu Ile Leu Ser Glu Val Gln Ala Gln Leu
                245                 250                 255

Asn Val Glu Ala Lys Asp Val Asp Ala Leu Ser Arg Thr Arg Thr Val
            260                 265                 270
```

-continued

```
Gly Glu Val Val Asn Ala Met Lys Ala Glu Ile Ala Gly Ser Ser Gly
            275                 280                 285

Ala Ala Ala Ala Ala Pro Ala Pro Val Ala Ala Pro Ala Pro Val
290                 295                 300

Ala Ala Ala Ala Pro Ala Val Ser Ser Ala Leu Leu Glu Lys Ala Glu
305                 310                 315                 320

Ser Val Val Met Glu Val Leu Ala Ala Lys Thr Gly Tyr Glu Thr Asp
                    325                 330                 335

Met Ile Glu Ala Asp Met Glu Leu Glu Thr Glu Leu Gly Ile Asp Ser
                340                 345                 350

Ile Lys Arg Val Glu Ile Leu Ser Glu Val Gln Ala Gln Leu Asn Val
                    355                 360                 365

Glu Ala Lys Asp Val Asp Ala Leu Ser Arg Thr Arg Thr Val Gly Glu
        370                 375                 380

Val Val Asn Ala Met Lys Ala Glu Ile Ala Gly Ser Ser Gly Ala Ala
385                 390                 395                 400

Ala Pro Ala Pro Val Ala Ala Pro Ala Pro Val Ala Ala Ala
                    405                 410                 415

Pro Ala Val Asn Ser Ala Leu Leu Glu Lys Ala Glu Thr Val Val Met
                420                 425                 430

Glu Val Leu Ala Ala Lys Thr Gly Tyr Glu Thr Asp Met Ile Glu Pro
                435                 440                 445

Asp Met Glu Leu Glu Thr Glu Leu Gly Ile Asp Ser Ile Lys Arg Val
        450                 455                 460

Glu Ile Leu Ser Glu Val Gln Ala Gln Leu Asn Val Glu Ala Lys Asp
465                 470                 475                 480

Val Asp Ala Leu Ser Arg Thr Arg Thr Val Gly Glu Val Val Asn Ala
                    485                 490                 495

Met Lys Ala Glu Ile Ala Gly Ser Ser Gly Ala Ala Ala Ala Pro
                500                 505                 510

Ala Pro Val Ala Ala Pro Ala Pro Val Ala Ala Pro Ala Val Ser
            515                 520                 525

Ser Ala Leu Leu Glu Lys Ala Glu Ser Val Val Met Glu Val Leu Ala
        530                 535                 540

Ala Lys Thr Gly Tyr Glu Thr Asp Met Ile Glu Ala Asp Met Glu Leu
545                 550                 555                 560

Glu Thr Glu Leu Gly Ile Asp Ser Ile Lys Arg Val Glu Ile Leu Ser
                    565                 570                 575

Glu Val Gln Ala Gln Leu Asn Val Glu Ala Lys Asp Val Asp Ala Leu
                580                 585                 590

Ser Arg Thr Arg Thr Val Gly Glu Val Val Asn Ala Met Lys Ala Glu
            595                 600                 605

Ile Ala Gly Ser Ser Gly Ala Ala Ala Ala Pro Ala Pro Val Ala
        610                 615                 620

Ala Ser Pro Ala Pro Val Ala Ala Ala Pro Ala Val Ser Ser Ala
625                 630                 635                 640

Leu Leu Glu Lys Ala Glu Ser Val Val Met Glu Val Leu Ala Ala Lys
                    645                 650                 655

Thr Gly Tyr Glu Thr Asp Met Ile Glu Ala Asp Met Glu Leu Glu Thr
                660                 665                 670

Glu Leu Gly Ile Asp Ser Ile Lys Arg Val Glu Ile Leu Ser Glu Val
            675                 680                 685

Gln Ala Met Leu Asn Val Glu Ala Lys Asp Val Asp Ala Leu Ser Arg
        690                 695                 700
```

-continued

```
Thr Arg Thr Val Gly Glu Val Val Asn Ala Met Lys Ala Glu Ile Ala
705                 710                 715                 720

Gly Ser Ser Gly Ala Ala Ala Ala Pro Ala Pro Val Ala Ala Ala
            725                 730                 735

Pro Ala Pro Val Thr Ala Ala Ala Pro Ala Val Ser Ser Ala Leu Leu
            740                 745                 750

Glu Lys Ala Glu Ser Val Val Met Glu Val Leu Ala Ala Lys Thr Gly
            755                 760                 765

Tyr Glu Thr Asp Met Ile Glu Ala Asp Met Glu Leu Glu Thr Glu Leu
            770                 775                 780

Gly Ile Asp Ser Ile Lys Arg Val Glu Ile Leu Ser Glu Val Gln Ala
785                 790                 795                 800

Met Leu Asn Val Glu Ala Lys Asp Val Asp Ala Leu Ser Arg Thr Arg
            805                 810                 815

Thr Val Gly Glu Val Val Asn Ala Met Lys Ala Glu Ile Ala Ser Ser
            820                 825                 830

Ser Gly Ala Ala Ala Pro Ala Pro Ala Ala Val Ala Pro Ala Pro
            835                 840                 845

Ala Ala Ala Pro Ala Val Ser Ser Ala Leu Leu Glu Lys Ala Glu Ser
            850                 855                 860

Val Val Met Glu Val Leu Ala Ala Lys Thr Gly Tyr Glu Thr Asp Met
865                 870                 875                 880

Ile Glu Ala Asp Met Glu Leu Glu Thr Glu Leu Gly Ile Asp Ser Ile
                885                 890                 895

Lys Arg Val Glu Ile Leu Ser Glu Val Gln Ala Met Leu Asn Val Glu
                900                 905                 910

Ala Lys Asp Val Asp Ala Leu Ser Arg Thr Arg Thr Val Gly Glu Val
            915                 920                 925

Val Asn Ala Met Lys Ala Glu Ile Ala Ser Ser Ser Gly Ala Ala Ala
            930                 935                 940

Pro Ala Pro Ala Ala Ala Ala Pro Ala Pro Ala Ala Ala Pro Ala
945                 950                 955                 960

Val Ser Ser Ala Leu Leu Glu Lys Ala Glu Ser Val Val Met Glu Val
            965                 970                 975

Leu Ala Ala Lys Thr Gly Tyr Glu Thr Asp Met Ile Glu Ala Asp Met
            980                 985                 990

Glu Leu Glu Thr Glu Leu Gly Ile Asp Ser Ile Lys Arg Val Glu Ile
            995                 1000                1005

Leu Ser Glu Val Gln Ala Met Leu Asn Val Glu Ala Lys Asp Val
    1010                1015                1020

Asp Ala Leu Ser Arg Thr Arg Thr Val Gly Glu Val Val Asn Ala
    1025                1030                1035

Met Lys Ala Glu Ile Ala Ser Ser Ser Gly Ala Ala Ala Pro Ala
    1040                1045                1050

Pro Ala Ala Ala Ala Pro Ala Pro Ala Ala Ala Pro Ala Val
    1055                1060                1065

Ser Ser Ala Leu Leu Glu Lys Ala Glu Ser Val Val Met Glu Val
    1070                1075                1080

Leu Ala Ala Lys Thr Gly Tyr Glu Thr Asp Met Ile Glu Ala Asp
    1085                1090                1095

Met Glu Leu Glu Thr Glu Leu Gly Ile Asp Ser Ile Lys Arg Val
    1100                1105                1110

Glu Ile Leu Ser Glu Val Gln Ala Met Leu Asn Val Glu Ala Lys
```

-continued

```
                 1115                1120                1125

Asp Val  Asp Ala Leu Ser Arg  Thr Arg Thr Val Gly  Glu Val Val
         1130                1135                1140

Asn Ala  Met Lys Ala Glu Ile  Ala Gly Ser Ser Gly  Ala Ala Thr
         1145                1150                1155

Ala Ser  Ala Pro Ala Ala Ala  Ala Ala Pro Ala
         1160                1165                1170

<210> SEQ ID NO 35
<211> LENGTH: 73
<212> TYPE: PRT
<213> ORGANISM: Ulkenia sp.

<400> SEQUENCE: 35

Leu Leu Ala Lys Ala Glu Ser Val Val Met Glu Val Leu Ala Ala Lys
1               5                   10                  15

Thr Gly Tyr Glu Thr Asp Met Ile Glu Pro Asp Met Glu Leu Glu Thr
            20                  25                  30

Glu Leu Gly Ile Asp Ser Ile Lys Arg Val Glu Ile Leu Ser Glu Val
        35                  40                  45

Gln Ala Gln Leu Asn Val Glu Ala Lys Asp Val Asp Ala Leu Ser Arg
    50                  55                  60

Thr Arg Thr Val Gly Glu Val Val Asn
65                  70

<210> SEQ ID NO 36
<211> LENGTH: 73
<212> TYPE: PRT
<213> ORGANISM: Ulkenia sp.

<400> SEQUENCE: 36

Leu Leu Ala Lys Ala Glu Thr Val Val Met Glu Val Leu Ala Ala Lys
1               5                   10                  15

Thr Gly Tyr Glu Thr Asp Met Ile Glu Pro Asp Met Glu Leu Glu Thr
            20                  25                  30

Glu Leu Gly Ile Asp Ser Ile Lys Arg Val Glu Ile Leu Ser Glu Val
        35                  40                  45

Gln Ala Gln Leu Asn Val Glu Ala Lys Asp Val Asp Ala Leu Ser Arg
    50                  55                  60

Thr Arg Thr Val Gly Glu Val Val Asn
65                  70

<210> SEQ ID NO 37
<211> LENGTH: 73
<212> TYPE: PRT
<213> ORGANISM: Ulkenia sp.

<400> SEQUENCE: 37

Leu Leu Glu Lys Ala Glu Ser Val Val Met Glu Val Leu Ala Ala Lys
1               5                   10                  15

Thr Gly Tyr Glu Thr Asp Met Ile Glu Ala Asp Met Glu Leu Glu Thr
            20                  25                  30

Glu Leu Gly Ile Asp Ser Ile Lys Arg Val Glu Ile Leu Ser Glu Val
        35                  40                  45

Gln Ala Gln Leu Asn Val Glu Ala Lys Asp Val Asp Ala Leu Ser Arg
    50                  55                  60

Thr Arg Thr Val Gly Glu Val Val Asn
65                  70
```

-continued

<210> SEQ ID NO 38
<211> LENGTH: 73
<212> TYPE: PRT
<213> ORGANISM: Ulkenia sp.

<400> SEQUENCE: 38

Leu Leu Glu Lys Ala Glu Thr Val Val Met Glu Val Leu Ala Ala Lys
1               5                   10                  15

Thr Gly Tyr Glu Thr Asp Met Ile Glu Pro Asp Met Glu Leu Glu Thr
            20                  25                  30

Glu Leu Gly Ile Asp Ser Ile Lys Arg Val Glu Ile Leu Ser Glu Val
        35                  40                  45

Gln Ala Gln Leu Asn Val Glu Ala Lys Asp Val Asp Ala Leu Ser Arg
    50                  55                  60

Thr Arg Thr Val Gly Glu Val Val Asn
65                  70

<210> SEQ ID NO 39
<211> LENGTH: 73
<212> TYPE: PRT
<213> ORGANISM: Ulkenia sp.

<400> SEQUENCE: 39

Leu Leu Glu Lys Ala Glu Ser Val Val Met Glu Val Leu Ala Ala Lys
1               5                   10                  15

Thr Gly Tyr Glu Thr Asp Met Ile Glu Ala Asp Met Glu Leu Glu Thr
            20                  25                  30

Glu Leu Gly Ile Asp Ser Ile Lys Arg Val Glu Ile Leu Ser Glu Val
        35                  40                  45

Gln Ala Gln Leu Asn Val Glu Ala Lys Asp Val Asp Ala Leu Ser Arg
    50                  55                  60

Thr Arg Thr Val Gly Glu Val Val Asn
65                  70

<210> SEQ ID NO 40
<211> LENGTH: 73
<212> TYPE: PRT
<213> ORGANISM: Ulkenia sp.

<400> SEQUENCE: 40

Leu Leu Glu Lys Ala Glu Ser Val Val Met Glu Val Leu Ala Ala Lys
1               5                   10                  15

Thr Gly Tyr Glu Thr Asp Met Ile Glu Ala Asp Met Glu Leu Glu Thr
            20                  25                  30

Glu Leu Gly Ile Asp Ser Ile Lys Arg Val Glu Ile Leu Ser Glu Val
        35                  40                  45

Gln Ala Met Leu Asn Val Glu Ala Lys Asp Val Asp Ala Leu Ser Arg
    50                  55                  60

Thr Arg Thr Val Gly Glu Val Val Asn
65                  70

<210> SEQ ID NO 41
<211> LENGTH: 73
<212> TYPE: PRT
<213> ORGANISM: Ulkenia sp.

<400> SEQUENCE: 41

Leu Leu Glu Lys Ala Glu Ser Val Val Met Glu Val Leu Ala Ala Lys
1               5                   10                  15

```
Thr Gly Tyr Glu Thr Asp Met Ile Glu Ala Asp Met Glu Leu Glu Thr
            20                  25                  30

Glu Leu Gly Ile Asp Ser Ile Lys Arg Val Glu Ile Leu Ser Glu Val
            35                  40                  45

Gln Ala Met Leu Asn Val Glu Ala Lys Asp Val Asp Ala Leu Ser Arg
 50                  55                  60

Thr Arg Thr Val Gly Glu Val Val Asn
 65                  70

<210> SEQ ID NO 42
<211> LENGTH: 73
<212> TYPE: PRT
<213> ORGANISM: Ulkenia sp.

<400> SEQUENCE: 42

Leu Leu Glu Lys Ala Glu Ser Val Val Met Glu Val Leu Ala Ala Lys
 1               5                  10                  15

Thr Gly Tyr Glu Thr Asp Met Ile Glu Ala Asp Met Glu Leu Glu Thr
            20                  25                  30

Glu Leu Gly Ile Asp Ser Ile Lys Arg Val Glu Ile Leu Ser Glu Val
            35                  40                  45

Gln Ala Met Leu Asn Val Glu Ala Lys Asp Val Asp Ala Leu Ser Arg
 50                  55                  60

Thr Arg Thr Val Gly Glu Val Val Asn
 65                  70

<210> SEQ ID NO 43
<211> LENGTH: 73
<212> TYPE: PRT
<213> ORGANISM: Ulkenia sp.

<400> SEQUENCE: 43

Leu Leu Glu Lys Ala Glu Ser Val Val Met Glu Val Leu Ala Ala Lys
 1               5                  10                  15

Thr Gly Tyr Glu Thr Asp Met Ile Glu Ala Asp Met Glu Leu Glu Thr
            20                  25                  30

Glu Leu Gly Ile Asp Ser Ile Lys Arg Val Glu Ile Leu Ser Glu Val
            35                  40                  45

Gln Ala Met Leu Asn Val Glu Ala Lys Asp Val Asp Ala Leu Ser Arg
 50                  55                  60

Thr Arg Thr Val Gly Glu Val Val Asn
 65                  70

<210> SEQ ID NO 44
<211> LENGTH: 73
<212> TYPE: PRT
<213> ORGANISM: Ulkenia sp.

<400> SEQUENCE: 44

Leu Leu Glu Lys Ala Glu Ser Val Val Met Glu Val Leu Ala Ala Lys
 1               5                  10                  15

Thr Gly Tyr Glu Thr Asp Met Ile Glu Ala Asp Met Glu Leu Glu Thr
            20                  25                  30

Glu Leu Gly Ile Asp Ser Ile Lys Arg Val Glu Ile Leu Ser Glu Val
            35                  40                  45

Gln Ala Met Leu Asn Val Glu Ala Lys Asp Val Asp Ala Leu Ser Arg
 50                  55                  60

Thr Arg Thr Val Gly Glu Val Val Asn
 65                  70
```

<210> SEQ ID NO 45
<211> LENGTH: 203
<212> TYPE: PRT
<213> ORGANISM: Ulkenia sp.

<400> SEQUENCE: 45

```
Lys Lys Leu Val Gly Thr Ile Ala Gly Ala Arg Glu Val Arg Ser Ser
1               5                   10                  15

Ile Ala Asn Ile Glu Ala Leu Gly Gly Lys Ala Ile Tyr Ser Ser Cys
                20                  25                  30

Asp Val Asn Ser Ala Ala Asp Val Ala Lys Ala Val Arg Glu Ala Glu
            35                  40                  45

Ala Gln Leu Gly Ala Arg Val Thr Gly Val Val His Ala Ser Gly Val
        50                  55                  60

Leu Arg Asp Arg Leu Ile Glu Gln Lys Arg Pro Asp Glu Phe Asp Ala
65                  70                  75                  80

Val Phe Gly Thr Lys Val Thr Gly Leu Glu Asn Leu Phe Gly Ala Ile
                85                  90                  95

Asp Met Ala Asn Leu Lys His Leu Val Leu Phe Ser Ser Leu Ala Gly
            100                 105                 110

Phe His Gly Asn Ile Gly Gln Ser Asp Tyr Ala Met Ala Asn Glu Ala
        115                 120                 125

Leu Asn Lys Met Gly Leu Glu Leu Ser Asp Arg Val Ser Val Lys Ser
130                 135                 140

Ile Cys Phe Gly Pro Trp Asp Gly Gly Met Val Thr Pro Gln Leu Lys
145                 150                 155                 160

Lys Gln Phe Gln Ser Met Gly Val Gln Ile Ile Pro Arg Glu Gly Gly
                165                 170                 175

Ala Asp Thr Val Ala Arg Ile Val Leu Gly Ser Ser Pro Ala Glu Ile
            180                 185                 190

Leu Val Gly Asn Trp Thr Thr Pro Thr Lys Lys
        195                 200
```

<210> SEQ ID NO 46
<211> LENGTH: 780
<212> TYPE: DNA
<213> ORGANISM: Ulkenia sp.

<400> SEQUENCE: 46

```
aagcgcattg ccgtggtggg catggccgtg caatacgcgg gctgcaaaga caaggaagag      60
ttctggaaag tagtcatggg cggtgaggct gcatggacta agattagcga taaacgcctc     120
ggatccaaca agcgagccga gcacttcaaa gcagagcgta gcaaatttgc agataccttt     180
tgcaacgaga actacggctg cgtcgatgac tccgtcgata cgaacacga gcttctcctt      240
aagctctcca gaaggctctc tccgagaca tcggtctccg actctacaag gtgcggtatt      300
gtgagcggat gcctgtcctt tcccatggac aacctccagg gcgaactcct caatgtgtac     360
caaaaccacg tcgaaaagaa actcggcgct cgcgtcttca aggatgcctc caagtggtcc     420
gagcgtgagc agtcgcagaa ccccgaggct ggtgaccgcc gcatctttat ggacccggca     480
tccttcgtag cagaagagct caacctcggt cctcttcact actctgtcga tgctgcctgt     540
gccaccgccc tttacgtcct tcgcctcgcc caggaccacc tcgtttccgg tgctgctgat     600
gtcatgctcg ctggtgcaac ttgcttcccg gagccctttt tcattctctc cggattctcc     660
actttccagg ccatgcctgt atcgggagac ggcatctcgt acccgcttca caaggacagt     720
```

```
cagggtctca cccctggtga aggtggtgcc attatggttc tcaagcgcct tgacgacgct    780
```

<210> SEQ ID NO 47
<211> LENGTH: 51
<212> TYPE: DNA
<213> ORGANISM: Ulkenia sp.

<400> SEQUENCE: 47

```
cctcttcact actctgtcga tgctgcctgt gccaccgccc tttacgtcct t             51
```

<210> SEQ ID NO 48
<211> LENGTH: 12
<212> TYPE: DNA
<213> ORGANISM: Ulkenia sp.

<400> SEQUENCE: 48

```
gatgctgcct gt                                                        12
```

<210> SEQ ID NO 49
<211> LENGTH: 477
<212> TYPE: DNA
<213> ORGANISM: Ulkenia sp.

<400> SEQUENCE: 49

```
tacggtactc tgctcggtgc taccatcagc aatgctggct gtggtcttcc cctcaagccg    60
cacttgccca gcgagaagtc ctgcctcatt gatacctaca gcgcgtcaa cgtgcacccg    120
cacaagatcc agtacgtcga gtgccacgca acgggtactc cccagggaga ccgcgttgag   180
attgatgccg tcaaggcttg cttcgagggc aaggtgcctc gctttggaag ctccaagggt   240
aactttggcc acacactcgt tgcagctggt ttcgcaggca tgtgcaaggt actccttgcc   300
atgaagcatg gtgtgatccc gcccactcct ggtgtcgatg gatcttccca aatggacccg   360
cttgtggtct ctgagcccat cccatggccc gacactgagg gcgagcccaa gcgcgctggt   420
ctctccgctt tcggctttgg tggcaccaac gcccacgcag tctttgagga gtttgac      477
```

<210> SEQ ID NO 50
<211> LENGTH: 1278
<212> TYPE: DNA
<213> ORGANISM: Ulkenia sp.

<400> SEQUENCE: 50

```
aagcgcattg ccgtggtggg catggccgtg caatacgcgg gctgcaaaga caaggaagag    60
ttctggaaag tagtcatggg cggtgaggct gcatggacta agattagcga taaacgcctc   120
ggatccaaca gcgagccga gcacttcaaa gcagagcgta gcaaatttgc agataccttt   180
tgcaacgaga actacggctg cgtcgatgac tccgtcgata cgaacacga gcttctcctt   240
aagctctcca agaaggctct ctccgagaca tcggtctccg actctacaag gtgcggtatt   300
gtgagcggat gcctgtcctt tcccatggac aacctccagg gcgaactcct caatgtgtac   360
caaaaccacg tcgaaaagaa actcggcgct cgcgtcttca aggatgcctc caagtggtcc   420
gagcgtgagc agtcgcagaa ccccgaggct ggtgaccgcc gcatctttat ggacccggca   480
tccttcgtag cagaagagct caacctcggt cctcttcact actctgtcga tgctgcctgt   540
gccaccgccc tttacgtcct tcgcctcgcc caggaccacc tcgtttccgg tgctgctgat   600
gtcatgctcg ctggtgcaac ttgcttcccg gagcctttt tcattctctc cggattctcc   660
actttccagg ccatgcctgt atcgggagac ggcatctcgt acccgcttca caaggacagt   720
cagggtctca cccctggtga aggtggtgcc attatggttc tcaagcgcct tgacgacgct   780
```

```
attcgcgatg gagaccacat ttacggtact ctgctcggtg ctaccatcag caatgctggc      840
tgtggtcttc ccctcaagcc gcacttgccc agcgagaagt cctgcctcat tgatacctac      900
aagcgcgtca acgtgcaccc gcacaagatc cagtacgtcg agtgccacgc aacgggtact      960
ccccagggag accgcgttga gattgatgcc gtcaaggctt gcttcgaggg caaggtgcct     1020
cgctttggaa gctccaaggg taactttggc cacacactcg ttgcagctgg tttcgcaggc     1080
atgtgcaagg tactccttgc catgaagcat ggtgtgatcc cgcccactcc tggtgtcgat     1140
ggatcttccc aaatggaccc gcttgtggtc tctgagccca tcccatggcc cgacactgag     1200
ggcgagccca gcgcgctgg tctctccgct ttcggctttg gtggcaccaa cgcccacgca     1260
gtctttgagg agtttgac                                                  1278

<210> SEQ ID NO 51
<211> LENGTH: 801
<212> TYPE: DNA
<213> ORGANISM: Ulkenia sp.

<400> SEQUENCE: 51
atgcgcattg ctattaccgg tatggatgcc accttcggct ccctcaaggg cctggacgcc       60
tttgagcgtg ccatctacaa tggccaacat ggtgctgtgc cattgcctga aagcgctgg      120 cgtttccttg gtaaagacaa ggactttttg gacctgtgcg gtgtcaagga ggtgccccac      180
ggatgctaca ttgaggacgt cgaggtggac tttagccgcc tgcgcacgcc catgacgcca      240
gacgacatgt tgcgccccat gcagctactt gctgtcacaa ccatcgaccg tgccattctc      300
aactctggcc tcaagaaggg aggtaaggtc gctgtcttcg tcggccttgg cactgacctt      360
gagctctacc gtcaccgcgc ccgcgttgcc ctcaaggagc gtgctcgtcc cgaagccgct      420
tcagccctca atgatatgat gtcctacatc aacgattgcg gtaccgctac ctcgtacaca      480
tcctacatcg gcaacctcgt ggccacccgc gtgtcttcac aatggggttt cgagggtcct      540
tctttcacca tcacagaggg caacaactcc gtctaccgtt gcgcagagtt gggcaagtac      600
ttgctcgaga ctggcgaggt cgaggccgta gtgatcgccg gtgtggatct ttgcgccagc      660
gctgagaatc tctacgtgaa gtcgcgtcgt ttcaaggtct cggagcagga gagcccgcgg      720
gccagcttcg actccggcgc tgacggctac tttgttggtg agggatgtgg tgccctcgtc      780
ctcaagcgcg agagcgactg c                                                801

<210> SEQ ID NO 52
<211> LENGTH: 792
<212> TYPE: DNA
<213> ORGANISM: Ulkenia sp.

<400> SEQUENCE: 52
gctgctttcg gactgagcct tggagagatt tccatggttt ttgcctttt tgagaagaac        60 ggccttgtct ctgaggagct gacaactaaa ctccgcaact cggaggtctg gcgtaaggcc      120
ctcgctgttg agtttgacgc cctccgcaag gcctggaata ttccccaaga taccctgtc      180 agcgagttct ggcaaggata cgtggtacgt ggaacccgcg aggccgttga agcggccatc      240
ggccccaaca ataagtacgt gcacttgacc attgtcaacg atgccaacag tgctctcatc      300
agtggcaagc ctgaagattg caaggctgcc attgctcgcc tgagcagcaa cctccctgct      360
ttgcccgtgg accttggtat gtgtggccac tgccccgtgg tcgagccgta cggcaagcag      420
atcgctgaga tccatagcgt cctcgagatt cccgaggttg ccggccttga cctgtacacg      480
agcgtcaacc agaagaagct tgttaacaag tccactggag ccagcgacga gtacgcaccc      540
```

```
agctttggtg aatacgcagc acagctgtac actgttcagg cagactttcc taagatcgcc    600
aagaccgtta gcgacaagaa ctttgacgtc tttgttgaga ctggtcccaa cgcccaccgt    660
agcgccgcaa ttcgcgccac ccttggaaat agcaagcctt tgtcaccgg atccatggac     720 cgccagaacg agaatgcttg gacaaccatg gtcaagctgg ttgcctctct ccaagcccac    780
cgcgtgcctg gc                                                         792
```

<210> SEQ ID NO 53
<211> LENGTH: 1302
<212> TYPE: DNA
<213> ORGANISM: Ulkenia sp.

<400> SEQUENCE: 53

```
agccgtgcct tcatggagac atatggtgta tccgccccca tgtacaccgg cgccatggca      60
aagggcattg catccgctga gatggttatc gctgccggaa agcgcggcat ccttggttct     120
ctcggtgctg tggtcttcc tatcgccacc gtacgcaagg ctctcgaagc tatccaggct     180
gaactgccca agggcccta cgctgtcaac ctcatccact ctcccttcga cagcaacctc     240
gagaagggta acgtcgacct cttcctcgag aagggcgtca ctgtcgttga agcctccgcc    300
tttatgacct tgaccccgca gctcgtgcgc taccgtgctg caggtctctc tcgcgctgct    360
gatggctcca cggttattaa gaaccgcgtc atcggtaagg tttctcgcac agagcttgcc    420
gcaatgttta tccgtcccgc gcccgagaat ctcctcgaga agctgctgaa gtccggcgag    480
atcacccaag agcaggctgc tctcgcacgc acagtgcctg tggcagacga cattgccgtt    540
gaggcggact ccggtggcca caccgataac cgccccatcc acgtcatcct ccctctcatt    600
gtcaacctcc gtgatcgtct gcacaaggag tgcggctacc ctgcccacct tcgcgttcgc    660
gttggtgctg tggtggcat tggatgccct caggccgcca ttgccacctt caacatgggc    720
gcggccttca tcgtcactgg taccgtaaac cagatgagta agcaagctgg aacctgtgac    780
accgttcgca agcagctctc acaagccacc tactccgaca tctgcatggc cccagcagct    840 gacatgttg aggaaggtgt caagctccag gtgctcaaga agggaactat gttcccctcg     900
cgtgccaaca agctctatga gctcttcgtc aagtatgact cctttgagtc catggctcct    960
ggagagctgg aacgtgtgga gaagcgcatt ttcaagaagt ctctgtcaga gtttgggaa    1020 gagaccaagg acttctacat caacaggttg cagaacccgg agaagattga gcgcgcggag  1080
cgtgacccca gcttaagat gtccttgtgc ttccgctggt accttggttt ggcgagcttc   1140
tgggcaaacg ctggcatccc ggaccgtgcc atggactacc aggtttggtg tggcccagcg  1200
attggatctt tcaacgactt catcaagggt acctaccttg accccgccgt tgccaacgag  1260 tacccgcgatg ttgtgcaaat caacttgcag atcctccgtg gt                    1302
```

<210> SEQ ID NO 54
<211> LENGTH: 260
<212> TYPE: PRT
<213> ORGANISM: Ulkenia sp.

<400> SEQUENCE: 54

```
Lys Arg Ile Ala Val Gly Met Ala Val Gln Tyr Ala Gly Cys Lys
1               5                   10                  15

Asp Lys Glu Glu Phe Trp Lys Val Val Met Gly Gly Glu Ala Ala Trp
                20                  25                  30

Thr Lys Ile Ser Asp Lys Arg Leu Gly Ser Asn Lys Arg Ala Glu His
            35                  40                  45

Phe Lys Ala Glu Arg Ser Lys Phe Ala Asp Thr Phe Cys Asn Glu Asn
```

```
                50                  55                  60
Tyr Gly Cys Val Asp Asp Ser Val Asp Asn Glu His Glu Leu Leu Leu
 65                  70                  75                  80

Lys Leu Ser Lys Lys Ala Leu Ser Glu Thr Ser Val Ser Asp Ser Thr
                 85                  90                  95

Arg Cys Gly Ile Val Ser Gly Cys Leu Ser Phe Pro Met Asp Asn Leu
            100                 105                 110

Gln Gly Glu Leu Leu Asn Val Tyr Gln Asn His Val Glu Lys Lys Leu
            115                 120                 125

Gly Ala Arg Val Phe Lys Asp Ala Ser Lys Trp Ser Glu Arg Glu Gln
        130                 135                 140

Ser Gln Asn Pro Glu Ala Gly Asp Arg Arg Ile Phe Met Asp Pro Ala
145                 150                 155                 160

Ser Phe Val Ala Glu Glu Leu Asn Leu Gly Pro Leu His Tyr Ser Val
                165                 170                 175

Asp Ala Ala Cys Ala Thr Ala Leu Tyr Val Leu Arg Leu Ala Gln Asp
            180                 185                 190

His Leu Val Ser Gly Ala Ala Asp Val Met Leu Ala Gly Ala Thr Cys
        195                 200                 205

Phe Pro Glu Pro Phe Phe Ile Leu Ser Gly Phe Ser Thr Phe Gln Ala
    210                 215                 220

Met Pro Val Ser Gly Asp Gly Ile Ser Tyr Pro Leu His Lys Asp Ser
225                 230                 235                 240

Gln Gly Leu Thr Pro Gly Glu Gly Gly Ala Ile Met Val Leu Lys Arg
                245                 250                 255

Leu Asp Asp Ala
            260

<210> SEQ ID NO 55
<211> LENGTH: 17
<212> TYPE: PRT
<213> ORGANISM: Ulkenia sp.

<400> SEQUENCE: 55

Pro Leu His Tyr Ser Val Asp Ala Ala Cys Ala Thr Ala Leu Tyr Val
 1               5                  10                  15

Leu

<210> SEQ ID NO 56
<211> LENGTH: 4
<212> TYPE: PRT
<213> ORGANISM: Ulkenia sp.

<400> SEQUENCE: 56

Asp Ala Ala Cys
 1

<210> SEQ ID NO 57
<211> LENGTH: 159
<212> TYPE: PRT
<213> ORGANISM: Ulkenia sp.

<400> SEQUENCE: 57

Tyr Gly Thr Leu Leu Gly Ala Thr Ile Ser Asn Ala Gly Cys Gly Leu
 1               5                  10                  15

Pro Leu Lys Pro His Leu Pro Ser Glu Lys Ser Cys Leu Ile Asp Thr
                20                  25                  30

Tyr Lys Arg Val Asn Val His Pro His Lys Ile Gln Tyr Val Glu Cys
```

```
                35                  40                  45
His Ala Thr Gly Thr Pro Gln Gly Asp Arg Val Glu Ile Asp Ala Val
 50                  55                  60

Lys Ala Cys Phe Glu Gly Lys Val Pro Arg Phe Gly Ser Ser Lys Gly
65                  70                  75                  80

Asn Phe Gly His Thr Leu Val Ala Ala Gly Phe Ala Gly Met Cys Lys
                85                  90                  95

Val Leu Leu Ala Met Lys His Gly Val Ile Pro Pro Thr Pro Gly Val
            100                 105                 110

Asp Gly Ser Ser Gln Met Asp Pro Leu Val Val Ser Glu Pro Ile Pro
        115                 120                 125

Trp Pro Asp Thr Glu Gly Glu Pro Lys Arg Ala Gly Leu Ser Ala Phe
130                 135                 140

Gly Phe Gly Gly Thr Asn Ala His Ala Val Phe Glu Glu Phe Asp
145                 150                 155

<210> SEQ ID NO 58
<211> LENGTH: 426
<212> TYPE: PRT
<213> ORGANISM: Ulkenia sp.

<400> SEQUENCE: 58

Lys Arg Ile Ala Val Val Gly Met Ala Val Gln Tyr Ala Gly Cys Lys
1               5                   10                  15

Asp Lys Glu Glu Phe Trp Lys Val Val Met Gly Gly Glu Ala Ala Trp
            20                  25                  30

Thr Lys Ile Ser Asp Lys Arg Leu Gly Ser Asn Lys Arg Ala Glu His
        35                  40                  45

Phe Lys Ala Glu Arg Ser Lys Phe Ala Asp Thr Phe Cys Asn Glu Asn
    50                  55                  60

Tyr Gly Cys Val Asp Asp Ser Val Asp Asn Glu His Glu Leu Leu Leu
65                  70                  75                  80

Lys Leu Ser Lys Lys Ala Leu Ser Glu Thr Ser Val Ser Asp Ser Thr
                85                  90                  95

Arg Cys Gly Ile Val Ser Gly Cys Leu Ser Phe Pro Met Asp Asn Leu
            100                 105                 110

Gln Gly Glu Leu Leu Asn Val Tyr Gln Asn His Val Gly Lys Lys Leu
        115                 120                 125

Gly Ala Arg Val Phe Lys Asp Ala Ser Lys Trp Ser Glu Arg Glu Gln
    130                 135                 140

Ser Gln Asn Pro Glu Ala Gly Asp Arg Arg Ile Phe Met Asp Pro Ala
145                 150                 155                 160

Ser Phe Val Ala Glu Glu Leu Asn Leu Gly Pro Leu His Tyr Ser Val
                165                 170                 175

Asp Ala Ala Cys Ala Thr Ala Leu Tyr Val Leu Arg Leu Ala Gln Asp
            180                 185                 190

His Leu Val Ser Gly Ala Ala Asp Val Met Leu Ala Gly Ala Thr Cys
        195                 200                 205

Phe Pro Glu Pro Phe Phe Ile Leu Ser Gly Phe Ser Thr Phe Gln Ala
    210                 215                 220

Met Pro Val Ser Gly Asp Gly Ile Ser Tyr Pro Leu His Lys Asp Ser
225                 230                 235                 240

Gln Gly Leu Thr Pro Gly Glu Gly Gly Ala Ile Met Val Leu Lys Arg
                245                 250                 255

Leu Asp Asp Ala Ile Arg Asp Gly Asp His Ile Tyr Gly Thr Leu Leu
```

```
            260                 265                 270
Gly Ala Thr Ile Ser Asn Ala Gly Cys Gly Leu Pro Leu Lys Pro His
        275                 280                 285
Leu Pro Ser Glu Lys Ser Cys Leu Ile Asp Thr Tyr Lys Arg Val Asn
        290                 295                 300
Val His Pro His Lys Ile Gln Tyr Val Glu Cys His Ala Thr Gly Thr
305                 310                 315                 320
Pro Gln Gly Asp Arg Val Glu Ile Asp Ala Val Lys Ala Cys Phe Glu
                325                 330                 335
Gly Lys Val Pro Arg Phe Gly Ser Ser Lys Gly Asn Phe Gly His Thr
                340                 345                 350
Leu Val Ala Ala Gly Phe Ala Gly Met Cys Lys Val Leu Leu Ala Met
                355                 360                 365
Lys His Gly Val Ile Pro Pro Thr Pro Gly Val Asp Gly Ser Ser Gln
        370                 375                 380
Met Asp Pro Leu Val Val Ser Glu Pro Ile Pro Trp Pro Asp Thr Glu
385                 390                 395                 400
Gly Glu Pro Lys Arg Ala Gly Leu Ser Ala Phe Gly Phe Gly Gly Thr
                405                 410                 415
Asn Ala His Ala Val Phe Glu Glu Phe Asp
                420                 425

<210> SEQ ID NO 59
<211> LENGTH: 267
<212> TYPE: PRT
<213> ORGANISM: Ulkenia sp.

<400> SEQUENCE: 59

Met Arg Ile Ala Ile Thr Gly Met Asp Ala Thr Phe Gly Ser Leu Lys
1               5                   10                  15
Gly Leu Asp Ala Phe Glu Arg Ala Ile Tyr Asn Gly Gln His Gly Ala
                20                  25                  30
Val Pro Leu Pro Glu Lys Arg Trp Arg Phe Leu Gly Lys Asp Lys Asp
            35                  40                  45
Phe Leu Asp Leu Cys Gly Val Lys Glu Val Pro His Gly Cys Tyr Ile
    50                  55                  60
Glu Asp Val Glu Val Asp Phe Ser Arg Leu Arg Thr Pro Met Thr Pro
65                  70                  75                  80
Asp Asp Met Leu Arg Pro Met Gln Leu Leu Ala Val Thr Thr Ile Asp
                85                  90                  95
Arg Ala Ile Leu Asn Ser Gly Leu Lys Lys Gly Gly Lys Val Ala Val
                100                 105                 110
Phe Val Gly Leu Gly Thr Asp Leu Glu Leu Tyr Arg His Arg Ala Arg
            115                 120                 125
Val Ala Leu Lys Glu Arg Ala Arg Pro Glu Ala Ala Ser Ala Leu Asn
    130                 135                 140
Asp Met Met Ser Tyr Ile Asn Asp Cys Gly Thr Ala Thr Ser Tyr Thr
145                 150                 155                 160
Ser Tyr Ile Gly Asn Leu Val Ala Thr Arg Val Ser Ser Gln Trp Gly
                165                 170                 175
Phe Glu Gly Pro Ser Phe Thr Ile Thr Glu Gly Asn Asn Ser Val Tyr
                180                 185                 190
Arg Cys Ala Glu Leu Gly Lys Tyr Leu Leu Glu Thr Gly Glu Val Glu
            195                 200                 205
Ala Val Val Ile Ala Gly Val Asp Leu Cys Ala Ser Ala Glu Asn Leu
```

```
            210                 215                 220
Tyr Val Lys Ser Arg Arg Phe Lys Val Ser Glu Gln Glu Ser Pro Arg
225                 230                 235                 240

Ala Ser Phe Asp Ser Gly Ala Asp Gly Tyr Phe Val Gly Glu Gly Cys
                245                 250                 255

Gly Ala Leu Val Leu Lys Arg Glu Ser Asp Cys
                260                 265
```

<210> SEQ ID NO 60
<211> LENGTH: 264
<212> TYPE: PRT
<213> ORGANISM: Ulkenia sp.

<400> SEQUENCE: 60

```
Ala Ala Phe Gly Leu Ser Leu Gly Glu Ile Ser Met Val Phe Ala Phe
1               5                   10                  15

Ser Glu Lys Asn Gly Leu Val Ser Glu Leu Thr Thr Lys Leu Arg
                20                  25                  30

Asn Ser Glu Val Trp Arg Lys Ala Leu Ala Val Glu Phe Asp Ala Leu
                35                  40                  45

Arg Lys Ala Trp Asn Ile Pro Gln Asp Thr Pro Val Ser Glu Phe Trp
    50                  55                  60

Gln Gly Tyr Val Val Arg Gly Thr Arg Glu Ala Val Glu Ala Ala Ile
65                  70                  75                  80

Gly Pro Asn Asn Lys Tyr Val His Leu Thr Ile Val Asn Asp Ala Asn
                85                  90                  95

Ser Ala Leu Ile Ser Gly Lys Pro Glu Asp Cys Lys Ala Ala Ile Ala
                100                 105                 110

Arg Leu Ser Ser Asn Leu Pro Ala Leu Pro Val Asp Leu Gly Met Cys
                115                 120                 125

Gly His Cys Pro Val Val Glu Pro Tyr Gly Lys Gln Ile Ala Glu Ile
                130                 135                 140

His Ser Val Leu Glu Ile Pro Glu Val Ala Gly Leu Asp Leu Tyr Thr
145                 150                 155                 160

Ser Val Asn Gln Lys Lys Leu Val Asn Lys Ser Thr Gly Ala Ser Asp
                165                 170                 175

Glu Tyr Ala Pro Ser Phe Gly Tyr Ala Ala Gln Leu Tyr Thr Val
                180                 185                 190

Gln Ala Asp Phe Pro Lys Ile Ala Lys Thr Val Ser Asp Lys Asn Phe
                195                 200                 205

Asp Val Phe Val Glu Thr Gly Pro Asn Ala His Arg Ser Ala Ala Ile
                210                 215                 220

Arg Ala Thr Leu Gly Asn Ser Lys Pro Phe Val Thr Gly Ser Met Asp
225                 230                 235                 240

Arg Gln Asn Glu Asn Ala Trp Thr Thr Met Val Lys Leu Val Ala Ser
                245                 250                 255

Leu Gln Ala His Arg Val Pro Gly
                260
```

<210> SEQ ID NO 61
<211> LENGTH: 434
<212> TYPE: PRT
<213> ORGANISM: Ulkenia sp.

<400> SEQUENCE: 61

```
Ser Arg Ala Phe Met Glu Thr Tyr Gly Val Ser Ala Pro Met Tyr Thr
1               5                   10                  15
```

```
Gly Ala Met Ala Lys Gly Ile Ala Ser Ala Glu Met Val Ile Ala Ala
             20                  25                  30
Gly Lys Arg Gly Ile Leu Gly Ser Leu Gly Ala Gly Gly Leu Pro Ile
         35                  40                  45
Ala Thr Val Arg Lys Ala Leu Glu Ala Ile Gln Ala Glu Leu Pro Lys
 50                  55                  60
Gly Pro Tyr Ala Val Asn Leu Ile His Ser Pro Phe Asp Ser Asn Leu
 65                  70                  75                  80
Glu Lys Gly Asn Val Asp Leu Phe Leu Glu Lys Gly Val Thr Val Val
                 85                  90                  95
Glu Ala Ser Ala Phe Met Thr Leu Thr Pro Gln Leu Val Arg Tyr Arg
                100                 105                 110
Ala Ala Gly Leu Ser Arg Ala Ala Asp Gly Ser Thr Val Ile Lys Asn
            115                 120                 125
Arg Val Ile Gly Lys Val Ser Arg Thr Glu Leu Ala Ala Met Phe Ile
        130                 135                 140
Arg Pro Ala Pro Glu Asn Leu Leu Glu Lys Leu Leu Lys Ser Gly Glu
145                 150                 155                 160
Ile Thr Gln Glu Gln Ala Ala Leu Ala Arg Thr Val Pro Val Ala Asp
                165                 170                 175
Asp Ile Ala Val Glu Ala Asp Ser Gly Gly His Thr Asp Asn Arg Pro
            180                 185                 190
Ile His Val Ile Leu Pro Leu Ile Val Asn Leu Arg Asp Arg Leu His
        195                 200                 205
Lys Glu Cys Gly Tyr Pro Ala His Leu Arg Val Arg Val Gly Ala Gly
210                 215                 220
Gly Gly Ile Gly Cys Pro Gln Ala Ala Ile Ala Thr Phe Asn Met Gly
225                 230                 235                 240
Ala Ala Phe Ile Val Thr Gly Thr Val Asn Gln Met Ser Lys Gln Ala
                245                 250                 255
Gly Thr Cys Asp Thr Val Arg Lys Gln Leu Ser Gln Ala Thr Tyr Ser
            260                 265                 270
Asp Ile Cys Met Ala Pro Ala Ala Asp Met Phe Glu Glu Gly Val Lys
        275                 280                 285
Leu Gln Val Leu Lys Lys Gly Thr Met Phe Pro Ser Arg Ala Asn Lys
290                 295                 300
Leu Tyr Glu Leu Phe Val Lys Tyr Asp Ser Phe Glu Ser Met Ala Pro
305                 310                 315                 320
Gly Glu Leu Glu Arg Val Glu Lys Arg Ile Phe Lys Lys Ser Leu Ser
                325                 330                 335
Glu Val Trp Glu Glu Thr Lys Asp Phe Tyr Ile Asn Arg Leu Gln Asn
            340                 345                 350
Pro Glu Lys Ile Glu Arg Ala Glu Arg Asp Pro Lys Leu Lys Met Ser
        355                 360                 365
Leu Cys Phe Arg Trp Tyr Leu Gly Leu Ala Ser Phe Trp Ala Asn Ala
370                 375                 380
Gly Ile Pro Asp Arg Ala Met Asp Tyr Gln Val Trp Cys Gly Pro Ala
385                 390                 395                 400
Ile Gly Ser Phe Asn Asp Phe Ile Lys Gly Thr Tyr Leu Asp Pro Ala
                405                 410                 415
Val Ala Asn Glu Tyr Pro Asp Val Val Gln Ile Asn Leu Gln Ile Leu
            420                 425                 430
Arg Gly
```

<210> SEQ ID NO 62
<211> LENGTH: 2000
<212> TYPE: DNA
<213> ORGANISM: Ulkenia sp.

<400> SEQUENCE: 62

| | | | | | |
|---|---|---|---|---|---|
| gagcacgcac | catcttctct | ccacgcgtaa | agaagagcag | agccagaggc | aggtaggtat | 60 |
| ctccacccat | ctcaggctgt | gacttctttg | tttctttctt | tctttgcttg | ttttctgttc | 120 |
| tctctctgtg | ctctgtccac | acgagaaaga | gaaagagaga | gagaaagaac | cacgggttta | 180 |
| tagagcgcac | tcgtccttcc | tgcttcagca | gaaagcactg | cgtaggagaa | ctacggggga | 240 |
| ggaggaagca | cgcacggagg | aggcgtggaa | ggaaggagga | gacagagaga | gagagacact | 300 |
| gagggacaga | gggggagagg | cagagggaga | ggcatctgat | gtttgcgaga | aaccaataag | 360 |
| ttttgaaagt | gatttgattt | agctgattga | ctgatctatg | gcctgaaaga | aagcttttaa | 420 |
| agcggaggga | gatagatgac | gagggcagct | gcgatgcgt | acggcgcatc | cgtctctctc | 480 |
| tgtgtctctc | tctctttctc | tctcgtcagg | gcgtggagac | ctcggaagct | gcacgcggcg | 540 |
| cggtgaggag | gcagggcagc | agagggagag | gagagatccc | agagtcgaag | agcattgatt | 600 |
| gattgcagat | gatcttgggc | aacgcgcgtc | agcttgagcg | aggaatgctt | tggacttcag | 660 |
| gttcttcgct | tctgtgtttc | attctttctc | gaagaaagaa | agaatgaaag | aaagagagaa | 720 |
| agaaagaaag | aaagaaagaa | agaaagaaag | aaagaaagaa | tgaatgaatg | aaagaaagag | 780 |
| agaaagaaag | aacgaatgaa | agaaagagag | aagaatcaa | agaaagcg | cattcgcagt | 840 |
| tcttcttcgt | gaaagaaaag | gaaaagagag | gcgatggtag | gctctgatct | catcatttct | 900 |
| ggtttctctg | ttgtacctgt | actctgtgct | tgtggccttg | cgaaggctga | agacgccatg | 960 |
| cagacaacca | cgcctccgca | gagactttgc | gggaaagcag | agggcttctc | gccactctcg | 1020 |
| aagaaacgag | ctcgccagtt | ttcggggttg | ttctcagaat | tgcgagtgtt | ggctttatat | 1080 |
| gggatgatgg | tatggcactt | cgtcatcgtt | actctcgctc | gcttgcttac | gaagattttc | 1140 |
| aaaagggcga | agaagtgct | cagcttttaa | aataaagtca | caccaaagac | taggccgcat | 1200 |
| agcagaaagc | taaagtaaac | ccaatctgtc | tgaagagagt | gtcgtggtta | gatacttacg | 1260 |
| caagagttta | aaagctgtaa | atagtacagg | aacaaaaaca | aataaatata | tatatattct | 1320 |
| tttttattag | taaaacatga | aaccaaaaaa | ctcctttaaa | ataaaataaa | ataaaataaa | 1380 |
| ataaaataaa | ataaaataaa | tttactacta | tatatacata | tatatataca | ataaataaaa | 1440 |
| acaactttt | cagaccagaa | aaagactgag | aaaaaaggaa | actaatgact | ctcgagcacc | 1500 |
| gagagcgata | taagagtgga | ttatatttgc | taggcccacc | acgagtgagt | cccctaggag | 1560 |
| gaagcgccct | ctgagacagg | agcagaggcg | tcgctggtgc | tccaaaaagc | gacggcgaat | 1620 |
| ggaaagcaaa | acccttcga | gggaggcttg | tggccgtgac | tattcaaatc | tccagcatct | 1680 |
| cagctccagc | acagcagaag | ctacctcgct | tctcagctct | agctatcaca | tcgatcgcag | 1740 |
| catctagctc | gtagacagct | agcgccgcac | cttccccaa | atcaacttgg | gcaacttaac | 1800 |
| tcttttttca | ccagaactcc | tcttttcctt | taatcttcga | aaagaagacg | aataaaagag | 1860 |
| ataatcctct | gccgcagcac | attctaaaag | aaaagcggca | tactggcgta | ggcaagactt | 1920 |
| tcaagctctt | cctcgcctcc | accccgtatt | tccctgttca | tctttgtgaa | acgaggaaac | 1980 |
| aagaaatttt | ataggacaag | | | | | 2000 |

<210> SEQ ID NO 63
<211> LENGTH: 2000

<212> TYPE: DNA
<213> ORGANISM: Ulkenia sp.

<400> SEQUENCE: 63

| | | | | | |
|---|---|---|---|---|---|
| agttgtgagg | ctgtcttgtc | ttgtcagtcg | cgaaagtgta | agcaagaact | ttgtcataca | 60 |
| aagaagcaac | caacttccga | accaacacac | cttgtaggat | tacaaccaca | actttctata | 120 |
| aatagtgcgc | aagaataacc | agtaagctat | ccttcgtgta | cctgttacaa | caacgacatt | 180 |
| tttacttgat | cttcctactt | gtgatgggta | gtcccggctt | gtactgacag | tgatgccaca | 240 |
| gcagagtaga | tcactgtgaa | taagtaaata | agcctactta | ttatattccc | aaagtactcg | 300 |
| ctgggatatt | attagtatca | cgaaaagtga | tatgttttat | aactcgcttg | tcttgccaag | 360 |
| atctaacctt | ttttttttaa | atggccaaaa | agtcgccaga | acacatctta | caataaacaa | 420 |
| aaatttagat | tatatcgtat | gtataatgta | taatatatta | tattattata | tacatacgat | 480 |
| ataatctaaa | gccattccag | acttattcgg | tgatgaaaaa | tgctttccca | gctttataca | 540 |
| aactattcaa | aaagttgcat | gacccatttt | cagatatatt | taatagtata | agattatgtc | 600 |
| catttgttttt | caaagttatt | caagagttta | catcttgaag | tttcatccct | ttactactac | 660 |
| actgttttttc | gtttgggttt | tttctctaac | ggcgaaagaa | acaagtcacc | aagcttaact | 720 |
| agtaggcatc | tttgtggtga | cgaaattaaa | gttgaatata | taaattatag | ttagtcatta | 780 |
| tggaatctca | gtttgaacga | agctaagcta | tttataaaaa | tcactgcatg | gagataaatac | 840 |
| ttgaattttg | atgatagtgt | ttatgaagaa | gtttaatctt | gctttttatt | aatgttattc | 900 |
| tctaatatag | aaatatttca | ataaaaaaat | catatgaagg | gataataaat | acagagaatg | 960 |
| atcgttatca | tttgatatgt | cgaacgctaa | tctatcatct | tatctaggaa | acaaaggtgg | 1020 |
| aaataaagga | aagccctaca | cgagttaatt | cctcaaacga | actactttgg | attatcaaat | 1080 |
| ccaactgctg | acactggata | catgcatgta | tttagtgggt | gttactgtac | ttccttatttt | 1140 |
| cctttaattc | aattgtcttg | attttttactt | cggagattct | acttgaaaat | catctccctt | 1200 |
| cacttccggt | tatacagaaa | gaccettcaa | ttcgaatgct | ggccaggtac | aataactatc | 1260 |
| agcgattccc | ctccactaga | catgaccgac | tgtaagcacc | tcaacccgat | ttcaagcaac | 1320 |
| acatgatgac | tagctgtttc | cgcaaaacaa | caaataagag | aggtagtgga | aaacacccag | 1380 |
| ttcgctcgag | ctcccctagt | agattcgaca | ttcactttct | atttgattgc | taattgtggg | 1440 |
| tccggctatt | taaggaaaga | actgatgaaa | gtccacctca | cgcaatcaaa | tcgcggtcta | 1500 |
| gttggaagct | acaatggccg | acgtatgcgc | gcctctatct | tttaggattg | tagaacaggg | 1560 |
| cggcaatctg | ctaacataaa | tttaataccctt | tgctcaagct | gctttccata | cttttcaatc | 1620 |
| catttgtgat | aatcttgcaa | tggaccaatc | tccaaatctg | tagaagcaat | aacaaggaca | 1680 |
| tcgcagggtc | ccggttcgtt | tgcatgctcg | tcttctggtg | ccacaacaat | gctgcctgtt | 1740 |
| attatctcat | gagagtcttt | tatactgcgga | tccgtggcta | tagcgtgaat | aaacgttgtg | 1800 |
| cgcaagccta | tatcctcgcg | atggagatac | tggcctgcta | cagtttgcgt | tcgtctgcct | 1860 |
| acgacaacgc | atggaacatt | ctttggtgtg | cgagtgggcc | gtagcgttcg | accctgggca | 1920 |
| aggaagccat | gcagacgtga | ttccgagagg | ccatctcgcg | tgtaagactt | atcccaattt | 1980 |
| tctggatcct | ctaatttcca | | | | | 2000 |

<210> SEQ ID NO 64
<211> LENGTH: 2000
<212> TYPE: DNA
<213> ORGANISM: Ulkenia sp.

<400> SEQUENCE: 64

```
aaattaatga atgaatcaat gaatgaatca atgaataatg ccaatgcaat gcgatgcgat      60
gctgcttcga gccatcgcac ggcggccatt gcgcgcttgc gtcagtcatg tcattccatt     120
cggagcggcg tgcgcgaggg agggagggag ggagggagaa gacgaggagc aggcggagag     180
agaggaggat gggcgggcgg gcggcgtcgt cggcgtcgtc gtcgtcgtgg gcctccgtag     240
tcgctgggaa ggagggcttt gattccaaat gaggattttg gtgcactgct ttcgagactt     300
tctcgcctga ttcggaattc ctcctcttct tcttcttttt agctgtgctt tctgcgtatt     360
cattgcgtgg gtttggcttg gttttcaaat caattagcag tctagtaact aacaaactaa     420
caaacagata aacagacaaa cagacaaaca aacaaaacaa acaaaacaaa caaaacaaag     480
caggaaagaa agaaacaaac aaatatacaa acaaagaaag aaagaagtgg tgggaactag     540
ggaaatcaat gtgtttgctt ctttcgcacc tttgcttttc ttgcttttct tggttctcaa     600
gtaagcgttt atcgcgccct cagaaaacaa aataaaatga tctaacataa catgaattta     660
tatttatttt atttgtttat taaataaata ttttttgtaa accagaattt cactctactt     720
ttgcaacact gagagagtgc catctgcata ataagtggca gtgttttttt gtttatttc     780 aaattaatta tacttgaact gctaggtcaa gaggccgcag cagcctgatg agataaggac     840
agagtaggca aggatggcag aagatcgcga aaaagcgag aaaggcaaac gagcaggccc     900
gaaggtgagg tggagctgct tgtcaaggtc gcgaggtttg tttgacagtt ataacagcaa     960
gaactaaggc aatttcaaga atgaagagca ctcgaataaa ccgatgaagc aaagtgtgta    1020
catacaaaca tacatacgta cagatgaaaa gaacagattt tcaataaaaa tgacttttta    1080
gtttaaacaa tgtttctgtt tgttgtttcg cttttcatta atttgttgca aattattttg    1140
ttttggtttt tgttttttgtt tttgaaaatc ataaaagaga tgctgccgca gacgtctgcg    1200
cgtctcatag ttgattgggt aatcgttttg ttgagttttg aaaatgtaaa cttcacttag    1260
ttgctcattt atcctcattc gtttgcccat ttgttctctg tttgaagcag agttttgact    1320
tctcgcattc gtggaatcca ccccttgctt gctttgcttg cttgcttgct tgcttgcttg    1380
cctgcttgct ttgcttgctt gcttgaccag cgtgcgcgct ttcgccagcc tagccttcga    1440
gacctcttga agacccttttg gagcgtctag ttcgaggttc tttctatttg cttcaagaga    1500
gacaaaataa caaagaaaaa gagagaaaaa acaagcaaag aaagaaacaa ggaaacaaac    1560
cacaaagcac gcatcgtgca tccaaacttt catccccca ctctctctct ctctctctct    1620
ctctctctcc ttcctcggaa aaggagtgag acaaaggcag acagcctcta gcttggcagc    1680
ctcgcagctc gtgcggcgcc agttcctaca gcttcgcgct gtccaaacgc cagtccatcg    1740
cagcttcggc tagctagttg gctgattgat tgattgattg attgatagcc tttattacgg    1800
cgttgattaa ctgattgatt atttgattgc tctggcatcc ctgtaatcac ttgctcaagg    1860
tagtcaatca catcatttat acatctcctc caaagcaaac catctacacg accgcttttt    1920
gatcgatcta aaagtgccgg tcaggtgaca cgcaagctct tttttttgtt tacagtaagc    1980
agcaacaaga aagcaaaaag                                                 2000

<210> SEQ ID NO 65
<211> LENGTH: 2000
<212> TYPE: DNA
<213> ORGANISM: Ulkenia sp.

<400> SEQUENCE: 65 gcccaattttg ctcctgatct gttcccatga ttatgatagg gataggtagt agttatagct      60
agactcattc cattcactta atccacatat gcaaattata attttatgtg tcgcatataa     120
```

```
actttccaaa ctttaaaatt ttcatttgca ttttatatat agatcacctg tgatcccttt      180
ctcgcccctt tcaacttcca aagtttacct actatcatat ggcatggcgc agccaatgca      240
ctctataaca tataagtaac agagatagtt tttgccgcat catttactct ttactcttgc      300
tatacaaggt aagcgccaag agagttaatt acatctgttt tatcggttcc tagtggaaat      360
aatagtgaca actataatta gtaggagtcc ttattgaccc tagtcatttg agcttgcacc      420
agatttgatg ttttttgcaaa cgaccttgac gcagagtgac gagcgaaaat tggatcccct      480
tggttgaagt ctaaactagc ttaaaatata tatgctcttc atataatata aagctgtttt      540
agattctatc aaataagaaa ttgatgactt tgagcaaatt aatatttggt atgggctccg      600
gcatctctga aaacgcttaa atgaagcttt tattcaccac gattcgacaa ctaaggttat      660
tttccacata attataactt ttcctacata actgtgctgt cgactcacac cttctttata      720
tatatagcct cgtagggatt cgaaactatg aattaagact cgttgaagtt tgatttatcc      780
attattttgc tgcacaaact atcgctaaga tataaagatc gtgcccagag cctgctatag      840
ggtcctaatg gcatgcttag cccggatttc cacgataaag ctgcattgta ttgagtatat      900
gcactcagag agtaaacttt aattgcaacg aacaatcttt ggcaagtcat atctcagcca      960
tcaatacatg tattgtgttc aaacgaattg cagcatatca ctcaaattat tttggtctag     1020
ttcagcggaa tcttttggtt gttttagtaa gagttgagta gagtatgttg gatgagtgtg     1080
tccacaaggt tatttgaata gggtatttac attctacaac atagtcagta agctctcgtg     1140
tgataaactg tatcaaaatc gacacaataa caggctagtg gtgccctgtg cacgtttta     1200 ccataacatg acagctacag catcagaaac aggtgtggtg cgcattttgg ttattctgat     1260
cctgaaacct aagaacaatt ttcatcgtct tgctagattg tgttttctgt attccatttg     1320
tggagcttca acatccatgc tgctgagtat tttcacatga agatcatagt gttagaatgt     1380
ttagtaagcc tattactaag ttttgaggta taggtgcttg ttgttgtcct tacataaata     1440
catgctgtct ttagtgctta gaccaacgtt gagtgtatcg tgctcttggc agaagaatag     1500
acatttataa cattatggtg aaaggcgatg gtctcgcttg catgttctcg cttgcgtttg     1560
cgtatcccta tacacttaac cgttgtttat gtgtacctaa gctatcatgc tgcatcttta     1620
caattttata caaataaatt tattttggaa tatataattg gtcactattt caggccagtt     1680
gacagtcctt aagatttgta gttgcgctgt tctcgtagtg agaatgaaga agcggaatct     1740
acatccatct gtgattgcat aagagcttgc ataagagtga agtaggtgaa agtcacagag     1800
aatatcttcc ctactatcct aaaggcaagg aatactacta tacacgaaca tagtaatgga     1860
attttacaca acagaagtac ccttgtctcc tgcctccttt tattattcca ttatgctctg     1920
ttatataatg aatgaagacg acttttaaca tcatttgatt ctcgagcagg cacgcacaat     1980
atagaggaag gattggcgtc                                                 2000
```

<210> SEQ ID NO 66
<211> LENGTH: 1212
<212> TYPE: DNA
<213> ORGANISM: Ulkenia sp.

<400> SEQUENCE: 66

```
ggcaagaacg tcgttttcga ctatgacgag ctccttgagt tcgccgaggg tgacatcagc       60
aaggtcttcg gccccgaatt cagccagatc gaccagtaca agcgtcgcgt tcgtctcccc      120 gccccgcgagt acctcctcgt cacccgcgtc accctcatgg acgccgaggt caacaactac      180
cgcgtcggtg cccgcatggt cactgagtac gacctccccg tcaacggtga gctctctgag      240
```

```
ggtggtgact gcccctgggc cgtgctcgtc gagagtggtc agtgtgatct catgctcatc      300
tcctacatgg gtattgactt ccagaacaag agcgaccgcg tctaccgtct gctcaacacc      360
accctcacct tctacggtgt tgcccaggag ggcgagaccc tggagtacga catccgcgtg      420
accggcttcg ccaagcgtct cgacggtgac atctccatgt tcttcttcga gtacgactgc      480
tacgtcaacg gccgtctcct catcgagatg cgcgacggct gtgccggttt cttcaccaac      540
gaggagctcg ccgccggcaa gggtgtcgtc tttacccgcg ctgatctcct cgcccgcgag      600
aagaccaaga agcaggacat caccccgtac gccattgccc gcgtcttaa  caagaccgtt      660 ctcaacgaga ctgagatgca gtccctcgtg acaagaact  ggaccaaggt tttcggcccc      720
gagaacggca tggaccagat caactacaaa ctctgcgccc gtaagatgct catgattgac      780
cgcgtcacca agattgacta caccggtggc ccctacggcc ttggtcttct cgttggtgag      840
aagatcctcg agcgcgacca ctggtacttt ccgtgccact cgtcggaga  ccaggtcatg      900 gctggatccc tcgtgtctga cggctgcagc cagctcctca agatgtacat gctctggctc      960
ggcctccacc ttaagaccgg tcccttcgac ttccgccccg tcaacggcca ccccaacaag     1020
gtccgctgcc gtggccagat ctccccgcac aagggtaagc tcgtatacgt catggagatc     1080
aaggagatgg gctacgacga ggctggtgac ccgtacgcca tcgccgatgt caacattctc     1140
gacattgact tcgagaaggg ccagactttc gaccttgcca acctccacga gtacggcaag     1200
ggcgacctca ac                                                         1212
```

<210> SEQ ID NO 67
<211> LENGTH: 21
<212> TYPE: DNA
<213> ORGANISM: Ulkenia sp.

<400> SEQUENCE: 67

```
tggtactttc cgtgccactt c                                                 21
```

<210> SEQ ID NO 68
<211> LENGTH: 1197
<212> TYPE: DNA
<213> ORGANISM: Ulkenia sp.

<400> SEQUENCE: 68

```
gtgcccggcg agatgccgct ctcgtggtac aacatggctg agttcatggc cggcaaggtc       60
agcctctgcc tcggccctga gttcgccaag ttcgatgact ccaacaccag ccgcagccct      120
gcatgggacc ttgctcttgt gactcgtgtg gtctccgttt ctgacatgga gtgggtccag      180
tggaagaacg tggactgcaa cccgtccaag ggaaccatgg ttggcgagtt cgactgcccc      240
atcgacgcct ggttcttcca gggatcttgt aacgacggcc acatgccgta ctccatcctc      300
atggagatcg ccctccagac ctctggtgtc ctcacctctg tgctcaaggc ccgctcacc      360 atggagaaga aggacattct cttccgcaac cttgacgcca cgccgagat  ggttcgctct      420 gatattgacc tccgcggcaa gaccatccac aacctcacca gtgtaccgg  ctacagcatg      480 ctcggagaca tgggtgtcca ccgcttcagc ttcgagctct ctgttgatgg tgtagtcttc      540
tacaagggta ccacctcctt cggctggttc gtccctgagg tcttcatctc ccagactggt      600
ctcgacaacg gtcgccgcac ccagccctgg cacattgagt ccaaggtgcc ttccgcccag      660
gtcctcacct acgacgttac ccccaacggt gccggtcgca cccagctcta cgccaacgcc      720
cccaagggcg ctcagctcac tcgccgctgg aaccagtgcc agtaccttga caccatcgac      780
cttgtggtcg ccggtggctc cgccggtctt ggctacggtc atggccgcaa gcaggtgaac      840
```

```
cccaaggact ggttcttctc gtgccacttc tggttcgact ccgtcatgcc cggctcgctc    900
ggtgtggagt ctatgttcca gctcgtcgag tccatcgctg tcaagcagga cctcgccggc    960
aagtacggca tcaccaaccc gaccttcgct catgctccgg gcaagatctc ctggaagtac   1020
cgtggtcagc tcaccccac ctccaagttc atggactccg aggcccacat tgtctccatc   1080
gaggcccacg acggcgtcgt cgacatcgtt gccaatggta acctctgggc tgatggcctc   1140
cgcgtctaca acgtcagcaa catccgtgtg cgcattgttg ctggcgccgc ccctgct      1197
```

<210> SEQ ID NO 69
<211> LENGTH: 21
<212> TYPE: DNA
<213> ORGANISM: Ulkenia sp.

<400> SEQUENCE: 69

```
tggttcttct cgtgccactt c                                               21
```

<210> SEQ ID NO 70
<211> LENGTH: 90
<212> TYPE: DNA
<213> ORGANISM: Ulkenia sp.

<400> SEQUENCE: 70

```
gctggcgccg ccctgctgc tgctgctgct gctgctgctg ttgctgctcc ggctgccgcc     60
cctgctccgg ttgctgcatc tggccctgcc                                      90
```

<210> SEQ ID NO 71
<211> LENGTH: 1299
<212> TYPE: DNA
<213> ORGANISM: Ulkenia sp.

<400> SEQUENCE: 71

```
gaaggcttca tgaagaccta cggtgttgtg gctcctctct acaccggtgc catggccaag     60
ggtattgcct ctgctgacct tgtgattgcc actggtaagc gcaagatcct cggttccttc   120
ggtgctggcg gtctccccat gcacattgtc cgtgccgctg ttgagaagat ccaggctgag   180
ctcccgaacg gccccttcgc cgtcaacctc atccactccc ccttcgatag caaccttgag   240
aagggcaacg ttgacctctt cctcgagaag ggcgttactg tcgtcgaggc ctccgccttc   300
atgaccttga ccccgcaagt cgtccgctac cgtgctgctg gtctttcccg taacgctgat   360
ggctccatta acatcaagaa ccgcatcatc ggtaaggtct cccgtaccga gctcgctgag   420
atgttcatcc gccctgcccc gcagaacctc ctcgacaagc tcatccagtc tggtgagatt   480
accaaggagc aggctgagct tgccaagctc gtccccgtcg ccgacgacat cgccgtcgag   540
gccgactctg gtggccacac cgacaaccgc cccatccacg tcatcctccc ccttatcatc   600
aacctccgca accgcctcca caaggagtgc ggctaccccg ctcacctccg cgtgcgcgtt   660
ggagctggtg gtggtgttgg atgccccag gccgctgccg ctgctctcgc tatgggtgct   720
gccttccttg ttaccggcac tgtcaaccag gtcgccaagc agtccggcac ctgcgacaat   780
gtccgcaagc agctctgcat ggccacctac tctgacgtct gcatggctcc cgctgctgac   840
atgttcgagg agggcgtcaa gctccaggtc ctcaagaagg gaaccatgtt cccgtccagg   900
gctaacaagc tctacgagct cttctgcaag tacgactcct tcgagtccat gctgccaca    960 gagctcgagc gtgttgagaa gcgcatcttc cagtgccctc ttgctgatgt ctgggctgag   1020
acctccgact tctacatcaa ccgcctccac aaccgggaga agatcacccg tgccgagcgt   1080
gaccccaagc tcaagatgtc tctctgcttc cgctggtacc ttggtcttgc ctctcgctgg   1140
```

```
gccaacaccg gtgaggctgg acgcgtcatg gactaccagg tctggtgtgg ccctgccatt    1200
ggagccttca acgacttcat caagggctcc taccttgacc cggccgtctc tggtgagtac    1260
ccggacgtcg tgcagatcaa cttgcagatc cttcgcggt                           1299
```

<210> SEQ ID NO 72
<211> LENGTH: 404
<212> TYPE: PRT
<213> ORGANISM: Ulkenia sp.

<400> SEQUENCE: 72

```
Gly Lys Asn Val Val Phe Asp Tyr Asp Glu Leu Leu Glu Phe Ala Glu
1               5                   10                  15

Gly Asp Ile Ser Lys Val Phe Gly Pro Glu Phe Ser Gln Ile Asp Gln
            20                  25                  30

Tyr Lys Arg Arg Val Arg Leu Pro Ala Arg Glu Tyr Leu Leu Val Thr
        35                  40                  45

Arg Val Thr Leu Met Asp Ala Glu Val Asn Asn Tyr Arg Val Gly Ala
    50                  55                  60

Arg Met Val Thr Glu Tyr Asp Leu Pro Val Asn Gly Glu Leu Ser Glu
65                  70                  75                  80

Gly Gly Asp Cys Pro Trp Ala Val Leu Val Glu Ser Gly Gln Cys Asp
                85                  90                  95

Leu Met Leu Ile Ser Tyr Met Gly Ile Asp Phe Gln Asn Lys Ser Asp
            100                 105                 110

Arg Val Tyr Arg Leu Leu Asn Thr Thr Leu Thr Phe Tyr Gly Val Ala
        115                 120                 125

Gln Glu Gly Glu Thr Leu Glu Tyr Asp Ile Arg Val Thr Gly Phe Ala
    130                 135                 140

Lys Arg Leu Asp Gly Asp Ile Ser Met Phe Phe Phe Glu Tyr Asp Cys
145                 150                 155                 160

Tyr Val Asn Gly Arg Leu Leu Ile Glu Met Arg Asp Gly Cys Ala Gly
                165                 170                 175

Phe Phe Thr Asn Glu Glu Leu Ala Ala Gly Lys Gly Val Val Phe Thr
            180                 185                 190

Arg Ala Asp Leu Leu Ala Arg Glu Lys Thr Lys Gln Asp Ile Thr
        195                 200                 205

Pro Tyr Ala Ile Ala Pro Arg Leu Asn Lys Thr Val Leu Asn Glu Thr
    210                 215                 220

Glu Met Gln Ser Leu Val Asp Lys Asn Trp Thr Lys Val Phe Gly Pro
225                 230                 235                 240

Glu Asn Gly Met Asp Gln Ile Asn Tyr Lys Leu Cys Ala Arg Lys Met
                245                 250                 255

Leu Met Ile Asp Arg Val Thr Lys Ile Asp Tyr Thr Gly Gly Pro Tyr
            260                 265                 270

Gly Leu Gly Leu Leu Val Gly Glu Lys Ile Leu Glu Arg Asp His Trp
        275                 280                 285

Tyr Phe Pro Cys His Phe Val Asp Gln Val Met Ala Gly Ser Leu
    290                 295                 300

Val Ser Asp Gly Cys Ser Gln Leu Leu Lys Met Tyr Met Leu Trp Leu
305                 310                 315                 320

Gly Leu His Leu Lys Thr Gly Pro Phe Asp Phe Arg Pro Val Asn Gly
                325                 330                 335

His Pro Asn Lys Val Arg Cys Arg Gly Gln Ile Ser Pro His Lys Gly
            340                 345                 350
```

```
Lys Leu Val Tyr Val Met Glu Ile Lys Glu Met Gly Tyr Asp Glu Ala
            355                 360                 365

Gly Asp Pro Tyr Ala Ile Ala Asp Val Asn Ile Leu Asp Ile Asp Phe
        370                 375                 380

Glu Lys Gly Gln Thr Phe Asp Leu Ala Asn Leu His Glu Tyr Gly Lys
385                 390                 395                 400

Gly Asp Leu Asn

<210> SEQ ID NO 73
<211> LENGTH: 7
<212> TYPE: PRT
<213> ORGANISM: Ulkenia sp.

<400> SEQUENCE: 73

Trp Tyr Phe Pro Cys His Phe
1               5

<210> SEQ ID NO 74
<211> LENGTH: 399
<212> TYPE: PRT
<213> ORGANISM: Ulkenia sp.

<400> SEQUENCE: 74

Val Pro Gly Glu Met Pro Leu Ser Trp Tyr Asn Met Ala Glu Phe Met
1               5                   10                  15

Ala Gly Lys Val Ser Leu Cys Leu Gly Pro Glu Phe Ala Lys Phe Asp
            20                  25                  30

Asp Ser Asn Thr Ser Arg Ser Pro Ala Trp Asp Leu Ala Leu Val Thr
        35                  40                  45

Arg Val Val Ser Val Ser Asp Met Glu Trp Val Gln Trp Lys Asn Val
50                  55                  60

Asp Cys Asn Pro Ser Lys Gly Thr Met Val Gly Glu Phe Asp Cys Pro
65                  70                  75                  80

Ile Asp Ala Trp Phe Phe Gln Gly Ser Cys Asn Asp Gly His Met Pro
            85                  90                  95

Tyr Ser Ile Leu Met Glu Ile Ala Leu Gln Thr Ser Gly Val Leu Thr
            100                 105                 110

Ser Val Leu Lys Ala Pro Leu Thr Met Glu Lys Asp Ile Leu Phe
            115                 120                 125

Arg Asn Leu Asp Ala Asn Ala Glu Met Val Arg Ser Asp Ile Asp Leu
        130                 135                 140

Arg Gly Lys Thr Ile His Asn Leu Thr Lys Cys Thr Gly Tyr Ser Met
145                 150                 155                 160

Leu Gly Asp Met Gly Val His Arg Phe Ser Phe Glu Leu Ser Val Asp
            165                 170                 175

Gly Val Val Phe Tyr Lys Gly Thr Thr Ser Phe Gly Trp Phe Val Pro
            180                 185                 190

Glu Val Phe Ile Ser Gln Thr Gly Leu Asp Asn Gly Arg Arg Thr Gln
            195                 200                 205

Pro Trp His Ile Glu Ser Lys Val Pro Ser Ala Gln Val Leu Thr Tyr
        210                 215                 220

Asp Val Thr Pro Asn Gly Ala Gly Arg Thr Gln Leu Tyr Ala Asn Ala
225                 230                 235                 240

Pro Lys Gly Ala Gln Leu Thr Arg Arg Trp Asn Gln Cys Gln Tyr Leu
            245                 250                 255

Asp Thr Ile Asp Leu Val Val Ala Gly Gly Ser Ala Gly Leu Gly Tyr
```

-continued

```
                260                 265                 270
Gly His Gly Arg Lys Gln Val Asn Pro Lys Asp Trp Phe Ser Cys
                275                 280                 285
His Phe Trp Phe Asp Ser Val Met Pro Gly Ser Leu Gly Val Glu Ser
                290                 295                 300
Met Phe Gln Leu Val Glu Ser Ile Ala Val Lys Gln Asp Leu Ala Gly
305                 310                 315                 320
Lys Tyr Gly Ile Thr Asn Pro Thr Phe Ala His Ala Pro Gly Lys Ile
                325                 330                 335
Ser Trp Lys Tyr Arg Gly Gln Leu Thr Pro Thr Ser Lys Phe Met Asp
                340                 345                 350
Ser Glu Ala His Ile Val Ser Ile Glu Ala His Asp Gly Val Val Asp
                355                 360                 365
Ile Val Ala Asn Gly Asn Leu Trp Ala Asp Gly Leu Arg Val Tyr Asn
                370                 375                 380
Val Ser Asn Ile Arg Val Arg Ile Val Ala Gly Ala Ala Pro Ala
385                 390                 395

<210> SEQ ID NO 75
<211> LENGTH: 7
<212> TYPE: PRT
<213> ORGANISM: Ulkenia sp.

<400> SEQUENCE: 75

Trp Phe Phe Ser Cys His Phe
1               5

<210> SEQ ID NO 76
<211> LENGTH: 30
<212> TYPE: PRT
<213> ORGANISM: Ulkenia sp.

<400> SEQUENCE: 76

Ala Gly Ala Ala Pro Ala Ala Ala Ala Ala Ala Ala Val Ala Ala
1               5                   10                  15
Pro Ala Ala Ala Pro Ala Pro Val Ala Ala Ser Gly Pro Ala
                20                  25                  30

<210> SEQ ID NO 77
<211> LENGTH: 433
<212> TYPE: PRT
<213> ORGANISM: Ulkenia sp.

<400> SEQUENCE: 77

Glu Gly Phe Met Lys Thr Tyr Gly Val Val Ala Pro Leu Tyr Thr Gly
1               5                   10                  15
Ala Met Ala Lys Gly Ile Ala Ser Ala Asp Leu Val Ile Ala Thr Gly
                20                  25                  30
Lys Arg Lys Ile Leu Gly Ser Phe Gly Ala Gly Leu Pro Met His
                35                  40                  45
Ile Val Arg Ala Ala Val Glu Lys Ile Gln Ala Glu Leu Pro Asn Gly
    50                  55                  60
Pro Phe Ala Val Asn Leu Ile His Ser Pro Phe Asp Ser Asn Leu Glu
65                  70                  75                  80
Lys Gly Asn Val Asp Leu Phe Leu Glu Lys Gly Val Thr Val Val Glu
                85                  90                  95
Ala Ser Ala Phe Met Thr Leu Thr Pro Gln Val Val Arg Tyr Arg Ala
                100                 105                 110
```

```
Ala Gly Leu Ser Arg Asn Ala Asp Gly Ser Ile Asn Ile Lys Asn Arg
            115                 120                 125

Ile Ile Gly Lys Val Ser Arg Thr Glu Leu Ala Glu Met Phe Ile Arg
        130                 135                 140

Pro Ala Pro Gln Asn Leu Leu Asp Lys Leu Ile Gln Ser Gly Glu Ile
145                 150                 155                 160

Thr Lys Glu Gln Ala Glu Leu Ala Lys Leu Val Pro Val Ala Asp Asp
                165                 170                 175

Ile Ala Val Glu Ala Asp Ser Gly Gly His Thr Asp Asn Arg Pro Ile
            180                 185                 190

His Val Ile Leu Pro Leu Ile Ile Asn Leu Arg Asn Arg Leu His Lys
        195                 200                 205

Glu Cys Gly Tyr Pro Ala His Leu Arg Val Arg Val Gly Ala Gly Gly
    210                 215                 220

Gly Val Gly Cys Pro Gln Ala Ala Ala Ala Leu Ala Met Gly Ala
225                 230                 235                 240

Ala Phe Leu Val Thr Gly Thr Val Asn Gln Val Ala Lys Gln Ser Gly
                245                 250                 255

Thr Cys Asp Asn Val Arg Lys Gln Leu Cys Met Ala Thr Tyr Ser Asp
            260                 265                 270

Val Cys Met Ala Pro Ala Ala Asp Met Phe Glu Glu Gly Val Lys Leu
        275                 280                 285

Gln Val Leu Lys Lys Gly Thr Met Phe Pro Ser Arg Ala Asn Lys Leu
290                 295                 300

Tyr Glu Leu Phe Cys Lys Tyr Asp Ser Phe Glu Ser Met Pro Ala Thr
305                 310                 315                 320

Glu Leu Glu Arg Val Glu Lys Arg Ile Phe Gln Cys Pro Leu Ala Asp
                325                 330                 335

Val Trp Ala Glu Thr Ser Asp Phe Tyr Ile Asn Arg Leu His Asn Pro
            340                 345                 350

Glu Lys Ile Thr Arg Ala Glu Arg Asp Pro Lys Leu Lys Met Ser Leu
        355                 360                 365

Cys Phe Arg Trp Tyr Leu Gly Leu Ala Ser Arg Trp Ala Asn Thr Gly
    370                 375                 380

Glu Ala Gly Arg Val Met Asp Tyr Gln Val Trp Cys Gly Pro Ala Ile
385                 390                 395                 400

Gly Ala Phe Asn Asp Phe Ile Lys Gly Ser Tyr Leu Asp Pro Ala Val
                405                 410                 415

Ser Gly Glu Tyr Pro Asp Val Val Gln Ile Asn Leu Gln Ile Leu Arg
            420                 425                 430

Gly

<210> SEQ ID NO 78
<211> LENGTH: 2000
<212> TYPE: DNA
<213> ORGANISM: Ulkenia sp.

<400> SEQUENCE: 78
gcacgtagag caagaaagaa tgaaagaaag aacgaaagaa agaaagagag agagagagag     60
agagagagag agaaagcgaa gatgatagcg gagagaactc ttcttcgcag tcactctgtt    120
tctcagtcag tcccgcaacc aataacaact cgaactcgca gcagtgttct tcggagtgcc    180
agcgctcgct cgcactgcgt cggcacagca gcagcagcag caggccccgc gctcgctgca    240
ctcagcccgg gcaggagcaa cagctgctga gcagctgagg ccagctggct ggcggctcgc    300
```

```
ctcgcctcgc ctcgcgtcgc gtcgcgagag aaagcgatcg accaactgtc aatcgattat    360
tcgagtcctt cgagcgcttt atagggcact gattgatcac tcattgattc attgactcat    420
ttattctttg cgtggtcagc caaacggcgt tagcattggg caaagcgggt ctttgctttg    480
ctctaaaata gatttgctcg cgagagtacg tacttgcagg agtaggtagg ctctgcctag    540
tacctgggca tttgaatatt tgaacttcga acttcgttga gtatctgaat atttgaatat    600
ctgaatattt gaatttcgaa agtttgaata tttgaatatt tgaattttgg aatattggaa    660
tagctgggtt tggagataag acttactaag ctaagcgccg acgtaagagc ggcgagtaaa    720
tccacacaca agagagaggc agagagagag ggagggagac aactcgcgca ggcaagctga    780
gcccactgga cgcacggggc gcgtccccccc tgacgggcgc tctggtggtg cgtgtttgg    840 gagggttttg catgcttgtg ataggggctc tggcgcgggc tctgtacggt gcttggagat    900
gcacgggcag ggcgagagag gggacgggtt cccgggaggc gctgcttgga ggtgctgaga    960
gggagggaga aggcgtgctt tgcgatgcgc ggggcgacct aggcgctgct gcgcggtgca   1020
gcagcaggga cctcggacgt gagtcgaagc cgtctgcaga ggagatggta gaagggccgc   1080
ggattggtag cagagaagag gaaatagaag aagaagaaga aatagaagaa gaagaaatag   1140
aagaagaaga aatagaagaa gaagaggagg acgggcaggc gggaaagatg gagaaaggac   1200
tcgcggcggg aaaacaagag aatgtgaact tgggcttgaa cttggtttg aatttgaatg   1260 tggagaacga ggggttgaat ttgagtttga atttgaaaga aaacttacgg aaagaaagtt   1320
tagttgaaag tgagaaagaa aaaaatgaga agaaaaaga gaagaaaaa gagaaagaaa   1380 aagagaaaga aaagagaaa gaaaagaga agaaaaaga gaaagaaaaa gagaaagaaa   1440
aagagaaaga aaagagaaa gaaaagaga agaaaaaga gaaagaaaaa gagaagaaa   1500 aagaagaaga aaagagaaa gaaaagaga agaaaaaga gaaagaaaaa gaagaaggag   1560
atttaaaaag ttgtttagtt gaaaaggag aggaggaag aagcagcgac agcggcagaa   1620
gaagaagtag ttgttgtaag aggggaacgg aggcagtagc agtggagcag gcggaggcga   1680
cagcaaacct cgaactcgac cccgtcgagc cgcagcaaga acaagagccc gaccaggtgg   1740
acgaggacga ggtccgcttg ttgtcaggaa caacagaagt tgcaggacta gccgagagtg   1800
ctaccactgc aattcttaga tccacagacg caagagcaga aaacttacaa ctgctcgcca   1860
caacacaaga accaccttca gatacaacca ggttcgagaa ctccacaagt ctagaagcag   1920
caacagctct agcagataat caaacaggtc cagaaaaagc tacgactaga agagaaatta   1980
tcgagtcgca acttgcaacc                                               2000
```

<210> SEQ ID NO 79
<211> LENGTH: 4683
<212> TYPE: DNA
<213> ORGANISM: Ulkenia sp.

<400> SEQUENCE: 79

```
gcgagttata tctgtctaga aaacttggca tggctagcaa tttatgtcta gctattccat     60
acacacggta atgccagtag cctgttagtt atagctcttt tggttgttgt ctcacaatac    120
actgacatca gcagaacaaa atgaaagggg ccttggctac catgaaatca atacttcaaa    180
aggtctcttg gtttctttac tcgcatgtcg ctatttactt acattcctcg agtacataac    240
atatcataca tcaaagaaat taaaaagaaa acaaacattc aaatatgcat tactttccct    300
actgtactag taagtacgtt tctggtatta agttgttttt tctcaaaaga acaatgtgct    360
tacttgtaaa atccacagct gcttacttgt aagcctcaac tagttagtga tgtgattatc    420
```

```
ataaaatgtt cgacactgta cctcctttcc agctatcttc ctacacctcc tctgacgcag    480
gttgacggag gaggcgtggg ggttgattga agtgcaacac aacgttttgt ttaagatatt    540
ccttgccttg gccgactcca aatggatagc acagaagcct aatgataatt tgaattaatt    600
ttatttcgag cttatttaat gctcttatca gagtccgtag gtatctcttt tcctactaat    660
tgttgaaaaa ggatgttttg gacatagcag gtcatcatac tatttggttc catcaaattc    720
atatccattt ctttcgttca agtgcttccc ttcctactta ttatatatat tatatatcca    780
taaatgtaaa agagacgatt acgaatactt tgcatacatg tatagcgaaa cagagatggt    840
agcaaaagtt caccttcact aatctaagaa tctctccacg tgggtaaaaa cttcagcagt    900
aagattgtaa atgatgtcca agaacaaaac gtcatgctag tccaggggtt actgagctaa    960
cgattaataa tgtttcgtag tcttcctaat tgcaccatca aaacttgtct gcacaagttt   1020
taaagtattg gagcctttac tgaagaatca gaggacatag atggggcacg ttcgccttga   1080
aaaaaatagt cttctttacc tgcatggtgt tacaaacaaa aacgagttga aaatagctgt   1140
gcaaggaggc aaacatgatt ggaaaagaaa aacgagggga cccttataca ggagggcgcc   1200
acatagtaga atgagtagat tgttagagta gggtacgctt tatgtgattg attgaatggg   1260
cgagtgaaag ttgctgtcaa ggttctaaac aaaaggatgt ttgagtttgt gagtattgtt   1320
tgcggcaaaa agattcagta gagagaaatg cacaaaaaga taatacgtgt gtagggcgat   1380
tatggaggca tgcatttggg ggaaatcatc gcatgcgcat gagtttctcc atctgccgaa   1440
tctttgcaaa ggcattttca agctccattt gcatagcgta ggcttgctgc tcaaactgag   1500
cgcgctgatg cgccagattt tcttcatgtc ttttgttcaa actacgctca agaccctcaa   1560
gagccgcaac cttgagcttg cgttcctttt gctgaatctc cataactctt cgtttcacct   1620
ggagctcaat ttctgcagca tccgtggtct ttgcagcggc ctgtgcgtct tgtgcggcct   1680
gtgcgttgtt tgcgagctcc tttcgcagct cctccatctc cgcgttcttt ttctcctcca   1740
tccatttggc accgagtttg gcagcttgat cgatgcggcc cttgagaact tcttcgttct   1800
cctcaagttc tgcgatacgc gcgtgtaagc cgaggatctc ctccgagaca gcctcgccat   1860
tgatcattat ttcacttccc gagtcttgaa tgacaacatc agccttggtg ccaggttcac   1920
cggtatctcg ctcgcaaccc tgctggcgca tagacagcat aaggcgcgca ttatcctcac   1980
gcagatcatc cacctgttct gataaaagtt tgactgcctg ctcaagatta cggggggttca   2040 cttcgtgaaa aatttcttga aggtctcgaa gctcagaaag cttggcagag caagtgtgca   2100
tcgctctgca cttttttaaga cgtgcaagtg catcatcaag tttggcatta tttaccttca   2160
tggaggcttc agctacttcg gcttcttcga ttacaatttt ctgcagctct acaacatcat   2220
ggccaattaa cttgcgatgc agctcggcaa tcaccccatg catctttttcg gtatggcctg   2280 gacgcgcctc atcctgcgtt cttcggatct cctcctctag ttctcgattt agacgaaggg   2340
ctggtccaag gggcgggtaa ttagcctgag tcaagccaag ctctgttgct agtccaaggc   2400
agtcggaaag tcgcagccgg tccctatcag aaacagcctt ttgcaagtct acgctcaaac   2460
gcacttcttg agccttgcgc accatcttcg gttctgcctg tcgcagaagt ttcgagtcgt   2520
agccagcttg ccacgctagc acgatggcac gcgcaagtga cctcagttga ccgctgttca   2580
tggcagactt gagcaacatt tgatttgca caaatacctc atctgattca tcatcttcag   2640
cttcctcaag ctctgcaggt gtcttgcgct ctccagagac ttgaagagca gggttcaaac   2700
cgccctccag gacctcgctc gcaagcgcct cctctgtctc agctttgcgc aatagcgcag   2760
cagcattctc cgccattgtg tttgtcactc acgagattaa tatcgttgcc agagtatacg   2820
```

```
gtaatgcgag ttaaggattc acagaatctc tcaaattaat ctttcaccct aatgatatcc    2880
acaaaacgtt gcaatcgctc agcccaacga caagcgtgct tcttgtttta agactgcaac    2940
tgctcctttt tctattagtc aatatggacc gtcctccaaa cgtccagaaa atagcacaga    3000
atttaccagc agccgctgca gacaagaagt gcaagagagc aggcaagcaa gtgagggttt    3060
gagcaaatag gccaacctct ccacgcagaa ttctagggtc gcaaccggaa ctcacagtcc    3120
ttagaaaccg tgcgaagccc tgggctcaac ttcaatttgt ccacgggacc ttcagcaagc    3180
accaagctca gcagcgtgaa ggcaggcgct gaccacagtt tgagctcaga gggcttggtg    3240
tgcctcgcga ttgatattga agtcaattgc gcaggacggc agcaacggac caggtggtga    3300
agaaggtaat ctccagcgga gtgatgatgg agctcgaccg actactccgg aatcgaccag    3360
gggaggtgcg ggcgcccttc acaagcgggc gagaggcagg ggagagaagg ctcgactcca    3420
cgtcttgaag cgtgtacgtg tgcgcgctca cgcgtgcgac acgccggcaa gggcgcctta    3480
gtggcctgct gctgctgctg gtcgccacgc tgcgagccca agagatttga attgaactcg    3540
aagaaaataa ctatcattta tcaattccaa tcaatcaatg cattatgaag cacctctgaa    3600
gtgaactatt ctcctctcca atatacaaca aaaacacac acagtgggtt ttaccctata    3660
acctattgtt ccgcgagcga tcaactactc tatagagcga atgaccagtt tttcttctt    3720
tcttctttc tttctttctt tcttctttc ttctttctt tcttctttc tttcttctg    3780
ttttcctatc taataacccc tttaatcgag gaaaccttttc gatttaaaag gaaagctctg    3840
tctgtatata tctgttacag atactgctat catgccatgc agaaagaaac acaaagaaa    3900
aacaaaagaa agagagaaag agagaaagaa agagagaaag aaagaaagaa agaaagaaag    3960
aagagcttt ctcaatcggt ttcctcatcg accgctcaca tatctacgat tgtggcaaag    4020
aaagaaagaa agaaagaagg aaagcctcag cagagtccgc acgaaagcct tcattgagcc    4080
accatgtcgt ggtccgctgc agtcagtgcc gcctctctgt gaattgagtg agtgagtgag    4140
tgagtgagtt ggttggttag ttagttagtg cctcttcagc tcaaagcctt tcacggtcgc    4200
tcttcgagcg tttgcttttt cataaacaaa taaacaaacc atcgaacgaa ccatcgaacg    4260
aacgaacaat ggtaccccag aatagacgga attaattgct aagtaaacca gtaacagtaa    4320
gttagtgttt ctgacctgag ccgttttctt tatttattcc tctcagctct gtgaagagaa    4380
tttgggatga aaagaaacgt tttatttat ttaaagttt agtaacaaga aaacatggt    4440
ccctcttctt ccttcatgta aaaataagta agtaaaaaaa agaaagaaa aaaaaaaag    4500
cttttaaagt agtaaagcga ggtagagata aagttctttt ctcagggctc ctagtaggca    4560
cttaggaggt acgtctaaga ccgcctcgtg ggaagaaaag agaaacaag aagagaaaag    4620
agagagagaa acagcgctga cccgagaggc tcatgcgcag agcccaaatc tgcccaactt    4680
tgg                                                                 4683
```

<210> SEQ ID NO 80  
<211> LENGTH: 1848  
<212> TYPE: PRT  
<213> ORGANISM: Ulkenia sp.

<400> SEQUENCE: 80

```
Met Leu Val Ile Gly Ala Leu Ala Arg Ala Leu Tyr Gly Ala Trp Arg
1               5                   10                  15

Cys Thr Gly Arg Ala Arg Glu Gly Thr Gly Ser Arg Glu Ala Leu Leu
            20                  25                  30

Gly Gly Ala Glu Arg Glu Gly Glu Val Leu Cys Asp Ala Arg Gly
        35                  40                  45
```

```
Asp Leu Gly Ala Ala Ala Arg Cys Ser Ser Arg Asp Leu Gly Arg Glu
    50                  55                  60

Ser Lys Pro Ser Ala Glu Glu Met Val Glu Gly Pro Arg Ile Gly Ser
65              70                  75                  80

Arg Glu Glu Glu Ile Glu Glu Glu Glu Ile Glu Glu Glu Glu Glu Ile
                85                  90                  95

Glu Glu Glu Glu Ile Glu Glu Glu Glu Glu Asp Gly Gln Ala Gly Lys
                100                 105                 110

Met Glu Lys Gly Leu Ala Ala Gly Lys Gln Glu Asn Val Asn Leu Gly
        115                 120                 125

Leu Asn Phe Gly Leu Asn Leu Asn Val Glu Asn Glu Gly Leu Asn Leu
    130                 135                 140

Ser Leu Asn Leu Lys Glu Asn Leu Arg Lys Glu Ser Leu Val Glu Ser
145                 150                 155                 160

Glu Lys Glu Lys Asn Glu Lys Glu Lys Glu Lys Glu Lys Glu Lys Glu
                165                 170                 175

Lys Glu Lys Glu Lys Glu Lys Glu Lys Glu Lys Glu Lys Glu Lys Glu
                180                 185                 190

Lys Glu Lys Glu Lys Glu Lys Glu Lys Glu Lys Glu Lys Glu Lys Glu
                195                 200                 205

Lys Glu Lys Glu Lys Glu Glu Lys Glu Glu Lys Glu Lys Glu
                210                 215                 220

Lys Glu Lys Glu Lys Glu Lys Glu Glu Gly Asp Leu Lys Ser
225                 230                 235                 240

Cys Leu Val Glu Lys Gly Glu Gly Gly Arg Ser Ser Asp Ser Gly Arg
                245                 250                 255

Arg Arg Ser Ser Cys Cys Lys Arg Gly Thr Glu Ala Val Ala Val Glu
                260                 265                 270

Gln Ala Glu Ala Thr Ala Asn Leu Glu Leu Asp Pro Val Glu Pro Gln
            275                 280                 285

Gln Glu Gln Glu Pro Asp Gln Val Asp Glu Asp Glu Val Arg Leu Leu
        290                 295                 300

Ser Gly Thr Thr Glu Val Ala Gly Leu Ala Glu Ser Ala Thr Thr Ala
305                 310                 315                 320

Ile Leu Arg Ser Thr Asp Ala Arg Ala Glu Asn Leu Gln Leu Leu Ala
            325                 330                 335

Thr Thr Gln Glu Pro Pro Ser Asp Thr Thr Arg Phe Glu Asn Ser Thr
        340                 345                 350

Ser Leu Glu Ala Ala Thr Ala Leu Ala Asp Asn Gln Thr Gly Pro Glu
        355                 360                 365

Lys Ala Thr Thr Arg Arg Glu Ile Ile Glu Ser Gln Leu Ala Thr Met
    370                 375                 380

Ala Thr Arg Val Lys Thr Asn Lys Lys Pro Cys Trp Glu Met Thr Lys
385                 390                 395                 400

Glu Glu Leu Thr Ser Gly Lys Asn Val Val Phe Asp Tyr Asp Glu Leu
                405                 410                 415

Leu Glu Phe Ala Glu Gly Asp Ile Ser Lys Val Phe Gly Pro Glu Phe
            420                 425                 430

Ser Gln Ile Asp Gln Tyr Lys Arg Arg Val Arg Leu Pro Ala Arg Glu
        435                 440                 445

Tyr Leu Leu Val Thr Arg Val Thr Leu Met Asp Ala Glu Val Asn Asn
    450                 455                 460

Tyr Arg Val Gly Ala Arg Met Val Thr Glu Tyr Asp Leu Pro Val Asn
```

```
                465                 470                 475                 480
Gly Glu Leu Ser Glu Gly Gly Asp Cys Pro Trp Ala Val Leu Val Glu
                    485                 490                 495

Ser Gly Gln Cys Asp Leu Met Leu Ile Ser Tyr Met Gly Ile Asp Phe
                500                 505                 510

Gln Asn Lys Ser Asp Arg Val Tyr Arg Leu Leu Asn Thr Thr Leu Thr
            515                 520                 525

Phe Tyr Gly Val Ala Gln Glu Gly Glu Thr Leu Glu Tyr Asp Ile Arg
        530                 535                 540

Val Thr Gly Phe Ala Lys Arg Leu Asp Gly Asp Ile Ser Met Phe Phe
545                 550                 555                 560

Phe Glu Tyr Asp Cys Tyr Val Asn Gly Arg Leu Leu Ile Glu Met Arg
                565                 570                 575

Asp Gly Cys Ala Gly Phe Phe Thr Asn Glu Glu Leu Ala Ala Gly Lys
                580                 585                 590

Gly Val Val Phe Thr Arg Ala Asp Leu Leu Ala Arg Glu Lys Thr Lys
            595                 600                 605

Lys Gln Asp Ile Thr Pro Tyr Ala Ile Ala Pro Arg Leu Asn Lys Thr
        610                 615                 620

Val Leu Asn Glu Thr Glu Met Gln Ser Leu Val Asp Lys Asn Trp Thr
625                 630                 635                 640

Lys Val Phe Gly Pro Glu Asn Gly Met Asp Gln Ile Asn Tyr Lys Leu
                645                 650                 655

Cys Ala Arg Lys Met Leu Met Ile Asp Arg Val Thr Lys Ile Asp Tyr
                660                 665                 670

Thr Gly Gly Pro Tyr Gly Leu Gly Leu Leu Val Gly Glu Lys Ile Leu
            675                 680                 685

Glu Arg Asp His Trp Tyr Phe Pro Cys His Phe Val Gly Asp Gln Val
        690                 695                 700

Met Ala Gly Ser Leu Val Ser Asp Gly Cys Ser Gln Leu Leu Lys Met
705                 710                 715                 720

Tyr Met Leu Trp Leu Gly Leu His Leu Lys Thr Gly Pro Phe Asp Phe
                725                 730                 735

Arg Pro Val Asn Gly His Pro Asn Lys Val Arg Cys Arg Gly Gln Ile
                740                 745                 750

Ser Pro His Lys Gly Lys Leu Val Tyr Val Met Glu Ile Lys Glu Met
            755                 760                 765

Gly Tyr Asp Glu Ala Gly Asp Pro Tyr Ala Ile Ala Asp Val Asn Ile
        770                 775                 780

Leu Asp Ile Asp Phe Glu Lys Gly Gln Thr Phe Asp Leu Ala Asn Leu
785                 790                 795                 800

His Glu Tyr Gly Lys Gly Asp Leu Asn Lys Lys Ile Val Val Asp Phe
                805                 810                 815

Lys Gly Ile Ala Leu Lys Leu Gln Lys Arg Ser Gly Pro Ala Val Val
                820                 825                 830

Ala Pro Glu Lys Pro Leu Ala Leu Asn Lys Asp Leu Cys Ala Pro Ala
            835                 840                 845

Val Glu Ala Ile Pro Glu His Ile Leu Lys Gly Asp Ala Leu Ala Pro
        850                 855                 860

Asn Gln Met Thr Trp His Pro Met Ser Lys Ile Ala Gly Asn Pro Thr
865                 870                 875                 880

Pro Ser Phe Ser Pro Ser Ala Tyr Pro Pro Arg Pro Ile Thr Phe Thr
                885                 890                 895
```

```
Pro Phe Pro Gly Asn Lys Asn Asp Asn Asn His Val Pro Gly Glu Met
            900                 905                 910
Pro Leu Ser Trp Tyr Asn Met Ala Glu Phe Met Ala Gly Lys Val Ser
            915                 920                 925
Leu Cys Leu Gly Pro Glu Phe Ala Lys Phe Asp Ser Asn Thr Ser
    930                 935                 940
Arg Ser Pro Ala Trp Asp Leu Ala Leu Val Thr Arg Val Val Ser Val
945                 950                 955                 960
Ser Asp Met Glu Trp Val Gln Trp Lys Asn Val Asp Cys Asn Pro Ser
            965                 970                 975
Lys Gly Thr Met Val Gly Glu Phe Asp Cys Pro Ile Asp Ala Trp Phe
            980                 985                 990
Phe Gln Gly Ser Cys Asn Asp Gly His Met Pro Tyr Ser Ile Leu Met
            995                 1000                1005
Glu Ile Ala Leu Gln Thr Ser Gly Val Leu Thr Ser Val Leu Lys
    1010                1015                1020
Ala Pro Leu Thr Met Glu Lys Lys Asp Ile Leu Phe Arg Asn Leu
    1025                1030                1035
Asp Ala Asn Ala Glu Met Val Arg Ser Asp Ile Asp Leu Arg Gly
    1040                1045                1050
Lys Thr Ile His Asn Leu Thr Lys Cys Thr Gly Tyr Ser Met Leu
    1055                1060                1065
Gly Asp Met Gly Val His Arg Phe Ser Phe Glu Leu Ser Val Asp
    1070                1075                1080
Gly Val Val Phe Tyr Lys Gly Thr Thr Ser Phe Gly Trp Phe Val
    1085                1090                1095
Pro Glu Val Phe Ile Ser Gln Thr Gly Leu Asp Asn Gly Arg Arg
    1100                1105                1110
Thr Gln Pro Trp His Ile Glu Ser Lys Val Pro Ser Ala Gln Val
    1115                1120                1125
Leu Thr Tyr Asp Val Thr Pro Asn Gly Ala Gly Arg Thr Gln Leu
    1130                1135                1140
Tyr Ala Asn Ala Pro Lys Gly Ala Gln Leu Thr Arg Arg Trp Asn
    1145                1150                1155
Gln Cys Gln Tyr Leu Asp Thr Ile Asp Leu Val Val Ala Gly Gly
    1160                1165                1170
Ser Ala Gly Leu Gly Tyr Gly His Gly Arg Lys Gln Val Asn Pro
    1175                1180                1185
Lys Asp Trp Phe Phe Ser Cys His Phe Trp Phe Asp Ser Val Met
    1190                1195                1200
Pro Gly Ser Leu Gly Val Glu Ser Met Phe Gln Leu Val Glu Ser
    1205                1210                1215
Ile Ala Val Lys Gln Asp Leu Ala Gly Lys Tyr Gly Ile Thr Asn
    1220                1225                1230
Pro Thr Phe Ala His Ala Pro Gly Lys Ile Ser Trp Lys Tyr Arg
    1235                1240                1245
Gly Gln Leu Thr Pro Thr Ser Lys Phe Met Asp Ser Glu Ala His
    1250                1255                1260
Ile Val Ser Ile Glu Ala His Asp Gly Val Val Asp Ile Val Ala
    1265                1270                1275
Asn Gly Asn Leu Trp Ala Asp Gly Leu Arg Val Tyr Asn Val Ser
    1280                1285                1290
Asn Ile Arg Val Arg Ile Val Ala Gly Ala Ala Pro Ala Ala Ala
    1295                1300                1305
```

```
Ala Ala Ala Ala Ala Val Ala Pro Ala Ala Pro Ala Pro
    1310            1315            1320

Val Ala Ala Ser Gly Pro Ala Gln Thr Ile Thr Leu Lys Gln Leu
    1325            1330            1335

Lys Ala Glu Leu Leu Asp Val Glu Lys Pro Leu Tyr Ile Ser Ser
    1340            1345            1350

Ser Asn Gly Gln Val Lys Lys His Ala Asp Val Ala Gly Gly Gln
    1355            1360            1365

Ala Thr Ile Val Gln Ala Cys Ser Leu Ser Asp Leu Gly Asp Glu
    1370            1375            1380

Gly Phe Met Lys Thr Tyr Gly Val Val Ala Pro Leu Tyr Thr Gly
    1385            1390            1395

Ala Met Ala Lys Gly Ile Ala Ser Ala Asp Leu Val Ile Ala Thr
    1400            1405            1410

Gly Lys Arg Lys Ile Leu Gly Ser Phe Gly Ala Gly Gly Leu Pro
    1415            1420            1425

Met His Ile Val Arg Ala Ala Val Glu Lys Ile Gln Ala Glu Leu
    1430            1435            1440

Pro Asn Gly Pro Phe Ala Val Asn Leu Ile His Ser Pro Phe Asp
    1445            1450            1455

Ser Asn Leu Glu Lys Gly Asn Val Asp Leu Phe Leu Glu Lys Gly
    1460            1465            1470

Val Thr Val Val Glu Ala Ser Ala Phe Met Thr Leu Thr Pro Gln
    1475            1480            1485

Val Val Arg Tyr Arg Ala Ala Gly Leu Ser Arg Asn Ala Asp Gly
    1490            1495            1500

Ser Ile Asn Ile Lys Asn Arg Ile Ile Gly Lys Val Ser Arg Thr
    1505            1510            1515

Glu Leu Ala Glu Met Phe Ile Arg Pro Ala Pro Gln Asn Leu Leu
    1520            1525            1530

Asp Lys Leu Ile Gln Ser Gly Glu Ile Thr Lys Glu Gln Ala Glu
    1535            1540            1545

Leu Ala Lys Leu Val Pro Val Ala Asp Asp Ile Ala Val Glu Ala
    1550            1555            1560

Asp Ser Gly Gly His Thr Asp Asn Arg Pro Ile His Val Ile Leu
    1565            1570            1575

Pro Leu Ile Ile Asn Leu Arg Asn Arg Leu His Lys Glu Cys Gly
    1580            1585            1590

Tyr Pro Ala His Leu Arg Val Arg Val Gly Ala Gly Gly Gly Val
    1595            1600            1605

Gly Cys Pro Gln Ala Ala Ala Ala Ala Leu Ala Met Gly Ala Ala
    1610            1615            1620

Phe Leu Val Thr Gly Thr Val Asn Gln Val Ala Lys Gln Ser Gly
    1625            1630            1635

Thr Cys Asp Asn Val Arg Lys Gln Leu Cys Met Ala Thr Tyr Ser
    1640            1645            1650

Asp Val Cys Met Ala Pro Ala Ala Asp Met Phe Glu Glu Gly Val
    1655            1660            1665

Lys Leu Gln Val Leu Lys Lys Gly Thr Met Phe Pro Ser Arg Ala
    1670            1675            1680

Asn Lys Leu Tyr Glu Leu Phe Cys Lys Tyr Asp Ser Phe Glu Ser
    1685            1690            1695

Met Pro Ala Thr Glu Leu Glu Arg Val Glu Lys Arg Ile Phe Gln
```

```
                      1700                1705                1710

Cys Pro Leu Ala Asp Val Trp Ala Glu Thr Ser Asp Phe Tyr Ile
    1715                1720                1725

Asn Arg Leu His Asn Pro Glu Lys Ile Thr Arg Ala Glu Arg Asp
    1730                1735                1740

Pro Lys Leu Lys Met Ser Leu Cys Phe Arg Trp Tyr Leu Gly Leu
    1745                1750                1755

Ala Ser Arg Trp Ala Asn Thr Gly Glu Ala Gly Arg Val Met Asp
    1760                1765                1770

Tyr Gln Val Trp Cys Gly Pro Ala Ile Gly Ala Phe Asn Asp Phe
    1775                1780                1785

Ile Lys Gly Ser Tyr Leu Asp Pro Ala Val Ser Gly Glu Tyr Pro
    1790                1795                1800

Asp Val Val Gln Ile Asn Leu Gln Ile Leu Arg Gly Ala Cys Tyr
    1805                1810                1815

Leu Arg Arg Leu Asn Val Ile Arg Asn Asp Pro Arg Val Ser Ile
    1820                1825                1830

Glu Val Glu Asp Ala Glu Phe Val Tyr Glu Pro Thr Asn Ala Leu
    1835                1840                1845

<210> SEQ ID NO 81
<211> LENGTH: 18
<212> TYPE: DNA
<213> ORGANISM: artificial sequence
<220> FEATURE:
<223> OTHER INFORMATION: completely synthesized oligonucleotide MOF1
<220> FEATURE:
<221> NAME/KEY: misc_feature
<222> LOCATION: (1)..(18)

<400> SEQUENCE: 81
ctcggcattg actccatc                                                   18

<210> SEQ ID NO 82
<211> LENGTH: 18
<212> TYPE: DNA
<213> ORGANISM: artificial sequence
<220> FEATURE:
<223> OTHER INFORMATION: completely synthesized oligonucleotide MOR1
<220> FEATURE:
<221> NAME/KEY: misc_feature
<222> LOCATION: (1)..(18)

<400> SEQUENCE: 82
gagaatctcg acacgctt                                                   18

<210> SEQ ID NO 83
<211> LENGTH: 21
<212> TYPE: DNA
<213> ORGANISM: artificial sequence
<220> FEATURE:
<223> OTHER INFORMATION: completely synthesized oligonucleotide PSF2
<220> FEATURE:
<221> NAME/KEY: misc_feature
<222> LOCATION: (1)..(21)

<400> SEQUENCE: 83
attactcctc tctgcatccg t                                               21

<210> SEQ ID NO 84
<211> LENGTH: 21
<212> TYPE: DNA
<213> ORGANISM: artificial sequence
<220> FEATURE:
```

-continued

```
<223> OTHER INFORMATION: completely synthesized oligonucleotide PSR2
<220> FEATURE:
<221> NAME/KEY: misc_feature
<222> LOCATION: (1)..(21)

<400> SEQUENCE: 84
gccgaagaca gcatcaaact c                                              21

<210> SEQ ID NO 85
<211> LENGTH: 21
<212> TYPE: DNA
<213> ORGANISM: artificial sequence
<220> FEATURE:
<223> OTHER INFORMATION: completely synthesized oligonucleotide CFOR1
<220> FEATURE:
<221> NAME/KEY: misc_feature
<222> LOCATION: (1)..(21)

<400> SEQUENCE: 85
gtcgagagtg gccagtgcga t                                              21

<210> SEQ ID NO 86
<211> LENGTH: 21
<212> TYPE: DNA
<213> ORGANISM: artificial sequence
<220> FEATURE:
<223> OTHER INFORMATION: completely synthesized oligonucleotide CREV3
<220> FEATURE:
<221> NAME/KEY: misc_feature
<222> LOCATION: (1)..(21)

<400> SEQUENCE: 86
aaagtggcag ggaaagtacc a                                              21

<210> SEQ ID NO 87
<211> LENGTH: 2910
<212> TYPE: PRT
<213> ORGANISM: Schizochytrium sp.

<400> SEQUENCE: 87

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45

Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Lys Asn Ile
        115                 120                 125

Gly Cys Val Leu Gly Ile Gly Gly Gln Lys Ser Ser His Glu Phe
        130                 135                 140

Tyr Ser Arg Leu Asn Tyr Val Val Val Glu Lys Val Leu Arg Lys Met
145                 150                 155                 160

Gly Met Pro Glu Glu Asp Val Lys Val Ala Val Glu Lys Tyr Lys Ala
                165                 170                 175
```

-continued

```
Asn Phe Pro Glu Trp Arg Leu Asp Ser Phe Pro Gly Phe Leu Gly Asn
            180                 185                 190

Val Thr Ala Gly Arg Cys Thr Asn Thr Phe Asn Leu Asp Gly Met Asn
            195                 200                 205

Cys Val Asp Ala Ala Cys Ala Ser Ser Leu Ile Ala Val Lys Val
            210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
            260                 265                 270

Thr Lys Gly Met Leu Ile Gly Glu Gly Ser Ala Met Leu Val Leu Lys
            275                 280                 285

Arg Tyr Ala Asp Ala Val Arg Asp Gly Asp Glu Ile His Ala Val Ile
            290                 295                 300

Arg Gly Cys Ala Ser Ser Ser Asp Gly Lys Ala Ala Gly Ile Tyr Thr
305                 310                 315                 320

Pro Thr Ile Ser Gly Gln Glu Glu Ala Leu Arg Arg Ala Tyr Asn Arg
                325                 330                 335

Ala Cys Val Asp Pro Ala Thr Val Thr Leu Val Glu Gly His Gly Thr
            340                 345                 350

Gly Thr Pro Val Gly Asp Arg Ile Glu Leu Thr Ala Leu Arg Asn Leu
            355                 360                 365

Phe Asp Lys Ala Tyr Gly Glu Gly Asn Thr Glu Lys Val Ala Val Gly
            370                 375                 380

Ser Ile Lys Ser Ser Ile Gly His Leu Lys Ala Val Ala Gly Leu Ala
385                 390                 395                 400

Gly Met Ile Lys Val Ile Met Ala Leu Lys His Lys Thr Leu Pro Gly
                405                 410                 415

Thr Ile Asn Val Asp Asn Pro Pro Asn Leu Tyr Asp Asn Thr Pro Ile
            420                 425                 430

Asn Glu Ser Ser Leu Tyr Ile Asn Thr Met Asn Arg Pro Trp Phe Pro
            435                 440                 445

Pro Pro Gly Val Pro Arg Arg Ala Gly Ile Ser Ser Phe Gly Phe Gly
450                 455                 460

Gly Ala Asn Tyr His Ala Val Leu Glu Glu Ala Glu Pro Glu His Thr
465                 470                 475                 480

Thr Ala Tyr Arg Leu Asn Lys Arg Pro Gln Pro Val Leu Met Met Ala
                485                 490                 495

Ala Thr Pro Ala Ala Leu Gln Ser Leu Cys Glu Ala Gln Leu Lys Glu
            500                 505                 510

Phe Glu Ala Ala Ile Lys Glu Asn Glu Thr Val Lys Asn Thr Ala Tyr
            515                 520                 525

Ile Lys Cys Val Lys Phe Gly Glu Gln Phe Lys Phe Pro Gly Ser Ile
            530                 535                 540

Pro Ala Thr Asn Ala Arg Leu Gly Phe Leu Val Lys Asp Ala Glu Asp
545                 550                 555                 560

Ala Cys Ser Thr Leu Arg Ala Ile Cys Ala Gln Phe Ala Lys Asp Val
                565                 570                 575

Thr Lys Glu Ala Trp Arg Leu Pro Arg Glu Gly Val Ser Phe Arg Ala
            580                 585                 590

Lys Gly Ile Ala Thr Asn Gly Ala Val Ala Ala Leu Phe Ser Gly Gln
            595                 600                 605
```

```
Gly Ala Gln Tyr Thr His Met Phe Ser Glu Val Ala Met Asn Trp Pro
    610                 615                 620
Gln Phe Arg Gln Ser Ile Ala Ala Met Asp Ala Ala Gln Ser Lys Val
625                 630                 635                 640
Ala Gly Ser Asp Lys Asp Phe Glu Arg Val Ser Gln Val Leu Tyr Pro
                645                 650                 655
Arg Lys Pro Tyr Glu Arg Glu Pro Gln Asp His Lys Lys Ile Ser
                660                 665                 670
Leu Thr Ala Tyr Ser Gln Pro Ser Thr Leu Ala Cys Ala Leu Gly Ala
            675                 680                 685
Phe Glu Ile Phe Lys Glu Ala Gly Phe Thr Pro Asp Phe Ala Ala Gly
    690                 695                 700
His Ser Leu Gly Glu Phe Ala Ala Leu Tyr Ala Ala Gly Cys Val Asp
705                 710                 715                 720
Arg Asp Glu Leu Phe Glu Leu Val Cys Arg Arg Ala Arg Ile Met Gly
                725                 730                 735
Gly Lys Asp Ala Pro Ala Thr Pro Lys Gly Cys Met Ala Ala Val Ile
            740                 745                 750
Gly Pro Asn Ala Glu Asn Ile Lys Val Gln Ala Ala Asn Val Trp Leu
    755                 760                 765
Gly Asn Ser Asn Ser Pro Ser Gln Thr Val Ile Thr Gly Ser Val Glu
770                 775                 780
Gly Ile Gln Ala Glu Ser Ala Arg Leu Gln Lys Glu Gly Phe Arg Val
785                 790                 795                 800
Val Pro Leu Ala Cys Glu Ser Ala Phe His Ser Pro Gln Met Glu Asn
                805                 810                 815
Ala Ser Ser Ala Phe Lys Asp Val Ile Ser Lys Val Ser Phe Arg Thr
            820                 825                 830
Pro Lys Ala Glu Thr Lys Leu Phe Ser Asn Val Ser Gly Glu Thr Tyr
    835                 840                 845
Pro Thr Asp Ala Arg Glu Met Leu Thr Gln His Met Thr Ser Ser Val
850                 855                 860
Lys Phe Leu Thr Gln Val Arg Asn Met His Gln Ala Gly Ala Arg Ile
865                 870                 875                 880
Phe Val Glu Phe Gly Pro Lys Gln Val Leu Ser Lys Leu Val Ser Glu
                885                 890                 895
Thr Leu Lys Asp Asp Pro Ser Val Val Thr Val Ser Val Asn Pro Ala
            900                 905                 910
Ser Gly Thr Asp Ser Asp Ile Gln Leu Arg Asp Ala Ala Val Gln Leu
    915                 920                 925
Val Val Ala Gly Val Asn Leu Gln Gly Phe Asp Lys Trp Asp Ala Pro
930                 935                 940
Asp Ala Thr Arg Met Gln Ala Ile Lys Lys Arg Thr Thr Leu Arg
945                 950                 955                 960
Leu Ser Ala Ala Thr Tyr Val Ser Asp Lys Thr Lys Lys Val Arg Asp
                965                 970                 975
Ala Ala Met Asn Asp Gly Arg Cys Val Thr Tyr Leu Lys Gly Ala Ala
            980                 985                 990
Pro Leu Ile Lys Ala Pro Glu Pro Val Val Asp Glu Ala Ala Lys Arg
    995                 1000                1005
Glu Ala Glu Arg Leu Gln Lys Glu Leu Gln Asp Ala Gln Arg Gln
    1010                1015                1020
Leu Asp Asp Ala Lys Arg Ala Ala Ala Glu Ala Asn Ser Lys Leu
```

-continued

```
            1025                1030                1035

Ala Ala Ala Lys Glu Glu Ala Lys Thr Ala Ala Ala Ser Ala Lys
        1040                1045                1050

Pro Ala Val Asp Thr Ala Val Val Glu Lys His Arg Ala Ile Leu
        1055                1060                1065

Lys Ser Met Leu Ala Glu Leu Asp Gly Tyr Gly Ser Val Asp Ala
        1070                1075                1080

Ser Ser Leu Gln Gln Gln Gln Gln Gln Thr Ala Pro Ala Pro
        1085                1090                1095

Val Lys Ala Ala Ala Pro Ala Ala Pro Val Ala Ser Ala Pro Ala
        1100                1105                1110

Pro Ala Val Ser Asn Glu Leu Leu Glu Lys Ala Glu Thr Val Val
        1115                1120                1125

Met Glu Val Leu Ala Ala Lys Thr Gly Tyr Glu Thr Asp Met Ile
        1130                1135                1140

Glu Ala Asp Met Glu Leu Glu Thr Glu Leu Gly Ile Asp Ser Ile
        1145                1150                1155

Lys Arg Val Glu Ile Leu Ser Glu Val Gln Ala Met Leu Asn Val
        1160                1165                1170

Glu Ala Lys Asp Val Asp Ala Leu Ser Arg Thr Arg Thr Val Gly
        1175                1180                1185

Glu Val Val Asn Ala Met Lys Ala Glu Ile Ala Gly Ser Ser Ala
        1190                1195                1200

Pro Ala Pro Ala Ala Ala Pro Ala Pro Ala Lys Ala Ala Pro
        1205                1210                1215

Ala Ala Ala Ala Pro Ala Val Ser Asn Glu Leu Leu Glu Lys Ala
        1220                1225                1230

Glu Thr Val Val Met Glu Val Leu Ala Ala Lys Thr Gly Tyr Glu
        1235                1240                1245

Thr Asp Met Ile Glu Ser Asp Met Glu Leu Glu Thr Glu Leu Gly
        1250                1255                1260

Ile Asp Ser Ile Lys Arg Val Glu Ile Leu Ser Glu Val Gln Ala
        1265                1270                1275

Met Leu Asn Val Glu Ala Lys Asp Val Asp Ala Leu Ser Arg Thr
        1280                1285                1290

Arg Thr Val Gly Glu Val Val Asn Ala Met Lys Ala Glu Ile Ala
        1295                1300                1305

Gly Gly Ser Ala Pro Ala Pro Ala Ala Ala Ala Pro Gly Pro Ala
        1310                1315                1320

Ala Ala Ala Pro Ala Pro Ala Ala Ala Pro Ala Val Ser Asn
        1325                1330                1335

Glu Leu Leu Glu Lys Ala Glu Thr Val Val Met Glu Val Leu Ala
        1340                1345                1350

Ala Lys Thr Gly Tyr Glu Thr Asp Met Ile Glu Ser Asp Met Glu
        1355                1360                1365

Leu Glu Thr Glu Leu Gly Ile Asp Ser Ile Lys Arg Val Glu Ile
        1370                1375                1380

Leu Ser Glu Val Gln Ala Met Leu Asn Val Glu Ala Lys Asp Val
        1385                1390                1395

Asp Ala Leu Ser Arg Thr Arg Thr Val Gly Glu Val Val Asp Ala
        1400                1405                1410

Met Lys Ala Glu Ile Ala Gly Gly Ser Ala Pro Ala Pro Ala Ala
        1415                1420                1425
```

```
Ala Ala Pro Ala Pro Ala Ala Ala Ala Pro Pro Ala Ala Pro
    1430            1435            1440

Ala Pro Ala Val Ser Ser Glu Leu Leu Glu Lys Ala Glu Thr Val
    1445            1450            1455

Val Met Glu Val Leu Ala Ala Lys Thr Gly Tyr Glu Thr Asp Met
    1460            1465            1470

Ile Glu Ser Asp Met Glu Leu Glu Thr Glu Leu Gly Ile Asp Ser
    1475            1480            1485

Ile Lys Arg Val Glu Ile Leu Ser Glu Val Gln Ala Met Leu Asn
    1490            1495            1500

Val Glu Ala Lys Asp Val Asp Ala Leu Ser Arg Thr Arg Thr Val
    1505            1510            1515

Gly Glu Val Val Asp Ala Met Lys Ala Glu Ile Ala Gly Gly Ser
    1520            1525            1530

Ala Pro Ala Pro Ala Ala Ala Ala Pro Ala Pro Ala Ala Ala Ala
    1535            1540            1545

Pro Ala Pro Ala Ala Pro Ala Pro Ala Ala Pro Ala Pro Ala Val
    1550            1555            1560

Ser Ser Glu Leu Leu Glu Lys Ala Glu Thr Val Val Met Glu Val
    1565            1570            1575

Leu Ala Ala Lys Thr Gly Tyr Glu Thr Asp Met Ile Glu Ser Asp
    1580            1585            1590

Met Glu Leu Glu Thr Glu Leu Gly Ile Asp Ser Ile Lys Arg Val
    1595            1600            1605

Glu Ile Leu Ser Glu Val Gln Ala Met Leu Asn Val Glu Ala Lys
    1610            1615            1620

Asp Val Asp Ala Leu Ser Arg Thr Arg Thr Val Gly Glu Val Val
    1625            1630            1635

Asp Ala Met Lys Ala Glu Ile Ala Gly Ser Ser Ala Ser Ala Pro
    1640            1645            1650

Ala Ala Ala Ala Pro Ala Pro Ala Ala Ala Ala Pro Ala Pro Ala
    1655            1660            1665

Ala Ala Ala Pro Ala Val Ser Asn Glu Leu Leu Glu Lys Ala Glu
    1670            1675            1680

Thr Val Val Met Glu Val Leu Ala Ala Lys Thr Gly Tyr Glu Thr
    1685            1690            1695

Asp Met Ile Glu Ser Asp Met Glu Leu Glu Thr Glu Leu Gly Ile
    1700            1705            1710

Asp Ser Ile Lys Arg Val Glu Ile Leu Ser Glu Val Gln Ala Met
    1715            1720            1725

Leu Asn Val Glu Ala Lys Asp Val Asp Ala Leu Ser Arg Thr Arg
    1730            1735            1740

Thr Val Gly Glu Val Val Asp Ala Met Lys Ala Glu Ile Ala Gly
    1745            1750            1755

Gly Ser Ala Pro Ala Pro Ala Ala Ala Pro Ala Pro Ala Ala
    1760            1765            1770

Ala Ala Pro Ala Val Ser Asn Glu Leu Leu Glu Lys Ala Glu Thr
    1775            1780            1785

Val Val Met Glu Val Leu Ala Ala Lys Thr Gly Tyr Glu Thr Asp
    1790            1795            1800

Met Ile Glu Ser Asp Met Glu Leu Glu Thr Glu Leu Gly Ile Asp
    1805            1810            1815

Ser Ile Lys Arg Val Glu Ile Leu Ser Glu Val Gln Ala Met Leu
    1820            1825            1830
```

```
Asn Val Glu Ala Lys Asp Val Asp Ala Leu Ser Arg Thr Arg Thr
    1835            1840                1845
Val Gly Glu Val Val Asp Ala Met Lys Ala Glu Ile Ala Gly Ser
    1850            1855                1860
Ser Ala Pro Ala Pro Ala Ala Ala Pro Ala Pro Ala Ala Ala
    1865            1870                1875
Ala Pro Ala Pro Ala Ala Ala Ala Pro Ala Val Ser Ser Glu Leu
    1880            1885                1890
Leu Glu Lys Ala Glu Thr Val Val Met Glu Val Leu Ala Ala Lys
    1895            1900                1905
Thr Gly Tyr Glu Thr Asp Met Ile Glu Ser Asp Met Glu Leu Glu
    1910            1915                1920
Thr Glu Leu Gly Ile Asp Ser Ile Lys Arg Val Glu Ile Leu Ser
    1925            1930                1935
Glu Val Gln Ala Met Leu Asn Val Glu Ala Lys Asp Val Asp Ala
    1940            1945                1950
Leu Ser Arg Thr Arg Thr Val Gly Glu Val Val Asp Ala Met Lys
    1955            1960                1965
Ala Glu Ile Ala Gly Gly Ser Ala Pro Ala Pro Ala Ala Ala
    1970            1975                1980
Pro Ala Pro Ala Ala Ala Ala Pro Ala Val Ser Asn Glu Leu Leu
    1985            1990                1995
Glu Lys Ala Glu Thr Val Val Met Glu Val Leu Ala Ala Lys Thr
    2000            2005                2010
Gly Tyr Glu Thr Asp Met Ile Glu Ser Asp Met Glu Leu Glu Thr
    2015            2020                2025
Glu Leu Gly Ile Asp Ser Ile Lys Arg Val Glu Ile Leu Ser Glu
    2030            2035                2040
Val Gln Ala Met Leu Asn Val Glu Ala Lys Asp Val Asp Ala Leu
    2045            2050                2055
Ser Arg Thr Arg Thr Val Gly Glu Val Val Asp Ala Met Lys Ala
    2060            2065                2070
Glu Ile Ala Gly Gly Ser Ala Pro Ala Pro Ala Ala Ala Pro
    2075            2080                2085
Ala Ser Ala Gly Ala Ala Pro Ala Val Lys Ile Asp Ser Val His
    2090            2095                2100
Gly Ala Asp Cys Asp Asp Leu Ser Leu Met His Ala Lys Val Val
    2105            2110                2115
Asp Ile Arg Arg Pro Asp Glu Leu Ile Leu Glu Arg Pro Glu Asn
    2120            2125                2130
Arg Pro Val Leu Val Val Asp Asp Gly Ser Glu Leu Thr Leu Ala
    2135            2140                2145
Leu Val Arg Val Leu Gly Ala Cys Ala Val Val Leu Thr Phe Glu
    2150            2155                2160
Gly Leu Gln Leu Ala Gln Arg Ala Gly Ala Ala Ile Arg His
    2165            2170                2175
Val Leu Ala Lys Asp Leu Ser Ala Glu Ser Ala Glu Lys Ala Ile
    2180            2185                2190
Lys Glu Ala Glu Gln Arg Phe Gly Ala Leu Gly Gly Phe Ile Ser
    2195            2200                2205
Gln Gln Ala Glu Arg Phe Glu Pro Ala Glu Ile Leu Gly Phe Thr
    2210            2215                2220
Leu Met Cys Ala Lys Phe Ala Lys Ala Ser Leu Cys Thr Ala Val
```

```
                    2225                 2230                 2235
Ala Gly Gly Arg Pro Ala Phe Ile Gly Val Ala Arg Leu Asp Gly
2240                 2245                 2250

Arg Leu Gly Phe Thr Ser Gln Gly Thr Ser Asp Ala Leu Lys Arg
2255                 2260                 2265

Ala Gln Arg Gly Ala Ile Phe Gly Leu Cys Lys Thr Ile Gly Leu
2270                 2275                 2280

Glu Trp Ser Glu Ser Asp Val Phe Ser Arg Gly Val Asp Ile Ala
2285                 2290                 2295

Gln Gly Met His Pro Glu Asp Ala Val Ala Ile Val Arg Glu
2300                 2305                 2310

Met Ala Cys Ala Asp Ile Arg Ile Arg Glu Val Gly Ile Gly Ala
2315                 2320                 2325

Asn Gln Gln Arg Cys Thr Ile Arg Ala Ala Lys Leu Glu Thr Gly
2330                 2335                 2340

Asn Pro Gln Arg Gln Ile Ala Lys Asp Asp Val Leu Leu Val Ser
2345                 2350                 2355

Gly Gly Ala Arg Gly Ile Thr Pro Leu Cys Ile Arg Glu Ile Thr
2360                 2365                 2370

Arg Gln Ile Ala Gly Gly Lys Tyr Ile Leu Leu Gly Arg Ser Lys
2375                 2380                 2385

Val Ser Ala Ser Glu Pro Ala Trp Cys Ala Gly Ile Thr Asp Glu
2390                 2395                 2400

Lys Ala Val Gln Lys Ala Ala Thr Gln Glu Leu Lys Arg Ala Phe
2405                 2410                 2415

Ser Ala Gly Glu Gly Pro Lys Pro Thr Pro Arg Ala Val Thr Lys
2420                 2425                 2430

Leu Val Gly Ser Val Leu Gly Ala Arg Glu Val Arg Ser Ser Ile
2435                 2440                 2445

Ala Ala Ile Glu Ala Leu Gly Gly Lys Ala Ile Tyr Ser Ser Cys
2450                 2455                 2460

Asp Val Asn Ser Ala Ala Asp Val Ala Lys Ala Val Arg Asp Ala
2465                 2470                 2475

Glu Ser Gln Leu Gly Ala Arg Val Ser Gly Ile Val His Ala Ser
2480                 2485                 2490

Gly Val Leu Arg Asp Arg Leu Ile Glu Lys Lys Leu Pro Asp Glu
2495                 2500                 2505

Phe Asp Ala Val Phe Gly Thr Lys Val Thr Gly Leu Glu Asn Leu
2510                 2515                 2520

Leu Ala Ala Val Asp Arg Ala Asn Leu Lys His Met Val Leu Phe
2525                 2530                 2535

Ser Ser Leu Ala Gly Phe His Gly Asn Val Gly Gln Ser Asp Tyr
2540                 2545                 2550

Ala Met Ala Asn Glu Ala Leu Asn Lys Met Gly Leu Glu Leu Ala
2555                 2560                 2565

Lys Asp Val Ser Val Lys Ser Ile Cys Phe Gly Pro Trp Asp Gly
2570                 2575                 2580

Gly Met Val Thr Pro Gln Leu Lys Lys Gln Phe Gln Glu Met Gly
2585                 2590                 2595

Val Gln Ile Ile Pro Arg Glu Gly Gly Ala Asp Thr Val Ala Arg
2600                 2605                 2610

Ile Val Leu Gly Ser Ser Pro Ala Glu Ile Leu Val Gly Asn Trp
2615                 2620                 2625
```

-continued

Arg Thr Pro Ser Lys Lys Val Gly Ser Asp Thr Ile Thr Leu His
2630                2635                2640

Arg Lys Ile Ser Ala Lys Ser Asn Pro Phe Leu Glu Asp His Val
2645                2650                2655

Ile Gln Gly Arg Arg Val Leu Pro Met Thr Leu Ala Ile Gly Ser
2660                2665                2670

Leu Ala Glu Thr Cys Leu Gly Leu Phe Pro Gly Tyr Ser Leu Trp
2675                2680                2685

Ala Ile Asp Asp Ala Gln Leu Phe Lys Gly Val Thr Val Asp Gly
2690                2695                2700

Asp Val Asn Cys Glu Val Thr Leu Thr Pro Ser Thr Ala Pro Ser
2705                2710                2715

Gly Arg Val Asn Val Gln Ala Thr Leu Lys Thr Phe Ser Ser Gly
2720                2725                2730

Lys Leu Val Pro Ala Tyr Arg Ala Val Ile Val Leu Ser Asn Gln
2735                2740                2745

Gly Ala Pro Pro Ala Asn Ala Thr Met Gln Pro Pro Ser Leu Asp
2750                2755                2760

Ala Asp Pro Ala Leu Gln Gly Ser Val Tyr Asp Gly Lys Thr Leu
2765                2770                2775

Phe His Gly Pro Ala Phe Arg Gly Ile Asp Asp Val Leu Ser Cys
2780                2785                2790

Thr Lys Ser Gln Leu Val Ala Lys Cys Ser Ala Val Pro Gly Ser
2795                2800                2805

Asp Ala Ala Arg Gly Glu Phe Ala Thr Asp Thr Asp Ala His Asp
2810                2815                2820

Pro Phe Val Asn Asp Leu Ala Phe Gln Ala Met Leu Val Trp Val
2825                2830                2835

Arg Arg Thr Leu Gly Gln Ala Ala Leu Pro Asn Ser Ile Gln Arg
2840                2845                2850

Ile Val Gln His Arg Pro Val Pro Gln Asp Lys Pro Phe Tyr Ile
2855                2860                2865

Thr Leu Arg Ser Asn Gln Ser Gly Gly His Ser Gln His Lys His
2870                2875                2880

Ala Leu Gln Phe His Asn Glu Gln Gly Asp Leu Phe Ile Asp Val
2885                2890                2895

Gln Ala Ser Val Ile Ala Thr Asp Ser Leu Ala Phe
2900                2905                2910

<210> SEQ ID NO 88
<211> LENGTH: 2059
<212> TYPE: PRT
<213> ORGANISM: Schizochytrium sp.

<400> SEQUENCE: 88

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

-continued

```
Gly Thr Leu Asp Glu Asn Glu Ile Asp Asn Glu His Glu Leu Leu Leu
                 85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
            180                 185                 190

Asp Ala Ala Cys Ala Thr Ala Leu Tyr Val Leu Arg Leu Ala Gln Asp
        195                 200                 205

His Leu Val Ser Gly Ala Ala Asp Val Met Leu Cys Gly Ala Thr Cys
    210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Gly Ser Ile Met Val Leu Lys
            260                 265                 270

Arg Leu Asp Asp Ala Ile Arg Asp Gly Asp His Ile Tyr Gly Thr Leu
        275                 280                 285

Leu Gly Ala Asn Val Ser Asn Ser Gly Thr Gly Leu Pro Leu Lys Pro
    290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
            340                 345                 350

Glu Gly Lys Val Pro Arg Phe Gly Thr Thr Lys Gly Asn Phe Gly His
        355                 360                 365

Thr Leu Val Ala Ala Gly Phe Ala Gly Met Cys Lys Val Leu Leu Ser
    370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
                405                 410                 415

Thr Asn Gly Glu Pro Lys Arg Ala Gly Leu Ser Ala Phe Gly Phe Gly
            420                 425                 430

Gly Thr Asn Ala His Ala Val Phe Glu Glu His Asp Pro Ser Asn Ala
        435                 440                 445

Ala Cys Thr Gly His Asp Ser Ile Ser Ala Leu Ser Ala Arg Cys Gly
    450                 455                 460

Gly Glu Ser Asn Met Arg Ile Ala Ile Thr Gly Met Asp Ala Thr Phe
465                 470                 475                 480

Gly Ala Leu Lys Gly Leu Asp Ala Phe Glu Arg Ala Ile Tyr Thr Gly
                485                 490                 495

Ala His Gly Ala Ile Pro Leu Pro Glu Lys Arg Trp Arg Phe Leu Gly
            500                 505                 510
```

-continued

```
Lys Asp Lys Asp Phe Leu Asp Leu Cys Gly Val Lys Ala Thr Pro His
        515                 520                 525
Gly Cys Tyr Ile Glu Asp Val Glu Val Asp Phe Gln Arg Leu Arg Thr
        530                 535                 540
Pro Met Thr Pro Glu Asp Met Leu Leu Pro Gln Gln Leu Leu Ala Val
545                 550                 555                 560
Thr Thr Ile Asp Arg Ala Ile Leu Asp Ser Gly Met Lys Lys Gly Gly
                565                 570                 575
Asn Val Ala Val Phe Val Gly Leu Gly Thr Asp Leu Glu Leu Tyr Arg
                580                 585                 590
His Arg Ala Arg Val Ala Leu Lys Glu Arg Val Arg Pro Glu Ala Ser
            595                 600                 605
Lys Lys Leu Asn Asp Met Met Gln Tyr Ile Asn Asp Cys Gly Thr Ser
        610                 615                 620
Thr Ser Tyr Thr Ser Tyr Ile Gly Asn Leu Val Ala Thr Arg Val Ser
625                 630                 635                 640
Ser Gln Trp Gly Phe Thr Gly Pro Ser Phe Thr Ile Thr Glu Gly Asn
                645                 650                 655
Asn Ser Val Tyr Arg Cys Ala Glu Leu Gly Lys Tyr Leu Leu Glu Thr
                660                 665                 670
Gly Glu Val Asp Gly Val Val Ala Gly Val Asp Leu Cys Gly Ser
            675                 680                 685
Ala Glu Asn Leu Tyr Val Lys Ser Arg Arg Phe Lys Val Ser Thr Ser
        690                 695                 700
Asp Thr Pro Arg Ala Ser Phe Asp Ala Ala Asp Gly Tyr Phe Val
705                 710                 715                 720
Gly Glu Gly Cys Gly Ala Phe Val Leu Lys Arg Glu Thr Ser Cys Thr
                725                 730                 735
Lys Asp Asp Arg Ile Tyr Ala Cys Met Asp Ala Ile Val Pro Gly Asn
                740                 745                 750
Val Pro Ser Ala Cys Leu Arg Glu Ala Leu Asp Gln Ala Arg Val Lys
            755                 760                 765
Pro Gly Asp Ile Glu Met Leu Glu Leu Ser Ala Asp Ser Ala Arg His
        770                 775                 780
Leu Lys Asp Pro Ser Val Leu Pro Lys Glu Leu Thr Ala Glu Glu
785                 790                 795                 800
Ile Gly Gly Leu Gln Thr Ile Leu Arg Asp Asp Lys Leu Pro Arg
                805                 810                 815
Asn Val Ala Thr Gly Ser Val Lys Ala Thr Val Gly Asp Thr Gly Tyr
                820                 825                 830
Ala Ser Gly Ala Ala Ser Leu Ile Lys Ala Ala Leu Cys Ile Tyr Asn
            835                 840                 845
Arg Tyr Leu Pro Ser Asn Gly Asp Asp Trp Asp Glu Pro Ala Pro Glu
        850                 855                 860
Ala Pro Trp Asp Ser Thr Leu Phe Ala Cys Gln Thr Ser Arg Ala Trp
865                 870                 875                 880
Leu Lys Asn Pro Gly Glu Arg Arg Tyr Ala Ala Val Ser Gly Val Ser
                885                 890                 895
Glu Thr Arg Ser Cys Tyr Ser Val Leu Leu Ser Glu Ala Glu Gly His
            900                 905                 910
Tyr Glu Arg Glu Asn Arg Ile Ser Leu Asp Glu Glu Ala Pro Lys Leu
        915                 920                 925
Ile Val Leu Arg Ala Asp Ser His Glu Glu Ile Leu Gly Arg Leu Asp
```

```
                930           935           940
Lys Ile Arg Glu Arg Phe Leu Gln Pro Thr Gly Ala Ala Pro Arg Glu
945                 950                 955                 960
Ser Glu Leu Lys Ala Gln Ala Arg Arg Ile Phe Leu Glu Leu Leu Gly
                965                 970                 975
Glu Thr Leu Ala Gln Asp Ala Ala Ser Ser Gly Ser Gln Lys Pro Leu
                980                 985                 990
Ala Leu Ser Leu Val Ser Thr Pro Ser Lys Leu Gln Arg Glu Val Glu
            995                 1000                1005
Leu Ala Ala Lys Gly Ile Pro Arg Cys Leu Lys Met Arg Arg Asp
    1010                1015                1020
Trp Ser Ser Pro Ala Gly Ser Arg Tyr Ala Pro Glu Pro Leu Ala
    1025                1030                1035
Ser Asp Arg Val Ala Phe Met Tyr Gly Glu Gly Arg Ser Pro Tyr
    1040                1045                1050
Tyr Gly Ile Thr Gln Asp Ile His Arg Ile Trp Pro Glu Leu His
    1055                1060                1065
Glu Val Ile Asn Glu Lys Thr Asn Arg Leu Trp Ala Glu Gly Asp
    1070                1075                1080
Arg Trp Val Met Pro Arg Ala Ser Phe Lys Ser Glu Leu Glu Ser
    1085                1090                1095
Gln Gln Gln Glu Phe Asp Arg Asn Met Ile Glu Met Phe Arg Leu
    1100                1105                1110
Gly Ile Leu Thr Ser Ile Ala Phe Thr Asn Leu Ala Arg Asp Val
    1115                1120                1125
Leu Asn Ile Thr Pro Lys Ala Ala Phe Gly Leu Ser Leu Gly Glu
    1130                1135                1140
Ile Ser Met Ile Phe Ala Phe Ser Lys Lys Asn Gly Leu Ile Ser
    1145                1150                1155
Asp Gln Leu Thr Lys Asp Leu Arg Glu Ser Asp Val Trp Asn Lys
    1160                1165                1170
Ala Leu Ala Val Glu Phe Asn Ala Leu Arg Glu Ala Trp Gly Ile
    1175                1180                1185
Pro Gln Ser Val Pro Lys Asp Glu Phe Trp Gln Gly Tyr Ile Val
    1190                1195                1200
Arg Gly Thr Lys Gln Asp Ile Glu Ala Ala Ile Ala Pro Asp Ser
    1205                1210                1215
Lys Tyr Val Arg Leu Thr Ile Ile Asn Asp Ala Asn Thr Ala Leu
    1220                1225                1230
Ile Ser Gly Lys Pro Asp Ala Cys Lys Ala Ala Ile Ala Arg Leu
    1235                1240                1245
Gly Gly Asn Ile Pro Ala Leu Pro Val Thr Gln Gly Met Cys Gly
    1250                1255                1260
His Cys Pro Glu Val Gly Pro Tyr Thr Lys Asp Ile Ala Lys Ile
    1265                1270                1275
His Ala Asn Leu Glu Phe Pro Val Val Asp Gly Leu Asp Leu Trp
    1280                1285                1290
Thr Thr Ile Asn Gln Lys Arg Leu Val Pro Arg Ala Thr Gly Ala
    1295                1300                1305
Lys Asp Glu Trp Ala Pro Ser Ser Phe Gly Glu Tyr Ala Gly Gln
    1310                1315                1320
Leu Tyr Glu Lys Gln Ala Asn Phe Pro Gln Ile Val Glu Thr Ile
    1325                1330                1335
```

-continued

| | | | | | | | | | | | |
|---|---|---|---|---|---|---|---|---|---|---|---|
| Tyr | Lys | Gln | Asn | Tyr | Asp | Val | Phe | Val | Glu | Val | Gly | Pro | Asn | Asn |
| | 1340 | | | | 1345 | | | | 1350 | | |
| His | Arg | Ser | Thr | Ala | Val | Arg | Thr | Thr | Leu | Gly | Pro | Gln | Arg | Asn |
| 1355 | | | | | 1360 | | | | | 1365 | | |
| His | Leu | Ala | Gly | Ala | Ile | Asp | Lys | Gln | Asn | Glu | Asp | Ala | Trp | Thr |
| 1370 | | | | | 1375 | | | | | 1380 | | |
| Thr | Ile | Val | Lys | Leu | Val | Ala | Ser | Leu | Lys | Ala | His | Leu | Val | Pro |
| 1385 | | | | | 1390 | | | | | 1395 | | |
| Gly | Val | Thr | Ile | Ser | Pro | Leu | Tyr | His | Ser | Lys | Leu | Val | Ala | Glu |
| 1400 | | | | | 1405 | | | | | 1410 | | |
| Ala | Glu | Ala | Cys | Tyr | Ala | Ala | Leu | Cys | Lys | Gly | Glu | Lys | Pro | Lys |
| 1415 | | | | | 1420 | | | | | 1425 | | |
| Lys | Asn | Lys | Phe | Val | Arg | Lys | Ile | Gln | Leu | Asn | Gly | Arg | Phe | Asn |
| 1430 | | | | | 1435 | | | | | 1440 | | |
| Ser | Lys | Ala | Asp | Pro | Ile | Ser | Ser | Ala | Asp | Leu | Ala | Ser | Phe | Pro |
| 1445 | | | | | 1450 | | | | | 1455 | | |
| Pro | Ala | Asp | Pro | Ala | Ile | Glu | Ala | Ala | Ile | Ser | Ser | Arg | Ile | Met |
| 1460 | | | | | 1465 | | | | | 1470 | | |
| Lys | Pro | Val | Ala | Pro | Lys | Phe | Tyr | Ala | Arg | Leu | Asn | Ile | Asp | Glu |
| 1475 | | | | | 1480 | | | | | 1485 | | |
| Gln | Asp | Glu | Thr | Arg | Asp | Pro | Ile | Leu | Asn | Lys | Asp | Asn | Ala | Pro |
| 1490 | | | | | 1495 | | | | | 1500 | | |
| Ser | Ser | Ser | Ser | Ser | Ser | Ser | Ser | Ser | Ser | Ser | Ser | Ser | Ser | Ser |
| 1505 | | | | | 1510 | | | | | 1515 | | |
| Pro | Ser | Pro | Ala | Pro | Ser | Ala | Pro | Val | Gln | Lys | Lys | Ala | Ala | Pro |
| 1520 | | | | | 1525 | | | | | 1530 | | |
| Ala | Ala | Glu | Thr | Lys | Ala | Val | Ala | Ser | Ala | Asp | Ala | Leu | Arg | Ser |
| 1535 | | | | | 1540 | | | | | 1545 | | |
| Ala | Leu | Leu | Asp | Leu | Asp | Ser | Met | Leu | Ala | Leu | Ser | Ser | Ala | Ser |
| 1550 | | | | | 1555 | | | | | 1560 | | |
| Ala | Ser | Gly | Asn | Leu | Val | Glu | Thr | Ala | Pro | Ser | Asp | Ala | Ser | Val |
| 1565 | | | | | 1570 | | | | | 1575 | | |
| Ile | Val | Pro | Pro | Cys | Asn | Ile | Ala | Asp | Leu | Gly | Ser | Arg | Ala | Phe |
| 1580 | | | | | 1585 | | | | | 1590 | | |
| Met | Lys | Thr | Tyr | Gly | Val | Ser | Ala | Pro | Leu | Tyr | Thr | Gly | Ala | Met |
| 1595 | | | | | 1600 | | | | | 1605 | | |
| Ala | Lys | Gly | Ile | Ala | Ser | Ala | Asp | Leu | Val | Ile | Ala | Ala | Gly | Arg |
| 1610 | | | | | 1615 | | | | | 1620 | | |
| Gln | Gly | Ile | Leu | Ala | Ser | Phe | Gly | Ala | Gly | Gly | Leu | Pro | Met | Gln |
| 1625 | | | | | 1630 | | | | | 1635 | | |
| Val | Val | Arg | Glu | Ser | Ile | Glu | Lys | Ile | Gln | Ala | Ala | Leu | Pro | Asn |
| 1640 | | | | | 1645 | | | | | 1650 | | |
| Gly | Pro | Tyr | Ala | Val | Asn | Leu | Ile | His | Ser | Pro | Phe | Asp | Ser | Asn |
| 1655 | | | | | 1660 | | | | | 1665 | | |
| Leu | Glu | Lys | Gly | Asn | Val | Asp | Leu | Phe | Leu | Glu | Lys | Gly | Val | Thr |
| 1670 | | | | | 1675 | | | | | 1680 | | |
| Phe | Val | Glu | Ala | Ser | Ala | Phe | Met | Thr | Leu | Thr | Pro | Gln | Val | Val |
| 1685 | | | | | 1690 | | | | | 1695 | | |
| Arg | Tyr | Arg | Ala | Ala | Gly | Leu | Thr | Arg | Asn | Ala | Asp | Gly | Ser | Val |
| 1700 | | | | | 1705 | | | | | 1710 | | |
| Asn | Ile | Arg | Asn | Arg | Ile | Ile | Gly | Lys | Val | Ser | Arg | Thr | Glu | Leu |
| 1715 | | | | | 1720 | | | | | 1725 | | |
| Ala | Glu | Met | Phe | Met | Arg | Pro | Ala | Pro | Glu | His | Leu | Leu | Gln | Lys |
| 1730 | | | | | 1735 | | | | | 1740 | | |

Leu Ile Ala Ser Gly Glu Ile Asn Gln Glu Gln Ala Glu Leu Ala
    1745                1750                1755

Arg Arg Val Pro Val Ala Asp Asp Ile Ala Val Glu Ala Asp Ser
    1760                1765                1770

Gly Gly His Thr Asp Asn Arg Pro Ile His Val Ile Leu Pro Leu
    1775                1780                1785

Ile Ile Asn Leu Arg Asp Arg Leu His Arg Glu Cys Gly Tyr Pro
    1790                1795                1800

Ala Asn Leu Arg Val Arg Val Gly Ala Gly Gly Ile Gly Cys
    1805                1810                1815

Pro Gln Ala Ala Leu Ala Thr Phe Asn Met Gly Ala Ser Phe Ile
    1820                1825                1830

Val Thr Gly Thr Val Asn Gln Val Ala Lys Gln Ser Gly Thr Cys
    1835                1840                1845

Asp Asn Val Arg Lys Gln Leu Ala Lys Ala Thr Tyr Ser Asp Val
    1850                1855                1860

Cys Met Ala Pro Ala Ala Asp Met Phe Glu Glu Gly Val Lys Leu
    1865                1870                1875

Gln Val Leu Lys Lys Gly Thr Met Phe Pro Ser Arg Ala Asn Lys
    1880                1885                1890

Leu Tyr Glu Leu Phe Cys Lys Tyr Asp Ser Phe Glu Ser Met Pro
    1895                1900                1905

Pro Ala Glu Leu Ala Arg Val Glu Lys Arg Ile Phe Ser Arg Ala
    1910                1915                1920

Leu Glu Glu Val Trp Asp Glu Thr Lys Asn Phe Tyr Ile Asn Arg
    1925                1930                1935

Leu His Asn Pro Glu Lys Ile Gln Arg Ala Glu Arg Asp Pro Lys
    1940                1945                1950

Leu Lys Met Ser Leu Cys Phe Arg Trp Tyr Leu Ser Leu Ala Ser
    1955                1960                1965

Arg Trp Ala Asn Thr Gly Ala Ser Asp Arg Val Met Asp Tyr Gln
    1970                1975                1980

Val Trp Cys Gly Pro Ala Ile Gly Ser Phe Asn Asp Phe Ile Lys
    1985                1990                1995

Gly Thr Tyr Leu Asp Pro Ala Val Ala Asn Glu Tyr Pro Cys Val
    2000                2005                2010

Val Gln Ile Asn Lys Gln Ile Leu Arg Gly Ala Cys Phe Leu Arg
    2015                2020                2025

Arg Leu Glu Ile Leu Arg Asn Ala Arg Leu Ser Asp Gly Ala Ala
    2030                2035                2040

Ala Leu Val Ala Ser Ile Asp Asp Thr Tyr Val Pro Ala Glu Lys
    2045                2050                2055

Leu

<210> SEQ ID NO 89
<211> LENGTH: 1502
<212> TYPE: PRT
<213> ORGANISM: Schizochytrium sp.

<400> SEQUENCE: 89

Met Ala Leu Arg Val Lys Thr Asn Lys Lys Pro Cys Trp Glu Met Thr
  1               5                  10                  15

Lys Glu Glu Leu Thr Ser Gly Lys Thr Glu Val Phe Asn Tyr Glu Glu
             20                  25                  30

-continued

```
Leu Leu Glu Phe Ala Glu Gly Asp Ile Ala Lys Val Phe Gly Pro Glu
        35                  40                  45

Phe Ala Val Ile Asp Lys Tyr Pro Arg Arg Val Arg Leu Pro Ala Arg
 50                  55                  60

Glu Tyr Leu Leu Val Thr Arg Val Thr Leu Met Asp Ala Glu Val Asn
 65                  70                  75                  80

Asn Tyr Arg Val Gly Ala Arg Met Val Thr Glu Tyr Asp Leu Pro Val
                 85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
            115                 120                 125

Phe Gln Asn Gln Gly Asp Arg Val Tyr Arg Leu Leu Asn Thr Thr Leu
130                 135                 140

Thr Phe Tyr Gly Val Ala His Glu Gly Glu Thr Leu Glu Tyr Asp Ile
145                 150                 155                 160

Arg Val Thr Gly Phe Ala Lys Arg Leu Asp Gly Gly Ile Ser Met Phe
                165                 170                 175

Phe Phe Glu Tyr Asp Cys Tyr Val Asn Gly Arg Leu Leu Ile Glu Met
            180                 185                 190

Arg Asp Gly Cys Ala Gly Phe Phe Thr Asn Glu Glu Leu Asp Ala Gly
            195                 200                 205

Lys Gly Val Val Phe Thr Arg Gly Asp Leu Ala Ala Arg Ala Lys Ile
210                 215                 220

Pro Lys Gln Asp Val Ser Pro Tyr Ala Val Ala Pro Cys Leu His Lys
225                 230                 235                 240

Thr Lys Leu Asn Glu Lys Glu Met Gln Thr Leu Val Asp Lys Asp Trp
                245                 250                 255

Ala Ser Val Phe Gly Ser Lys Asn Gly Met Pro Glu Ile Asn Tyr Lys
            260                 265                 270

Leu Cys Ala Arg Lys Met Leu Met Ile Asp Arg Val Thr Ser Ile Asp
            275                 280                 285

His Lys Gly Gly Val Tyr Gly Leu Gly Gln Leu Val Gly Glu Lys Ile
        290                 295                 300

Leu Glu Arg Asp His Trp Tyr Phe Pro Cys His Phe Val Lys Asp Gln
305                 310                 315                 320

Val Met Ala Gly Ser Leu Val Ser Asp Gly Cys Ser Gln Met Leu Lys
                325                 330                 335

Met Tyr Met Ile Trp Leu Gly Leu His Leu Thr Thr Gly Pro Phe Asp
            340                 345                 350

Phe Arg Pro Val Asn Gly His Pro Asn Lys Val Arg Cys Arg Gly Gln
        355                 360                 365

Ile Ser Pro His Lys Gly Lys Leu Val Tyr Val Met Glu Ile Lys Glu
        370                 375                 380

Met Gly Phe Asp Glu Asp Asn Asp Pro Tyr Ala Ile Ala Asp Val Asn
385                 390                 395                 400

Ile Ile Asp Val Asp Phe Glu Lys Gly Gln Asp Phe Ser Leu Asp Arg
                405                 410                 415

Ile Ser Asp Tyr Gly Lys Gly Asp Leu Asn Lys Lys Ile Val Val Asp
            420                 425                 430

Phe Lys Gly Ile Ala Leu Lys Met Gln Lys Arg Ser Thr Asn Lys Asn
            435                 440                 445

Pro Ser Lys Val Gln Pro Val Phe Ala Asn Gly Ala Ala Thr Val Gly
        450                 455                 460
```

```
Pro Glu Ala Ser Lys Ala Ser Ser Gly Ala Ser Ala Ser Ala Ser Ala
465                 470                 475                 480

Ala Pro Ala Lys Pro Ala Phe Ser Ala Asp Val Leu Ala Pro Lys Pro
            485                 490                 495

Val Ala Leu Pro Glu His Ile Leu Lys Gly Asp Ala Leu Ala Pro Lys
                500                 505                 510

Glu Met Ser Trp His Pro Met Ala Arg Ile Pro Gly Asn Pro Thr Pro
            515                 520                 525

Ser Phe Ala Pro Ser Ala Tyr Lys Pro Arg Asn Ile Ala Phe Thr Pro
        530                 535                 540

Phe Pro Gly Asn Pro Asn Asp Asn Asp His Thr Pro Gly Lys Met Pro
545                 550                 555                 560

Leu Thr Trp Phe Asn Met Ala Glu Phe Met Ala Gly Lys Val Ser Met
                565                 570                 575

Cys Leu Gly Pro Glu Phe Ala Lys Phe Asp Asp Ser Asn Thr Ser Arg
            580                 585                 590

Ser Pro Ala Trp Asp Leu Ala Leu Val Thr Arg Ala Val Ser Val Ser
        595                 600                 605

Asp Leu Lys His Val Asn Tyr Arg Asn Ile Asp Leu Asp Pro Ser Lys
                610                 615                 620

Gly Thr Met Val Gly Glu Phe Asp Cys Pro Ala Asp Ala Trp Phe Tyr
625                 630                 635                 640

Lys Gly Ala Cys Asn Asp Ala His Met Pro Tyr Ser Ile Leu Met Glu
            645                 650                 655

Ile Ala Leu Gln Thr Ser Gly Val Leu Thr Ser Val Leu Lys Ala Pro
                660                 665                 670

Leu Thr Met Glu Lys Asp Asp Ile Leu Phe Arg Asn Leu Asp Ala Asn
        675                 680                 685

Ala Glu Phe Val Arg Ala Asp Leu Asp Tyr Arg Gly Lys Thr Ile Arg
690                 695                 700

Asn Val Thr Lys Cys Thr Gly Tyr Ser Met Leu Gly Glu Met Gly Val
705                 710                 715                 720

His Arg Phe Thr Phe Glu Leu Tyr Val Asp Asp Val Leu Phe Tyr Lys
            725                 730                 735

Gly Ser Thr Ser Phe Gly Trp Phe Val Pro Glu Val Phe Ala Ala Gln
                740                 745                 750

Ala Gly Leu Asp Asn Gly Arg Lys Ser Glu Pro Trp Phe Ile Glu Asn
        755                 760                 765

Lys Val Pro Ala Ser Gln Val Ser Ser Phe Asp Val Arg Pro Asn Gly
770                 775                 780

Ser Gly Arg Thr Ala Ile Phe Ala Asn Ala Pro Ser Gly Ala Gln Leu
785                 790                 795                 800

Asn Arg Arg Thr Asp Gln Gly Gln Tyr Leu Asp Ala Val Asp Ile Val
            805                 810                 815

Ser Gly Ser Gly Lys Lys Ser Leu Gly Tyr Ala His Gly Ser Lys Thr
                820                 825                 830

Val Asn Pro Asn Asp Trp Phe Phe Ser Cys His Phe Trp Phe Asp Ser
        835                 840                 845

Val Met Pro Gly Ser Leu Gly Val Glu Ser Met Phe Gln Leu Val Glu
850                 855                 860

Ala Ile Ala Ala His Glu Asp Leu Ala Gly Lys His Gly Ile Ala Asn
865                 870                 875                 880

Pro Thr Phe Val His Ala Pro Gly Lys Ile Ser Trp Lys Tyr Arg Gly
```

-continued

```
                885                 890                 895
Gln Leu Thr Pro Lys Ser Lys Lys Met Asp Ser Glu Val His Ile Val
            900                 905                 910

Ser Val Asp Ala His Asp Gly Val Val Asp Leu Val Ala Asp Gly Phe
            915                 920                 925

Leu Trp Ala Asp Ser Leu Arg Val Tyr Ser Val Ser Asn Ile Arg Val
            930                 935                 940

Arg Ile Ala Ser Gly Glu Ala Pro Ala Ala Ser Ser Ala Ala Ser
945                 950                 955                 960

Val Gly Ser Ser Ala Ser Ser Val Glu Arg Thr Arg Ser Ser Pro Ala
            965                 970                 975

Val Ala Ser Gly Pro Ala Gln Thr Ile Asp Leu Lys Gln Leu Lys Thr
            980                 985                 990

Glu Leu Leu Glu Leu Asp Ala Pro  Leu Tyr Leu Ser Gln  Asp Pro Thr
            995                 1000                1005

Ser Gly  Gln Leu Lys Lys His  Thr Asp Val Ala Ser  Gly Gln Ala
    1010                1015                1020

Thr Ile  Val Gln Pro Cys Thr  Leu Gly Asp Leu Gly  Asp Arg Ser
    1025                1030                1035

Phe Met  Glu Thr Tyr Gly Val  Val Ala Pro Leu Tyr  Thr Gly Ala
    1040                1045                1050

Met Ala  Lys Gly Ile Ala Ser  Ala Asp Leu Val Ile  Ala Ala Gly
    1055                1060                1065

Lys Arg  Lys Ile Leu Gly Ser  Phe Gly Ala Gly Gly  Leu Pro Met
    1070                1075                1080

His His  Val Arg Ala Ala Leu  Glu Lys Ile Gln Ala  Ala Leu Pro
    1085                1090                1095

Gln Gly  Pro Tyr Ala Val Asn  Leu Ile His Ser Pro  Phe Asp Ser
    1100                1105                1110

Asn Leu  Glu Lys Gly Asn Val  Asp Leu Phe Leu Glu  Lys Gly Val
    1115                1120                1125

Thr Val  Val Glu Ala Ser Ala  Phe Met Thr Leu Thr  Pro Gln Val
    1130                1135                1140

Val Arg  Tyr Arg Ala Ala Gly  Leu Ser Arg Asn Ala  Asp Gly Ser
    1145                1150                1155

Val Asn  Ile Arg Asn Arg Ile  Ile Gly Lys Val Ser  Arg Thr Glu
    1160                1165                1170

Leu Ala  Glu Met Phe Ile Arg  Pro Ala Pro Glu His  Leu Leu Glu
    1175                1180                1185

Lys Leu  Ile Ala Ser Gly Glu  Ile Thr Gln Glu Gln  Ala Glu Leu
    1190                1195                1200

Ala Arg  Arg Val Pro Val Ala  Asp Asp Ile Ala Val  Glu Ala Asp
    1205                1210                1215

Ser Gly  Gly His Thr Asp Asn  Arg Pro Ile His Val  Ile Leu Pro
    1220                1225                1230

Leu Ile  Ile Asn Leu Arg Asn  Arg Leu His Arg Glu  Cys Gly Tyr
    1235                1240                1245

Pro Ala  His Leu Arg Val Arg  Val Gly Ala Gly Gly  Gly Val Gly
    1250                1255                1260

Cys Pro  Gln Ala Ala Ala Ala  Ala Leu Thr Met Gly  Ala Ala Phe
    1265                1270                1275

Ile Val  Thr Gly Thr Val Asn  Gln Val Ala Lys Gln  Ser Gly Thr
    1280                1285                1290
```

```
Cys Asp Asn Val Arg Lys Gln Leu Ser Gln Ala Thr Tyr Ser Asp
1295                1300                1305

Ile Cys Met Ala Pro Ala Ala Asp Met Phe Glu Glu Gly Val Lys
    1310                1315                1320

Leu Gln Val Leu Lys Lys Gly Thr Met Phe Pro Ser Arg Ala Asn
1325                1330                1335

Lys Leu Tyr Glu Leu Phe Cys Lys Tyr Asp Ser Phe Asp Ser Met
1340                1345                1350

Pro Pro Ala Glu Leu Glu Arg Ile Glu Lys Arg Ile Phe Lys Arg
1355                1360                1365

Ala Leu Gln Glu Val Trp Glu Thr Lys Asp Phe Tyr Ile Asn
1370                1375                1380

Gly Leu Lys Asn Pro Glu Lys Ile Gln Arg Ala Glu His Asp Pro
1385                1390                1395

Lys Leu Lys Met Ser Leu Cys Phe Arg Trp Tyr Leu Gly Leu Ala
1400                1405                1410

Ser Arg Trp Ala Asn Met Gly Ala Pro Asp Arg Val Met Asp Tyr
1415                1420                1425

Gln Val Trp Cys Gly Pro Ala Ile Gly Ala Phe Asn Asp Phe Ile
1430                1435                1440

Lys Gly Thr Tyr Leu Asp Pro Ala Val Ser Asn Glu Tyr Pro Cys
1445                1450                1455

Val Val Gln Ile Asn Leu Gln Ile Leu Arg Gly Ala Cys Tyr Leu
1460                1465                1470

Arg Arg Leu Asn Ala Leu Arg Asn Asp Pro Arg Ile Asp Leu Glu
1475                1480                1485

Thr Glu Asp Ala Ala Phe Val Tyr Glu Pro Thr Asn Ala Leu
1490                1495                1500

<210> SEQ ID NO 90
<211> LENGTH: 2910
<212> TYPE: PRT
<213> ORGANISM: Schizochytrium sp.

<400> SEQUENCE: 90

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45

Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Asn Ile
        115                 120                 125

Gly Cys Val Leu Gly Ile Gly Gly Gln Lys Ser Ser His Glu Phe
    130                 135                 140

Tyr Ser Arg Leu Asn Tyr Val Val Val Glu Lys Val Leu Arg Lys Met
145                 150                 155                 160
```

```
Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
            180                 185                 190

Val Thr Ala Gly Arg Cys Thr Asn Thr Phe Asn Leu Asp Gly Met Asn
        195                 200                 205

Cys Val Val Asp Ala Ala Cys Ala Ser Ser Leu Ile Ala Val Lys Val
    210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
            260                 265                 270

Thr Lys Gly Met Leu Ile Gly Glu Gly Ser Ala Met Leu Val Leu Lys
        275                 280                 285

Arg Tyr Ala Asp Ala Val Arg Asp Gly Asp Glu Ile His Ala Val Ile
    290                 295                 300

Arg Gly Cys Ala Ser Ser Asp Gly Lys Ala Ala Gly Ile Tyr Thr
305                 310                 315                 320

Pro Thr Ile Ser Gly Gln Glu Ala Leu Arg Arg Ala Tyr Asn Arg
                325                 330                 335

Ala Cys Val Asp Pro Ala Thr Val Thr Leu Val Glu Gly His Gly Thr
            340                 345                 350

Gly Thr Pro Val Gly Asp Arg Ile Glu Leu Thr Ala Leu Arg Asn Leu
        355                 360                 365

Phe Asp Lys Ala Tyr Gly Glu Gly Asn Thr Glu Lys Val Ala Val Gly
370                 375                 380

Ser Ile Lys Ser Ser Ile Gly His Leu Lys Ala Val Ala Gly Leu Ala
385                 390                 395                 400

Gly Met Ile Lys Val Ile Met Ala Leu Lys His Lys Thr Leu Pro Gly
                405                 410                 415

Thr Ile Asn Val Asp Asn Pro Asn Leu Tyr Asp Asn Thr Pro Ile
            420                 425                 430

Asn Glu Ser Ser Leu Tyr Ile Asn Thr Met Asn Arg Pro Trp Phe Pro
        435                 440                 445

Pro Pro Gly Val Pro Arg Arg Ala Gly Ile Ser Ser Phe Gly Phe Gly
    450                 455                 460

Gly Ala Asn Tyr His Ala Val Leu Glu Glu Ala Glu Pro Glu His Thr
465                 470                 475                 480

Thr Ala Tyr Arg Leu Asn Lys Arg Pro Gln Pro Val Leu Met Met Ala
                485                 490                 495

Ala Thr Pro Ala Ala Leu Gln Ser Leu Cys Glu Ala Gln Leu Lys Glu
            500                 505                 510

Phe Glu Ala Ala Ile Lys Glu Asn Glu Thr Val Lys Asn Thr Ala Tyr
        515                 520                 525

Ile Lys Cys Val Lys Phe Gly Glu Gln Phe Lys Phe Pro Gly Ser Ile
    530                 535                 540

Pro Ala Thr Asn Ala Arg Leu Gly Phe Leu Val Lys Asp Ala Glu Asp
545                 550                 555                 560

Ala Cys Ser Thr Leu Arg Ala Ile Cys Ala Gln Phe Ala Lys Asp Val
                565                 570                 575

Thr Lys Glu Ala Trp Arg Leu Pro Arg Glu Gly Val Ser Phe Arg Ala
            580                 585                 590
```

Lys Gly Ile Ala Thr Asn Gly Ala Val Ala Ala Leu Phe Ser Gly Gln
              595                 600                 605

Gly Ala Gln Tyr Thr His Met Phe Ser Glu Val Ala Met Asn Trp Pro
    610                 615                 620

Gln Phe Arg Gln Ser Ile Ala Ala Met Asp Ala Ala Gln Ser Lys Val
625                 630                 635                 640

Ala Gly Ser Asp Lys Asp Phe Glu Arg Val Ser Gln Val Leu Tyr Pro
                645                 650                 655

Arg Lys Pro Tyr Glu Arg Glu Pro Glu Gln Asp His Lys Lys Ile Ser
            660                 665                 670

Leu Thr Ala Tyr Ser Gln Pro Ser Thr Leu Ala Cys Ala Leu Gly Ala
        675                 680                 685

Phe Glu Ile Phe Lys Glu Ala Gly Phe Thr Pro Asp Phe Ala Ala Gly
    690                 695                 700

His Ser Leu Gly Glu Phe Ala Ala Leu Tyr Ala Ala Gly Cys Val Asp
705                 710                 715                 720

Arg Asp Glu Leu Phe Glu Leu Val Cys Arg Arg Ala Arg Ile Met Gly
                725                 730                 735

Gly Lys Asp Ala Pro Ala Thr Pro Lys Gly Cys Met Ala Ala Val Ile
            740                 745                 750

Gly Pro Asn Ala Glu Asn Ile Lys Val Gln Ala Ala Asn Val Trp Leu
        755                 760                 765

Gly Asn Ser Asn Ser Pro Ser Gln Thr Val Ile Thr Gly Ser Val Glu
    770                 775                 780

Gly Ile Gln Ala Glu Ser Ala Arg Leu Gln Lys Glu Gly Phe Arg Val
785                 790                 795                 800

Val Pro Leu Ala Cys Glu Ser Ala Phe His Ser Pro Gln Met Glu Asn
                805                 810                 815

Ala Ser Ser Ala Phe Lys Asp Val Ile Ser Lys Val Ser Phe Arg Thr
            820                 825                 830

Pro Lys Ala Glu Thr Lys Leu Phe Ser Asn Val Ser Gly Glu Thr Tyr
        835                 840                 845

Pro Thr Asp Ala Arg Glu Met Leu Thr Gln His Met Thr Ser Ser Val
    850                 855                 860

Lys Phe Leu Thr Gln Val Arg Asn Met His Gln Ala Gly Ala Arg Ile
865                 870                 875                 880

Phe Val Glu Phe Gly Pro Lys Gln Val Leu Ser Lys Leu Val Ser Glu
                885                 890                 895

Thr Leu Lys Asp Asp Pro Ser Val Val Thr Val Ser Val Asn Pro Ala
            900                 905                 910

Ser Gly Thr Asp Ser Asp Ile Gln Leu Arg Asp Ala Ala Val Gln Leu
        915                 920                 925

Val Val Ala Gly Val Asn Leu Gln Gly Phe Asp Lys Trp Asp Ala Pro
    930                 935                 940

Asp Ala Thr Arg Met Gln Ala Ile Lys Lys Arg Thr Thr Leu Arg
945                 950                 955                 960

Leu Ser Ala Ala Thr Tyr Val Ser Asp Lys Thr Lys Val Arg Asp
                965                 970                 975

Ala Ala Met Asn Asp Gly Arg Cys Val Thr Tyr Leu Gly Ala Ala
            980                 985                 990

Pro Leu Ile Lys Ala Pro Glu Pro  Val Val Asp Glu Ala  Ala Lys Arg
        995                 1000                1005

Glu Ala  Glu Arg Leu Gln Lys  Glu Leu Gln Asp Ala  Gln Arg Gln

```
                       1010                1015                1020

Leu Asp Asp Ala Lys Arg Ala Ala Glu Ala Asn Ser Lys Leu
    1025                1030                1035

Ala Ala Ala Lys Glu Glu Ala Lys Thr Ala Ala Ser Ala Lys
    1040                1045                1050

Pro Ala Val Asp Thr Ala Val Val Glu Lys His Arg Ala Ile Leu
    1055                1060                1065

Lys Ser Met Leu Ala Glu Leu Asp Gly Tyr Gly Ser Val Asp Ala
    1070                1075                1080

Ser Ser Leu Gln Gln Gln Gln Gln Gln Thr Ala Pro Ala Pro
    1085                1090                1095

Val Lys Ala Ala Ala Pro Ala Ala Pro Val Ala Ser Ala Pro Ala
    1100                1105                1110

Pro Ala Val Ser Asn Glu Leu Leu Glu Lys Ala Glu Thr Val Val
    1115                1120                1125

Met Glu Val Leu Ala Ala Lys Thr Gly Tyr Glu Thr Asp Met Ile
    1130                1135                1140

Glu Ala Asp Met Glu Leu Glu Thr Glu Leu Gly Ile Asp Ser Ile
    1145                1150                1155

Lys Arg Val Glu Ile Leu Ser Glu Val Gln Ala Met Leu Asn Val
    1160                1165                1170

Glu Ala Lys Asp Val Asp Ala Leu Ser Arg Thr Arg Thr Val Gly
    1175                1180                1185

Glu Val Val Asn Ala Met Lys Ala Glu Ile Ala Gly Ser Ser Ala
    1190                1195                1200

Pro Ala Pro Ala Ala Ala Pro Ala Pro Ala Lys Ala Ala Pro
    1205                1210                1215

Ala Ala Ala Ala Pro Ala Val Ser Asn Glu Leu Leu Glu Lys Ala
    1220                1225                1230

Glu Thr Val Val Met Glu Val Leu Ala Ala Lys Thr Gly Tyr Glu
    1235                1240                1245

Thr Asp Met Ile Glu Ser Asp Met Glu Leu Glu Thr Glu Leu Gly
    1250                1255                1260

Ile Asp Ser Ile Lys Arg Val Glu Ile Leu Ser Glu Val Gln Ala
    1265                1270                1275

Met Leu Asn Val Glu Ala Lys Asp Val Asp Ala Leu Ser Arg Thr
    1280                1285                1290

Arg Thr Val Gly Glu Val Val Asn Ala Met Lys Ala Glu Ile Ala
    1295                1300                1305

Gly Gly Ser Ala Pro Ala Pro Ala Ala Ala Ala Pro Gly Pro Ala
    1310                1315                1320

Ala Ala Ala Pro Ala Pro Ala Ala Ala Pro Ala Val Ser Asn
    1325                1330                1335

Glu Leu Leu Glu Lys Ala Glu Thr Val Val Met Glu Val Leu Ala
    1340                1345                1350

Ala Lys Thr Gly Tyr Glu Thr Asp Met Ile Glu Ser Asp Met Glu
    1355                1360                1365

Leu Glu Thr Glu Leu Gly Ile Asp Ser Ile Lys Arg Val Glu Ile
    1370                1375                1380

Leu Ser Glu Val Gln Ala Met Leu Asn Val Glu Ala Lys Asp Val
    1385                1390                1395

Asp Ala Leu Ser Arg Thr Arg Thr Val Gly Glu Val Val Asp Ala
    1400                1405                1410
```

```
Met Lys Ala Glu Ile Ala Gly Gly Ser Ala Pro Ala Pro Ala Ala
1415                1420                1425

Ala Ala Pro Ala Pro Ala Ala Ala Pro Ala Pro Ala Ala Pro
1430                1435                1440

Ala Pro Ala Val Ser Ser Glu Leu Leu Glu Lys Ala Glu Thr Val
1445                1450                1455

Val Met Glu Val Leu Ala Ala Lys Thr Gly Tyr Glu Thr Asp Met
1460                1465                1470

Ile Glu Ser Asp Met Glu Leu Glu Thr Glu Leu Gly Ile Asp Ser
1475                1480                1485

Ile Lys Arg Val Glu Ile Leu Ser Glu Val Gln Ala Met Leu Asn
1490                1495                1500

Val Glu Ala Lys Asp Val Asp Ala Leu Ser Arg Thr Arg Thr Val
1505                1510                1515

Gly Glu Val Val Asp Ala Met Lys Ala Glu Ile Ala Gly Gly Ser
1520                1525                1530

Ala Pro Ala Pro Ala Ala Ala Pro Ala Pro Ala Ala Ala
1535                1540                1545

Pro Ala Pro Ala Ala Pro Ala Pro Ala Ala Pro Ala Pro Ala Val
1550                1555                1560

Ser Ser Glu Leu Leu Glu Lys Ala Glu Thr Val Val Met Glu Val
1565                1570                1575

Leu Ala Ala Lys Thr Gly Tyr Glu Thr Asp Met Ile Glu Ser Asp
1580                1585                1590

Met Glu Leu Glu Thr Glu Leu Gly Ile Asp Ser Ile Lys Arg Val
1595                1600                1605

Glu Ile Leu Ser Glu Val Gln Ala Met Leu Asn Val Glu Ala Lys
1610                1615                1620

Asp Val Asp Ala Leu Ser Arg Thr Arg Thr Val Gly Glu Val Val
1625                1630                1635

Asp Ala Met Lys Ala Glu Ile Ala Gly Ser Ser Ala Ser Ala Pro
1640                1645                1650

Ala Ala Ala Ala Pro Ala Pro Ala Ala Ala Ala Pro Ala Pro Ala
1655                1660                1665

Ala Ala Ala Pro Ala Val Ser Asn Glu Leu Leu Glu Lys Ala Glu
1670                1675                1680

Thr Val Val Met Glu Val Leu Ala Ala Lys Thr Gly Tyr Glu Thr
1685                1690                1695

Asp Met Ile Glu Ser Asp Met Glu Leu Glu Thr Glu Leu Gly Ile
1700                1705                1710

Asp Ser Ile Lys Arg Val Glu Ile Leu Ser Glu Val Gln Ala Met
1715                1720                1725

Leu Asn Val Glu Ala Lys Asp Val Asp Ala Leu Ser Arg Thr Arg
1730                1735                1740

Thr Val Gly Glu Val Val Asp Ala Met Lys Ala Glu Ile Ala Gly
1745                1750                1755

Gly Ser Ala Pro Ala Pro Ala Ala Ala Pro Ala Pro Ala Ala
1760                1765                1770

Ala Ala Pro Ala Val Ser Asn Glu Leu Leu Glu Lys Ala Glu Thr
1775                1780                1785

Val Val Met Glu Val Leu Ala Ala Lys Thr Gly Tyr Glu Thr Asp
1790                1795                1800

Met Ile Glu Ser Asp Met Glu Leu Glu Thr Glu Leu Gly Ile Asp
1805                1810                1815
```

```
Ser Ile Lys Arg Val Glu Ile Leu Ser Glu Val Gln Ala Met Leu
    1820            1825                1830

Asn Val Glu Ala Lys Asp Val Asp Ala Leu Ser Arg Thr Arg Thr
    1835            1840                1845

Val Gly Glu Val Val Asp Ala Met Lys Ala Glu Ile Ala Gly Ser
    1850            1855                1860

Ser Ala Pro Ala Pro Ala Ala Ala Ala Pro Ala Pro Ala Ala Ala
    1865            1870                1875

Ala Pro Ala Pro Ala Ala Ala Ala Pro Ala Val Ser Ser Glu Leu
    1880            1885                1890

Leu Glu Lys Ala Glu Thr Val Val Met Glu Val Leu Ala Ala Lys
    1895            1900                1905

Thr Gly Tyr Glu Thr Asp Met Ile Glu Ser Asp Met Glu Leu Glu
    1910            1915                1920

Thr Glu Leu Gly Ile Asp Ser Ile Lys Arg Val Glu Ile Leu Ser
    1925            1930                1935

Glu Val Gln Ala Met Leu Asn Val Glu Ala Lys Asp Val Asp Ala
    1940            1945                1950

Leu Ser Arg Thr Arg Thr Val Gly Glu Val Val Asp Ala Met Lys
    1955            1960                1965

Ala Glu Ile Ala Gly Gly Ser Ala Pro Ala Pro Ala Ala Ala Ala
    1970            1975                1980

Pro Ala Pro Ala Ala Ala Ala Pro Ala Val Ser Asn Glu Leu Leu
    1985            1990                1995

Glu Lys Ala Glu Thr Val Val Met Glu Val Leu Ala Ala Lys Thr
    2000            2005                2010

Gly Tyr Glu Thr Asp Met Ile Glu Ser Asp Met Glu Leu Glu Thr
    2015            2020                2025

Glu Leu Gly Ile Asp Ser Ile Lys Arg Val Glu Ile Leu Ser Glu
    2030            2035                2040

Val Gln Ala Met Leu Asn Val Glu Ala Lys Asp Val Asp Ala Leu
    2045            2050                2055

Ser Arg Thr Arg Thr Val Gly Glu Val Val Asp Ala Met Lys Ala
    2060            2065                2070

Glu Ile Ala Gly Gly Ser Ala Pro Ala Pro Ala Ala Ala Ala Pro
    2075            2080                2085

Ala Ser Ala Gly Ala Ala Pro Ala Val Lys Ile Asp Ser Val His
    2090            2095                2100

Gly Ala Asp Cys Asp Asp Leu Ser Leu Met His Ala Lys Val Val
    2105            2110                2115

Asp Ile Arg Arg Pro Asp Glu Leu Ile Leu Glu Arg Pro Glu Asn
    2120            2125                2130

Arg Pro Val Leu Val Val Asp Asp Gly Ser Glu Leu Thr Leu Ala
    2135            2140                2145

Leu Val Arg Val Leu Gly Ala Cys Ala Val Val Leu Thr Phe Glu
    2150            2155                2160

Gly Leu Gln Leu Ala Gln Arg Ala Gly Ala Ala Ala Ile Arg His
    2165            2170                2175

Val Leu Ala Lys Asp Leu Ser Ala Glu Ser Ala Glu Lys Ala Ile
    2180            2185                2190

Lys Glu Ala Glu Gln Arg Phe Gly Ala Leu Gly Gly Phe Ile Ser
    2195            2200                2205

Gln Gln Ala Glu Arg Phe Glu Pro Ala Glu Ile Leu Gly Phe Thr
```

```
               2210                2215                2220

Leu Met Cys Ala Lys Phe Ala  Lys Ala Ser Leu Cys  Thr Ala Val
    2225                2230                2235

Ala Gly Gly Arg Pro Ala Phe  Ile Gly Val Ala Arg  Leu Asp Gly
    2240                2245                2250

Arg Leu Gly Phe Thr Ser Gln  Gly Thr Ser Asp Ala  Leu Lys Arg
    2255                2260                2265

Ala Gln Arg Gly Ala Ile Phe  Gly Leu Cys Lys Thr  Ile Gly Leu
    2270                2275                2280

Glu Trp Ser Glu Ser Asp Val  Phe Ser Arg Gly Val  Asp Ile Ala
    2285                2290                2295

Gln Gly Met His Pro Glu Asp  Ala Ala Val Ala Ile  Val Arg Glu
    2300                2305                2310

Met Ala Cys Ala Asp Ile Arg  Ile Arg Glu Val Gly  Ile Gly Ala
    2315                2320                2325

Asn Gln Gln Arg Cys Thr Ile  Arg Ala Ala Lys Leu  Glu Thr Gly
    2330                2335                2340

Asn Pro Gln Arg Gln Ile Ala  Lys Asp Asp Val Leu  Leu Val Ser
    2345                2350                2355

Gly Gly Ala Arg Gly Ile Thr  Pro Leu Cys Ile Arg  Glu Ile Thr
    2360                2365                2370

Arg Gln Ile Ala Gly Gly Lys  Tyr Ile Leu Leu Gly  Arg Ser Lys
    2375                2380                2385

Val Ser Ala Ser Glu Pro Ala  Trp Cys Ala Gly Ile  Thr Asp Glu
    2390                2395                2400

Lys Ala Val Gln Lys Ala Ala  Thr Gln Glu Leu Lys  Arg Ala Phe
    2405                2410                2415

Ser Ala Gly Glu Gly Pro Lys  Pro Thr Pro Arg Ala  Val Thr Lys
    2420                2425                2430

Leu Val Gly Ser Val Leu Gly  Ala Arg Glu Val Arg  Ser Ser Ile
    2435                2440                2445

Ala Ala Ile Glu Ala Leu Gly  Gly Lys Ala Ile Tyr  Ser Ser Cys
    2450                2455                2460

Asp Val Asn Ser Ala Ala Asp  Val Ala Lys Ala Val  Arg Asp Ala
    2465                2470                2475

Glu Ser Gln Leu Gly Ala Arg  Val Ser Gly Ile Val  His Ala Ser
    2480                2485                2490

Gly Val Leu Arg Asp Arg Leu  Ile Glu Lys Lys Leu  Pro Asp Glu
    2495                2500                2505

Phe Asp Ala Val Phe Gly Thr  Lys Val Thr Gly Leu  Glu Asn Leu
    2510                2515                2520

Leu Ala Ala Val Asp Arg Ala  Asn Leu Lys His Met  Val Leu Phe
    2525                2530                2535

Ser Ser Leu Ala Gly Phe His  Gly Asn Val Gly Gln  Ser Asp Tyr
    2540                2545                2550

Ala Met Ala Asn Glu Ala Leu  Asn Lys Met Gly Leu  Glu Leu Ala
    2555                2560                2565

Lys Asp Val Ser Val Lys Ser  Ile Cys Phe Gly Pro  Trp Asp Gly
    2570                2575                2580

Gly Met Val Thr Pro Gln Leu  Lys Lys Gln Phe Gln  Glu Met Gly
    2585                2590                2595

Val Gln Ile Ile Pro Arg Glu  Gly Gly Ala Asp Thr  Val Ala Arg
    2600                2605                2610
```

-continued

```
Ile Val Leu Gly Ser Ser Pro Ala Glu Ile Leu Val Gly Asn Trp
2615                2620                2625

Arg Thr Pro Ser Lys Lys Val Gly Ser Asp Thr Ile Thr Leu His
2630                2635                2640

Arg Lys Ile Ser Ala Lys Ser Asn Pro Phe Leu Glu Asp His Val
2645                2650                2655

Ile Gln Gly Arg Arg Val Leu Pro Met Thr Leu Ala Ile Gly Ser
2660                2665                2670

Leu Ala Glu Thr Cys Leu Gly Leu Phe Pro Gly Tyr Ser Leu Trp
2675                2680                2685

Ala Ile Asp Asp Ala Gln Leu Phe Lys Gly Val Thr Val Asp Gly
2690                2695                2700

Asp Val Asn Cys Glu Val Thr Leu Thr Pro Ser Thr Ala Pro Ser
2705                2710                2715

Gly Arg Val Asn Val Gln Ala Thr Leu Lys Thr Phe Ser Ser Gly
2720                2725                2730

Lys Leu Val Pro Ala Tyr Arg Ala Val Ile Val Leu Ser Asn Gln
2735                2740                2745

Gly Ala Pro Pro Ala Asn Ala Thr Met Gln Pro Pro Ser Leu Asp
2750                2755                2760

Ala Asp Pro Ala Leu Gln Gly Ser Val Tyr Asp Gly Lys Thr Leu
2765                2770                2775

Phe His Gly Pro Ala Phe Arg Gly Ile Asp Asp Val Leu Ser Cys
2780                2785                2790

Thr Lys Ser Gln Leu Val Ala Lys Cys Ser Ala Val Pro Gly Ser
2795                2800                2805

Asp Ala Ala Arg Gly Glu Phe Ala Thr Asp Thr Asp Ala His Asp
2810                2815                2820

Pro Phe Val Asn Asp Leu Ala Phe Gln Ala Met Leu Val Trp Val
2825                2830                2835

Arg Arg Thr Leu Gly Gln Ala Ala Leu Pro Asn Ser Ile Gln Arg
2840                2845                2850

Ile Val Gln His Arg Pro Val Pro Gln Asp Lys Pro Phe Tyr Ile
2855                2860                2865

Thr Leu Arg Ser Asn Gln Ser Gly Gly His Ser Gln His Lys His
2870                2875                2880

Ala Leu Gln Phe His Asn Glu Gln Gly Asp Leu Phe Ile Asp Val
2885                2890                2895

Gln Ala Ser Val Ile Ala Thr Asp Ser Leu Ala Phe
2900                2905                2910

<210> SEQ ID NO 91
<211> LENGTH: 2910
<212> TYPE: PRT
<213> ORGANISM: Schizochytrium sp.

<400> SEQUENCE: 91

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
                20                  25                  30

Arg Glu Ser Trp Glu Thr Ile Arg Ala Gly Ile Asp Cys Leu Ser Asp
            35                  40                  45

Leu Pro Glu Asp Arg Val Asp Val Thr Ala Tyr Phe Asp Pro Val Lys
        50                  55                  60
```

-continued

```
Thr Thr Lys Asp Lys Ile Tyr Cys Lys Arg Gly Gly Phe Ile Pro Glu
 65                  70                  75                  80

Tyr Asp Phe Asp Ala Arg Glu Phe Gly Leu Asn Met Phe Gln Met Glu
                 85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Lys Asn Ile
            115                 120                 125

Gly Cys Val Leu Gly Ile Gly Gly Gln Lys Ser His Glu Phe
            130                 135                 140

Tyr Ser Arg Leu Asn Tyr Val Val Glu Lys Val Leu Arg Lys Met
145                 150                 155                 160

Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
            180                 185                 190

Val Thr Ala Gly Arg Cys Thr Asn Thr Phe Asn Leu Asp Gly Met Asn
            195                 200                 205

Cys Val Val Asp Ala Ala Cys Ala Ser Ser Leu Ile Ala Val Lys Val
            210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
            260                 265                 270

Thr Lys Gly Met Leu Ile Gly Glu Gly Ser Ala Met Leu Val Leu Lys
            275                 280                 285

Arg Tyr Ala Asp Ala Val Arg Asp Gly Asp Glu Ile His Ala Val Ile
            290                 295                 300

Arg Gly Cys Ala Ser Ser Ser Asp Gly Lys Ala Ala Gly Ile Tyr Thr
305                 310                 315                 320

Pro Thr Ile Ser Gly Gln Glu Glu Ala Leu Arg Arg Ala Tyr Asn Arg
                325                 330                 335

Ala Cys Val Asp Pro Ala Thr Val Thr Leu Val Glu Gly His Gly Thr
            340                 345                 350

Gly Thr Pro Val Gly Asp Arg Ile Glu Leu Thr Ala Leu Arg Asn Leu
            355                 360                 365

Phe Asp Lys Ala Tyr Gly Glu Gly Asn Thr Glu Lys Val Ala Val Gly
            370                 375                 380

Ser Ile Lys Ser Ser Ile Gly His Leu Lys Ala Val Ala Gly Leu Ala
385                 390                 395                 400

Gly Met Ile Lys Val Ile Met Ala Leu Lys His Lys Thr Leu Pro Gly
                405                 410                 415

Thr Ile Asn Val Asp Asn Pro Asn Leu Tyr Asp Asn Thr Pro Ile
            420                 425                 430

Asn Glu Ser Ser Leu Tyr Ile Asn Thr Met Asn Arg Pro Trp Phe Pro
            435                 440                 445

Pro Pro Gly Val Pro Arg Arg Ala Gly Ile Ser Ser Phe Gly Phe Gly
            450                 455                 460

Gly Ala Asn Tyr His Ala Val Leu Glu Glu Ala Glu Pro His Thr
465                 470                 475                 480

Thr Ala Tyr Arg Leu Asn Lys Arg Pro Gln Pro Val Leu Met Met Ala
            485                 490                 495
```

```
Ala Thr Pro Ala Ala Leu Gln Ser Leu Cys Glu Ala Gln Leu Lys Glu
            500                 505                 510

Phe Glu Ala Ala Ile Lys Glu Asn Glu Thr Val Lys Asn Thr Ala Tyr
            515                 520                 525

Ile Lys Cys Val Lys Phe Gly Glu Gln Phe Lys Phe Pro Gly Ser Ile
        530                 535                 540

Pro Ala Thr Asn Ala Arg Leu Gly Phe Leu Val Lys Asp Ala Glu Asp
545                 550                 555                 560

Ala Cys Ser Thr Leu Arg Ala Ile Cys Ala Gln Phe Ala Lys Asp Val
                565                 570                 575

Thr Lys Glu Ala Trp Arg Leu Pro Arg Glu Gly Val Ser Phe Arg Ala
            580                 585                 590

Lys Gly Ile Ala Thr Asn Gly Ala Val Ala Ala Leu Phe Ser Gly Gln
        595                 600                 605

Gly Ala Gln Tyr Thr His Met Phe Ser Glu Val Ala Met Asn Trp Pro
        610                 615                 620

Gln Phe Arg Gln Ser Ile Ala Ala Met Asp Ala Ala Gln Ser Lys Val
625                 630                 635                 640

Ala Gly Ser Asp Lys Asp Phe Glu Arg Val Ser Gln Val Leu Tyr Pro
                645                 650                 655

Arg Lys Pro Tyr Glu Arg Glu Pro Gln Asp His Lys Lys Ile Ser
            660                 665                 670

Leu Thr Ala Tyr Ser Gln Pro Ser Thr Leu Ala Cys Ala Leu Gly Ala
        675                 680                 685

Phe Glu Ile Phe Lys Glu Ala Gly Phe Thr Pro Asp Phe Ala Ala Gly
        690                 695                 700

His Ser Leu Gly Glu Phe Ala Ala Leu Tyr Ala Ala Gly Cys Val Asp
705                 710                 715                 720

Arg Asp Glu Leu Phe Glu Leu Val Cys Arg Arg Ala Arg Ile Met Gly
                725                 730                 735

Gly Lys Asp Ala Pro Ala Thr Pro Lys Gly Cys Met Ala Ala Val Ile
            740                 745                 750

Gly Pro Asn Ala Glu Asn Ile Lys Val Gln Ala Ala Asn Val Trp Leu
        755                 760                 765

Gly Asn Ser Asn Ser Pro Ser Gln Thr Val Ile Thr Gly Ser Val Glu
        770                 775                 780

Gly Ile Gln Ala Glu Ser Ala Arg Leu Gln Lys Glu Gly Phe Arg Val
785                 790                 795                 800

Val Pro Leu Ala Cys Glu Ser Ala Phe His Ser Pro Gln Met Glu Asn
                805                 810                 815

Ala Ser Ser Ala Phe Lys Asp Val Ile Ser Lys Val Ser Phe Arg Thr
            820                 825                 830

Pro Lys Ala Glu Thr Lys Leu Phe Ser Asn Val Ser Gly Glu Thr Tyr
        835                 840                 845

Pro Thr Asp Ala Arg Glu Met Leu Thr Gln His Met Thr Ser Ser Val
        850                 855                 860

Lys Phe Leu Thr Gln Val Arg Asn Met His Gln Ala Gly Ala Arg Ile
865                 870                 875                 880

Phe Val Glu Phe Gly Pro Lys Gln Val Leu Ser Lys Leu Val Ser Glu
                885                 890                 895

Thr Leu Lys Asp Asp Pro Ser Val Val Thr Val Ser Val Asn Pro Ala
            900                 905                 910

Ser Gly Thr Asp Ser Asp Ile Gln Leu Arg Asp Ala Ala Val Gln Leu
```

-continued

```
            915                 920                 925
Val Val Ala Gly Val Asn Leu Gln Gly Phe Asp Lys Trp Asp Ala Pro
    930                 935                 940

Asp Ala Thr Arg Met Gln Ala Ile Lys Lys Arg Thr Thr Leu Arg
945                 950                 955                 960

Leu Ser Ala Ala Thr Tyr Val Ser Asp Lys Thr Lys Val Arg Asp
                965                 970                 975

Ala Ala Met Asn Asp Gly Arg Cys Val Thr Tyr Leu Lys Gly Ala Ala
                980                 985                 990

Pro Leu Ile Lys Ala Pro Glu Pro  Val Val Asp Glu Ala  Ala Lys Arg
            995                 1000                1005

Glu Ala  Glu Arg Leu Gln Lys  Glu Leu Gln Asp Ala  Gln Arg Gln
1010                1015                1020

Leu Asp  Asp Ala Lys Arg Ala  Ala Glu Ala Asn  Ser Lys Leu
    1025                1030                1035

Ala Ala  Ala Lys Glu Glu Ala  Lys Thr Ala Ala Ala  Ser Ala Lys
    1040                1045                1050

Pro Ala  Val Asp Thr Ala Val  Val Glu Lys His Arg  Ala Ile Leu
    1055                1060                1065

Lys Ser  Met Leu Ala Glu Leu  Asp Gly Tyr Gly Ser  Val Asp Ala
    1070                1075                1080

Ser Ser  Leu Gln Gln Gln Gln  Gln Gln Thr Ala  Pro Ala Pro
    1085                1090                1095

Val Lys  Ala Ala Ala Pro Ala  Ala Pro Val Ala Ser  Ala Pro Ala
    1100                1105                1110

Pro Ala  Val Ser Asn Glu Leu  Leu Glu Lys Ala Glu  Thr Val Val
    1115                1120                1125

Met Glu  Val Leu Ala Ala Lys  Thr Gly Tyr Glu Thr  Asp Met Ile
    1130                1135                1140

Glu Ala  Asp Met Glu Leu Glu  Thr Glu Leu Gly Ile  Asp Ser Ile
    1145                1150                1155

Lys Arg  Val Glu Ile Leu Ser  Glu Val Gln Ala Met  Leu Asn Val
    1160                1165                1170

Glu Ala  Lys Asp Val Asp Ala  Leu Ser Arg Thr Arg  Thr Val Gly
    1175                1180                1185

Glu Val  Val Asn Ala Met Lys  Ala Glu Ile Ala Gly  Ser Ser Ala
    1190                1195                1200

Pro Ala  Pro Ala Ala Ala Ala  Pro Ala Pro Ala Lys  Ala Ala Pro
    1205                1210                1215

Ala Ala  Ala Ala Pro Ala Val  Ser Asn Glu Leu Leu  Glu Lys Ala
    1220                1225                1230

Glu Thr  Val Val Met Glu Val  Leu Ala Ala Lys Thr  Gly Tyr Glu
    1235                1240                1245

Thr Asp  Met Ile Glu Ser Asp  Met Glu Leu Glu Thr  Glu Leu Gly
    1250                1255                1260

Ile Asp  Ser Ile Lys Arg Val  Glu Ile Leu Ser Glu  Val Gln Ala
    1265                1270                1275

Met Leu  Asn Val Glu Ala Lys  Asp Val Asp Ala Leu  Ser Arg Thr
    1280                1285                1290

Arg Thr  Val Gly Glu Val Val  Asn Ala Met Lys Ala  Glu Ile Ala
    1295                1300                1305

Gly Gly  Ser Ala Pro Ala Pro  Ala Ala Ala Ala Pro  Gly Pro Ala
    1310                1315                1320
```

-continued

```
Ala Ala Ala Pro Ala Pro Ala Ala Ala Pro Ala Val Ser Asn
    1325                1330            1335

Glu Leu Leu Glu Lys Ala Glu Thr Val Val Met Glu Val Leu Ala
    1340                1345            1350

Ala Lys Thr Gly Tyr Glu Thr Asp Met Ile Glu Ser Asp Met Glu
    1355                1360            1365

Leu Glu Thr Glu Leu Gly Ile Asp Ser Ile Lys Arg Val Glu Ile
    1370                1375            1380

Leu Ser Glu Val Gln Ala Met Leu Asn Val Glu Ala Lys Asp Val
    1385                1390            1395

Asp Ala Leu Ser Arg Thr Arg Thr Val Gly Glu Val Val Asp Ala
    1400                1405            1410

Met Lys Ala Glu Ile Ala Gly Gly Ser Ala Pro Ala Pro Ala Ala
    1415                1420            1425

Ala Ala Pro Ala Pro Ala Ala Ala Pro Ala Pro Ala Ala Pro
    1430                1435            1440

Ala Pro Ala Val Ser Ser Glu Leu Leu Glu Lys Ala Glu Thr Val
    1445                1450            1455

Val Met Glu Val Leu Ala Ala Lys Thr Gly Tyr Glu Thr Asp Met
    1460                1465            1470

Ile Glu Ser Asp Met Glu Leu Glu Thr Glu Leu Gly Ile Asp Ser
    1475                1480            1485

Ile Lys Arg Val Glu Ile Leu Ser Glu Val Gln Ala Met Leu Asn
    1490                1495            1500

Val Glu Ala Lys Asp Val Asp Ala Leu Ser Arg Thr Arg Thr Val
    1505                1510            1515

Gly Glu Val Val Asp Ala Met Lys Ala Glu Ile Ala Gly Gly Ser
    1520                1525            1530

Ala Pro Ala Pro Ala Ala Ala Pro Ala Pro Ala Ala Ala Ala
    1535                1540            1545

Pro Ala Pro Ala Ala Pro Ala Pro Ala Ala Pro Ala Pro Ala Val
    1550                1555            1560

Ser Ser Glu Leu Leu Glu Lys Ala Glu Thr Val Val Met Glu Val
    1565                1570            1575

Leu Ala Ala Lys Thr Gly Tyr Glu Thr Asp Met Ile Glu Ser Asp
    1580                1585            1590

Met Glu Leu Glu Thr Glu Leu Gly Ile Asp Ser Ile Lys Arg Val
    1595                1600            1605

Glu Ile Leu Ser Glu Val Gln Ala Met Leu Asn Val Glu Ala Lys
    1610                1615            1620

Asp Val Asp Ala Leu Ser Arg Thr Arg Thr Val Gly Glu Val Val
    1625                1630            1635

Asp Ala Met Lys Ala Glu Ile Ala Gly Ser Ser Ala Ser Ala Pro
    1640                1645            1650

Ala Ala Ala Ala Pro Ala Pro Ala Ala Ala Pro Ala Pro Ala
    1655                1660            1665

Ala Ala Ala Pro Ala Val Ser Asn Glu Leu Leu Glu Lys Ala Glu
    1670                1675            1680

Thr Val Val Met Glu Val Leu Ala Ala Lys Thr Gly Tyr Glu Thr
    1685                1690            1695

Asp Met Ile Glu Ser Asp Met Glu Leu Glu Thr Glu Leu Gly Ile
    1700                1705            1710

Asp Ser Ile Lys Arg Val Glu Ile Leu Ser Glu Val Gln Ala Met
    1715                1720            1725
```

```
Leu Asn Val Glu Ala Lys Asp Val Asp Ala Leu Ser Arg Thr Arg
    1730                1735                1740

Thr Val Gly Glu Val Val Asp Ala Met Lys Ala Glu Ile Ala Gly
    1745                1750                1755

Gly Ser Ala Pro Ala Pro Ala Ala Ala Pro Ala Pro Ala Ala
    1760                1765                1770

Ala Ala Pro Ala Val Ser Asn Glu Leu Leu Glu Lys Ala Glu Thr
    1775                1780                1785

Val Val Met Glu Val Leu Ala Ala Lys Thr Gly Tyr Glu Thr Asp
    1790                1795                1800

Met Ile Glu Ser Asp Met Glu Leu Glu Thr Glu Leu Gly Ile Asp
    1805                1810                1815

Ser Ile Lys Arg Val Glu Ile Leu Ser Glu Val Gln Ala Met Leu
    1820                1825                1830

Asn Val Glu Ala Lys Asp Val Asp Ala Leu Ser Arg Thr Arg Thr
    1835                1840                1845

Val Gly Glu Val Val Asp Ala Met Lys Ala Glu Ile Ala Gly Ser
    1850                1855                1860

Ser Ala Pro Ala Pro Ala Ala Ala Pro Ala Pro Ala Ala Ala
    1865                1870                1875

Ala Pro Ala Pro Ala Ala Ala Pro Ala Val Ser Ser Glu Leu
    1880                1885                1890

Leu Glu Lys Ala Glu Thr Val Val Met Glu Val Leu Ala Ala Lys
    1895                1900                1905

Thr Gly Tyr Glu Thr Asp Met Ile Glu Ser Asp Met Glu Leu Glu
    1910                1915                1920

Thr Glu Leu Gly Ile Asp Ser Ile Lys Arg Val Glu Ile Leu Ser
    1925                1930                1935

Glu Val Gln Ala Met Leu Asn Val Glu Ala Lys Asp Val Asp Ala
    1940                1945                1950

Leu Ser Arg Thr Arg Thr Val Gly Glu Val Val Asp Ala Met Lys
    1955                1960                1965

Ala Glu Ile Ala Gly Gly Ser Ala Pro Ala Pro Ala Ala Ala
    1970                1975                1980

Pro Ala Pro Ala Ala Ala Pro Ala Val Ser Asn Glu Leu Leu
    1985                1990                1995

Glu Lys Ala Glu Thr Val Val Met Glu Val Leu Ala Ala Lys Thr
    2000                2005                2010

Gly Tyr Glu Thr Asp Met Ile Glu Ser Asp Met Glu Leu Glu Thr
    2015                2020                2025

Glu Leu Gly Ile Asp Ser Ile Lys Arg Val Glu Ile Leu Ser Glu
    2030                2035                2040

Val Gln Ala Met Leu Asn Val Glu Ala Lys Asp Val Asp Ala Leu
    2045                2050                2055

Ser Arg Thr Arg Thr Val Gly Glu Val Val Asp Ala Met Lys Ala
    2060                2065                2070

Glu Ile Ala Gly Gly Ser Ala Pro Ala Pro Ala Ala Ala Pro
    2075                2080                2085

Ala Ser Ala Gly Ala Ala Pro Ala Val Lys Ile Asp Ser Val His
    2090                2095                2100

Gly Ala Asp Cys Asp Asp Leu Ser Leu Met His Ala Lys Val Val
    2105                2110                2115

Asp Ile Arg Arg Pro Asp Glu Leu Ile Leu Glu Arg Pro Glu Asn
```

```
                2120                2125                2130

Arg Pro Val Leu Val Val Asp Asp Gly Ser Glu Leu Thr Leu Ala
    2135                2140                2145

Leu Val Arg Val Leu Gly Ala Cys Ala Val Val Leu Thr Phe Glu
    2150                2155                2160

Gly Leu Gln Leu Ala Gln Arg Ala Gly Ala Ala Ala Ile Arg His
    2165                2170                2175

Val Leu Ala Lys Asp Leu Ser Ala Glu Ser Ala Glu Lys Ala Ile
    2180                2185                2190

Lys Glu Ala Glu Gln Arg Phe Gly Ala Leu Gly Gly Phe Ile Ser
    2195                2200                2205

Gln Gln Ala Glu Arg Phe Glu Pro Ala Glu Ile Leu Gly Phe Thr
    2210                2215                2220

Leu Met Cys Ala Lys Phe Ala Lys Ala Ser Leu Cys Thr Ala Val
    2225                2230                2235

Ala Gly Gly Arg Pro Ala Phe Ile Gly Val Ala Arg Leu Asp Gly
    2240                2245                2250

Arg Leu Gly Phe Thr Ser Gln Gly Thr Ser Asp Ala Leu Lys Arg
    2255                2260                2265

Ala Gln Arg Gly Ala Ile Phe Gly Leu Cys Lys Thr Ile Gly Leu
    2270                2275                2280

Glu Trp Ser Glu Ser Asp Val Phe Ser Arg Gly Val Asp Ile Ala
    2285                2290                2295

Gln Gly Met His Pro Glu Asp Ala Ala Val Ala Ile Val Arg Glu
    2300                2305                2310

Met Ala Cys Ala Asp Ile Arg Ile Arg Glu Val Gly Ile Gly Ala
    2315                2320                2325

Asn Gln Gln Arg Cys Thr Ile Arg Ala Ala Lys Leu Glu Thr Gly
    2330                2335                2340

Asn Pro Gln Arg Gln Ile Ala Lys Asp Asp Val Leu Leu Val Ser
    2345                2350                2355

Gly Gly Ala Arg Gly Ile Thr Pro Leu Cys Ile Arg Glu Ile Thr
    2360                2365                2370

Arg Gln Ile Ala Gly Gly Lys Tyr Ile Leu Leu Gly Arg Ser Lys
    2375                2380                2385

Val Ser Ala Ser Glu Pro Ala Trp Cys Ala Gly Ile Thr Asp Glu
    2390                2395                2400

Lys Ala Val Gln Lys Ala Ala Thr Gln Glu Leu Lys Arg Ala Phe
    2405                2410                2415

Ser Ala Gly Glu Gly Pro Lys Pro Thr Pro Arg Ala Val Thr Lys
    2420                2425                2430

Leu Val Gly Ser Val Leu Gly Ala Arg Glu Val Arg Ser Ser Ile
    2435                2440                2445

Ala Ala Ile Glu Ala Leu Gly Gly Lys Ala Ile Tyr Ser Ser Cys
    2450                2455                2460

Asp Val Asn Ser Ala Ala Asp Val Ala Lys Ala Val Arg Asp Ala
    2465                2470                2475

Glu Ser Gln Leu Gly Ala Arg Val Ser Gly Ile Val His Ala Ser
    2480                2485                2490

Gly Val Leu Arg Asp Arg Leu Ile Glu Lys Lys Leu Pro Asp Glu
    2495                2500                2505

Phe Asp Ala Val Phe Gly Thr Lys Val Thr Gly Leu Glu Asn Leu
    2510                2515                2520
```

```
Leu Ala Ala Val Asp Arg Ala Asn Leu Lys His Met Val Leu Phe
2525                2530                2535

Ser Ser Leu Ala Gly Phe His Gly Asn Val Gly Gln Ser Asp Tyr
2540                2545                2550

Ala Met Ala Asn Glu Ala Leu Asn Lys Met Gly Leu Glu Leu Ala
2555                2560                2565

Lys Asp Val Ser Val Lys Ser Ile Cys Phe Gly Pro Trp Asp Gly
2570                2575                2580

Gly Met Val Thr Pro Gln Leu Lys Lys Gln Phe Gln Glu Met Gly
2585                2590                2595

Val Gln Ile Ile Pro Arg Glu Gly Gly Ala Asp Thr Val Ala Arg
2600                2605                2610

Ile Val Leu Gly Ser Ser Pro Ala Glu Ile Leu Val Gly Asn Trp
2615                2620                2625

Arg Thr Pro Ser Lys Lys Val Gly Ser Asp Thr Ile Thr Leu His
2630                2635                2640

Arg Lys Ile Ser Ala Lys Ser Asn Pro Phe Leu Glu Asp His Val
2645                2650                2655

Ile Gln Gly Arg Arg Val Leu Pro Met Thr Leu Ala Ile Gly Ser
2660                2665                2670

Leu Ala Glu Thr Cys Leu Gly Leu Phe Pro Gly Tyr Ser Leu Trp
2675                2680                2685

Ala Ile Asp Asp Ala Gln Leu Phe Lys Gly Val Thr Val Asp Gly
2690                2695                2700

Asp Val Asn Cys Glu Val Thr Leu Thr Pro Ser Thr Ala Pro Ser
2705                2710                2715

Gly Arg Val Asn Val Gln Ala Thr Leu Lys Thr Phe Ser Ser Gly
2720                2725                2730

Lys Leu Val Pro Ala Tyr Arg Ala Val Ile Val Leu Ser Asn Gln
2735                2740                2745

Gly Ala Pro Pro Ala Asn Ala Thr Met Gln Pro Pro Ser Leu Asp
2750                2755                2760

Ala Asp Pro Ala Leu Gln Gly Ser Val Tyr Asp Gly Lys Thr Leu
2765                2770                2775

Phe His Gly Pro Ala Phe Arg Gly Ile Asp Asp Val Leu Ser Cys
2780                2785                2790

Thr Lys Ser Gln Leu Val Ala Lys Cys Ser Ala Val Pro Gly Ser
2795                2800                2805

Asp Ala Ala Arg Gly Glu Phe Ala Thr Asp Thr Asp Ala His Asp
2810                2815                2820

Pro Phe Val Asn Asp Leu Ala Phe Gln Ala Met Leu Val Trp Val
2825                2830                2835

Arg Arg Thr Leu Gly Gln Ala Ala Leu Pro Asn Ser Ile Gln Arg
2840                2845                2850

Ile Val Gln His Arg Pro Val Pro Gln Asp Lys Pro Phe Tyr Ile
2855                2860                2865

Thr Leu Arg Ser Asn Gln Ser Gly Gly His Ser Gln His Lys His
2870                2875                2880

Ala Leu Gln Phe His Asn Glu Gln Gly Asp Leu Phe Ile Asp Val
2885                2890                2895

Gln Ala Ser Val Ile Ala Thr Asp Ser Leu Ala Phe
2900                2905                2910
```

PUFA-PKS GENES FROM *ULKENIA*

The invention describes genes coding sequences specific for polyketide synthases (PKS). The PKS synthesized from them is characterized by its enzymatic capacity to produce PUFAs (polyunsaturated fatty acids). The invention furthermore comprises the identification of the corresponding DNA sequences as well as the use of nucleotide sequences for the production of recombinant and/or transgenic organisms.

The term PUFAs (polyunsaturated fatty acids) denotes multiply unsaturated long-chain fatty acids with a chain length>C12 and at least two double bonds. There are two main families of PUFA that differ according to the position of the first double bond, relative to the alkyl end, in omega-3 (n-3) and in omega-6 (n-6) fatty acids. They are important components of cell membranes, where they are present in the form of lipids, especially phospholipids. PUFAs also function as preliminary stages of important molecules in humans and in animals such as, e.g., prostaglandins, leukotrienes and prostacyclins (A. P. Simopoulos, essential fatty acids in health and chronic disease, Am. J. Clin. Nutr. 1999 (70), pp. 560-569). Important representatives of the group of omega-3 fatty acids are DHA (docosahexaenoic acid) and EPA (eicosapentaenoic acid), that can be found in fish oils and in marine microorganisms. An important representative of omega-6 fatty acids is ARA (arachidonic acid), that occurs, e.g., in filamentary fungi but can also be isolated from animal tissues such as liver and kidney. DHA and ARA occur next to one another in human mother's milk.

PUFAs are essential for a human as regards an appropriate development, in particular for the developing brain, tissue formation and its repair. Thus, DHA is an important component of human cell membranes, especially those of the nerves. It plays an important part in the maturing of brain function and is essential for the development of vision. Omega-3 PUFAs such as DHA and EPA are used as nutrient supplement since a balanced nourishment with a sufficient supply of DHA is advantageous for the prophylaxis of certain diseases (A. P. Simopoulos, Essential fatty acids in health and chronic disease, American Journal of Clinical Nutrition 1999 (70), pp. 560-569). For example, adults with non-insulin-dependent diabetes exhibit a deficiency or at least an unbalanced DHA balance related to cardiac problems occurring later. Likewise, neuronal diseases such as, e.g., Alzheimer's or schizophrenia are accompanied by low DHA levels.

There is a large number of sources for the commercial extraction of DHA, such as, e.g., oils from marine cold-water fish, egg yolk fractions or marine microorganisms. Microorganisms suitable for the extraction of n-3 PUFA are found, e.g., in bacteria in the in the genus *Vibrio* (e.g., *Vibrio marinus*) or in the dinoflagellates (*Dinophyta*), in which in particular the genus *Crypthecodinium*, such as *C. cohnii* or in the Stramenopiles (or *Labyrinthulomycota*), such as the Pinguiophyceae such as, e.g., *Glossomastix, Phaeomonas, Pinguiochrysis, Pinguiococcus* and *Polypodochrysis*. Other preferred microorganisms for producing PUFA belong in particular to the order Thraustochytriales, (Thraustchytriidea) with the genera *Japonochytrium, Schizochytrium, Thraustochytrium, Althornia, Labyrinthuloides, Aplanochytrium* and *Ulkenia*.

The oils extracted from commercially known PUFA sources such as plants or animals are often characterized by a very heterogeneous composition. The oils extracted in this manner must be subjected to expensive purification processes in order to be able to enrich one or several PUFAs. Furthermore, the supplying with PUFA from such sources is subjected to uncontrollable fluctuations. Thus, diseases and weather influences can reduce animal and also vegetable yields. The extraction of PUFA from fish is subject to seasonal fluctuations and can even be temporarily halted due to overfishing or climatic changes (e.g., el Niño). Animal oils, especially fish oils, can accumulate noxious substances from the environment via the food chain. It has become known that animals are highly stressed by organochlorides such as, e.g., polychlorinated biphenyls, in particular in commercial fish farms, that counteract the healthy aspects of fish consumption (Hites et al. 2004, Global assessment of organic contaminants in farmed salmon, Science 303, pp. 226-229). The resulting loss in quality of fish products results in a decreasing acceptance of consumers for fish and fish oils as omega-3 PUFA sources. Furthermore, the concentration of DHA from fish is relatively expensive on account of high technical requirements. On the other hand, DHA is present in a few marine microorganisms in amounts of approximately 50% of the total fat component of the cell and they can be cultivated relatively economically in large fermenters. Another advantage of microorganisms is a composition of the oils extracted from them that is limited to a few components.

Various biocatalytic paths are known for the biosynthesis of long-chain PUFA such as docosahexaenoic acid (DHA; 22:6, n-3) and eicosapentaenoic acid (EPA; 20:5, n-3). The conventional biosynthesis path for producing long-chain PUFA in eukaryotic organisms begins with the delta-6 desaturation of linoleic acid (LA; 18:2, n-6) and alphalinoleic acid. It results in the synthesis of gammalinoleic acid (GLA; 18:3, n-6) from linoleic acid and of octadecatetraenoic acid (OTA; 18:4, n-3) from alphalinoleic acid. This desaturation step is followed for the n-6 as well as for the n-3 fatty acids by an elongation step as well as a delta-5 desaturation, resulting in arachidonic acid (ARA; 20:4, n-6) and eicosapentaenoic acid (EPA; 20:5, n-3). The synthesis of docosahexaenoic acid (DHA; 22:6, n-3) starting from eicosapentaenoic acid (EPA; 20:5, n-3) can then take place via two different biosynthesis paths. In the so-called linear biosynthesis path an elongation of eicosapentaenoic acid (EPA; 20:5, n-3) by two further carbon units takes place with a subsequent delta-4 desaturation for the formation of docosahexaenoic acid (DHA; 22:6, n-3). The existence of this biosynthesis path was able to be corroborated by the presence of a delta-4 desaturase in organisms such as *thraustochytrium* and *Euglena* (Qiu, et al., Identification of a delta 4 fatty acid desaturase from *Thraustochytrium* sp. involved in the biosynthesis of docosahexaenoic acid by heterologous expression in *Saccharomyces cerevisiae* and *Brassica juncea*., J. Biol. Chem. 276 (2001), pp. 31561-31,566 and Meyer et al., Biosynthesis of docosahexaenoic acid in *Euglena gracilis*: Biochemical and molecular evidence for the involvement of a delta 4 fatty acyl group desaturase. Biochemistry 42 (2003), pp. 9779-9788). The second path to the synthesis of docosahexaenoic acid (DHA; 22:6, n-3) starting from eicosapentaenoic acid (EPA; 20:5, n-3), the so-called Sprecher pathway, is independent of a delta-4 desaturation. It consists of two successive elongation steps by 2 carbon units to tetracosapentaenoic acid (24:5, n-3) and a subsequent delta-6 desaturation to tetracosahexaenoic acid (24:6, n-3). Then the formation of docosahexaenoic acid subsequently takes place by a shortening by two carbon units as a consequence of a peroxisomal β oxidation (H. Sprecher, Metabolism of highly unsaturated n-3 and n-6 fatty acids. Biochimica et Biophysica Acta 1486 (2000), pp. 219-231). This second biosynthesis path is the DHA synthesis path predominant in mammals (Leonard et al., Identification and expression of mammalian long-chain PUFA elongation enzymes. Lipids 37 (2002), pp. 733-740). An alternative biosynthesis path for the formation of C20 PUFA is present in a few organisms that lack a delta 6 denaturase activity. These organisms include, e.g., the protists *Acanthamoeba* sp. and *Euglena gracilis*. The first step in the alternative C20 PUFA synthesis consists in an elongation of the C18 fatty acids, linoleic acid (LA; 18:2, n-6) and alpha-linoleic acid (ALA; 18:3, n-3) by two carbon units. The resulting fatty acids eicosadienoic acid (20:2, n-6) and eicosatrienoic acid (20:3, n-3) are then converted by a delta 8 desaturation and a subsequent delta 5 desaturation into arachidonic acid (ARA; 20:4, n-6) and/or eicosapentaenoic acid (EPA; 20:5, n-3) (Sayanova and Napier, Eicosapentaenoic acid: Biosynthetic routes and the potential for synthesis in transgenic plants. Phytochemistry 65 (2004), pp. 147-158; Wallis and Browse; The delta-8 desaturase of *Euglena gracilis*: An alternate pathway for synthesis of 20-carbon polyunsaturated fatty acids. Arch. Biochem. Biophys. 362 (1999), pp. 307-316).

Higher plants to not have the ability to synthesize C20 PUFA from preliminary stages. They form, starting from stearic acid (18:0), oleic acid (C18:1; delta-9 desaturase), linoleic acid (18:2, n-6, delta 12 desaturase) and alpha linoleic acid (18:3, n-3; delta 15 desaturase) via various desaturases.

However, a certain number of marine microorganisms take a completely different biosynthesis path for the production of EPA and DHA. These PUFA-producing microorganisms include marine representatives of gamma proteobacteria as well as a few species of the cytophaga flavobacterium bacteroides group and up to the present a eukaryotic protist, *Schizochytrium* sp. ATCC 20888 (Metz et al. 2001, Production of polyunsaturated fatty acids by polyketide synthases in both prokaryotes and eukaryotes. Science 293:290-293). They synthesize long-chain PUFA via so-called polyketide synthases (PKS). These PKSs represent large enzymes that catalyze the synthesis of secondary metabolites consisting of ketide units (G. W. Wallis, J. L. Watts and J. Browse, Polyunsaturated fatty acid synthesis: what will they think of next? Trends in Biochemical Sciences 27 (9) pp. 467-473). The synthesis of polyketides contains a number of enzymatic reactions that are analogous to those of fatty acid synthesis (Hopwood & Sherman Annu. Rev. Genet. 24 (1990) pp. 37-66; Katz & Donadio Annu. Rev. of Microbiol. 47 (1993) pp. 875-912).

Gene sequences of different PUFA-PKSs (PUFA-synthesizing PKSs) are already known. Thus, a 38 kb genomic fragment was isolated from the marine bacterium *Shewanella* sp. that contains the information for the production of eicosapentaenoic acid (EPA). Subsequent sequencing of this fragment resulted in the identification of 8 open reading frames (ORFs) (H. Takeyama et al., Microbiology 143 (1997) pp. 2725-2731). Five of these open reading frames from *Shewanella* are closely related to polyketide synthase genes. Likewise, U.S. Pat. No. 5,798,259 describes the EPA gene cluster from *Shewanella putrefaciens* SCRC-2874. PUFA-PKS genes were also found in the marine prokaryotes *Photobacterium profundum* strain SS9 (Allen and Bartlett, Microbiology 2002, 148 pp. 1903-1913) and *Moritella marina* strain MP-1, earlier *Vibrio marinus* (Tanaka at al., Biotechnol. Letters 1999, 21, pp. 939-945). Analogous PUFA-producing, PKS-like ORFs were also able to be identified in the eukaryotic protist *Schizochytrium* (Metz et al, Science 293 (2001) pp. 290-293 and U.S. Pat. No. 6,556,583, WO02/083870 A2). Three ORFs were determined in *Schizochytrium* that display partial identities with the EPA gene cluster from *Shewanella*. The existence of these preserved PKS genes in a few prokaryotes and the eukaryote *Schizochytrium* furnishes an indication for a possible horizontal gene transfer of PUFA-PKS genes between pro- and eukaryotes.

Even the transgenic production of PUFAs using isolated gene clusters in microorganisms that normally do not generate PUFAs was able to be shown already. Thus, the five above-named ORFs (open reading frames) present in a cluster from *Shewanella* sp. SCRC-2738 are sufficient for producing measurable amounts of EPA in the non-IPA producers *E. coli* and *Synechoccus* sp. (Yazawa, Lipids 1996, 31, pp. 297-300 and Takayama et al., Microbiology 1997, 143, pp. 2725-2731).

In general, there is always a need for new PUFA producers for the large-scale production of PUFAs. It is immaterial at first whether this production takes place, e.g., in a prokaryote, a protist or in a plant. The goal is always to produce high-quality PUFAs in large amounts as economically as possible and in a manner that protects the environment as much as possible. The present invention pursues this goal in that it describes the appropriate PUFA-PKS genes from an especially efficient PUFA producer, *Ulkenia* sp.

In consideration of the state of the art, the present invention therefore had the task of identifying and isolating further PUFA-PKS genes from the microorganism *Ulkenia* sp. producing DHA that are splendidly suited for the production of PUFAs. In addition, knowledge about the position and arrangement of such genes as well as their regulatory elements should be gained. The knowledge obtained from this, especially the nucleic acid material obtained from this, should make possible the reinforced expression of PUFA-PKS genes in a syngeneic as well as in a transgenic organism.

These tasks as well as others not explicitly named that can be readily derived or concluded, however, from the connections initially discussed here, are solved by the subject matter defined in the claims of the present invention.

1. PUFA-PKS, characterized in that they
   a. include at least one of the amino acid sequences represented in SEQ ID No. 6 (ORF 1), 7 (ORF 2), 8 and/or 80 (ORF 3) and have sequences homologous to them with at least 70%, preferably 80%, especially preferably at least 90% and more especially preferably at least 99% and most preferably 100% sequence homology that have the biological activity of at least one domain of the PUFA-PKS, or
   b. include at least one of the amino acid sequences represented in SEQ ID No. 32, 34, 45, 58, 59, 60, 61, 72, 74 and/or 77 and have sequences homologous to them with at least 70%, preferably 80%, especially preferably at least 90% and more especially preferably at least 99% and most preferably 100% sequence homology and that have the biological activity of at least one domain of the PUFA-PKS 2. Isolated PUFA-PKS according to claim 1 with 10 or more ACP domains.

Furthermore, the invention concerns under a preferred aspect such a PUFA-PKS that comprises at least one amino acid sequence with at least 70%, preferably at least 80%, especially preferably at least 90% and more especially preferably at least 99% identity with at least 500 directly successive amino acids of the sequences SEQ ID No. 6 (ORF 1), 7 (ORF 2) and/or 8 and/or 80 (ORF 3).

Furthermore, the invention concerns under a preferred aspect an amino acid sequence with at least 70%, preferably at least 80%, especially preferably at least 90% and more especially preferably at least 99% identity with at least 500 directly successive amino acids of the sequences SEQ ID No. 6 (ORF 1), 7 (ORF 2) and/or 8 and/or 80 (ORF 3).

Under a further preferred aspect, the invention concerns an isolated DNA molecule coding for a PUFA-PKS according to one of the foregoing claims.

The latter is preferably characterized in that it codes an amino acid sequence that is at least 70% identical to at least 500 directly successive amino acids of the sequences SEQ ID No. 6 (ORF 1), 7 (ORF 2) and/or 8 and/or 80 (ORF 3).

Furthermore, the present invention concerns such an isolated DNA molecule that has at least 70%, preferably at least 80%, especially preferably at least 90% and more especially preferably at least 95% identity with at least 500 successive nucleotides from the sequences SEQ ID No. 3, 4, 5 and/or 9.

Under a further preferred aspect, the invention concerns a recombinant DNA molecule comprising one of the previously described DNA molecules connected functionally with at least one DNA sequence that controls the transcription, preferably selected from the group consisting of SEQ ID No. 3, 4 and 5 and/or 9 or parts thereof from at least 500 nucleotides as well as functional variants of them.

Under yet a further preferred aspect the invention concerns a recombinant host cell comprising a previously described recombinant DNA molecule.

Under a further preferred viewpoint the invention concerns a recombinant host cell that endogenically expresses the PUFA-PKS in accordance with the invention with at least 10 ACP domains.

Furthermore, under yet a further preferred aspect the invention concerns a method for the production of oil containing PUFA, preferably DHA, comprising the cultivation of such a recombinant host cell, as well as the oil produced in this manner.

Furthermore, under yet a further preferred aspect the invention concerns a method for the production of biomass containing PUFA, preferably DHA, comprising the cultivation of such a recombinant host cell, as well as the biomass produced in this manner.

Therefore, under yet a further preferred aspect the invention also concerns a recombinant biomass produced according to a method for producing biomass containing PUFA, preferably DHA, comprising the cultivation of a host cell which is a recombinant host cell comprising a recombinant DNA molecule comprising an isolated DNA molecule coding for an amino acid sequence PUFA-PKS comprising at least one of the amino acid sequences represented in SEQ ID No. 6 (ORF 1), 7 (ORF 2), 8 and/or 80 (ORF 3) and have sequences homologous to them with at least 70%, preferably 80%, especially preferably at least 90% and more especially preferably at least 99% and most preferably 100% sequence homology that have the biological activity of at least one domain of the PUFA-PKS, or comprise at least one of the amino acid sequences represented in SEQ ID No 32, 34, 45, 58, 59, 60, 61, 72, 74 and/or 77 and have sequences homologous to them with at least 70%, preferably 80%, especially preferably at least 90% and more especially preferably at least 99% and most preferably 100% sequence homology and that have the biological activity of at least one domain of the PUFA-PKS and DNA completely complementary with it, functionally connected with at least one DNA sequence that controls the transcription, preferably selected from the group consisting of SEQ ID No. XX-YY (terminators/promoters) or parts thereof from at least 500 nucleotides as well as functional variants of them, comprising a nucleic acid comprising an isolated DNA molecule coding for an amino acid sequence PUFA-PKS comprising at least one of the amino acid sequences represented in SEQ ID No. 6 (ORF 1), 7 (ORF 2), 8 and/or 80 (ORF 3) and have sequences homologous to them with at least 70%, preferably 80%, especially preferably at least 90% and more especially preferably at least 99% and most preferably 100% sequence homology that have the biological activity of at least one domain of the PUFA-PKS, or comprise at least one of the amino acid sequences represented in SEQ ID No. 32, 34, 45, 58, 59, 60, 61, 72, 74 and/or 77 and have sequences homologous to them with at least 70%, preferably 80%, especially preferably at least 90% and more especially preferably at least 99% and most preferably 100% sequence homology and that have the biological activity of at least one domain of the PUFA-PKS and DNA completely complementary with it, functionally connected with at least one DNA sequence that controls the transcription, preferably selected from the group consisting of SEQ ID No XX-YY (terminators/promoters) or parts thereof from at least 500 nucleotides as well as functional variants of them, and/or an amino acid sequence PUFA-PKS comprising at least one of the amino acid sequences represented in SEQ ID No 6 (ORF 1), 7 (ORF 2), 8 and/or 80 (ORF 3) and have sequences homologous to them with at least 70%, preferably 80%, especially preferably at least 90% and more especially preferably at least 99% and most preferably 100% sequence homology that have the biological activity of at least one domain of the PUFA-PKS, or comprise at least one of the amino acid sequences represented in SEQ ID No. 32, 34, 45, 58, 59, 60, 61, 72, 74 and/or 77 and have sequences homologous to them with at least 70%, preferably 80%, especially preferably at least 90% and more especially preferably at least 99% and most preferably 100% sequence homology and that nave the biological activity of at least one domain of the PUFA-PKS or parts of at least 500 successive amino acids homologous to it.

The invention also concerns under yet a further preferred aspect the use of individual enzyme domains from PUFA-PKS comprising SEQ ID No. 6, 7, 8 and/or 80, represented in SEQ ID No. 32, 33, 34, 45, 58, 59, 60, 61, 72, 74 and/or 77 for producing artificial polyketides, e.g., polyketide antibiotics and/or new, changed fatty acids.

According to the invention, identity in the case of nucleic acids denotes the same base pairs at the particular position of the strands to be compared. However, gaps are possible. A possibility for calculating the identity values in % is represented by the programs blastn and fasta.

As far as amino acids are concerned, the concept homology comprises, e.g., also conservative exchanges in the amino acid sequence that does not appreciably influence the function and/or the structure of the protein. Even such homology values are calculated by programs known an expert in the art such as, e.g., blastp, Matrix PAM30, Gap Penalties: 9, Extension: 1 (Altschul at al., NAR 25, 3389-3402).

The sequence information of PUFA-PKS genes from *Ulkenia* sp. is made available by the nucleic acid sequences and amino acid sequences defined in SEQ ID No. 3 to 5 and/or 9. SEQ ID No. 1 and 2 represent the entire genomic DNA sequence on the two cosmids presently isolated (see examples 2 and 3). The latter contain for their part the information for the three relevant open reading frames ORFs 1-3 essential for PUFA synthesis as well as their flanking regulatory sequences. Furthermore, the protein sequences that can be derived from the genomic sequences are represented as a result thereof.

The invention furthermore comprises a method for the homologous and heterologous transformation of host organisms with nucleic acids in accordance with the invention for the production of highly pure PUFAs. The isolated open reading frames preferably result in the syngeneic as well as in the transgenic organism in the production of PUFA, especially of DHA, EPA and DPA.

The PUFAs produced thereby are preferably present as component of the biomass or as oil.

Prior to the present invention, only the PUFA-PKS genes of a eukaryotic organism, the protist *Schizochytrium*, were known (U.S. Pat. No. 6,566,583, WO02/083870). The sequence data then determined stems partially from cDNA and from chromosomal DNA. For the first time, all PUFA-PKS genes of a eukaryotic protist essential for the PUFA synthesis are completely described from chromosomal DNA in the present invention. This results not only in the determination of the previously unknown PUFA-PKS-coding gene information from *Ulkenia* sp., but also additionally supplies data about flanking regulatory elements such as promoters and terminators of the transcription. In addition, the chromosomal sequence information makes possible an insight into the position and arrangement of the individual PUFA-PKS genes.

It was here completely surprising that the cluster as such, as it was previously known from the prokaryotic PUFA-PKS representatives such as *Shewanella, Photobacterium* or *Moritella*, is no longer present. The cosmid (Seq ID No. 1) identified at first showed that the linear arrangement of the individual ORFs is interrupted in *Ulkenia* and also that the reading direction of individual ORFs is oppositely directed (FIG. 1). This is possibly the consequence of massive gene transpositions. The individual ORFs also display clearly greater intervals from each other as a consequence of the transpositions. Thus, the two ORFs 1 and 2 have an interval of approximately 13 kb. The third ORF was not able to be identified in this context until on a further cosmid (Seq ID No. 2) and no partial identities between the two cosmids (Seq ID No. 1 and 2) were able to be found (FIG. 1). That means that ORF from *Ulkenia* sp. is no longer located spatially in the vicinity of the two ORFs 1 and 2. This allows the conclusion that the PUFA gene cluster, as it is known from the above-named prokaryotic representatives, no longer exists in the eukaryote *Ulkenia* sp. The position and arrangement of the individual PUFA-PKS genes of the protist *Schizochytrium* on the genome has been partially determined (WO 02/083870) and also shows an opposite orientation of the two ORFs A and B. However, they are separated from one another only by 4224 base pairs. This sequence section is discussed as an intergenic region with bidirectional promoter element in Patent Application WO 02/083870. A bidirectional promoter element between homologous ORFs 1 and 2, at least for *Ulkenia*, appears improbable on account of the interval of 12.95 kb determined for *Ulkenia*. No further obvious ORFs are present within the 12.95 kb region between ORF1 and ORF2 from *Ulkenia*. This speaks for a region in which massive recombinations and/or transposition events have taken place. Transposase-like events can also have taken place based on a few repetitive sequence repetitions.

It was more especially surprising that the PUFA-PKS from *Ulkenia* sp. has the greatest number of repetitions of the acyl carrier protein with 10 ACP domains in comparison to the PUFA-PKS of the EPA producers *Shewanella* (6×ACP) and *Photobacterium* (5×ACP) as well as those of the DHA producers *Moritella* (5×ACP) and *Schizochytrium* (9×ACP) (FIG. 3). This means that the PUFA-PKS isolated from *Ulkenia* sp. not only has a deviating amino acid sequence relative to the PUFA-PKS from the related protist *Schizochytrium* but is also structurally unique. Another particularity is the fact that the third ORF from *Ulkenia* sp. is shortened by 38 amino acids relative to ORF C from *Schizochytrium* and additionally contains an alanine-rich domain that is not present in this manner in *Schizochytrium* (FIG. 6). Interestingly, this sequence resembles the regions present between the individual ACT domains from ORF 1 and possibly represents a linker region. The similarity consists both in the length of the sequence as well as in the fact that the alanine successions are interrupted only by individual prolines and valines. The greatest part of the amino acids in ORF 3 lacking relative to *Schizochytrium* ORF C is the consequence of a deletion, 30 amino acids long, between the dehydrase/isomerase domains (FIG. 6). As a result, these domains are located on the corresponding protein at a short interval from each other, which can have in influence on the enzymatic activity. For ORF 3, even further 5'-located ATG codons are conceivable as start codons, so that theoretically even an ORF maximally 1848 amino acids long can be present (Seq ID No. 9 and 80). Even simultaneously occurring variants of ORF 3 are possible in this context.

In particular, ORF 1 from *Ulkenia* sp. (Seq ID No. 3 and 6) contains on the one hand a so-called beta ketoacyl synthase domain (Seq ID No. 14 and 32) that is characterized by the motive (DXAC) (Seq ID No. 12 and 30). This motive for the active center of the enzymatic domain in *Ulkenia* ORF 1 can be expanded in a preferred form to a range of 17 amino acids (GMNCVVDAACASSLIAV) Seq ID No. 11 and 29). The entire beta ketoacyl synthase domain can be divided into an N terminal (Seq ID No. 10 and 28) and into a C terminal (Seq ID No. 13 and 31) section. The biological function of the beta ketoacyl synthase domain is the catalysis of the condensation reaction in the fatty acid- and/or PKS synthesis. The acyl group intended for the elongation is bound via a thioester bond to the cysteine group of the active center of the enzymatic domain and transferred in several steps to carbon atom 2 of the malonyl group on the acyl carrier protein, releasing $CO_2$. The beta ketoacyl synthase domain is followed by a malonylCoA-ACP transferase domain (Seq ID No. 15 and 33). This domain catalyzes the transfer of malonylCoA to the 4'-phosphopantetheine group on the acyl carrier protein (ACP). MalonylCoA-ACP transferase domains also transfer methyl- or ethyl malonate to the ACP, during which they can introduce branches into the otherwise linear carbon chain. A linker region is then followed by an alanine-rich sequence section (Seq ID No. 16 and 34) that contains 10 repetitions of an acyl carrier protein domain (ACP domain) (17-26 and 35-44). These ACP domains are separated from each other for their part by linker regions consisting primarily of alanines and prolines. Each of the ACP domains is characterized by a bonding motive for a 4'-phosphopantetheine molecule (LGXDS(L/I)). The 4'-phosphopantetheine molecule is bound here to the preserved serine inside the motive, The ACP domains serve via the 4'-phosphopantetheine group as carrier for the growing fatty acid and/or polyketide chain. A sequence with partial identities to ketoreductases (Seq ID No. 27 and 45) subsequently follows. The biological function of these domains consists in the NADPH-dependent reduction of 3-ketoacyl-ACP compounds. It represents the first reduction reaction in the fatty acid biosynthesis. This reaction also takes place frequently in the polyketide synthesis (see also FIG. 3).

ORF 2 from *Ulkenia* sp. (Seq ID No. 4 and 7) also begins with a beta ketoacyl synthase domain (Seq ID No. 50 and 58) that is characterized by the motive (DXAC) (Seq ID No. 48 and 56). This motive for the active center of the enzyme domains in *Ulkenia* ORF 2 can be expanded in a preferred form to a range of 17 amino acids (PLHYSVDAACATA-LYVL) (Seq ID No. 47 and 55). The entire beta ketoacyl synthase domain can be divided into an N-terminal (Seq ID No. 46 and 54) and a C-terminal (Seq ID No. 49 and 57) section. The biological activity of this domain corresponds to the beta ketoacyl synthase domain described in ORF 1.

Kethosynthases play a key part in the elongation cycle and show higher substrate specificity than other enzymes of the fatty acid synthesis. This is followed again by a sequence section with smaller partial identities to a beta ketoacyl synthase domain. Furthermore, this domain lacks motive DXAC for the active center. It has properties of a so-called chain length factor (CLF) from type II PKS-similar systems (Seq ID No. 51 and 59). CLF amino acid sequences have partial identities to ketosynthases but have no characteristic active center with a corresponding cysteine group. The part of CLFs in PKS systems is currently being discussed in a controversial manner. Recent results indicate that the part of the CLF domain consists in the decarboxylation of malonyl ACP. The acetyl group produced can subsequently bond to the active center of a beta ketoacyl synthase domain and thus represents the so-called priming molecule of the initial condensation reaction. CLF-homologous sequences are also found as load domains in molecular PKS systems. Domains with CLF sequence properties are present in all previously known PUFA-PKS systems. This is followed by an acyl transferase domain (Seq ID No. 52 and 60). This domain catalyzes a number of acyl transfers such as the transfer from acyl to coenzymeA or to ACP domains. The terminating domain from ORF 2 shows partial identities to oxidoreductases (Seq ID No. 53 and 61) and represents an enoyl reductase domain with high probability. The biological activity of the enoyl reductase domain resides in the second reduction reaction of the fatty acid synthesis. It catalyzes the reduction of the trans double bond of the fatty acid acyl ACP (see also FIG. 2).

ORF 3 from *Ulkenia* sp. (Seq ID No. 5 and 8) consists of two dehydrase/isomerase domains (Seq ID No. 66, 68, 72 and 74). Both domains contain an "active site" histidine with a directly adjacent cysteine (Seq ID No. 67 and 73 as well as Seq ID No. 69 and 75). The biological function of these domains is the insertion of trans double bonds into the fatty acid or polyketide molecule with the splitting off of $H_2O$ and the subsequent conversion of the double bond into the cis isomeric form. The second dehydrase/isomerase domain merges into an alanine-rich region (Seq ID No. 70 and 76) without a known function but that possibly represents a linker region. This is followed by an enoyl reductase domain (Seq ID No. 71 and 77) with high partial identity to the enoyl reductase domain from *Ulkenia* already present in ORF 2. Its biological function corresponds to the enoyl reductase domain already described above (see also FIG. 2).

Preferably 2000 bp (Sequence ID No. 62) are present as promoter sequence in front of the start ATG codon for ORF 1 from *Ulkenia* sp. They are especially preferably 1500 bp, more especially preferably 1000 bp in front of the start.

Preferably 2000 bp (Sequence ID No. 63) can be present after the stop codon TAA as termination sequence for ORF 1. 1500 bp are especially preferred and 1000 bp are more especially preferred after the stop. A potential termination signal for the mRNA synthesis of ORF 1, with the base sequence AATAAA, is present 412 bp after stop codon TAA.

Preferably 2000 bp (Sequence ID No. 64) are present as promoter sequence in front of the start ATG codon for ORF 2 from *Ulkenia* sp. They are especially preferably 1500 bp, more especially preferably 1000 bp in front of the start.

Preferably 2000 bp (Sequence ID No. 65) can be present after the stop codon TAA as termination sequence for ORF 2. A potential termination signal for the mRNA synthesis of ORF 2, with the base sequence AATAAA, is present 1650 bp after stop codon TAA.

Preferably 2000 bp (Sequence ID No. 78) are present as promoter sequence in front of the start ATG codon for ORF 3 from *Ulkenia* sp. They are especially preferably 1500 bp, more especially preferably 1000 bp in front of the start.

Preferably 2000 bp (Sequence ID No. 79) can be present after the stop codon TAA as termination sequence for ORF 3. A potential termination signal for the mRNA synthesis of ORF 3, with the base sequence AATAAA, is present 4229 bp after stop codon TAA.

PUFA such as, e.g., DHA can be produced homologously in *Ulkenia* sp. as well as also heterologously in a host such as, e.g., *E. coli* using the sequence information determined in the present invention. The nucleic acid sequences in accordance with the invention can be used to increase the production of PUFA in that they are used, e.g., to increase the number of PUFA-PKS genes in the PUFA-producing organism. Naturally, even individual nucleic acid sections such as, e.g., the sequence sections coding for the ACP domains can be multiplied in a homologous or also heterologous production organism. In particular, the ACP domains present themselves for increasing the production as bonding sites for the cofactor 4-phosphapantheteine essential for PUFA synthesis. Naturally, even the use of different regulatory elements such as, e.g., promoters, terminators and enhancer elements can result in an increase in production in genetically modified PUFA producers. Genetic modifications in individual sequence sections can result in a changing of the structure of the resulting product and thus in the production of different PUFAs. Moreover, the similarity of PUFA synthases to polyketide synthases makes possible the construction of mixed systems. This so-called combinatory biosynthesis permits the production of new artificial bioactive substances. For example, new polyketide antibiotics that are produced in transgenic microorganisms by a mixed system of PKS- and PUFA-PKS units are conceivable.

Hosts suitable for the heterologous expression of the PUFA genes present here are, in addition to *E. coli*, e.g., yeasts such as *Saccharomyces cerevisiae* and *Pichia Pastoris* or filamentary fungi such as, e.g., *Aspergillus nidulans* and *Acremonium chrysogenum*. PUFA-producing plants can be generated by introducing the genes in accordance with the invention in, e.g., soy, rape, sunflower, flax or other, preferably oil-rich plants. For an effective heterologous expression of PUFA genes even other accessory genes such as, e.g., 4-phosphopantheteine transferases can also be used. Moreover, host-specific promoter/operator systems can be used for reinforced or inducible gene expression.

A plurality of prokaryotic expression systems can be used for the heterologous production of PUFA. Expression vectors that also contain, in addition to the corresponding PUFA genes, promoters, ribosome bonding sites and transcription terminators can be constructed. The promoter/operator region of *E. coli* tryptophan biosynthesis and promoters of the lambda phage are cited as examples for such regulatory elements in *E. coli*. Likewise, selectable markers such as, e.g., resistances to ampicillin, tetracycline or chloramphenicol can be used on the appropriate vectors. Very suitable vectors for the transformation of *E. coli* are pBR322, pCQV2 and the pUC plasmid as well as their derivatives. These plasmids can contain viral as well as bacterial elements. Every strain stemming from *E. coli* K12 such as, e.g., JM 101, JM109, RR1, HB101, DH1 or AG1 can be used as *E. coli* host strain. Naturally, all other customary prokaryotic expression systems are also conceivable for heterologous PUFA production (see also Sambrook et al.). The use of oil-building bacteria as host systems is also conceivable.

Mammalian, plant and insect cells as well as fungi such as, e.g., yeasts can be used as eukaryotic expression systems. In the case of the yeast system transcription initiation elements from genes from enzymes from the glycolysis can be used. This includes regulatory elements of alcohol dehydrogenase, glycerol aldehyde-3-phosphate dehydrogenase, phosphoglukoisomerase, phosphoglycerate kinase, etc. However, even regulatory elements from genes such as from acidic phosphatase, lactase, metallothionein or glucoamylase can be used. Promoters are also used here that permit a reinforced or inducible expression. Promoters inducible by galactose (GAL1, GAL7 and GAL10) are also of particular interest (Lue et al. 1987 Mol. Cell. Biol. 7, p. 3446 ff. and Johnston 1987 Mircobiol. Rev. 51, p. 458 ff.). The 3' termination sequence preferably also stems from a yeast. Since nucleotide sequences immediately around the start codon (ATG) influence the expression of genes in yeasts, efficient translation initiation sequences from the yeast are also preferred. In instances in which yeast plasmids are used, they contain a replication origin from yeasts and contain a selection marker. This selection marker is preferably an auxotrophy marker such as, e.g., LEU, TRP or HIS. Such yeast plasmids are the so-called YRps (Yeast Replicating plasmids), YCps (Yeast Centromere plasmids) and YEps (Yeast Episomal plasmids). Plasmids without replication origin are the Yips (Yeast Integrating plasmids), that are used for the integration of transformed DNA into the genome. The plasmids pYES2 and pYX424 as well as the pPICZ plasmids are of special interest.

If filamentous fungi such as, e.g., *Aspergillus nidulans* are used as heterologous PUFA producers, promoters from the corresponding organism can also be used. The gpdA promoter for a reinforced expression and the alcA promoter for an inducible expression can be used as examples. Yeast plasmids such as pHELP (D. J. Balance and G. Turner (1985) Development of a high-frequency transforming vector for *Aspergillus nidulans*. Gene 36, 321-331) and selectable markers such as ura, bio or paba are preferably used for the transformation of filamentous fungi. Even 3' regulatory elements from filamentous fungi are preferred.

The production of PUFA in insect cells can take place by the baculovirus expression system. Such expression systems are commercially available, e.g., from Clonetech or Invitrogen.

Vectors such as, e.g., the Ti plasmid from *Agrobacterium* or entire viruses such as Cauliflower MosaicVirus (CaMV), Geminivirus, Tomato golden MosaicVirus or Tobacco MosaicVirus (TMV) can be used for the transformation of plants. A preferred promoter is, e.g., the 35S promoter of CaMV. Further possibilities for the transformation of plants are the calcium phosphate method, the polyethylene glycol method, microinjection, electroporation or lipofection of protoplasts. The transformation by bombarding with the DNA-charged microparticles (gene gun) is also preferred. An alternative PUFA production in plants results from the transformation of chloroplasts. For example, N-terminal Leader peptides make possible a transport of proteins in chloroplasts. A preferred Leader peptide stems from the small subunit of ribulose biphosphate carboxylase but Leader peptides of other chloroplastidary proteins can also be used. Another possibility is offered by the stable transformation of the chloroplast genome. In particular biolistic but also other methods can be considered for this (Blowers et al. Plant Cell 1989 1 pp. 123-132, Kline et al. Nature 1987 327 pp. 70-73 and Schrier et al. Embo J. 4 pp. 25-32.

Commercially available expression systems can also be used for mammalian cells. Among others, viral and non-viral transformation- and expression systems such as, e.g., the lentiviral or adenoviral systems or the T-Rex system of Invitrogen can be used as examples. The Flp-In system, also from Invitrogen, presents itself for the purposeful integration of DNA in mammalian cells.

The nucleic acid and amino acids constituting the basis for the method in accordance with the invention are described in the following using a few examples. However, the sequences and the invention are not limited to these examples.

This specification incorporates-by reference the material contained on the CD-ROM containing the file named SEQUENCE LISTING 112310 which was created on Nov. 23, 2010 and is 327 kilobytes in size.

BRIEF DESCRIPTION OF THE FIGURES

FIG. 4 contains a sequence comparison of ORF 1 from *Ulkenia* sp. (SEQ. ID Nos 3 and 6) with ORF A from *Schizochytrium* (SEQ. ID No 87). The degree of partial identity of both sequences is approximately 81.5%.

FIG. 5 contains a sequence comparison of ORF 2 from *Ulkenia* sp. (SEQ. ID Nos 4 and 7) with ORF B from *Schizochytrium* (SEQ. ID No 88). The degree of partial identity of both sequences is approximately 75.9%.

Figure 6B:
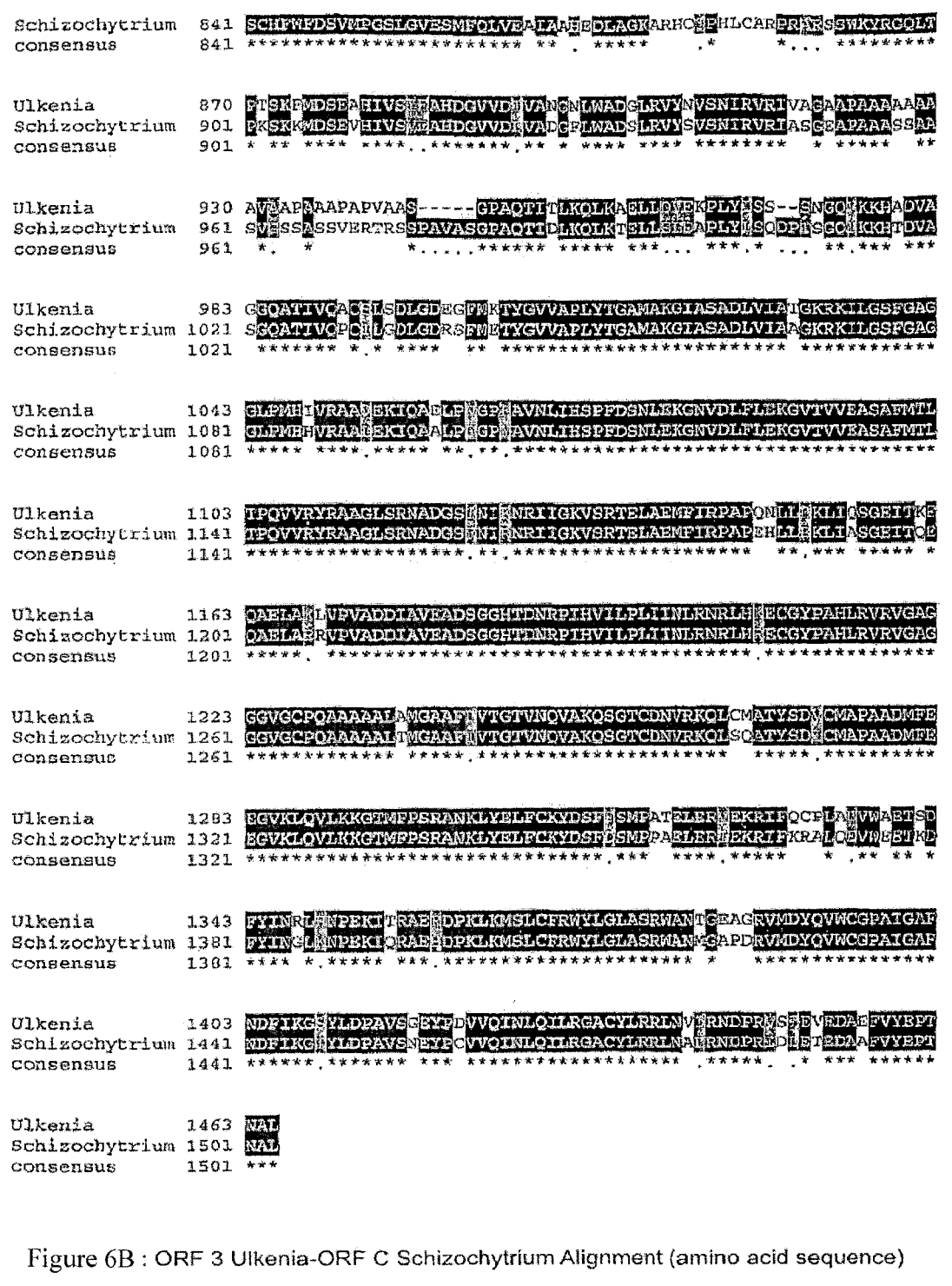

FIG. 6 contains a sequence comparison of ORF 3 from *Ulkenia* sp. (SEQ. ID Nos 5 and with ORF C from *Schizochytrium* (SEQ. ID No 89). The degree of partial identity of both sequences is approximately 80.0%.

FIG. 7 describes a sequence comparison, performed with FASTAX, of the PCR product described in Example 1 (SEQ. ID Nos 81 and 82) with databank sequences (Swiss-PROT All library) (SEQ. ID No 90).

FIG. 9 describes a sequence comparison, performed with BLASTX, of the PCR product described in Example 3 (SEQ. ID Nos 85 and 86) with databank sequences (Swiss-PROT All library) (SEQ. ID No 91).

EXAMPLES

Example 1

Figure 1:
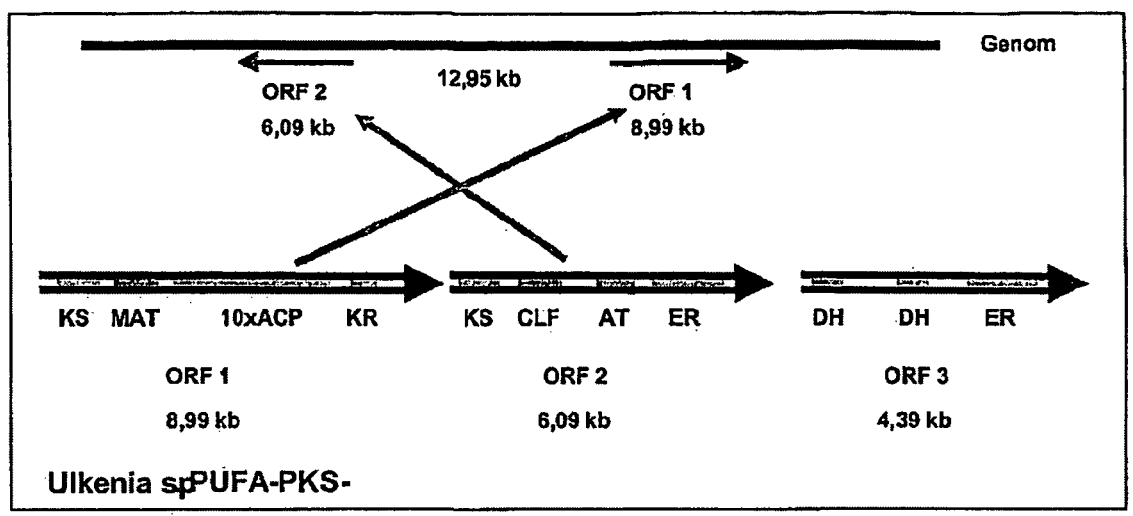
FIG. 1 describes the position of PUFA-PKS genes from *Ulkenia* sp. on the genome. Furthermore, the individual domains of the PUFA-PKS coded by these genes are shown. KS: Keto Synthase, MAT: Malonyl-CoA:ACP Acyl transferase, ACP: Acyl Carrier Protein, KR: Keto Reductase, CLF: Chain Length Factor, AT: Acyl transferase, ER: Enoyl Reductase and DH: Dehydrase/Isomerase.
Figure 2:
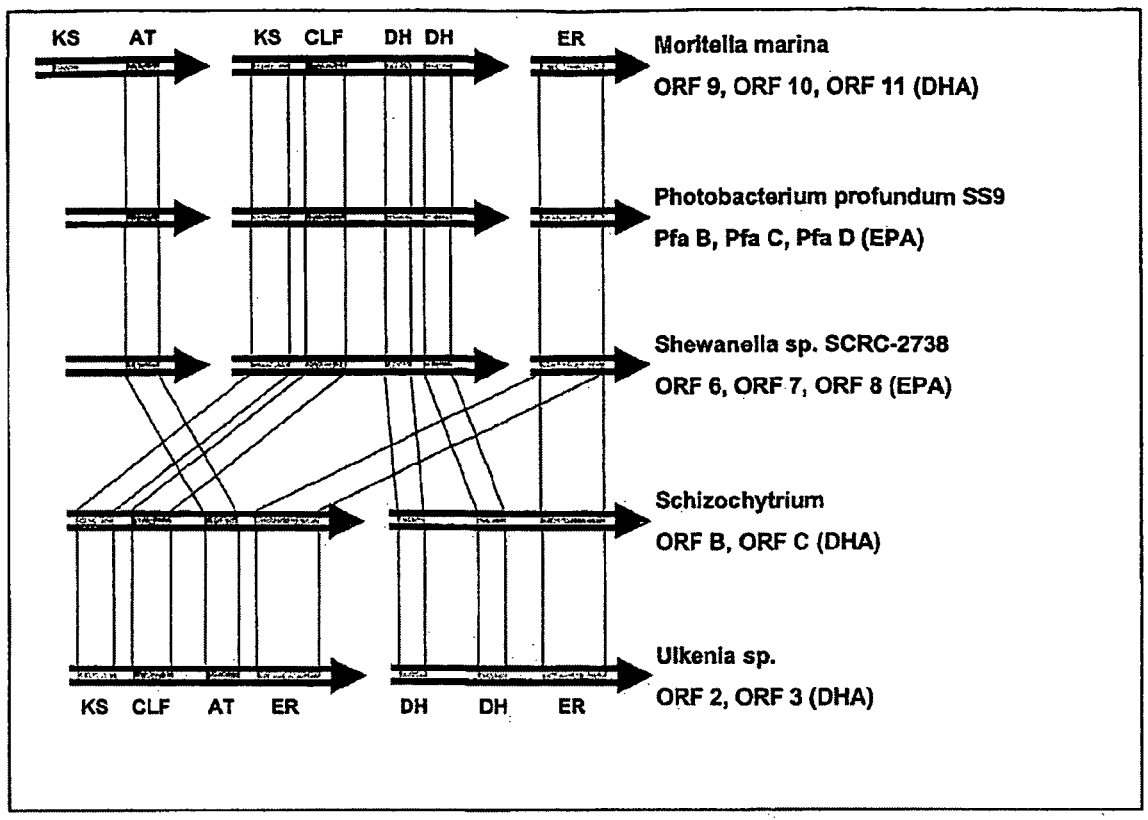
FIG. 2 shows a comparison of ORF 2 and ORF 3 from *Ulkenia* sp. with the corresponding homologous ORFs from *Moritella marina* (GenBank accession no.: AB025342.1), *Photobacterium profundum* SS9 (GenBank accession no.: AF409100), *Shewanella* sp. SCRC-2783 (GenBank accession no.: U73935.1) and *Schizochytrium* (GenBank accession nos.: AF378327, AF378328, AF378329). The gene transpositions in and between the individual ORFs in the course of the evolution are also indicated next to the domain structure.
Figure 3:
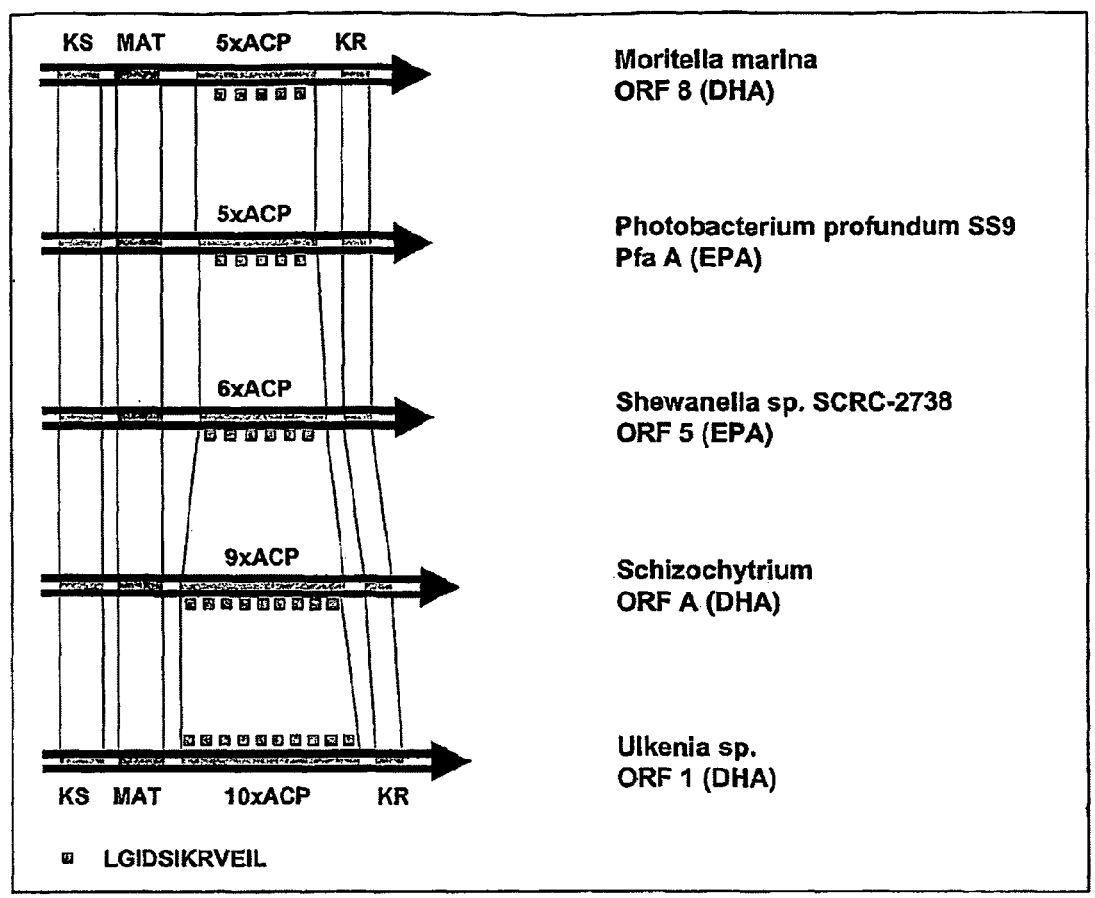
FIG. 3 shows a comparison of ORF 1 from *Ulkenia* sp. with the corresponding homologous ORFs from *Moritella marina* (GenGank accession no.: AB025342.1), *Photobacterium profundum* SS9 (GenBank accession no.: AF409100), *Shewanella* sp. SCRC-2783 (GenBank accession no.: U73935.1) and *Schizochytrium* (GenBank accession nos.: AF378327, AF378328, AF378329). The number of ACP domains and the repetitions of the amino acid succession LGIDSIKRVEIL are emphasized.

Amplification of a PUFA-PKS Specific Sequence from DNA Isolated from *Ulkenia* sp. SAM2179

1.1 Isolation of Genomic DNA Containing Genes Coding for PUFA-PKS 50 ml DH1 medium (50 g/l glucose; 12.5 g/l yeast extract; 16.65 g/l Tropic Marin; pH 6.0) was inoculated in a 250 ml Erlenmeyer flask with flow spoiler with *Ulkenia* sp. SAM 2179 and cultivated 48 h at 28° C. and 150 rpm. The cells were subsequently washed with sterile tap water, centrifuged off and the cell sediment frozen at −85° C. For the further workup the cell sediment was then transferred into a mortar and comminuted under liquid nitrogen with a pestle to a fine powder. Then, $\frac{1}{10}^{th}$ of the pulverized cell material was compounded with 2 ml lysis buffer (50 mM tris/Cl pH 7.2; 50 mM EDTA; 3% (v/v) SDA; 0.01% (v/v) 2-mercaptoethanol) and incubated 1 h at 68° C. 2 ml phenol/chloroform/isoamylalcohol (25:24:1) were subsequently added, agitated and centrifuged 20 min at 100000 rpm. After removal of the upper aqueous phase the latter was transferred into two new reaction vessels at 600 μl each and again compounded with 600 μl each phenol/chloroform/isoamylalcohol (25:24:1), agitated and centrifuged 15 min at 13000 rpm. Each 400 μl of a particular upper phase was then transferred into a new reaction vessel and inverted two to three times after the addition of 1 ml ethanol (100%) in each instance. Then, the precipitated DNA was wound on a glass rod, washed with 70% ethanol, dried and dissolved in 50 μl $H_2O_{dist}$. The DNA extracted in this manner was compounded with 2 μl RNase A and stored at 4° C. until further use.

1.2 PCR Reaction Using Motive-Specific Oligonucleotides

The PCR primers MOF1 and MOR1 were used as motive-specific oligonucleotides.

MOF1: 5'-CTC GGC ATT GAC TCC ATC-3' (Seq ID No. 81) MOR1: 5'-GAG AAT CTC GAC ACG CTT-3' (Seq ID No. 82). The genomic DNA from *Ulkenia* sp. 2179 as described in Paragraph 1.1 above was diluted 1:100. 2 μl of this dilution were then transferred into a 50 μl volume PCR reaction mixture (1× buffer (Sigma); dNTPs (200 μM each); MOF1 (20 pmol), MOR1 (20 pmol) and 2.5 U Taq-DNA polymerase (Sigma). The PCR was carried out under the following conditions: Initial denaturing 94° C. for 3 min, followed subsequently by 30 cycles at 94° C. each for 1 min, 55° C. for 1 min, 72° C. 1 min and finally 8 min 72° C. The PCR products were then analyzed by gel electrophoresis and fragments with an appropriate size incorporated into vector pCR2.1 TOPO via T/A cloning (Invitrogen). After transformation of *E. coli* TOP10F', plasmid DNA was isolated (Qiaprep Spin, QUAGEN) and sequenced.

The sequence data obtained was compared with the officially accessible EMBL Nucleotide Sequence Database and evaluated. The sequence comparisons obtained with FASTAX yielded for the main product of the PCR from *Ulkenia* sp. SAM 2179 a partial identity, that was approximately 90% on the amino acid level, with the acyl carrier protein of PUFA-PKS (ORF A; ORF: open reading frame) from *Schizochytrium* sp. ATCC 20888 (FIG. 7). Surprisingly, only a single PCR experiment had to be carried out in order to determine this PUFA-PKS in *Ulkenia* sp. SAM 2179. This speaks for an especially high effectiveness of the oligonucleotides used.

Example 2

Production of a Gene Bank from Genomic DNA from *Ulkenia* Sp. SAM 2179

Figure 8:
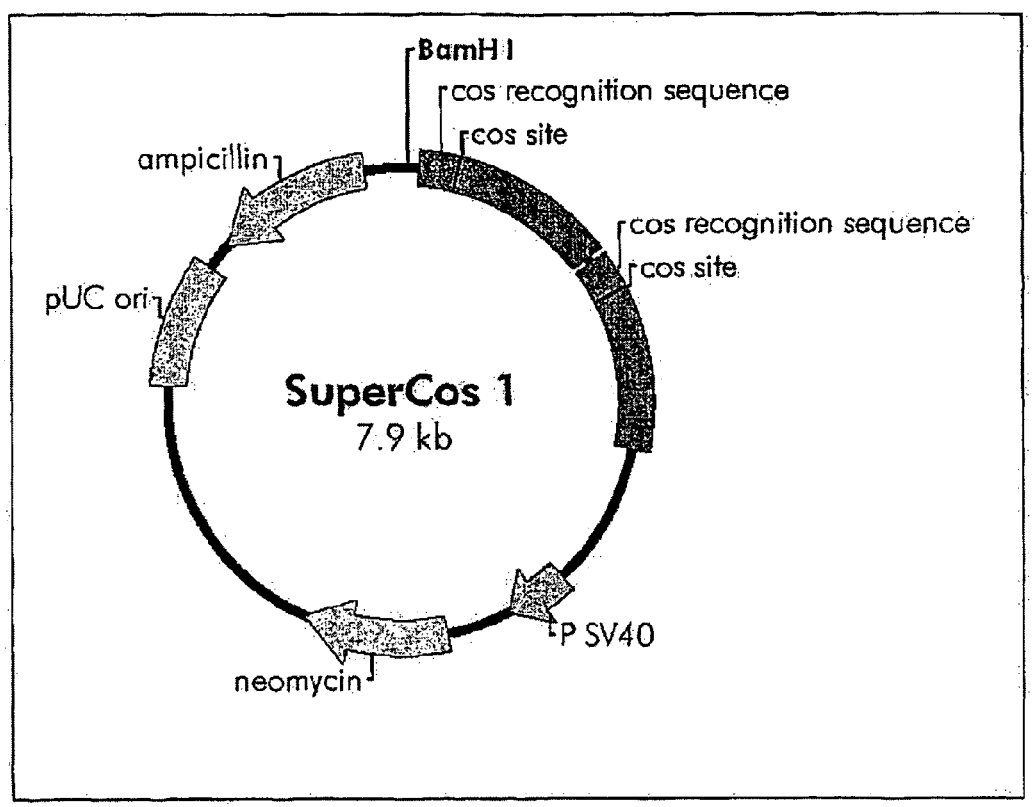
FIG. 8 shows a vector card of Cosmid SuperCosI (Stratagene), that was used to produce the cosmid bank from Example 2.

50 μg genomic DNA from *Ulkenia* sp. SAM 2179 were partially split in a volume of 500 μl with 2.5 U Sau3AI for 2 min at 37° C. and subsequently immediately precipitated with the same volume of phenol/chloroform, then precipitated with ethanol and taken up in $H_2O_{dist}$. Then, the Sau3AI split genomic DNA was dephosphorylated with SAP (Shrimp Alkaline Phosphatase; Roche) according to the instructions of the producer. Enzyme inactivation subsequently took place by heating the reaction batch for 20 minutes to 65° C. Cosmid Supercos I (Stratagene, FIG. 8) was used as vector. 10 μg Supercos I were completely split several hours with XbaI at 37° C. The enzyme was then heat-inactivated 20 min at 65° C. and the cleaved cosmid dephosphorylated with SAP (Shrimp Alkaline Phosphatase; Roche) according to the instructions of the producer. The enzyme inactivation also took place here by heating the reaction batch for 20 minutes at 65° C. XbaI split and dephosphorylated Supercos I cosmid was then completely split with BamHI for several hours at 37° C. The cleaved cosmid DNA was then precipitated with phenol/chloroform, precipitated with ethanol and subsequently taken up in $H_2O_{dist}$. For the ligation 1 μg cosmid DNA, split with XbaI and BamHI, and 3.5 μl Sau3AI split genomic DNA were combined in a volume of 20 μl and ligated with T4 ligase (Biolabs) in accordance with the instructions of the producer for several hours. Approximately $\frac{1}{3}^{th}$ of the ligation batch was subsequently packaged in phages using the Gigapack III XL Packaging Extract (Stratagene) in accordance with the instructions of the producer. The latter were then used for the transfection of *E. coli* XL1-Blue MR. The isolation of PUFA-PKS-specific cosmids from the gene bank took place subsequently by the QIAGEN company (Hilden, Germany) in the form of a PCR screening using the *Ulkenia*-PKS-specific oligonucleotides PSF2:5'-ATT ACT CCT CTC TGC ATC CGT-3' (Seq ID No. 83) and PSR2: 5'-GCC GAA GAC AGC ATC AAA CTC-3' (Seq ID No. 84). The cosmid DNA of cosmid clone C19F09 determined thereby was subsequently isolated and sequenced (Seq ID No. 1).

Example 3

Identification of ORF3 from *Ulkenia* Sp.

In order to identify ORF 3 from *Ulkenia* sp. SAM 2179, oligonucleotides were derived from highly preserved sequence sections of different PUFA-PKS. Interestingly, very high partial identities that appeared to be suitable for PCR amplification appeared in the area of the sequence sections coding for the dehydrase/isomerase between the individual species.

3.1 Isolation of Genomic DNA Containing Genes Coding for PUFA-PKS

See example 1.1

3.2 PCR Reactions Using PUFA-PKS-Specific Oligonucleotides

The following PCR primers were used as PUFA-PKS-specific oligonucleotides:

```
                                              (Seq No. 85)
CFOR1:   5'- GTC GAG AGT GGC CAG TGC GAT -3'

(Seq ID No. 86)
CREV3:   5'- AAA GTG GCA GGG AAA GTA CCA -3'.
```

The genomic DNA from *Ulkenia* sp. 2179 as described under Paragraph 3.1 above was diluted to a ratio of 1:10. 2 μl of this dilution were then transferred into a 50 μl volume PCR reaction mixture (1× and buffer (Sigma); dNTPs (200 μM each); CFOR1 (20 pmol), CREV3 (20 pmol) and 2.5 U Taq-DNA polymerase (Sigma). The PCR was carried out under the following conditions: Initial denaturing 94° C. for 3 min followed by 30 cycles at 94° C. each for 1 min, 60° C. for 1 min, 72° C. 1 min, and finally 8 min 72° C. The PCR products were then analyzed by gel electrophoresis and fragments with an appropriate size incorporated into vector pCR2.1 TOPO via T/A cloning (Invitrogen). After transformation of *E. coli* TOP10F', plasmid DNA was isolated (Qiaprep Spin, QUAGEN) and partially sequenced.

The sequence data obtained was compared with the officially accessible EMBL Nucleotide Sequence Database and evaluated. The sequence comparisons obtained with FASTAX yielded for the main product of the PCR from *Ulkenia* sp. SAM 2179 a partial identity that was approximately 80% on the amino acid level, with the ORF C of the PUFA-PKS synthase from *Schizochytrium* sp. ATCC 20888 (FIG. 9). Surprisingly, only a single PCR experiment had to be carried out in order to determine this PUFA-PKS in *Ulkenia* sp. SAM 2179. This speaks for an especially high effectiveness of the oligonucleotides used. The isolation of PUFA-PKS-specific cosmids from the gene bank described in Example 2 took place subsequently by the QIAGEN company (Hilden, Germany) in the form of a PCR screening using the oligonucleotides CFOR1: 5'-GTC GAG AGT GGC CAG TGC GAT-3' (Seq ID No. 85) and CREV3: 5'-AAA GTG GCA GGG AAA GTA CCA-3' (Seq ID No. 86) already used for the PCR. The cosmid DNA of cosmid clone 058G09 determined thereby was subsequently isolated and sequenced (Seq ID No. 2).

---

The invention claimed is:

1. An isolated and purified PUFA-PKS, comprising the amino acid sequence of SEQ ID NO:6 (ORF 1) or a sequence with at least 95% sequence homology to SEQ ID NO:6 that has PUFA-PKS enzymatic activity comprising keto synthase (KS), malonyl-CoA:ACP acyltransferase (MAT), acyl carrier protein (ACP), and keto reductase (KR).

2. The isolated PUFA-PKS according to claim 1 with 10 ACP domains.

3. An isolated and purified PUFA-PKS according to claim 1, characterized in that it comprises at least one amino acid sequence with at least 95% sequence homology with at least 500 successive amino acids of SEQ ID NO:6 (ORF 1) and has PUFA-PKS enzymatic activity selected from the group consisting of KS, MAT, ACP, and KR.

4. An isolated and purified amino acid sequence with at least 95% identity with at least 500 successive amino acids of SEQ ID NO:6 (ORF 1) and that has PUFA-PKS enzymatic activity selected from the group consisting of KS, MAT, ACP, and KR.

5. An isolated and purified PUFA-PKS comprising the amino acid sequence of SEQ ID NO: 32 or a sequence with at least 99% sequence homology to SEQ ID NO: 32 that has KS enzymatic activity of the PUFA-PKS, or
   at least one amino acid sequence of SEQ ID NO: 33, 34, and 45 or a sequence with at least 95% sequence homology to one of SEQ ID NO: 33, 34 and 45 that has PUFA-PKS enzymatic activity selected from the group consisting of MAT, ACP, and KR.

6. The isolated PUFA-PKS according to claim 5 with 10 ACP domains of SEQ ID NO:34.

* * * * *